US011667981B2

(12) United States Patent
Eyal et al.

(10) Patent No.: US 11,667,981 B2
(45) Date of Patent: *Jun. 6, 2023

(54) LIGNOCELLULOSIC CONVERSION PROCESSES AND PRODUCTS

(71) Applicant: Virdia, LLC, Danville, VA (US)

(72) Inventors: Aharon Eyal, Jerusalem (IL); Robert P. Jansen, Collinsville, IL (US)

(73) Assignee: VIRDIA, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/100,679

(22) Filed: Nov. 20, 2020

(65) Prior Publication Data
US 2021/0147952 A1    May 20, 2021

Related U.S. Application Data

(63) Continuation of application No. 15/334,147, filed on Oct. 25, 2016, now Pat. No. 10,876,178, which is a continuation of application No. 14/009,858, filed as application No. PCT/IL2012/050118 on Apr. 2, 2012, now Pat. No. 9,512,495.

(60) Provisional application No. 61/483,663, filed on May 7, 2011, provisional application No. 61/473,134, filed on Apr. 7, 2011.

(51) Int. Cl.
| | | |
|---|---|---|
| *C13K 1/02* | (2006.01) | |
| *C08H 8/00* | (2010.01) | |
| *C13K 13/00* | (2006.01) | |
| *A61L 15/42* | (2006.01) | |
| *C08H 7/00* | (2011.01) | |
| *C08L 97/02* | (2006.01) | |
| *D21C 3/00* | (2006.01) | |
| *D21H 11/00* | (2006.01) | |
| *C10L 1/00* | (2006.01) | |
| *C10L 1/02* | (2006.01) | |
| *C10L 1/04* | (2006.01) | |
| *C10L 1/06* | (2006.01) | |
| *C10L 1/08* | (2006.01) | |
| *C07C 57/04* | (2006.01) | |
| *C08K 3/20* | (2006.01) | |
| *C10L 1/18* | (2006.01) | |
| *C11D 3/382* | (2006.01) | |
| *C11D 3/386* | (2006.01) | |
| *A61L 15/20* | (2006.01) | |
| *C11D 1/66* | (2006.01) | |
| *C12P 7/10* | (2006.01) | |
| *C12P 7/18* | (2006.01) | |
| *C12P 7/56* | (2006.01) | |
| *D21C 5/02* | (2006.01) | |

(52) U.S. Cl.
CPC .............. *C13K 1/02* (2013.01); *A61L 15/20* (2013.01); *A61L 15/42* (2013.01); *C07C 57/04* (2013.01); *C08H 6/00* (2013.01); *C08H 8/00* (2013.01); *C08K 3/20* (2013.01); *C08L 97/02* (2013.01); *C10L 1/003* (2013.01); *C10L 1/02* (2013.01); *C10L 1/026* (2013.01); *C10L 1/04* (2013.01); *C10L 1/06* (2013.01); *C10L 1/08* (2013.01); *C10L 1/1802* (2013.01); *C11D 1/66* (2013.01); *C11D 3/382* (2013.01); *C11D 3/386* (2013.01); *C11D 3/38609* (2013.01); *C11D 3/38618* (2013.01); *C12P 7/10* (2013.01); *C12P 7/18* (2013.01); *C12P 7/56* (2013.01); *C13K 13/00* (2013.01); *C13K 13/002* (2013.01); *C13K 13/007* (2013.01); *D21C 3/00* (2013.01); *D21C 5/022* (2013.01); *D21H 11/00* (2013.01); *C12P 2201/00* (2013.01); *Y02E 50/10* (2013.01)

(58) Field of Classification Search
CPC ...... C13K 1/02; C13K 13/002; C13K 13/007; C08H 8/00; C08H 6/00; A61L 15/20; C12P 7/56; C12P 7/18; C12P 7/10; C12P 2201/00; C10L 1/026; C10L 1/02; C11D 1/66; C11D 3/386; D21C 5/022
USPC ....................................................... 536/124
See application file for complete search history.

(56) References Cited

U.S. PATENT DOCUMENTS

| | | | |
|---|---|---|---|
| 1,344,671 | A | 6/1920 | Bergius |
| 1,391,664 | A | 9/1921 | Bergius |
| 1,457,791 | A | 6/1923 | Norris et al. |
| 1,544,149 | A | 6/1925 | Hagglund |
| 1,547,893 | A | 7/1925 | Bergius |

(Continued)

FOREIGN PATENT DOCUMENTS

| | | |
|---|---|---|
| CA | 2735396 A1 | 3/2010 |
| CN | 1082115 A | 2/1994 |

(Continued)

OTHER PUBLICATIONS

Chen et al.; CN 101787398 A; Jul. 28, 2010 (Machine-English Translation).*

(Continued)

*Primary Examiner* — Shaojia A Jiang
*Assistant Examiner* — Michael C Henry
(74) *Attorney, Agent, or Firm* — DLA Piper LLP

(57) ABSTRACT

Processes for converting lignocellulose to feedstock and downstream products are disclosed. The processes may include acid treatment of lignocellulose to produce a fermentation feedstock. In various instances, the processes include recovery or recycling of acid, such as recovery of hydrochloric acid from concentrated and/or dilute streams. Downstream products may include acrylic acid-based products such as diapers, paper and paper-based products, ethanol, biofuels such as biodiesel and fuel additives, and detergents.

20 Claims, 1 Drawing Sheet

(56) References Cited

U.S. PATENT DOCUMENTS

| | | |
|---|---|---|
| 1,688,726 A | 10/1928 | Mckee |
| 1,699,177 A | 1/1929 | Bergius |
| 1,853,330 A | 4/1932 | Barstow et al. |
| 1,890,491 A | 12/1932 | Bergius et al. |
| 1,906,467 A | 5/1933 | Heath |
| 1,919,623 A | 7/1933 | Dreyfus |
| 2,008,284 A | 7/1935 | Koch et al. |
| 2,146,326 A | 2/1939 | Bergius et al. |
| 2,239,095 A | 4/1941 | Hasche |
| 2,293,724 A | 8/1942 | Faerber |
| 2,305,833 A | 12/1942 | Warth |
| 2,347,945 A | 5/1944 | Frey |
| 2,380,448 A * | 7/1945 | Katzen .................. C08H 6/00 530/507 |
| 2,391,149 A | 12/1945 | Frey |
| 2,440,442 A | 4/1948 | Hillyer et al. |
| 2,474,669 A | 6/1949 | Hereng |
| 2,692,291 A | 10/1954 | Bryan |
| 2,743,219 A | 4/1956 | Riehm |
| 2,752,270 A | 6/1956 | Specht |
| 2,778,751 A | 1/1957 | Richm |
| 2,890,972 A | 6/1959 | Wheaton |
| 2,917,390 A | 12/1959 | Apel et al. |
| 2,937,959 A | 5/1960 | Reents et al. |
| 2,944,923 A | 7/1960 | Riehm |
| 2,945,777 A | 7/1960 | Riehm |
| 2,951,775 A | 9/1960 | Apel |
| 2,989,569 A | 6/1961 | Apel |
| 3,067,065 A | 12/1962 | Kusama |
| 3,132,051 A | 5/1964 | Nobile et al. |
| 3,212,933 A | 10/1965 | Hess et al. |
| 3,251,716 A | 5/1966 | Porter |
| 3,311,450 A | 3/1967 | Alon et al. |
| 3,326,944 A | 6/1967 | Lew |
| 3,394,056 A | 7/1968 | Nadler et al. |
| 3,432,569 A | 3/1969 | Folz |
| 3,497,330 A | 2/1970 | Avraham et al. |
| 3,527,820 A | 9/1970 | Jules |
| 3,562,289 A | 2/1971 | Orlando et al. |
| 3,616,222 A | 10/1971 | Dasinger |
| 3,697,497 A | 10/1972 | Alfons |
| 3,808,192 A | 4/1974 | Dimitri |
| 3,839,318 A | 10/1974 | Mansfield |
| 4,008,285 A | 2/1977 | Melaja et al. |
| 4,018,637 A | 4/1977 | Kimmel et al. |
| 4,029,515 A | 6/1977 | Kiminki et al. |
| 4,036,939 A | 7/1977 | Duhayon et al. |
| 4,075,406 A | 2/1978 | Melaja et al. |
| 4,102,705 A | 7/1978 | Pfeiffer et al. |
| 4,111,928 A | 9/1978 | Holsopple et al. |
| 4,115,530 A | 9/1978 | Coenen et al. |
| 4,174,976 A | 11/1979 | Bose et al. |
| 4,184,845 A | 1/1980 | Lin |
| 4,206,302 A | 6/1980 | Favrot et al. |
| 4,230,681 A | 10/1980 | Coenen et al. |
| 4,237,110 A | 12/1980 | Forster et al. |
| 4,255,356 A | 3/1981 | Coenen et al. |
| 4,257,818 A | 3/1981 | Regnault et al. |
| 4,259,309 A | 3/1981 | Coenen et al. |
| 4,266,981 A | 5/1981 | Tsao et al. |
| 4,272,502 A | 6/1981 | Ziegenbein et al. |
| 4,277,626 A | 7/1981 | Forss et al. |
| 4,278,471 A | 7/1981 | Whittingham |
| 4,291,007 A | 9/1981 | Baniel |
| 4,299,677 A | 11/1981 | Venkatasubramanian et al. |
| 4,304,608 A | 12/1981 | Regnault et al. |
| 4,328,004 A | 5/1982 | Globus |
| 4,332,623 A | 6/1982 | Ando et al. |
| 4,374,738 A | 2/1983 | Kelley |
| 4,379,751 A | 4/1983 | Yoritomi et al. |
| 4,382,843 A | 5/1983 | Black |
| 4,384,897 A | 5/1983 | Brink |
| 4,395,543 A | 7/1983 | Wang et al. |
| 4,420,644 A | 12/1983 | Huibers et al. |
| 4,425,136 A | 1/1984 | Pearson et al. |
| 4,470,851 A | 9/1984 | Paszner et al. |
| 4,472,501 A | 9/1984 | Takasawa et al. |
| 4,496,426 A | 1/1985 | Baumeister et al. |
| 4,516,566 A | 5/1985 | Chao et al. |
| 4,520,105 A | 5/1985 | Sinner et al. |
| 4,525,218 A | 6/1985 | Chen et al. |
| 4,533,743 A | 8/1985 | Medeiros et al. |
| 4,556,430 A | 12/1985 | Converse et al. |
| 4,556,432 A | 12/1985 | Erckel et al. |
| 4,579,595 A | 4/1986 | Sachetto et al. |
| 4,608,245 A | 8/1986 | Gaddy et al. |
| 4,612,286 A | 9/1986 | Sherman et al. |
| 4,615,742 A | 10/1986 | Wright |
| 4,631,129 A | 12/1986 | Heikkila |
| 4,645,658 A | 2/1987 | Gaddy et al. |
| 4,647,704 A | 3/1987 | Engel et al. |
| 4,668,340 A | 5/1987 | Sherman |
| 4,677,198 A | 6/1987 | Linnett et al. |
| 4,701,414 A | 10/1987 | Van et al. |
| 4,713,413 A | 12/1987 | Tegge et al. |
| 4,746,401 A | 5/1988 | Roberts et al. |
| 4,764,596 A | 8/1988 | Lora et al. |
| 4,764,597 A | 8/1988 | Dilling |
| 4,814,015 A | 3/1989 | Quinlan |
| 4,837,315 A | 6/1989 | Kulprathipanja |
| 4,840,903 A | 6/1989 | Wu |
| 4,901,635 A | 2/1990 | Williams |
| 4,934,177 A | 6/1990 | Cuthbertson et al. |
| 4,946,946 A | 8/1990 | Fields et al. |
| 4,958,016 A | 9/1990 | Kerkenaar et al. |
| 4,966,650 A | 10/1990 | Delong et al. |
| 4,970,002 A | 11/1990 | Ando et al. |
| 4,990,696 A | 2/1991 | Stauffer |
| 4,992,308 A | 2/1991 | Sunol |
| 5,028,336 A | 7/1991 | Bartels et al. |
| 5,049,494 A | 9/1991 | Allenza |
| 5,081,026 A | 1/1992 | Heikkila et al. |
| 5,084,104 A | 1/1992 | Heikkila et al. |
| 5,093,004 A | 3/1992 | Hotier et al. |
| 5,102,553 A | 4/1992 | Kearney et al. |
| 5,114,491 A | 5/1992 | Sarhaddar |
| 5,114,590 A | 5/1992 | Hotier et al. |
| 5,132,476 A | 7/1992 | Osterburg et al. |
| 5,138,110 A | 8/1992 | Segall et al. |
| 5,142,023 A | 8/1992 | Gruber et al. |
| 5,174,865 A | 12/1992 | Stultz et al. |
| 5,176,832 A | 1/1993 | Dorta et al. |
| 5,188,673 A | 2/1993 | Clausen et al. |
| 5,196,460 A | 3/1993 | Lora et al. |
| 5,205,473 A | 4/1993 | Coffin, Sr. |
| 5,227,446 A | 7/1993 | Denzinger et al. |
| 5,238,826 A | 8/1993 | Leleu et al. |
| 5,244,553 A | 9/1993 | Goldstein |
| 5,247,058 A | 9/1993 | Gruber et al. |
| 5,247,059 A | 9/1993 | Gruber et al. |
| 5,258,488 A | 11/1993 | Gruber et al. |
| 5,274,073 A | 12/1993 | Gruber et al. |
| 5,332,842 A | 7/1994 | Dickakian |
| 5,338,405 A | 8/1994 | Patt et al. |
| 5,338,822 A | 8/1994 | Gruber et al. |
| 5,340,403 A | 8/1994 | Fields et al. |
| 5,357,035 A | 10/1994 | Gruber et al. |
| 5,359,026 A | 10/1994 | Gruber |
| 5,407,580 A | 4/1995 | Hester et al. |
| 5,411,594 A | 5/1995 | Brelsford |
| 5,421,964 A | 6/1995 | Mahler et al. |
| 5,446,123 A | 8/1995 | Gruber et al. |
| 5,475,080 A | 12/1995 | Gruber et al. |
| 5,480,490 A | 1/1996 | Toth et al. |
| 5,484,881 A | 1/1996 | Gruber et al. |
| 5,510,526 A | 4/1996 | Baniel et al. |
| 5,525,706 A | 6/1996 | Gruber et al. |
| 5,536,807 A | 7/1996 | Gruber et al. |
| 5,538,637 A | 7/1996 | Hester et al. |
| 5,539,081 A | 7/1996 | Gruber et al. |
| 5,571,378 A | 11/1996 | Elofson et al. |
| 5,580,389 A | 12/1996 | Farone et al. |
| 5,585,191 A | 12/1996 | Gruber et al. |
| 5,594,095 A | 1/1997 | Gruber et al. |

(56) References Cited

U.S. PATENT DOCUMENTS

| | | |
|---|---|---|
| 5,597,714 A | 1/1997 | Farone et al. |
| 5,602,286 A | 2/1997 | Muralidhara |
| 5,637,225 A | 6/1997 | Heikkila et al. |
| 5,696,195 A | 12/1997 | Tuminello et al. |
| 5,698,667 A | 12/1997 | Speaks et al. |
| 5,705,369 A | 1/1998 | Torget et al. |
| 5,711,817 A | 1/1998 | Titmas |
| 5,723,704 A | 3/1998 | Demail et al. |
| 5,726,046 A | 3/1998 | Farone et al. |
| 5,730,837 A | 3/1998 | Black et al. |
| 5,730,877 A | 3/1998 | Heikkila et al. |
| 5,767,330 A | 6/1998 | Metz et al. |
| 5,780,678 A | 7/1998 | Baniel et al. |
| 5,782,982 A | 7/1998 | Farone et al. |
| 5,807,952 A | 9/1998 | Agblevor |
| 5,820,687 A | 10/1998 | Farone et al. |
| 5,837,831 A | 11/1998 | Gruening et al. |
| 5,846,787 A | 12/1998 | Ladisch et al. |
| 5,847,238 A | 12/1998 | Muralidhara et al. |
| 5,859,270 A | 1/1999 | Kolstad et al. |
| 5,865,948 A | 2/1999 | Lora et al. |
| 5,876,505 A | 3/1999 | Klyosov et al. |
| 5,892,109 A | 4/1999 | Baniel et al. |
| 5,959,128 A | 9/1999 | Kolstad et al. |
| 5,969,195 A | 10/1999 | Stabel et al. |
| 5,980,593 A | 11/1999 | Friswell et al. |
| 5,998,607 A | 12/1999 | Heikkila et al. |
| 6,001,410 A | 12/1999 | Bolen et al. |
| 6,007,636 A | 12/1999 | Lightner |
| 6,063,204 A | 5/2000 | Hester et al. |
| 6,086,681 A | 7/2000 | Lindroos et al. |
| 6,087,532 A | 7/2000 | Baniel et al. |
| 6,093,217 A | 7/2000 | Froelich et al. |
| 6,093,326 A | 7/2000 | Heikkila et al. |
| 6,136,078 A | 10/2000 | Craig |
| 6,160,173 A | 12/2000 | Eyal et al. |
| 6,172,204 B1 | 1/2001 | Sarkanen et al. |
| 6,187,204 B1 | 2/2001 | Heikkild et al. |
| 6,187,951 B1 | 2/2001 | Baniel et al. |
| 6,207,209 B1 | 3/2001 | Jirjis et al. |
| 6,207,824 B1 | 3/2001 | Henkes et al. |
| 6,224,776 B1 | 5/2001 | Heikkila et al. |
| 6,229,046 B1 | 5/2001 | Eyal et al. |
| 6,230,477 B1 | 5/2001 | Caillouet |
| 6,239,274 B1 | 5/2001 | Heikkilä et al. |
| 6,258,175 B1 | 7/2001 | Lightner |
| 6,262,318 B1 | 7/2001 | Heikkilä et al. |
| 6,320,077 B1 | 11/2001 | Eyal et al. |
| 6,352,845 B1 | 3/2002 | Buchanan et al. |
| 6,361,990 B1 | 3/2002 | Porter et al. |
| 6,379,554 B1 | 4/2002 | Kearney et al. |
| 6,391,204 B1 | 5/2002 | Russo, Jr. |
| 6,409,841 B1 | 6/2002 | Lombard |
| 6,416,621 B1 | 7/2002 | Karstens |
| 6,419,788 B1 | 7/2002 | Wingerson |
| 6,419,828 B1 | 7/2002 | Russo, Jr. |
| 6,431,370 B1 | 8/2002 | Braunstein et al. |
| 6,451,123 B1 | 9/2002 | Saska et al. |
| 6,452,051 B1 | 9/2002 | Eyal |
| 6,512,110 B1 | 1/2003 | Heikkila et al. |
| 6,534,679 B2 | 3/2003 | Eyal et al. |
| 6,548,662 B1 | 4/2003 | Ohsaki et al. |
| 6,572,775 B2 | 6/2003 | Heikkila et al. |
| 6,610,867 B2 | 8/2003 | Jakel et al. |
| 6,620,292 B2 | 9/2003 | Wingerson |
| 6,663,780 B2 | 12/2003 | Heikkila et al. |
| 6,685,781 B2 | 2/2004 | Hyoky et al. |
| 6,692,578 B2 | 2/2004 | Schmidt et al. |
| 6,693,188 B2 | 2/2004 | Bohlmann et al. |
| 6,699,457 B2 | 3/2004 | Cortright et al. |
| 6,719,957 B2 | 4/2004 | Brady et al. |
| 6,747,076 B2 | 6/2004 | Schneider et al. |
| 6,752,902 B2 | 6/2004 | Heikkila et al. |
| 6,824,599 B2 | 11/2004 | Swatloski et al. |
| 6,833,149 B2 | 12/2004 | Jirjis et al. |
| 6,846,657 B2 | 1/2005 | Heikkila et al. |
| 6,852,345 B2 | 2/2005 | Hill et al. |
| 6,872,316 B2 | 3/2005 | Heikkila et al. |
| 6,875,349 B2 | 4/2005 | Heikkila et al. |
| 6,896,811 B2 | 5/2005 | Heikkila et al. |
| 6,911,565 B2 | 6/2005 | Heikkila et al. |
| 6,924,371 B2 | 8/2005 | Karki et al. |
| 6,936,110 B2 | 8/2005 | Thorre et al. |
| 6,942,754 B2 | 9/2005 | Izumi et al. |
| 6,953,873 B2 | 10/2005 | Cortright et al. |
| 6,964,757 B2 | 11/2005 | Cortright et al. |
| 6,964,758 B2 | 11/2005 | Cortright et al. |
| 6,987,183 B2 | 1/2006 | Heikkila et al. |
| 7,019,170 B2 | 3/2006 | Eyal et al. |
| 7,022,239 B2 | 4/2006 | Heikkila et al. |
| 7,026,152 B2 | 4/2006 | Ingram et al. |
| 7,037,378 B2 | 5/2006 | Jumppanen et al. |
| 7,109,005 B2 | 9/2006 | Eroma et al. |
| 7,144,977 B2 | 12/2006 | Eyal et al. |
| 7,186,856 B2 | 3/2007 | Meng et al. |
| 7,198,925 B2 | 4/2007 | Foody |
| 7,208,570 B2 | 4/2007 | Saviainen |
| 7,229,558 B2 | 6/2007 | Heikkila et al. |
| 7,314,528 B2 | 1/2008 | Koivikko et al. |
| 7,361,273 B2 | 4/2008 | Heikkila et al. |
| 7,399,323 B2 | 7/2008 | Renninger et al. |
| 7,449,313 B2 | 11/2008 | Rush |
| 7,465,791 B1 | 12/2008 | Hallberg et al. |
| 7,498,430 B2 | 3/2009 | Hollingsworth |
| 7,501,025 B2 | 3/2009 | Bakker et al. |
| 7,503,981 B2 | 3/2009 | Wyman et al. |
| 7,514,247 B2 | 4/2009 | Rush |
| 7,524,660 B2 | 4/2009 | Caimi et al. |
| 7,534,597 B2 | 5/2009 | Hause et al. |
| 7,557,262 B2 | 7/2009 | Lanahan et al. |
| 7,578,927 B2 | 8/2009 | Marker et al. |
| 7,618,612 B2 | 11/2009 | Cortright et al. |
| 7,625,728 B2 | 12/2009 | Eroma et al. |
| 7,629,010 B2 | 12/2009 | Passarelli et al. |
| 7,649,086 B2 | 1/2010 | Belanger et al. |
| 7,652,180 B2 | 1/2010 | Osterholt et al. |
| 7,662,617 B2 | 2/2010 | Rush |
| 7,670,813 B2 | 3/2010 | Foody et al. |
| 7,678,358 B2 | 3/2010 | Eckert et al. |
| 7,678,768 B2 | 3/2010 | Purpura et al. |
| 7,699,958 B2 | 4/2010 | Griffith et al. |
| 7,713,725 B2 | 5/2010 | England et al. |
| 7,717,364 B2 | 5/2010 | Wingerson |
| 7,718,070 B2 | 5/2010 | Wahnon et al. |
| 7,771,964 B2 | 8/2010 | Kim et al. |
| 7,794,824 B2 | 9/2010 | Eckert et al. |
| 7,834,092 B2 | 11/2010 | Uradnisheck et al. |
| 7,883,882 B2 | 2/2011 | Franklin et al. |
| 7,901,511 B2 | 3/2011 | Griffin et al. |
| 7,959,811 B2 | 6/2011 | Airaksinen et al. |
| 7,993,709 B2 | 8/2011 | Brunet |
| 8,003,352 B2 | 8/2011 | Foody et al. |
| 8,022,260 B2 | 9/2011 | O'Connor et al. |
| 8,052,953 B2 | 11/2011 | Chen |
| 8,101,808 B2 | 1/2012 | Evanko et al. |
| 8,163,092 B2 | 4/2012 | Baniel et al. |
| 8,247,203 B2 | 8/2012 | Foody et al. |
| 8,314,267 B2 | 11/2012 | Brandvold |
| 8,382,905 B2 | 2/2013 | Takeshima et al. |
| 8,404,355 B2 | 3/2013 | Jansen et al. |
| 8,500,910 B2 | 8/2013 | Brady et al. |
| 8,604,225 B2 | 12/2013 | Pedersen et al. |
| 8,637,660 B2 | 1/2014 | Fanselow et al. |
| 8,637,661 B2 | 1/2014 | Fanselow et al. |
| 8,657,960 B2 | 2/2014 | North |
| 8,685,685 B2 | 4/2014 | Retsina et al. |
| 8,722,878 B2 | 5/2014 | Raines et al. |
| 8,894,771 B2 | 11/2014 | Floyd et al. |
| 8,926,794 B2 | 1/2015 | Han et al. |
| 8,932,467 B2 | 1/2015 | Fosbol et al. |
| 8,999,065 B2 | 4/2015 | Kazachkin et al. |
| 9,115,467 B2 | 8/2015 | Jansen et al. |
| 9,200,337 B2 | 12/2015 | Colakyan et al. |
| 9,410,216 B2 | 8/2016 | Eyal et al. |

(56) References Cited

U.S. PATENT DOCUMENTS

| | | |
|---|---|---|
| 9,476,106 B2 | 10/2016 | Eyal et al. |
| 9,512,495 B2 | 12/2016 | Eyal |
| 9,617,608 B2 | 4/2017 | Eyal et al. |
| 9,650,687 B2 | 5/2017 | Jansen et al. |
| 9,663,836 B2 | 5/2017 | Jansen et al. |
| 9,765,478 B2 | 9/2017 | Brandt et al. |
| 9,783,861 B2 | 10/2017 | Jansen et al. |
| 9,845,514 B2 | 12/2017 | Eyal et al. |
| 9,963,673 B2 | 5/2018 | Eyal et al. |
| 9,976,194 B2 | 5/2018 | Eyal et al. |
| 10,041,138 B1 | 8/2018 | Eyal et al. |
| 10,240,217 B2 | 3/2019 | Jansen et al. |
| 10,752,878 B2 | 8/2020 | Eyal et al. |
| 10,760,138 B2 | 9/2020 | Eyal et al. |
| 2001/0003797 A1 | 6/2001 | Guevara et al. |
| 2002/0061950 A1 | 5/2002 | Yamamoto et al. |
| 2002/0069981 A1 | 6/2002 | Speaks et al. |
| 2002/0096274 A1 | 7/2002 | Lindstrom et al. |
| 2002/0153317 A1 | 10/2002 | Heikkila et al. |
| 2002/0164731 A1 | 11/2002 | Eroma et al. |
| 2003/0013606 A1 | 1/2003 | Hampden-Smith et al. |
| 2003/0094416 A1 | 5/2003 | Heikkila et al. |
| 2003/0121516 A1 | 7/2003 | Hyoeky et al. |
| 2003/0156970 A1 | 8/2003 | Oberkofler et al. |
| 2003/0192660 A1 | 10/2003 | Speaks et al. |
| 2003/0199049 A1 | 10/2003 | Nguyen et al. |
| 2003/0222021 A1 | 12/2003 | Ennelin et al. |
| 2004/0060673 A1 | 4/2004 | Phillips et al. |
| 2004/0074217 A1 | 4/2004 | Reaux |
| 2004/0108085 A1 | 6/2004 | Kettenbach et al. |
| 2004/0121446 A1 | 6/2004 | England et al. |
| 2004/0127371 A1 | 7/2004 | Arrowsmith et al. |
| 2004/0173533 A1 | 9/2004 | Farone et al. |
| 2004/0199025 A1 | 10/2004 | Stauffer |
| 2004/0199049 A1 | 10/2004 | Parasher et al. |
| 2004/0231661 A1 | 11/2004 | Griffin et al. |
| 2004/0237499 A1 | 12/2004 | Yogev et al. |
| 2005/0034823 A1 | 2/2005 | Brelid et al. |
| 2005/0136520 A1 | 6/2005 | Kinley et al. |
| 2005/0148056 A1 | 7/2005 | Levine et al. |
| 2005/0176110 A1 | 8/2005 | Leisola et al. |
| 2005/0211239 A1 | 9/2005 | Koivikko et al. |
| 2006/0024801 A1 | 2/2006 | Holtzapple et al. |
| 2006/0041059 A1 | 2/2006 | Fukasawa et al. |
| 2006/0051812 A1 | 3/2006 | Helin et al. |
| 2006/0134308 A1 | 6/2006 | Inglett |
| 2006/0207734 A1 | 9/2006 | Day et al. |
| 2007/0020375 A1 | 1/2007 | Jansen et al. |
| 2007/0031953 A1 | 2/2007 | Dunson et al. |
| 2007/0053987 A1 | 3/2007 | Bayer et al. |
| 2007/0112187 A1 | 5/2007 | Heikkila et al. |
| 2007/0178569 A1 | 8/2007 | Leschine et al. |
| 2007/0184555 A1 | 8/2007 | Banavali et al. |
| 2007/0197363 A1 | 8/2007 | Parrotta et al. |
| 2007/0219521 A1 | 9/2007 | Hird et al. |
| 2008/0021155 A1 | 1/2008 | Bono et al. |
| 2008/0029233 A1 | 2/2008 | Wingerson et al. |
| 2008/0032344 A1 | 2/2008 | Fallavollita |
| 2008/0033187 A1 | 2/2008 | Zhao et al. |
| 2008/0033188 A1 | 2/2008 | Dumesic et al. |
| 2008/0041366 A1 | 2/2008 | Wahnon et al. |
| 2008/0053870 A1 | 3/2008 | Marker et al. |
| 2008/0057555 A1 | 3/2008 | Nguyen |
| 2008/0060638 A1 | 3/2008 | Koivikko et al. |
| 2008/0168982 A1 | 7/2008 | Vente et al. |
| 2008/0182305 A1 | 7/2008 | Foody et al. |
| 2008/0193992 A1 | 8/2008 | Levine |
| 2008/0202504 A1 | 8/2008 | Hilst |
| 2008/0210393 A1 | 9/2008 | Gutierrez-Suarez et al. |
| 2008/0216391 A1 | 9/2008 | Cortright et al. |
| 2008/0227161 A1 | 9/2008 | Levie et al. |
| 2008/0274509 A1 | 11/2008 | Filho et al. |
| 2008/0274528 A1 | 11/2008 | Dixon et al. |
| 2008/0299606 A1 | 12/2008 | Pompejus et al. |
| 2008/0300434 A1 | 12/2008 | Cortright et al. |
| 2008/0300435 A1 | 12/2008 | Cortright et al. |
| 2008/0305210 A1 | 12/2008 | Petersen |
| 2008/0317661 A1 | 12/2008 | Eckert et al. |
| 2008/0318043 A1 | 12/2008 | Eckert et al. |
| 2009/0053783 A1 | 2/2009 | Gokarn et al. |
| 2009/0056707 A1 | 3/2009 | Foody et al. |
| 2009/0056889 A1 | 3/2009 | Ren et al. |
| 2009/0061486 A1 | 3/2009 | Edwards et al. |
| 2009/0061495 A1 | 3/2009 | Beatty et al. |
| 2009/0062232 A1 | 3/2009 | Fujikawa et al. |
| 2009/0069550 A1 | 3/2009 | Belanger et al. |
| 2009/0084511 A1 | 4/2009 | Lampinen et al. |
| 2009/0124829 A1 | 5/2009 | Gong |
| 2009/0142848 A1 | 6/2009 | Wyman et al. |
| 2009/0155873 A1 | 6/2009 | Kashiyama et al. |
| 2009/0173339 A1 | 7/2009 | Heikkilae et al. |
| 2009/0176286 A1 | 7/2009 | O'Connor et al. |
| 2009/0218055 A1 | 9/2009 | Uusitalo et al. |
| 2009/0226979 A1 | 9/2009 | Retsina et al. |
| 2009/0226993 A1 | 9/2009 | Kumar et al. |
| 2009/0229599 A1 | 9/2009 | Zhang et al. |
| 2009/0234142 A1 | 9/2009 | Mascal |
| 2009/0286295 A1 | 11/2009 | Medoff et al. |
| 2009/0305942 A1 | 12/2009 | Day et al. |
| 2010/0009408 A1 | 1/2010 | England et al. |
| 2010/0012010 A1 | 1/2010 | Gooijer et al. |
| 2010/0024807 A1 | 2/2010 | Burke et al. |
| 2010/0028557 A1 | 2/2010 | Nagano |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0055753 A1 | 3/2010 | Geros |
| 2010/0069626 A1 | 3/2010 | Kilambi |
| 2010/0083565 A1 | 4/2010 | Gruter et al. |
| 2010/0086981 A1 | 4/2010 | Latouf et al. |
| 2010/0093995 A1 | 4/2010 | Baniel et al. |
| 2010/0116267 A1 | 5/2010 | Mraz et al. |
| 2010/0124772 A1 | 5/2010 | Sabesan |
| 2010/0136642 A1 | 6/2010 | Belanger et al. |
| 2010/0144001 A1 | 6/2010 | Horton |
| 2010/0146844 A1 | 6/2010 | Dumenil |
| 2010/0151527 A1 | 6/2010 | Endo et al. |
| 2010/0151535 A1 | 6/2010 | Franklin et al. |
| 2010/0152509 A1 | 6/2010 | Ekman |
| 2010/0159566 A1 | 6/2010 | Leschine et al. |
| 2010/0160624 A1 | 6/2010 | Cunningham |
| 2010/0163019 A1 | 7/2010 | Chornet et al. |
| 2010/0167351 A1 | 7/2010 | Eyal et al. |
| 2010/0170504 A1 | 7/2010 | Zhang |
| 2010/0184151 A1 | 7/2010 | Tolan et al. |
| 2010/0184176 A1 | 7/2010 | Ishida et al. |
| 2010/0189706 A1 | 7/2010 | Chang et al. |
| 2010/0255554 A1 | 7/2010 | Benson et al. |
| 2010/0196979 A1 | 8/2010 | Birkmire et al. |
| 2010/0213130 A1 | 8/2010 | Airaksinen et al. |
| 2010/0233761 A1 | 9/2010 | Czartoski et al. |
| 2010/0249390 A1 | 9/2010 | Azuma et al. |
| 2010/0268000 A1 | 10/2010 | Parekh et al. |
| 2010/0269990 A1 | 10/2010 | Dottori et al. |
| 2010/0279354 A1 | 11/2010 | De |
| 2010/0279361 A1 | 11/2010 | South et al. |
| 2010/0279372 A1 | 11/2010 | Cho et al. |
| 2010/0287826 A1 | 11/2010 | Hoffman et al. |
| 2010/0305241 A1 | 12/2010 | Balakshin et al. |
| 2010/0305242 A1 | 12/2010 | Balakshin et al. |
| 2010/0305243 A1 | 12/2010 | Balakshin et al. |
| 2010/0305244 A1 | 12/2010 | Balakshin et al. |
| 2010/0313882 A1 | 12/2010 | Dottori et al. |
| 2011/0003348 A1 | 1/2011 | Genta et al. |
| 2011/0003352 A1 | 1/2011 | Retsina et al. |
| 2011/0016545 A1 | 1/2011 | Gray et al. |
| 2011/0020873 A1 | 1/2011 | Ren et al. |
| 2011/0020910 A1 | 1/2011 | Glass et al. |
| 2011/0002871 A1 | 2/2011 | Baniel et al. |
| 2011/0028672 A1 | 2/2011 | Dahlman et al. |
| 2011/0028710 A1 | 2/2011 | Baniel et al. |
| 2011/0033640 A1 | 2/2011 | Yamada et al. |
| 2011/0033896 A1 | 2/2011 | Boy et al. |

(56) References Cited

U.S. PATENT DOCUMENTS

| | | |
|---|---|---|
| 2011/0053238 A1 | 3/2011 | Ohgren et al. |
| 2011/0059316 A1 | 3/2011 | Kilambi et al. |
| 2011/0060132 A1 | 3/2011 | Lewis |
| 2011/0065159 A1 | 3/2011 | Raines et al. |
| 2011/0070131 A1 | 3/2011 | Schmidt et al. |
| 2011/0097776 A1 | 4/2011 | Johnson |
| 2011/0100359 A1 | 5/2011 | North |
| 2011/0105737 A1 | 5/2011 | Benjelloun et al. |
| 2011/0124057 A1 | 5/2011 | Genta et al. |
| 2011/0126448 A1 | 6/2011 | Dumenil |
| 2011/0129880 A1 | 6/2011 | Conners et al. |
| 2011/0129886 A1 | 6/2011 | Howard et al. |
| 2011/0143411 A1 | 6/2011 | Yuan et al. |
| 2011/0143412 A1 | 6/2011 | Kim et al. |
| 2011/0146138 A1 | 6/2011 | Berry et al. |
| 2011/0151516 A1 | 6/2011 | Van et al. |
| 2011/0155559 A1 | 6/2011 | Medoff |
| 2011/0172411 A1 | 7/2011 | Heikkila et al. |
| 2011/0178290 A1 | 7/2011 | Baniel et al. |
| 2011/0183394 A1 | 7/2011 | Bell et al. |
| 2011/0192560 A1 | 8/2011 | Heikkila et al. |
| 2011/0201059 A1 | 8/2011 | Hall et al. |
| 2011/0245491 A1 | 10/2011 | Airaksinen et al. |
| 2011/0256615 A1 | 10/2011 | Brady et al. |
| 2011/0262984 A1 | 10/2011 | Nguyen |
| 2011/0263811 A1 | 10/2011 | Sawai et al. |
| 2011/0271875 A1 | 11/2011 | Ahmed et al. |
| 2011/0274612 A1 | 11/2011 | Wohlmann et al. |
| 2011/0275860 A1 | 11/2011 | Beldring et al. |
| 2011/0281298 A1 | 11/2011 | Rawls et al. |
| 2011/0300617 A1 | 12/2011 | Genta et al. |
| 2011/0314726 A1 | 12/2011 | Jameel et al. |
| 2011/0318796 A1 | 12/2011 | Walther |
| 2012/0006320 A1 | 1/2012 | Nguyen |
| 2012/0021467 A1 | 1/2012 | Zhang et al. |
| 2012/0023810 A1 | 2/2012 | Fjare et al. |
| 2012/0036768 A1 | 2/2012 | Phillips et al. |
| 2012/0040408 A1 | 2/2012 | Decker et al. |
| 2012/0055466 A1 | 3/2012 | Cotti et al. |
| 2012/0058526 A1 | 3/2012 | Jansen et al. |
| 2012/0104313 A1 | 5/2012 | Garbero et al. |
| 2012/0116063 A1 | 5/2012 | Jansen et al. |
| 2012/0122170 A1 | 5/2012 | Ropars et al. |
| 2012/0134912 A1 | 5/2012 | Baniel et al. |
| 2012/0135489 A1 | 5/2012 | Weydahl |
| 2012/0149924 A1 | 6/2012 | De et al. |
| 2012/0156517 A1 | 6/2012 | Vuori et al. |
| 2012/0167874 A1 | 7/2012 | Jansen et al. |
| 2012/0184026 A1 | 7/2012 | Eyal |
| 2012/0227733 A1 | 9/2012 | Eyal et al. |
| 2012/0240921 A1 | 9/2012 | Fukuoka et al. |
| 2012/0264873 A1 | 10/2012 | Eyal et al. |
| 2012/0279497 A1 | 11/2012 | Jansen et al. |
| 2012/0282655 A1 | 11/2012 | Gibbs |
| 2012/0304529 A1 | 12/2012 | O'Connor et al. |
| 2012/0308991 A1 | 12/2012 | Eiteman et al. |
| 2012/0323053 A1 | 12/2012 | Qiao et al. |
| 2013/0012610 A1 | 1/2013 | Belanger et al. |
| 2013/0019859 A1 | 1/2013 | Qiao et al. |
| 2013/0028832 A1 | 1/2013 | Eyal et al. |
| 2013/0028833 A1 | 1/2013 | Eyal et al. |
| 2013/0047979 A1 | 2/2013 | Eyal et al. |
| 2013/0115653 A1 | 5/2013 | Peterson et al. |
| 2013/0167836 A1 | 7/2013 | Floyd et al. |
| 2013/0167837 A1 | 7/2013 | Floyd et al. |
| 2013/0183227 A1 | 7/2013 | Wohlmann et al. |
| 2013/0210101 A1 | 8/2013 | Parekh et al. |
| 2013/0216693 A1 | 8/2013 | Harrison et al. |
| 2013/0217070 A1 | 8/2013 | Zhao et al. |
| 2013/0252312 A1 | 9/2013 | Yoshikuni et al. |
| 2013/0276778 A1 | 10/2013 | Jansen et al. |
| 2013/0295628 A1 | 11/2013 | Retsina et al. |
| 2014/0011241 A1 | 1/2014 | Beatty et al. |
| 2014/0011248 A1 | 1/2014 | Medoff et al. |
| 2014/0014092 A1 | 1/2014 | Kazachkin et al. |
| 2014/0123973 A1 | 5/2014 | North |
| 2014/0154759 A1 | 6/2014 | Retsina et al. |
| 2014/0175331 A1 | 6/2014 | Jansen et al. |
| 2014/0190470 A1 | 7/2014 | Eyal et al. |
| 2014/0200365 A1 | 7/2014 | De et al. |
| 2014/0220651 A1 | 8/2014 | Raines et al. |
| 2014/0227161 A1 | 8/2014 | Manesh et al. |
| 2014/0271443 A1 | 9/2014 | Baker et al. |
| 2014/0275501 A1 | 9/2014 | Capanema et al. |
| 2014/0309416 A1 | 10/2014 | Teixeira et al. |
| 2014/0316162 A1 | 10/2014 | Gao et al. |
| 2014/0356915 A1 | 12/2014 | Retsina et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0087031 A1 | 3/2015 | Jansen et al. |
| 2015/0144126 A1 | 5/2015 | Jansen et al. |
| 2015/0176090 A1 | 6/2015 | Dumesic et al. |
| 2015/0197824 A1 | 7/2015 | Floyd et al. |
| 2015/0299738 A1 | 10/2015 | Wang et al. |
| 2016/0108481 A1 | 4/2016 | Eyal et al. |
| 2016/0108482 A1 | 4/2016 | Eyal et al. |
| 2016/0222477 A1 | 8/2016 | Jansen et al. |
| 2016/0376546 A1 | 12/2016 | Eyal et al. |
| 2017/0037486 A1 | 2/2017 | Eyal et al. |
| 2017/0130282 A1 | 5/2017 | Eyal et al. |
| 2017/0369957 A1 | 12/2017 | Jansen et al. |
| 2018/0148804 A1 | 5/2018 | Jansen et al. |
| 2018/0223383 A1 | 8/2018 | Eyal et al. |
| 2019/0153555 A1 | 5/2019 | Eyal et al. |

FOREIGN PATENT DOCUMENTS

| | | | |
|---|---|---|---|
| CN | 101001952 A | | 7/2007 |
| CN | 101016703 A | | 8/2007 |
| CN | 101120102 A | | 2/2008 |
| CN | 101279722 A | | 10/2008 |
| CN | 101313073 A | | 11/2008 |
| CN | 101550431 A | | 10/2009 |
| CN | 101787398 A | * | 7/2010 |
| CN | 101787398 A | | 7/2010 |
| CN | 101792822 A | | 8/2010 |
| CN | 102239184 A | | 11/2011 |
| CN | 102433358 B | | 10/2013 |
| CN | 103717622 A | | 4/2014 |
| CZ | 301471 B6 | | 3/2010 |
| DE | 4106373 A1 | | 9/1992 |
| DE | 19721301 C1 | | 10/1998 |
| DE | 102008064325 A1 | | 7/2010 |
| EP | 0018621 A1 | | 11/1980 |
| EP | 0317036 A1 | | 5/1989 |
| EP | 0224721 B1 | | 6/1991 |
| EP | 0247436 B1 | | 1/1992 |
| EP | 0493842 A2 | | 7/1992 |
| EP | 0504622 A1 | | 9/1992 |
| EP | 0560546 A1 | | 9/1993 |
| EP | 0446556 B1 | | 8/1995 |
| EP | 0700957 A1 | | 3/1996 |
| EP | 0878455 A1 | | 11/1998 |
| EP | 0690931 B1 | | 10/2001 |
| EP | 0697904 B1 | | 6/2002 |
| EP | 1253241 A2 | | 10/2002 |
| EP | 1272433 B1 | | 1/2004 |
| EP | 1253241 A3 | | 2/2004 |
| EP | 1721988 A2 | | 11/2006 |
| EP | 1878480 A1 | | 1/2008 |
| EP | 1918031 A1 | | 5/2008 |
| EP | 2336193 A1 | | 6/2011 |
| EP | 1458805 B1 | | 8/2011 |
| EP | 1733282 B1 | | 1/2012 |
| EP | 2325246 B1 | | 11/2013 |
| FR | 2604728 A1 | | 4/1988 |
| GB | 922685 A | | 4/1963 |
| GB | 1562682 A | | 3/1980 |
| GB | 2034291 A | | 6/1980 |
| GB | 2240053 A | | 7/1991 |
| GB | 2488918 B | | 3/2014 |
| JP | H11500912 A | | 1/1999 |
| JP | 2001226409 A | | 8/2001 |

(56) References Cited

FOREIGN PATENT DOCUMENTS

| | | | |
|---|---|---|---|
| JP | 2010501013 A | 1/2010 | |
| JP | 2010083850 A | 4/2010 | |
| JP | 2011223975 A | 11/2011 | |
| KR | 100564708 B1 | 3/2006 | |
| KR | 20140108301 A | 9/2014 | |
| WO | WO-8201723 A1 | 5/1982 | |
| WO | WO-8403304 A1 | 8/1984 | |
| WO | WO-9218557 A1 | 10/1992 | |
| WO | WO-9305186 A1 | 3/1993 | |
| WO | WO-9313265 A1 | 7/1993 | |
| WO | WO-9417213 A1 | 8/1994 | |
| WO | WO-9426380 A1 | 11/1994 | |
| WO | WO-9502726 A1 | 1/1995 | |
| WO | WO-9609350 A1 | 3/1996 | |
| WO | WO-9627028 A1 | 9/1996 | |
| WO | WO-9641052 A1 | 12/1996 | |
| WO | WO-9713732 A2 | 4/1997 | |
| WO | WO-9713732 A3 | 5/1997 | |
| WO | WO-9856958 A1 | 12/1998 | |
| WO | WO-9906133 A1 | 2/1999 | |
| WO | WO-9963145 A1 | 12/1999 | |
| WO | WO-0061276 A1 | 10/2000 | |
| WO | WO-0125143 A1 | 4/2001 | |
| WO | WO-0132715 A1 | 5/2001 | |
| WO | WO-0202826 A1 | 1/2002 | |
| WO | WO-03010339 A1 | 2/2003 | |
| WO | WO-03029329 A2 | 4/2003 | |
| WO | WO-03056038 A1 | 7/2003 | |
| WO | WO-03078540 A2 | 9/2003 | |
| WO | WO-03078540 A3 | 1/2004 | |
| WO | WO-2004050983 A1 | 6/2004 | |
| WO | WO-2004079017 A2 | 9/2004 | |
| WO | WO-2004079017 A3 | 8/2005 | |
| WO | WO-2006006164 A2 | 1/2006 | |
| WO | WO-2006034581 A1 | 4/2006 | |
| WO | WO-2006038863 A1 | 4/2006 | |
| WO | WO-2006056838 A1 | 6/2006 | |
| WO | WO-2006086861 A2 | 8/2006 | |
| WO | WO-2006086861 A3 | 10/2006 | |
| WO | WO-2006119357 A2 | 11/2006 | |
| WO | WO-2006119357 A3 | 1/2007 | |
| WO | WO-2007019505 A2 | 2/2007 | |
| WO | WO-2007019505 A3 | 6/2007 | |
| WO | WO-2007075476 A2 | 7/2007 | |
| WO | WO-2007102638 A1 | 9/2007 | |
| WO | WO-2007112314 A2 | 10/2007 | |
| WO | WO-2007120210 A2 | 10/2007 | |
| WO | WO-2007112314 A3 | 11/2007 | |
| WO | WO-2007124400 A2 | 11/2007 | |
| WO | WO-2007130984 A2 | 11/2007 | |
| WO | WO-2008017145 A1 | 2/2008 | |
| WO | WO-2008019468 A1 | 2/2008 | |
| WO | WO-2007075476 A3 | 3/2008 | |
| WO | WO-2008027699 A2 | 3/2008 | |
| WO | WO-2008069830 A2 | 6/2008 | |
| WO | WO-2008027699 A3 | 7/2008 | |
| WO | WO-2007124400 A3 | 8/2008 | |
| WO | WO-2008098036 A1 | 8/2008 | |
| WO | WO-2008109877 A1 | 9/2008 | |
| WO | WO-2008111045 A1 | 9/2008 | |
| WO | WO-2008123419 A1 | 10/2008 | |
| WO | WO-2008131229 A1 | 10/2008 | |
| WO | WO-2008069830 A3 | 11/2008 | |
| WO | WO-2008137639 A1 | 11/2008 | |
| WO | WO-2008140617 A2 | 11/2008 | |
| WO | WO-2008144903 A1 | 12/2008 | |
| WO | WO-2009002785 A1 | 12/2008 | |
| WO | WO-2009003167 A1 | 12/2008 | |
| WO | WO-2008140617 A3 | 1/2009 | |
| WO | WO-2009003292 A1 | 1/2009 | |
| WO | WO-2009015663 A2 | 2/2009 | |
| WO | WO-2009020459 A2 | 2/2009 | |
| WO | WO-2009021733 A2 | 2/2009 | |
| WO | WO-2009028969 A1 | 3/2009 | |
| WO | WO-2009030713 A1 | 3/2009 | |
| WO | WO-2009031164 A1 | 3/2009 |
| WO | WO-2009036674 A1 | 3/2009 |
| WO | WO-2009020459 A3 | 4/2009 |
| WO | WO-2006006164 A3 | 5/2009 |
| WO | WO-2009021733 A3 | 6/2009 |
| WO | WO-2009068711 A1 | 6/2009 |
| WO | WO-2009110374 A1 | 9/2009 |
| WO | WO-2009111026 A2 | 9/2009 |
| WO | WO-2009116885 A1 | 9/2009 |
| WO | WO-2009125400 A2 | 10/2009 |
| WO | WO-2009135480 A1 | 11/2009 |
| WO | WO-2009142837 A2 | 11/2009 |
| WO | WO-2009015663 A3 | 12/2009 |
| WO | WO-2009155982 A1 | 12/2009 |
| WO | WO-2009125400 A3 | 1/2010 |
| WO | WO-2010006840 A2 | 1/2010 |
| WO | WO-2010009343 A2 | 1/2010 |
| WO | WO-2010009515 A1 | 1/2010 |
| WO | WO-2010015404 A1 | 2/2010 |
| WO | WO-2010018105 A1 | 2/2010 |
| WO | WO-2010020977 A2 | 2/2010 |
| WO | WO-2009142837 A3 | 3/2010 |
| WO | WO-2010026244 A1 | 3/2010 |
| WO | WO-2010026572 A1 | 3/2010 |
| WO | WO-2010009343 A3 | 4/2010 |
| WO | WO-2010034055 A1 | 4/2010 |
| WO | WO-2010037109 A2 | 4/2010 |
| WO | WO-2010037178 A1 | 4/2010 |
| WO | WO-2010038021 A2 | 4/2010 |
| WO | WO-2010039152 A1 | 4/2010 |
| WO | WO-2010043424 A1 | 4/2010 |
| WO | WO-2010045576 A2 | 4/2010 |
| WO | WO-2010046532 A1 | 4/2010 |
| WO | WO-2010046619 A1 | 4/2010 |
| WO | WO-2010006840 A3 | 5/2010 |
| WO | WO-2010037109 A3 | 5/2010 |
| WO | WO-2010060183 A1 | 6/2010 |
| WO | WO-2010064229 A2 | 6/2010 |
| WO | WO-2010045576 A3 | 7/2010 |
| WO | WO-2010064229 A3 | 7/2010 |
| WO | WO-2010081231 A1 | 7/2010 |
| WO | WO-2010038021 A3 | 8/2010 |
| WO | WO-2010088486 A1 | 8/2010 |
| WO | WO-2010020977 A3 | 10/2010 |
| WO | WO-2010113129 A2 | 10/2010 |
| WO | WO-2010113130 A2 | 10/2010 |
| WO | WO-2010122554 A1 | 10/2010 |
| WO | WO-2010123932 A1 | 10/2010 |
| WO | WO-2010128272 A1 | 11/2010 |
| WO | WO-2010113129 A3 | 12/2010 |
| WO | WO-2010135804 A1 | 12/2010 |
| WO | WO-2010135805 A1 | 12/2010 |
| WO | WO-2010135806 A1 | 12/2010 |
| WO | WO-2010135807 A1 | 12/2010 |
| WO | WO-2010135832 A1 | 12/2010 |
| WO | WO-2010135833 A1 | 12/2010 |
| WO | WO-2010146331 A2 | 12/2010 |
| WO | WO-2010113130 A3 | 1/2011 |
| WO | WO-2011002660 A1 | 1/2011 |
| WO | WO-2011007043 A1 | 1/2011 |
| WO | WO-2011007369 A1 | 1/2011 |
| WO | WO-2011017587 A1 | 2/2011 |
| WO | WO-2011017797 A1 | 2/2011 |
| WO | WO-2011022840 A1 | 3/2011 |
| WO | WO-2011028554 A1 | 3/2011 |
| WO | WO-2011039751 A2 | 4/2011 |
| WO | WO-2011066487 A1 | 6/2011 |
| WO | WO-2011070602 A1 | 6/2011 |
| WO | WO-2011080131 A2 | 7/2011 |
| WO | WO-2011089589 A1 | 7/2011 |
| WO | WO-2011091044 A1 | 7/2011 |
| WO | WO-2011095977 A1 | 8/2011 |
| WO | WO-2011097719 A1 | 8/2011 |
| WO | WO-2011080131 A3 | 9/2011 |
| WO | WO-2011111189 A1 | 9/2011 |
| WO | WO-2011111190 A1 | 9/2011 |
| WO | WO-2010146331 A3 | 10/2011 |
| WO | WO-2011039751 A3 | 10/2011 |
| WO | WO-2011121181 A1 | 10/2011 |

(56) References Cited

FOREIGN PATENT DOCUMENTS

| WO | WO-2011124639 A1 | 10/2011 |
|---|---|---|
| WO | WO-2011140222 A1 | 11/2011 |
| WO | WO-2011151823 A1 | 12/2011 |
| WO | WO-2011154604 A1 | 12/2011 |
| WO | WO-2011154967 A1 | 12/2011 |
| WO | WO-2011161141 A1 | 12/2011 |
| WO | WO-2011161685 A2 | 12/2011 |
| WO | WO-2011163084 A1 | 12/2011 |
| WO | WO-2012001688 A2 | 1/2012 |
| WO | WO-2012015575 A1 | 2/2012 |
| WO | WO-2012018740 A1 | 2/2012 |
| WO | WO-2012031270 A1 | 3/2012 |
| WO | WO-2012044168 A1 | 4/2012 |
| WO | WO-2011161685 A3 | 5/2012 |
| WO | WO-2012060767 A1 | 5/2012 |
| WO | WO-2012061085 A2 | 5/2012 |
| WO | WO-2012079021 A2 | 6/2012 |
| WO | WO-2012085684 A2 | 6/2012 |
| WO | WO-2012106727 A1 | 8/2012 |
| WO | WO-2012018740 A1 | 9/2012 |
| WO | WO-2012137201 A1 | 10/2012 |
| WO | WO-2013024162 A1 | 2/2013 |
| WO | WO-2013026849 A1 | 2/2013 |
| WO | WO-2013038399 A1 | 3/2013 |
| WO | WO-2013040514 A1 | 3/2013 |
| WO | WO-2013040702 A1 | 3/2013 |
| WO | WO-2013055785 A1 | 4/2013 |
| WO | WO-2013070969 A2 | 5/2013 |
| WO | WO-2013071180 A1 | 5/2013 |
| WO | WO-2013083876 A2 | 6/2013 |
| WO | WO-2013166469 A2 | 11/2013 |
| WO | WO-2013192572 A1 | 12/2013 |
| WO | WO-2014044753 A1 | 3/2014 |
| WO | WO-2014076612 A1 | 5/2014 |
| WO | WO-2014081605 A1 | 5/2014 |
| WO | WO-2014106221 A1 | 7/2014 |
| WO | WO-2014126471 A1 | 8/2014 |
| WO | WO-2014138553 A1 | 9/2014 |
| WO | WO-2014169079 A2 | 10/2014 |
| WO | WO-2014178911 A1 | 11/2014 |
| WO | WO-2015139141 A1 | 9/2015 |
| WO | WO-2016112134 A1 | 7/2016 |
| WO | WO-2016191503 A1 | 12/2016 |

OTHER PUBLICATIONS

Sevcik et al. (Journal of Chromatography A, 1218 (2011) 1236-1243).*
Zhuang et al. (Nongye Gongcheng Xuebao (2007), 23(2), 177-182) (abstract sent).*
Abacherli, et al. Lignin Analytical Cluster, "Towards Standardisation of Methods". Rome, Forum 8, May 10-12, 2007.
Abacherli. Lignin structure and analytical methods. International Lignin Institute, Rue du Grand-Chêne 5, CH-1005 Lausanne, Switzerland Copyright ILI 2008, only for ILI members and only for personal use, Last update Jun. 20, 2008.
Abacherli. New lignins from agricultural plants. The international Lignin Institute, 5th international Forum' Sep. 7, 2000, Bordeaux (France).
Acevedo, et al. Surface Activity of Lignin Fractions isolated by Organic Solvents. Powerpoint. 2005.
Achyuthan, et al. Supramolecular Self-Assembled Chaos: Polyphenolic Lignin's Barrier to Cost-Effective Lignocellulosic Biofuels. Molecules. 2010; 15:8641-8688. doi:10.3390/molecules15118641.
Addi, et al. Flax lignin and lignans:Biosynthesis , Metabolism and Directed Modifications through a Genetic Engineering Approach. 2003.
Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy Laboratory Operated by Midwest Research Institute. Jun. 2002.
Adina, et al. Application of FTIR Spectroscopy for a Rapid Determination of Some Hydrolytic Enzymes Activity on Sea Buckthorn Substrate. Romanian Biotechnological Letters. 2010; 15(6):5738-5744.
ADM corn 42/43 syrup. Typical data information. Accessed Oct. 5, 2012.
Afanasiev, et al. Forecast of lignosulfonates properties as surfactant. 2005.
Afanasiev, et al. Stabilization effect of microparticles of sulfate lignin on water-oil emulsion. Powerpoint. 2005.
Agarwal, et al. FT raman spectroscopic study of softwood lignin. ISWPC. 1997.
Agarwal, et al. Near-IR surface-enhanced Raman spectrum of lignin. J. Raman Spectrosc. 2009;40:1527-1534.
Agarwal, et al. Raman spectra of lignin model compounds, incorporating the 13th ISWFPC (International Symposium on Wood, Fibre, and Pulping Chemistry), held in Auckland, New Zealand (May 16-19, 2005).Appita 2005, pp. 1-8.
Agblevor, et al. Analysis of biomass sugars using a novel HPLC method. Appl Biochem Biotechnol. Mar. 2007;136(3):309-26.
Ahlkvist.J. Formic and Levulinic Acid from Cellulose via Heterogeneous Catalysis. PhD Report. 2014, Sweden.
Ahmed, et al. A simplified method for accurate determination of cell wall uronide content. Journal of Food Biochemistry. 1977; 1:361-365.
Ahmed, et al. Preparation and studies on immobilized a-glucosidase from baker's yeast *Saccharomyces cerevisiae*. J. Serb. Chem. Soc. 2007; 72(12):1255-1263.
Albersheim. Metabolism of the Pectic Substances. For the degree of Doctor of Philosophy, California Institute of Technology Pasadena, California, 1959.
Albertson, et al. Addition Compounds of Sulfur Dioxide. Sep. 1943; 65:1687-1690.
Alizadeh, et al. Pretreatment of Switchgrass by Ammonia Fiber Explosion (AFEX). Applied Biochemistry and Biotechnology. 2005; 5(121-124):1133-1142.
Allosio-Ouarnier, et al. Application of High Performance Anion Exchange Chromatography to the Study of Carbohydrate Changes in Barley During Malting. Journal—Institute of Brewing 106(1):45-52. Jan. 2000.
Allsopp, et al. 130. The constitution of the cambium, the new wood and the mature sapwood of the common ash, the common elm and the scotch pine. May 10, 1940; 1078-1084.
Alonso-Fagundez, et al. Selective conversion of furfural to maleic anhydride and furan with VO(x)/Al(2)O(3) catalysts. 2012 ;5: 1984-1990.
Ambalkar, et al. Synthesis of Furfural from Lignocellulosic Biomass as Agricultural Residues : A Review. The International Journal of Engineering and Science. 2012; 1(1): 30-36.
Amidon, et al. Biorefinery: Conversion of Woody Biomass to Chemicals, Energy and Materials. Journal of Biobased Materials and Bioenergy. 2008; 2:100-120.
Anderson. The isolation of pectic substances from wood. 1935; 531-539.
Anellotech. Scaling up economical, non-food biomass derived Benzene, Toluene and Xylenes for major biobased polymers. Presentation by Anellotech; San Francisco. 2013.
Antonoplis, et al. High pressure HCl conversion of cellulose to glucose. Lawrence Berkeley National Laboratory, University of California, Paper LBL, 14221. Aug. 1981.
Arborgen. Purpose Grown Trees as an Economical and Sustainable Biomass Feedstock. Southeast Bioenergy conference, Presentation. 2010.
Argyropoulos. Oxidaton of Lignin in supercritical carbon dioxide. 2005.
Argyropoulus et al. Bioenergy Program. Presentation; NC State University. 2014.
ASTM Standards. Standard Test Method for Ash in Biomass. Designation: E1755-01 (Reapproved 2007).
Atalla, et al. Analysis of Lignin and Cellulose in Biological Energy Sources by Raman Microscopy. 2011.

(56) References Cited

OTHER PUBLICATIONS

Atchison, et al. Innovative Methods for Corn Stover Collecting, Handling, Storing and Transporting, Mar. 2003. National Renewable Energy Laboratory. Apr. 2004.
Atsuki. Action of highly concentrated hydrochloric acid on cellulose. Seniso Kogyo (1925), 153-61. CODEN: SKOGBJ ISSN: 0371-070X. Abstract only.
Badger. Ethanol from cellulose: a general review. Trends in new crops and new uses. 2002; 17-21.
Baker. Utilization of Sustainable Resources for Materials for Production of Carbon Fiber Structural and Energy Efficiency Applications. Oak Ridge National Laboratory, Tennessee, USA. Nordic Wood Biorefinery Conference, Stockholm, Sweden, Mar. 22-24, 2011.
Bakker. Advanced physical/chemical fractionation. Workshop of the EU FP6, Integrated Project Biosynergy. Nov. 17, 2011.
Baniel, et al. Porogen derived membranes.1. Concept description and analysis. J. of Membrane Science. 1990; 54:271-283.
Baniel. Reactions and processes in Liquidliquid (L/L) systems. Pure & Appl. Chem. 1986; 58(6):879-883.
Bao, et al. Preparation of 5-hydroxymethylfurfural by dehydration of fructose in the presence of acidic ionic liquid. Catalysis Communications; 2008; 9: 1383-1388.
Barneto, et al. Thermogravimetric characterization of eucaliptus wood. Artigo Tecnico 2011, 72(7), 53-56.
Barta, et al. Catalytic disassembly of an organosolv lignin via hydrogen transfer from supercritical methanol. Green Chem. 2010; 12:1640-1647.
Barton. "Table 18 Hoy's Cohesion Parameters for liquids (and solids and subcooled liquids) at 25° C." in CRC Handbook of solubility parameters and other cohesion parameters, Second Edition, Jan. 1, 1991. CRC Press, Boca Raton, FL. pp. 123-138.
Barton. CRC handbook of solubility parameters and other cohesion parameters. CRC Press. Boca Raton. 1991; 122-138.
Basak, et al. Thermal Properties of Jute Constituents and Flame Retardant Jute Fabrics. Textile Res. J. 1993, 63(11), 658-666.
Baumberger, et al. An overview of the analytical tools in the quali/quantitative analysis of functional groups and inter unit bondings in lignin.II. Interunit bondings characterization. COST E41—Roma—Jun. 7-8, 2007.
Baumberger, et al. Analytical methods for lignin characterisation, used by users (end-users and R&D companies). Compilation of all the protocols.
Bayat-Makooi, et al. Hydrolysis of cellulose with hydrochloric acid enhanced by cations. Dep. Wood Paper Sci., North Carolina State Univ., Raleigh, NC, USA. Editor(s): Kennedy, John F. Cellul. Its Deriv. (1985), 135-41. Publisher: Horwood, Chichester, UK CODEN: 54GPAW. Abstract only.
Beck, et al. Production of ethanol by bioconversion of wood sugars derived from two-stage dilute acid hydrolysis of hardwood. Biomass. 1984; 6:101-110.
Beg, et al. Cyclic transport of Fe3+ as H[FeCl4] and H[FeBr4] through a dibutyl ether-benzene membrane. Journal of Membrane Science. 1985; 24:97-100.
Berg, et al. The breaking of ternary acetate-alcohol-water azeotropes by extractive distillation. Chem. Eng. Commun. 1986; 48:93-101.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Berndes, et al. The contribution of biomass in the future global energy supply: a review of 17 studies. Biomass and Bioenergy. 2003; 25:1-28.
Berthold, et al. Association of water to polar groups; estimations by an adsorption model for ligno-cellulosic materials. Colloids Surfaces A:Physicochem. Eng. Aspects. 1996; 112:117-129.

Bilanicova, et al. Improvements in Enzymatic Preparation of Alkyl Glycosides. Czech J. Food Sci. 20101 28(1): 69-73.
Binder, et al. Mechanistic insights on the conversion of sugars into 5-hydroxymethylfurfural. Energy Environ. Sci., 2010; 3:765-771.
Binder, et al. Simple chemical transformation of lignocellulosic biomass into furans for fuels and chemicals. J Am Chem Soc. Feb. 2009 (5):1979-85. doi: 10.1021/ja808537j.
Bizzari, et al. CEH Marketing Research Report, Lignosulfonates. 671.5000 A. Jan. 2009.
Bizzari, et al. CEH Marketing research report: Lignosulfonates (2009) pp. 14-16.
Blommel, et al. Production of conventional liquid fuels from sugars. Virent energy systems. Aug. 25, 2008. 1-14.
Bo, et al. Mutual Solubilities for Water-o-Nitrotoluene System and Distribution Coefficients for Furfural and Acetic Acid in Water-o-Nitrotoluene System. J. Chem. Eng. Data; 2010;55;5191-5195.
Bochek. Effect of Hydrogen Bonding on Cellulose Solubility in Aqueous and Nonaqueous Solvents. Russian Journal of Applied Chemistry, vol. 76, No. 11, 2003, pp. 1711-1719.
Boeriu. Characterisation of structure-dependent functional properties. 2003.
Bonini, et al. Degradation and recovery of fine chemicals through singlet oxygen treatment of lignin. 2003.
Bonini, et al. New Materials from Lignin. 2005.
Bonini, et al. Qualitative 13C NMR spectra of lignin. Analytical methods for lignin characterisation. International Lignin Institute Version: 1.2, Last date of review: Aug. 2008.
Bonini. Low cost steam exploded lignin from straw: degradation and use. The international Lignin Institute, 5th international Forum' Sep. 7, 2000, Bordeaux (France).
Bourbonnais, et al. Lignin Oxidation by Laccase Isozymes from Trametes versicolor and Role of the Mediator 2,29-Azinobis(3-Ethylbenzthiazoline- 6-Sulfonate) in Kraft Lignin Depolymerization. Applied and environmental microbiology. May 1995; 61 (5):1876-1880.
Bozell et al. Top Value Added Chemicals from Biomass vol. I—Results of Screening for Potential Candidates from Sugars and Synthesis Gas Top Value Added Chemicals From Biomass vol. I : Results of Screening for Potential Candidates. NREL report.2004: 1-76.
Bozell. The Use of Renewable Feedstocks for the Production of Chemicals and Materials—A Brief Overview of Concepts. National Renewable Energy Laboratory, 1617 Cole Boulevard, Golden, CO 80401. 2010.
Braun, et al. Lignin-based carbon fibers: Oxidative thermostabilization of kraft lignin. Carbon.2005; 43:385-394.
Bridgwater, et al. Identification and market analysis of most promising added-value products to be co-produced with the fuels. Project No. 212831, Project end date: May 31, 2010; 1-132.
Brito, et al. Chemical composition changes in eucalyptus and pinus woods submitted to heat treatment. Bioresource Technology. 2008; 99:8545-8548.
Brodin, et al. Characteristics of lignin blends intended for carbon fibre production. 2008.
Brown, et al. Initial Market Assessment for Small-Scale Biomass-Based CHP, Prepared under Task No. WF6N.1050. National Renewable Energy Laboratory. Jan. 2008.
Brown. Determination of Dry Substance in Beet Sugar Juices, A Precision Method. Industrial and Engineering chemistry. Jul. 1924; 16(7):746-748.
Brown. Mixed acid recovery with the APU™ acid sorption system. ECO-TEC, Technical Paper 147, Jan. 1997.
Brownell, et al. Steam-Explosion Pretreatment of Wood: Effect of Chip Size, Acid, Moisture Content and Pressure Drop. Biotechnology and Bioengineering. 1986; XXVIII:792-801.
Brummer, et al. Understanding Carbohydrate Analysis. Chapter 2. Copyright 2005 by Taylor & Francis Group, LLC.
Brunner. Near critical and supercritical water. Part I. Hydrolytic and hydrothermal processes. J. of Supercritical Fluids. 2009; 47:373-381.
Bulushev, et al. Catalysis for conversion of biomass to fuels via pyrolysis and gasification: A review. Catalysts Today. 2001; 171: 1-13.

(56) References Cited

OTHER PUBLICATIONS

Bunker. The Wartime Production of Food Yeast in Germany. 2010.
Burchell, et al. The development of novel activated carbon composites. 17th Annual Conference on Fossil Energy Materials, Wyndham Baltimore Inner Harbor Hotel, Baltimore, Maryland, Apr. 22-24, 2003.
Busche. The Klason lignin determination as applied to aspenwood with special: reference to acid-soluble lignin. The Institute of Paper Chemistry, Appleton, Wisconsin,Doctor's Dissertation, A thesis submitted Jun. 1960.
Bustos, et al. Modeling of the Hydrolysis of Sugar Cane Bagasse with Hydrochloric Acid. Applied Biochemistry and Biotechnology. 2003; 104:51-68.
Bykov. Characterization of Natural and Technical Lignins using FTIR Spectroscopy. Master's Thesis, Division of Chemical Technology Department of Chemical Engineering and Geosciences, Lulea University of Technology. Feb. 2008.
Byrne. Expression, purification and crystallisation of membrane proteins. 2011.
Cai, et al. Integrated furfural production as a renewable fuel and chemical platform from lignocellulosic biomass. J. Chem. Technol. Biotechnol. 2014; 89: 2-10.
Campa et al. Capillary Electrophoresis of Neutral Carbohydrates. Methods in molecular biology.2008; 384:247-305.
Campa et al. Capillary electrophoresis of sugar acids. Methods in molecular biology. 2008; 384: 307-355.
Campbell et al. The bleaching action of alkaline hydrogen peroxide on wood. The Biochemical journal. 1938; 32(4): 702-707.
Campbell, et al. The Saccharification of Wood by the Bergius process at Suddeutschen Holzversucherung Werke A.G. Regensburg. Report on visit to Suddeutschen Holzversucherung Werke A.G. Regensburg.CIOS trip No. 764, this target was visited on Aug. 9, 1945.
Campbell. The Degradation of wood by simultaneous action of ethyl alcohol and hydrochloric acid. 1929; 1225-1232.
Campos. Calculations of VLE in electrolytes systems using chemical theory: aqueous acis chloridric system. 2nd Mercosur Congress on Chemical Engineering; 4th Mercosur Congress on Process Systems Engineering. 2008.
Canetti, et al. Thermal degradation behaviour of isotactic polypropylene with lignin. Polym. Degr. and stability 2006, 91, 494-498.
Capanema, et al. Quantitative characterization of a hardwood milled wood lignin by nuclear magnetic resonance spectroscopy. J Agr. Food. Chem. 2005; 53(25): 9639-9649.
Capraru, et al. Contribution to the modification and characterization of different types of lignins. Cellulose Chem. Technol. 2009; 43(9-10):409-418.
Cardona, et al. Production of bioethanol from sugarcane bagasse: Status and perspectives. Bioresource Technology. 2010; 101:4754-4766.
Carole, et al. Opportunities in the Industrial Biobased Products Industry. Applied Biochemistry and Biotechnology. 2004; 113-116:871-88.
Carr. The Biobased Revolution: How Biotechnology and Policy Are Changing the Way Materials Are Made. ASC Fall Convention & Expo. Oct. 11, 2005.
Carrott, et al. Lignin—from natural adsorbent to activated carbon: A review. Bioresource Technology 2007; 98:2301-2312.
Carvalheiro, et al. Hemicellulose biorefineries: a review on biomass pretreatments. Journal of Scientific and Industrial Research. 2008; 67:849-864.
Carvalho, et al. Comparison of different procedures for the detoxification of eucalyptus hemicellulosic hydrolysate for use in fermentative processes. J Chem Technol Biotechnol 2006; 81:152-157.
Castro, et al. Ecologically safe alkyl glucoside-based gemini surfactants. ARKIVOC 2005 (xii) 253-267, ISSN 1424-6376.
Cateto, et al. Lignin-based polyurethane materials. Proceedings of the 10th International Chemical and Biological Engineering Conference—CHEMPOR 2008 Braga, Portugal, Sep. 4-6, 2008 E.C. Ferreira and M. Mota (Eds.).
Cateto, et al. Monitoring of lignin-based polyurethane synthesis by FTIR-ATR. Barcelona, Apr. 27-28, 2005.
Cateto, et al. Oxypropylation of Lignins and Characterization of the Ensuing Polyols. Laboratory of Separation and Reaction Engineering, Bragança Polytechnic Institute, School of Engineering—University of Porto, Ecole Française de Papeterie et des Industries Graphiques, Institut National Polytechnique de Grenoble. 2007. Powerpoint.
Cateto, et al. Rigid Polyurethane foams from lignin-based polyols. Laboratory of Separation and Reaction Engineering. 2008.
Cayle, et al. The application of Mathews' Formula in Enzymatic Starch Conversions. Mar. 1966; 43:237-244.
Cazacu, et al. Lignin—component of complex materials. 2005; 64-71.
Cazacu, et al. Lignin characterization for its use in complex polymeric systems. Polymer Nanomaterials for Food Packaging, Characterization Needs, Safety and Environmental Issues, Sep. 1-2, 2010, London.
Celunol. EESI Congressional Briefing. Sep. 22, 2006.
Cetin, et al. Studies on Lignin-Based Adhesives for Particleboard Panels. Turk J Agric For. 2003;27:183-189.
Chakar, et al. Review of current and future softwood kraft lignin process chemistry. Industrial crops and products. 2004; 20:131-141.
Chalov, et al. Continuous hydrolysis of plant tissue polysaccharides with 46-48% hydrochloric acid. III. Absorption of hydrogen chloride by moist wood. Izvestiya Vysshikh Uchebnykh Zavedenii, Lesnoi Zhurnal (1966), 9(6), 139-43. CODEN: IVZLAL ISSN: 0536-1036. Abstract only.
Chalov, et al. Continuous hydrolysis of plant tissue polysaccharides with 46-48% hydrochloric acid. IV. The problem of the limit concentration of sugars in the hydrolyzate. Sbornik Trudov, Vsesoyuznyi Nauchno-Issledovatel'skii Institut Gidroliza Rastitel'nykh Materialov (1965), 1331-8. CODEN: SVGSAN ISSN: 0371-4322. Abstract only.
Chalov, et al. Continuous hydrolysis of plant tissues with 46-48% hydrochloric acid. VII. Composition of products of hydrolytic destruction of cellulose by concentrated hydrochloric acid. Zhurnal Prikladnoi Khimii (Sankt-Peterburg, Russian Federation) (1967), 40(4), 929-30. CODEN: ZPKHAB ISSN: 0044-4618. Abstract only.
Chalov, et al. Continuous hydrolysis of plant tissues with 46-48% hydrochloric acid. II. Effect of hydrogen chloride on oven-dry wood. Izv. Vysshikh Uchebn. Zavedenii, Lesn. Zh. (1963), 6(2), 141-4. Abstract only.
Chalov, et al. Continuous hydrolysis of wood with 46-48% hydrochloric acid. 1962), 5(No. B), 141-8. CODEN: IVZLAL ISSN: 0536-1036. Abstract only.
Chalov, et al. Differential hydrolysis of wood with concentrated hydrochloric acid in diffusion equipment. 1961), 4(6), 138-46. CODEN: IVZLAL ISSN: 0536-1036. Abstract only.
Chalov, et al. Equilibrium state in the system cellulose-hydrogen chloride-water-hydrolysis products. USSR. Sb. Tr. Vses. Nauch.-Issled. Inst. Gidroliza Rastit. Mater. (1968), 17 173-9. From: Ref. Zh., Khim. 1969, Abstr. No. 15p23. Abstract only.
Chalov, et al. Hydrolysis of difficult-to-hydro lyze polysaccharides of wood with 30-6% hydrochloric acid at 20-40.deg. USSR. Sb. Tr. Vses. Nauch.-Issled. Inst. Gidroliza Rast. Mater. (1969), 18 58-66. From: Ref. Zh., Khim. 1970, Abstr. No. 11P29. Abstract only.
Chalov, et al. Hydrolysis of hemicellulose components of pinewood with 30-36% hydrochloric acid at 30-40.deg. Gidroliznaya i Lesokhimicheskaya Promyshlennost (1968), 21(3), 4-6. CODEN: GLKPA2 ISSN: 0016-9706. Abstract only.
Chalov, et al. Hydrolysis of hemicellulose components of pinewood with 30-36% hydrochloric acid. Zhurnal Prikladnoi Khimii (Sankt-Peterburg, Russian Federation) (1961), 34 1601-8. CODEN: ZPKHAB ISSN: 0044-4618. Abstract only.
Chalov, et al. Hydrolysis of lignocellulose with 38-41% hydrochloric acid at 20°. Vysshikh Uchebn. Zavedenii, Lesn. Zh. (1964), 7(2), 137-43. Abstract only.
Chalov, et al. Hydrolysis of pinewood lignocellulose with 41 % hydrochloric acid in a [6-] diffuser unit. Izvest. Vysshikh Ucheb. Zavedenii, Lesnoi Zhur. (1961), 4(No. 2), 131-7. Abstract only.

(56) References Cited

OTHER PUBLICATIONS

Chalov, et al. Hydrolysis of polysaccharides of pinewood with 38-41% hydrochloric acid at 20°. Zhurnal Strukturnoi Khimii (1962), 35(No. 6), 1347-55. CODEN: ZSTKAI ISSN: 0136-7463. Abstract only.
Chalov, et al. Hydrolysis of polysaccharides of plant fiber in concentrated aqueous and gaseous hydrochloric acid. Zhurnal Prikladnoi Khimii (Sankt-Peterburg, Russian Federation) (1960), 33 2743-50. CODEN: ZPKHAB ISSN: 0044-4618. Abstract only.
Chalov, et al. Hydrolysis of wood with concentrated hydrochloric acid. Gidroliz. i Lesokhim. Prom. (1959), 12(No. 3), 3-5. Abstract only.
Chalov, et al. Hydrolysis of wood with concentrated hydrochloric acid. Gidroliznaya i Lesokhimicheskaya Promyshlennost (1959), 12(No. 4), 1-4. Abstract only.
Chalov, et al. Hydrolysis of wood with gaseous hydrochloric acid under atmospheric pressure. Gidroliznaya i Lesokhimicheskaya Promyshlennost (1959), 12 14-18. Abstract only.
Chalov, et al. Two-stage hydrolysis of wood by use of mechanochemical degradation of lignocellulose in the presence of hydrochloric acid. Sbornik Trudov. Gosudarstvennyi Nauchno-issledovatel'skii Institut Gidroliznoi i Sul'fitno-spirtovoi Promyshlennosti (1966), 15 189-98. CODEN: SGSSAC. Abstract only.
Chalov, et al. Withdrawal of the heat of absorption during hydrolysis of wood with gaseous hydrogen chloride. 1962), 5(No. 1), 155-62. CODEN: IVZLAL ISSN: 0536-1036. Abstract only.
Chalov. Sorption of Hydrogen Chloride by moist lignocellulose. SB. TR. VNII Gidroliza Rastitel'N. Mater. 1975; 25:41-49.
Chambost, et al. Guided tour: Implementing the forest biorefinery (FBR) at existing pulp and paper mills. Pulp & Paper Canada. 2008; 109(7):1-9.
Chandra, et al. Substrate Pretreatment: The Key to Effective Enzymatic Hydrolysis of Lignocellulosics? Adv Biochem Engin/Biotechnol. 2007; 108: 67-93.
Chang, et al. Modification of wood with isopropyl glycidyl ether and its effects on decay resistance and light stability. Bioresource Technology. 2006; 97:1265-1271.
Chaow-U-Thai et al. Removal of ash from sugarcane leaves and tops. International Journal of Biosciences.2012; 2(5): 12-17.
Chen, et al. Application of Molecular Fragments Variable Connectivity Index to Predicting Boiling Points of Alcohols. J. Iran. Chem. Soc. Dec. 2010; 7(4):1012-1020.
Cheng et al. A novel method to prepare L-arabinose from xylose mother liquor by yeast-mediated biopurification. Microbial cell factories.2011; 10 (43): 1-11.
Chevalier, et al. Vapor-Liquid Equilibrium Data for the Systems H2O-H2SO4-HCI, H2O-H2SO4-HBr, and H2O-HBrat 780 mmHg Pressure. J. Chem. Eng. Data. 1980; 25:271-273.
Chidambaram, et al. A two-step approach for the catalytic conversion of glucose to 2,5-dimethylfuran in ionic liquids. Green Chem. 2010; 12: 1254-1262.
Chinese Office action dated Dec. 3, 2014 for CN Application No. 2011800414270.
Choudhary et al. Conversion of Xylose to Furfural Using Lewis and Brønsted Acid Catalysts in Aqueous Media. ASC Catalysis.2012; 2: 2022-2028.
Choudhary et al. Highly efficient aqueous oxidation of furfural to succinic acid using reusable heterogeneous acid catalyst with hydrogen peroxide. Chem. Lett. 2012; 41: 409-411.
Christiernin. Composition of Lignin in Outer Cell-Wall Layers. Doctoral Thesis, Royal Institute of Technology. 2006.
Ciolacu, et al. New aspects concerning formulation of furan and lignin-based bio-adhesive. 2008.
Claricone Clarifiers and FiltraCone treatment plants. CB&I. Accessed Nov. 30, 2011.
Coetzee, et al. Determination of pectin content of eucalyptus wood. Holzforschung. 2011; 65:327-331.
Cognis. MCT Redbook. Solvent Extraction Reagents and Applications. Cognis miningchemicals technology. 2010.
Cole. XCV. The determination of reducing sugars by titration of ferricyanide. Biochem. 1933 xxvii, pp. 723-726.
Coma, et al. alpha-Glucosidase and N-Acetyl-p-o-glucosaminidase Isoenzymes in Serum. Clin. Chem. 1992; 38(2):223-226.
Compere, et al. Evaluation of Lignin from Alkaline-Pulped Hardwood Black Liquor. Oak Ridge National Laboratory, US Department of Energy, under contract DE-AC05-000R22725, ORNLITM-2005/88. May 2005.
Compere, et al. Improving the fundamental properties of lignin-based carbon fiber for transportation application. Oak Ridge National Lab. 2009.
Compere, et al. Low cost carbon fiber from renewable resources. Carbon. 1998; 36(7-8):1119-1124.
Conner, et al. Kinetic modeling of hardwood prehydrolysis. Part II. Xylan removal by dilute hydrochloric acid prehydrolysis. Wood and Fiber Science. 1985; 17(4):540-548.
Constantinescu, et al. Composites based on natural and recycled synthetic polymers. 2005.
Constantinescu, et al. Lignin hydrophobization by different esterification reactions. ILI—Forum 8 , May 10-12, 2007.
Constantinescu, et al. Study of the surface properties of some polyolefin/lignocellulosic composites treated by plasma. Cellulose Chem. Technol. 2007; 41(7-8):463-472.
Co-pending U.S. Appl. No. 15/573,801, filed Nov. 13, 2017.
Co-pending U.S. Appl. No. 17/100,672, filed Nov. 20, 2020.
Co-pending U.S. Appl. No. 17/177,098, filed Feb. 16, 2021.
Co-pending U.S. Appl. No. 15/261,560, filed Sep. 9, 2016.
Co-pending U.S. Appl. No. 15/298,145, filed Oct. 19, 2016.
Crittenden, et al. Extraction of hydrogene chloride from aqueous solutions. Industrial and Engineering Chemistry. Feb. 1954; 46(2):265-274.
Cui. Structural Analysis of Polysaccharides. Chapter 3. Copyright 2005 by Taylor & Francis Group, LLC.
Dave, et al. Molecular organization of lignin during carbonization. Polymer. 1993; 34(15):3144-3154.
David, et al. 31 P-NMR analysis of bio-oils obtained from the pyrolysis of biomass. Biofuels. 2010; 1(6):839-845.
David, et al. Cross-Polarization/Magic Angle Spinning (CP/MAS) 13C Nuclear Magnetic Resonance (NMR) Analysis of Chars from Alkaline-Treated Pyrolyzed Softwood. Energy & Fuels. 2009;23:498-501.
Dayton, et al. Biomass Hydropyrolysis in a Pressurized Fluidized Bed Reactor. Energy and Fuels.2013; 27: 3778-3785.
De Guzman. Bio-adipic acid prepares for entry. ICIS Chemical Business Sep. 27, 2010. www.icis.com.
De Jong, et al. Lignin as additive in paper production. Agrotechnology & Food Innovations, Wageningenur. Fibre and Paper Technology. Feb. 2005.
De Jong, et al. The simultaneous colouring and U.V. stabilisation of materials using dyed lignin. The international Lignin Institute, 5th international Forum' Sep. 7, 2000, Bordeaux (France).
De Los Rios, et al. Removal of Metal Ions from Aqueous Solutions by Extraction with Ionic Liquids. J. Chem. Eng. Data. 2010; 55:605-608.
De Wild, et al. Pyrolysis of Wheat Straw—Derived Organosolv Lignin. Ch. 5, pp. 101-122. 2011.
De Wild. Lignin Valorisation for Chemicals and Fuels by Catalytic Pyrolysis. International Biomass Valorisation Congress, Amsterdam—The Netherlands, Sep. 13-15, 2010.
Demirbas. Furfural Production from Fruit Shells by Acid-Catalyzed Hydrolysis, Energy Sources, Part A: Recovery, Utilization, and Environmental Effects. 2006; 28(2):157-165.
Demirbas. Products from lignocellulosic materials via degradation processes. Energy Sources, Part A. 2008; 30:27-37.
Diaz, et al. Variations in fiber length and some pulp chemical properties of Leucaena varieties. Industrial Crops and Products. 2007; 26(2): 142-150.
Dimmel et al. Electron transfer reactions in pulping systems ( II ): electrochemistry of Anthraquinone / Lignin model Quinonemethides. IPC Thechnical Paper series. 1984; 141: 1-22.
Dimmel et al. IPC Technical Paper Series No. 139 Electron Transfer Reactions in Pulping Systems ( I ): Theory and Applicability to Anthraquinone Pulping. 1984; 139: 1-15.

(56) References Cited

OTHER PUBLICATIONS

Dimmel, et al. Fundamentals of selectivity in pulping and bleaching: Delignification reactions. Members of the Institute of Paper Chemistry. The Institute of Paper Chemistry. 1986; Project 3475.
Dimov, et al. Influence of the amount and concentration of hydrochloric acid on the composition of wheat straw during prehydrolysis. Chem. Technol. Inst., Sofia, Bulg. Papier (Paris) (1960), 14 673-6. CODEN: PPERA3 ISSN: 0370-1174. Abstract only.
Diouf, et al. Radical Scavenging Capacity of Lignin Derivatives and Its Oxidative Stabilization Effect on Polyethylene. 2008.
Dipardo. Outlook for Biomass Ethanol Production and Demand. Energy Information Administration. 2008; 1-14.
Doorn, et al. CID-Based ICP-AES Instrumantation for Cntinuous On-Line Analysis of Aqueous Industrial Waste Streams. Conference report. 1997; Vancouver (Canada).
Draucker. Novel solvent systems for the development of sustainable technologies. Georgia Institute of Technology. Aug. 2007.
Drenkow. Wood Saccharification. A Modified Rheinau Process. 1976. DouglasDrenkow.com/write2a.html.
Drougge, et al. Application of Kraft lignin as metal binder. 2008.
Duque. Acid-functionalized nanoparticles for hydrolysis of lignocellulosic feedstocks. Master of Science, Department of Biological and Agricultural Engineering, College of Engineering, Kansas State University, Manhattan, Kansas. 2009.
Dutta et al. Direct conversion of cellulose and lignocellulosic biomass into chemicals and biofuel with metal chloride catalysts. Journal of Catalysis; 2012; 288; 8-15.
Dyadic. AlternaFuel® 200P, Product #326, (For considerations in biomass saccharification applications). 2010.
Dyadic. Enzyme Development for Fuel Ethanol Production from Pre-treated Biomass, Technical Report May 2010, Saccharification I.D: Sacc 05.17.10.
Eckert, et al. Tunable solvents for fine chemicals from the biorefinery. Green Chem. 2007; 9: 545-548.
Economy, et al. Activated carbon fibers—past, present, and future. 1996; 321-358.
Eggeman, et al. Process and economic analysis of pretreatment technologies. Bio. Tech. 2005;96:2019-2025.
Ehara, et al. A comparative study on chemical conversion of cellulose between the batch type and flow type systems in supercritical water. Cellulose. 2002; 9:301-311.
Elhanan, et al. Solvent Sublation of Iron( III) Chloride by Tri-n-Octylamine. Analytical chemistry. Apr. 1969; 40(4):671-674.
Elliott, et al. Pretreatment technologies for advancing anaerobic digestion of pulp and paper biotreatment residues. Water Research. 2007; 41:4273-4286.
Eminov et al. Highly selective and near-quantitative conversion of fructose to 5-hydroxymethylfurfural using mildly acidic ionic liquids. ACS Sustainable Chemistry & Engineering; 2014; 1-17.
EP18180953.4 Extended European Search Report dated Sep. 13, 2018.
Esteves, et al. Chemistry and ecotoxicity of heat-treated pine wood extractives. Wood Sci Technol. Jul. 11, 2010. DOI 10.1007/s00226-010-0356-0.
European search report dated May 4, 2015 for EP Application No. 12768483.5.
European search report dated Sep. 11, 2015 for EP Application No. 11797729.8.
European search report dated Oct. 9, 2015 for EP Application No. 12768483.5.
Excoffier, et al. Saccharification of Steam-Exploded Poplar Wood. Biotechnology and bioengineering. Dec. 20, 1991; 38(11):1308-1317.
Extended European search report dated Jan. 20, 2016 for EP Application No. 11797729.8.
Eyal, et al. A process for defluorination and purification of wet process phosphoric acids containing high al concentrations. Solvent Extraction and ion exchange. 1984; 2(4):677-697.
Eyal, et al. Extraction of Strong Mineral Acids by Organic Acid-Base Couples. Ind. Eng. Chem. Process Des. Dev. 1982, 21, 334-337.
Eyal, et al. pH dependence of carboxylicand mineral acid extraction by amine-based extractants: effects of pKa, Amine Basicity, and diluent properties. Ind. Eng. Chem. Res. 1995; 34:1789-1798.
Eyal, et al. Potassium Nitrate through Solvent Separation of Strong Acids. Ind. Eng. Chem. Process Des. 1985; 24:387-390.
Eyal, et al. Recovery and concentration of strong mineral acids from dilute solutions through LLX.I: review of parameters for adjusting extractant propert and analysis of process options. Solvent Extraction and ion exchange. 1991; 9(2):195-210.
Eyal, et al. Sulfuric acid recovery through solvent aided decomposition of ammonium sulfate. Solvent Extraction and ion exchange. 1986; 44:803-821.
Eyal, et al. Wet process phosphoric acid defluorination by aminebased extractants. Solvent Extraction and ion exchange. 1984; 2(4&5):659-675.
Fahim, et al. Liquid-Liquid Equilibria of the Ternary System Water + Acetic Acid + 1-Hexanol. J. Chem. Eng. Data. 1997; 42:183-186.
Farrell, et al. Solving Pitch Problems in Pulp and Paper Processes by the Use of Enzymes or Fungi. Advances in Biochemical Engineering/Biochemical Engineering/1997/pp. 198-212.
Feldman, et al. Lignin in blends with synthetic polymers. 2007.
Fenner, et al. Examination of the Thermal Decomposition of Kraft Pine Lignin by Fourier Transform Infrared Evolved Gas Analysis. J. Agric. Food Chem. 1981; 29:846-849.
Ferrari, et al., Ethanol production from eucalyptus wood hemicellulose hydrolysate by pichia stipitis, 1992, biotech and bioengineering, 40:753-759.
Ferraz, et al. Estimating the chemical composition of biodegraded pine and eucalyptus wood by DRIFT spectroscopy and multivariate analysis. Bioresource Technology. 2000; 74:201-212.
Fierro, et al. Methodical study of the chemical activation of Kraft lignin with KOH and NaOH. Microporous and Mesoporous Materials. 2007; 101:419-431.
Foran, et al. Beyond 2025: Transitions to the biomass-alcohol economy using ethanol and methanol. Working Paper Series 99/07. Dec. 1999.
Fox. Chemical and thermal charaterization of three industrial lignins and their corresponding lignin esters. A Thesis for the degree of Master of Science with a Major in Forest Products in the College of Graduate Studies University of Idaho, May 2006.
Foxit. Chemicals partition in wood. Mar. 2011.
Froass, et al. Nuclear Magnetic Resonance Studies. 4. Analysis of Residual Lignin after Kraft Pulping. Ind. Eng. Chem. Res. 1998; 37:3388-3394.
Funaoka, et al. Design and functions of structure controllable lignin-based polymers. 2005.
Fungsin, et al. Conversion of cassava waste into sugar using Aspergillus niger and Trichoderma reesei for ethanol production. 2010.
Gabilondo, et al. Lignin low molar mass fractions involvement in the synthesis of PF matrices. 2007.
Galbe, et al. A review of the production of ethanol from softwood. Appl Microbiol Biotechnol. 2002; 59:618-628.
Galbe, et al. Process Engineering Economics of Bioethanol Production. Adv Biochem Engin/Biotechnol. 2007; 108:303-327.
Galego, et al. Mechanism of the thermal resinification of pure furfural. Revista CENIC, Ciencias Fisicas. 1975; 6(1):163-180. Abstract only.
Gamez et al. Study of the hydrolysis of sugar cane bagasse using phosphoric acid. Journal of Food Engineering.2006; 74: 78-88.
Gani et al. Molecular Design of Solvents for Liquid Extraction Based on UNIFAC. Fluid Phase Equilibria. 1983; 13: 331-340.
Garna, et al. Kinetic of the hydrolysis of pectin galacturonic acid chains and quantification by ionic chromatography. Food Chemistry. 2006; 96:477-484.
Gaspar, et al. Oxidaton of Lignin in supercritical carbon dioxide. III meeting, Barcelona, Apr. 27-28, 2005.
Genencor. Enzyme Products for Fuel Ethanol Production. Genencor, 2007 Danisco US Inc.

(56) References Cited

OTHER PUBLICATIONS

Georgieva, et al. Enzymatic hydrolysis and ethanol fermentation of high dry matter wet-exploded wheat straw at low enzyme loading. Applied biochemistry and biotechnology. 2008;148:35-44.
Georgopoulos, et al. Thermoplastic polymers reinforced with fibrous agricultural residues. 2009.
Gibbs et al. An Economic Value Chain Using Nonfood Biomass Intermediates for Bioplastics Production. Presentation; General Biomass Company; 2013.
Glasser. Lignin retrospect and prospect. 2010.
Glazkova, et al. Effect of temperature on the extraction of pre-hydrolysis products from lignocellulose chips. Gidroliznaya i Lesokhimicheskaya Promyshlennost (1974), (6), 12-13. CODEN: GLKPA2 ISSN: 0016-9706. Abstract only.
Goldstein, et al. The hydrolysis of cellulose with superconcentrated hydrochloric acid. Biotechnology and Bioengineering Symposium (1984), Volume Date 1983, 13(Symp. Biotechnol. Fuels Chem., 5th, 1983), 17-25. CODEN: BIBSBR ISSN: 0572-6565. Abstract only.
Goldstein. Potential for Converting Wood into Plastics, Chemicals from wood may regain importance as the cost of petroleum continues to rise. Science, Sep. 12, 1975; 189(4206):847-852.
Goncalves, et al. Hydroxymethylation and oxidation of Organosolv lignins and utilization of the products. Bioresource Technology. 2001; 79:103-111.
Gonzalez-Serrano, et al. Development of Porosity upon Chemical Activation of Kraft Lignin with ZnCl2. Ind. Eng. Chem. Res. 1997; 36:4832-4838.
Gonzalez-Serrano, et al. Removal of water pollutants with activated carbons prepared from H3PO4 activation of lignin from kraft black liquors. Water Research. 2004; 38:3043-3050.
Gosselink, et al. Analysis of isolated lignin samples using organic and alkaline SEC and MALDI-TOF-MS. Agrotechnology & Food Sciences Group. 2006.
Gosselink, et al. Analytical protocols for characterisation of sulphur-free lignin. Industrial Crops and Products. 2004; 19:271-281.
Gosselink, et al. Characterisation and application of NovaFiber lignin. Industrial Crops and Products. 2004;20:191-203.
Gosselink, et al. Co-ordination network for lignin—standardisation, production and applications adapted to market requirements (EUROLIGNIN). Industrial Crops and Products 2004; 20:121-129.
Gosselink, et al. Development of lignin based products. Canada Biomass Business Day, Amstelveen (NL), Oct. 22, 2008.
Gosselink, et al. FT-IR characterisation of lignins with help of PCA. Cost E41 Spectrometric techniques used for the analysis of Carbohydrates, Lignin and Extractives Barcelona, Apr. 25, 26, 2005.
Gosselink, et al. Lignin depolymerization under supercritical process conditions. Agrotechnology & Food Sciences Group. 2008.
Gosselink, et al. Selective oxidation of lignin by periodate. ILI 8th Forum 11.05.2007 May 10-12, 2007.
Gosselink, et al. Valorization of biorefinery lignins. ILI Lignin workshop, Zürich/Dübendorf (CH), Oct. 28, 2008.
Gosselink, et al. Valorization of lignin resulting from biorefineries. Jun. 4, 2008, RRB4 Rotterdam.
Goto, et al. Supercritical Thermal Decomposition of Cellulose: Experiments and Modeling. Ind. Eng. Chem. Res. 1990; 29:1091-1095.
Grant, et al. Tall oil production and processing. Grant and Hockh's Chemical Dictionary 5th ed. 1987.
Gray, et al. Sugar Monomer and Oligomer Solubility, Data and Predictions for Application to Biomass Hydrolysis. Applied Biochemistry and Biotechnology. 2003; 105-108:179-193.
Greenwald. The dissociation of some calcium salts. Mar. 7, 1938; 437-452.
Grethlein, et al. The Cost of Ethanol Production from Lignocellulosic Biomass—A Comparison of Selected Alternative Processes. USDA. Specific Cooperative Agreement No. 58-1935-2-050. Apr. 30, 1993.
Gretland, et al. Characterisation of lignosulphonates and sulphonated kraft lignin by hydrophobic interaction chromatography. 2005.
Griffith, et al. Low cost carbon fiber for transportation application. USDE. 2003.
Grigoriev, et al. Polyoxometalate Oxidation of Phenolic Lignin Models. In: ACS Symposium Series 785. Oxidative delignification chemistry. Fundamentals and catalysis. Washington, DC: American Chemical Society. 2001; Chapter 18: 297-312.
Grinbaum. An Integrated method for Development and Scaling up of Extraction Processes. "Ion Exchange and Solvent Extraction", Y. Marcus, A. Sangupta (eds.), vol. 15, Elsevier, 2002.
Grzenia, et al. Membrane extraction for removal of acetic acid from biomass hydrolysates. J Membr Sci 2008;322:189-195.
Guerra, et al. On the Propensity of Lignins to Associate. Organic Chemistry of Wood Components Laboratory Department of Forest Biomaterials Science & Engineering North Carolina State Raleigh, North Carolina USA. 2007.
Guirguis, et al. Purification of phosphoric acid by a mixture of hydrophobic and hydrophilic extractants. Adv. Process. Met. Mater., Sohn Int. Sym. 2006; 3:451-465.
Gutierrez, et al. Analysis of Lipophilic extractives from wood and pitch deposits by solidphase extraction and gas chromatography. J. of Chromatography A. 1998; 823:449-455.
Gutierrez, et al. Enzymatic Removal of Free and Conjugated Sterols Forming Pitch Deposits in Environmentally Sound Bleaching of Eucalypt Paper Pulp. Environ. Sci. Technol. 2006; 40:3416-3422.
Gutierrez, et al. Fungal Degradation of Lipophilic Extractives in Eucalyptus globulus Wood. Applied and environmental microbiology. Apr. 1999; 65(4):1367-1371.
Gutierrez, et al. Microbial and enzymatic control of pitch in the pulp and paper industry. Appl Microbiol Biotechnol. 2009; 82:1005-1018.
Gutierrez, et al. The biotechnological control of pitch in paper pulp manufacturing. Trends in Biotechnology. 2001; 19(9):340-348.
Haensel, et al. Pyrolysis of wood-based polymer compounds. J. Anal. Appl. Pyrolysis. 2010; 87:124-128.
Hage, et al. Effects of process severity on the chemical structure of Miscanthus ethanol organosolv lignin. Polymer Degradation and Stability. 2010; 95:997-1003.
Hagglund. Hydrochloric acid lignin (preliminary communication). Berichte der Deutschen Chemischen Gesellschaft [Abteilung] B: Abhandlungen (1923), 56B 1866-8. CODEN: BDCBAD ISSN: 0365-9488. Abstract only.
Hagglund. Report of the research activities of the Cellulose Laboratory (Stockholm, Sweden) during the year 1941. Svensk Papperstidning (1942), 45 123-35. Abstract only.
Hagglund. The Decomposition of Wood by Acids wood Saccharification. Chemistry of Wood. New York: Academic Press, 1951. 631. Chapter IV. 390-413.
Hagglund. Wood Saccharification. A Modified Rheinau Process. 2011.
Hall, et al. Wood saccharification. USDA. Unasylva. 2007; 10(1).
Hall. Polyhydric alcohol from wood. US Department of Agriculture, Forest Service, Forest Products Laboratory, Madison, Wisconsin. No. 1984. Jul. 1954.
Hallac, et al. Biomass Characterization and Organosolv Pretreatment of Buddleja davidii. School of Chemistry and Biochemistry, Institute of Paper Science and Technology, Georgia Institute of Technology, Atlanta, GA. 2009.
Hallac, et al. Biomass Characterization of Buddleja davidii: A Potential Feedstock for Biofuel Production. J. Agric. Food Chem. 2009; 57(4):1275-1281.
Hallac, et al. Chemical Transformations of Buddleja davidii Lignin during Ethanol Organosolv Pretreatment. Energy Fuels. 2010; 24:2723-2732.
Hallac. Fundamental understanding of the biochemical conversion of buddleja davidii to fermentable sugars. Georgia Institute of Technology. May 2011.
Hallac. Lignin, a crash course. Dec. 23, 2009. Powerpoint.
Hallal et al. Electrochemical polymerization of furfural on a platinum electrode in aqueous solutions of potassium biphthalate. Materials Research; 2005; 8(1); 23-29.
Hamelinck, et al. Ethanol from lignocellulosic biomass: techno-economic performance in short-, middle- and long-term. Biomass and Bioenergy; 2005; 28; 384-410.

(56) References Cited

OTHER PUBLICATIONS

Hamelinck, et al. Production of advanced biofuels. International Sugar Journal. 2006; 108(1287):168-175.

Han, et al. Optimizing lignocellulosic feedstock for improved biofuel productivity and processing. Biofuels, Bioprod. Bioref. 2007; 1:135-146.

Hanchar, et al. Separation of glucose and pentose sugars by selective enzyme hydrolysis of AFEX-treated corn fiber. Appl Biochem Biotechnol. Apr. 2007;137-140(1-12):313-25. doi: 10.1007/s12010-007-9061-3.

Harada, et al. Formation of Isoamylase by Pseudomonas. Applied Microbiology. Oct. 1968; 16(10):1439-1444.

Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.

Harris, et al. The Madison Wood-Sugar Process. US Dept. of Agriculture. Jun. 1946; 1-21.

Harris. Derived products and chemical utilization of wood waste. Forest Products Laboratory; Forest Service US Department of Agriculture; Rept. No. R1666-10. Jun. 1949.

Harris. Progress in the Chemistry of Lignin 1943-1954, Report No. 2020. USDA. Mar. 1955.

Harrison. Clvii. A note on the solubilities of calcium soaps. 1924; 1222-1223.

Hasegawa, et al. New Pretreatment Methods Combining a Hot Water Treatment and Water/Acetone Extraction for Thermo-Chemical Conversion of Biomass. Energy & Fuels. 2004; 18:755-760.

Hatch, et al. acid retardation, A Simple Physical Method for Separation of Strong Acids from Their Salts. I & E C process design and development. Oct. 1963; 2(4):253-263.

Hatcher. Chemical structural studies of natural lignin by dipolar dephasing solid-state $^{13}$C nuclear magnetic resonance. Org. Geochem. 1987; 11 (1):31-39.

Hatcher. Dipolar-Dephasing $^{13}$C NMR Studies of Decomposed Wood and Coalified Xylem Tissue:Evidence for Chemical Structural Changes Associated with Defunctionalization of Lignin Structural Units during Coalification. Energy. Fuels. 1988; 2:48-58.

Havlik, et al. Atmospheric leaching of EAF dust with diluted sulphuric acid. Hydrometallurgy. 2004; doi:10.1016/j.hydromet.2004.10.008.

Hawley, et al. Comparison of hydrogen fluoride saccharification of lignocellulosic materials with other saccarification technologies. Energy in Agriculture. 1983; 2:219-244.

Hayashi, et al. Preparation of activated carbon from lignin by chemical activation. Carbon. 2000; 38:1873-1878.

Hayes, et al. The Biofine Process: Production of Levulinic Acid, Furfural and Formic Acid from Lignocellulosic Feedstocks. Biorefinery (8b). 2011.

Heinonen, et al. Chromatographic recovery of monosaccharides for the production of bioethanol from wood. Ind. Eng. Chem. Res. 2010; 49:2907-2915.

Held. Catalytic conversion of renewable plant sugars to fungible liquid hydrocarbon fuels using the bioforming process. TAPPI IBBC session 3. Virent Energy systems. Oct. 15, 2009.

Hellenbrand et al. Integration of Wet Oxidation and Nanofiltration for Treatment of Recalcitrant Organics in Wastewater. Kinetic, Catalysts and Reaction Engineering; 1997; 36; 5054-5062.

Hendriks, et al. Pretreatments to enhance the digestibility of lignocellulosic biomass. Bioresource Technology. 2009; 100:10-18.

Heppolette, et al. Effect of a-methylation on the parameters characterizing hydrolysis in water for a series of halides and sulfonates. Canadian Journal of Chemistry. 1966; 44:677-684.

Hergert. Infrared Spectra of Lignin and Related Compounds.11 Conifer Lignin and model compounds—Hergert in J. Org. Chem. 1960; 25:405-413.

Hernadez, et al. Role of lignin structure in foams formations and their stability. 2007.

Herrera, et al. Effect of the hydrochloric acid concentration on the hydrolysis of sorghum straw at atmospheric pressure. Journal of Food Engineering.2004; 63:103-109.

Herrera, et al. Production of Xylose from Sorghum Straw Using Hydrochloric Acid. Journal of Cereal Science. 2003; 37:267-274.

Herty. Advanced Materials Development Center. HCl Clean Tech Composite Sample—Extracted Wood Sample. 2010.

Hettenhaus et al. Cellulase Assessment Report and Recommendations for Future Work. Ethanol Production from Biomass Hydrolysis; NREL report; 1997.

Heuts, et al. Chrysosporium lucknowense cellulase production platform for applications in biorefineries. DYADIC ® Netherlands. 2010.

Higgins, et al. Hydrolysis of cellulose using HCL: A comparison between liquid phase and gaseous phase processes. Agricultural wastes. 1982; 4:97-116.

Hinz, et al. Hemicellulase production in Chrysosporium lucknowense C1. Journal of Cereal Science. 2009; 50(3):318-323. doi:10.1016/j.jcs.2009.07.005.

Hirajama et al. Semibatch Hydrothermal Hydrolysis of Cellulose in a Filter Paper by Dilute Organic Acids. Ind Eng Chem Res 54:6052-6059 (May 22, 2015).

Hirst, et al. CCCLXXXII.—The action of highly concentrated hydrochloric acid on cellulose and on some derivatives of glucose and of xylose. 1923; 3226-3235.

Hiwale, et al. Industrial Applications of Reactive Distillation: Recent Trends. International Journal of Chemical Reactor Engineering, vol. 2 [2004], Review R1. 1-54.

Hoareau et al. Sugar cane bagasse and curaua lignins oxidized by chlorine dioxide and reacted with furfuryl alcohol : characterization and stability. Polymer Degradation and Stability. 2004; 86: 567-576.

Hodge. Chemistry of Browning Reactions in Model Systems. Agricultural and Food Chemistry. Oct. 14, 1953; 1(15):928-943.

Holladay, et al. Top Value-Added Chemicals from Biomass vol. II—Results of Screening for Potential Candidates from Biorefinery Lignin. Pacific Northwest National Laboratory, Prepared for the U.S. Department of Energy. Oct. 2007.

Holm, et al. Ionic Liquids in the Pretreatment of Lignocellulosic Biomass, chapter 24, 545-560. 2011.

Holota, et al. One-stage hydrolysis of beechwood sawdust by gaseous hydrogen chloride. Vyskum (1967), (2), 105-18. CODEN: DRVYAP ISSN: 0012-6136. Abstract only.

Holtman, et al. An NMR Comparison of the Whole Lignin from Milled Wood, MWL, and REL Dissolved by the DMSO/NMI Procedure. Journal of Wood Chemistry and Technology. 2007; 27:179-200.

Holtman, et al. Quantitative 13C NMR Characterization of MWL isolated by milling techniques. J Wood Chem Technol. 2006; 26:21-34.

Horsley, et al. Azeotropic Data-II, No. 35, Advances in Chemistry Series. American Chemical Society, Washington, D.C. 1962.

Horvath, et al. IUPAC-NIST Solubility Data Series 68. Halogenated Aliphatic Hydrocarbon Compounds C3-C1 With Water. J. Phys. Chem. Ref. Data. 1999; 28(3):649-777.

Hou-Rui, et al. Novel Isolates for Biological Detoxification of Lignocellulosic Hydrolysate. Appl Biochem Biotechnol 2009; 152:199-212.

Howarth, et al. Methane and the greenhouse-gas footprint of natural gas from shale formations, A letter. Climatic Change, Accepted: Mar. 13, 2011, DOI 10.1007/s10584-011-0061-5.

Hu, et al. Chemical profiles of switchgrass. Bioresource Technology. 2010; 101:3253-3257.

Huang, et al. A review of separation technologies in current and future biorefineries. Separation and Purification Technology. 2008; 62:1-21.

Huber, et al. Synthesis of Transportation Fuels from Biomass: Chemistry, Catalysts, and Engineering. Chemical Reviews. Published on Web Jun. 27, 2006 Page Est: 54.3, 10.1021/cr068360d.

Huber. Breaking the Chemical and Engineering Barriers to Lignocellulosic Biofuels: Next Generation. Based on the: Jun. 25-26, 2007 ,Workshop, Washington D.C.

Hutchins, et al. Aqueous polar aprotic solvents. Efficient sources of nucleophilic oxygen. J. Org. Chem. 1983; 48:1360-1362.

(56) References Cited

OTHER PUBLICATIONS

Hyttinen et al. Comparison of VOC emissions between air-dried and heat-treated Norway spruce (Picea abies), Scots pine (Pinus sylvesteris) and European aspen (Populus tremula) wood. Atmospheric Environment. 2010; 44:5028-5033.

Ibarra, et al. Isolation of high-purity residual lignins from eucalypt paper pulps by cellulase and proteinase treatments followed by solvent extraction. Enzyme and Microbial Technology. 2004; 35:173-181.

Ibbc. Sequential Lignin Recovery & Purification (SLRP). Poster Session at the IBBC/BioPro Expo Mar. 14-16, 2011.

Ibrahim, et al. Comparison of alkaline pulping with steam explosion for glucose production from rice straw. Carbohydrate Polymers. 2011; 83:720-726.

Intechfibres. Microscopic Analysis of pulps, papers and boards: For a Fundamental Knowledge of Fibre Structure. IntechFibers, research in fibers Nov. 2007.

International search report and written opinion dated Mar. 9, 2012 for PCT/IL2011/000509.

International search report and written opinion dated May 23, 2012 for PCT Application No. US12/024033.

International search report and written opinion dated Jul. 18, 2012 for PCT/IB2011/003310.

International search report and written opinion dated Aug. 31, 2012 for PCT/IL2012/050118.

Iranmahboob, et al. Optimizing acid-hydrolysis: a critical step for production of ethanol from mixed wood chips. Biomass and Bioenergy. 2002; 22:401-404.

IsoClear 42% high fructose 80% solids corn syrup. Technical product information. Cargill. Updated Aug. 14, 2012.

Itzkowitz. Biodiesel from sugars. 2011.

Izydorczyk, et al. Polysaccharide Gums: Structures, Functional Properties, and Applications. Chapter 6. Copyright 2005 by Taylor & Francis Group, LLC.

Izydorczyk. Understanding the Chemistry of Food Carbohydrates. Chapter 1. Copyright 2005 by Taylor & Francis Group, LLC.

Jacobsen et al. Xylose Monomer and Oligomer Yields for Uncatalyzed Hydrolysis of Sugarcane Bagasse Hemicellulose at Varying Solids Concentration. Industrial & Engineering Chemistry Research; 2002; 41; 1454-1461.

Jacobsen, et al. Cellulose and Hemicellulose Hydrolysis Models for Application to Current and Novel Pretreatment Processes. Applied Biochemistry and Bio. 2000; 84-86:81-96.

Jiang, et al. Perdeuterated pyridinium molten salt (ionic liquid) for direct dissolution and NMR analysis of plant cell walls. Green Chem. 2009; 11:1762-1766.

Johannis. Rhenium- and molybdenum—catalyzed Dehydration Reactions. PhD Thesis. Utrecht University, The Netherlands, 1984.

Johnson, et al. Stability Patterns of Methoxy Phenols under Alkaline Hydrolysis Conditions. 2011.

Johnson, et al. Use of lignin in the biorefinery. 7th International Forum of the International Lignin Institute,Barcelona, Spain, Apr. 27-28, 2005.

Johnson. Effects of Dilute Acid Hydrolyzate Components on Glucose Degradation. National Bioenergy Center, NREL, 1617 Cole Blvd., Golden, Colorado 80401, USA. 2011.

Kadam, et al. Generating Process and Economic Data Needed for Preliminary Design of PureVision Biorefineries. DOE Project No. DE-FG36-05G085004, Final Nonproprietary Technical Report. Dec. 28, 2007.

Kadla, et al. Lignin-based carbon fibers for composite fiber applications. Carbon. 2002; 40:2913-2920.

Kaewwongsa, et al. Intestinal digestibility of the residual components of cassava pulp solid state fermentation by *Saccharomyces cerevisiae*. Suranaree J. Sci. Technol. 2009; 16(4):291-296.

Kamm et al. Internationale Bioraffinerie-Systeme Internationale Bioraffinerie-Systeme. Presentation; Brandenburgische Technische Universitat Cottbus; Frankfurt; 2006.

Kamm, et al. Chemical and biochemical generation of carbohydrates from lignocellulose-feedstock (Lupinus nootkatensis)—quantification of glucose. Chemosphere. 2006; 62:97-105.

Kamm, et al. Definition and technical status of Biorefineries. BioreFuture 2008, Tuesday Feb. 12, 2008, Brussels.

Karinen et al. Biorefining: heterogeneously catalyzed reactions of carbohydrates for the production of furfural and hydroxymethylfurfural. ChemSusChem; 2011; 4; 1002-1016.

Katzen, et al. A View of the History of Biochemical Engineering. Advances in Biochemical Engineering/Biotechnology. 2000; 70:77-91.

Kauko. Similarity of the action of hydrochloric acid upon cellulose and humus. Ann. acad. sci. Fennicae (1927), 26A(No. 15), 3-7. Abstract only.

Kauper. Sulfur-free lignin from alkaline pulping as emulsifiers. The international Lignin Institute, 5th international Forum' Sep. 7, 2000, Bordeaux (France).

Keller, et al. Microbial Pretreatment of Biomass, Potential for Reducing Severity. Applied Biochemistry and Biotechnology. 2003; 105-108:27-41.

Khan, et al. Kinetic Study on Palm Oil Waste Decomposition. Biofuel's Engineering Process Technology. 2011. Chapter 22, pp. 523-536.

Khan, et al. Protobind 1075—An Indigenous Economical and Eco-friendly Renewable Raw Material for the Plywood Industry. 2011.

Khezami, et al. Production and characterisation of activated carbon from wood components in powder: Cellulose, lignin, xylan. Powder Technology. 2005; 157:48-56.

Kim, et al. Continuous Countercurrent Extraction of Hemicellulose from Pretreated Wood Residues. Applied Biochemistry and Biotechnology. 2001; 91-93:253-267.

Kim, et al. Enzyme hydrolysis and ethanol fermentaion of liquid hot water and AFEX pretreated distillers' grains at high-solid loadings. Bio. Tech. 2008; 99:5206-5215.

Kim, et al. Pretreatment and fractionation of corn stover by ammonia recycle percolation process. Bioresource Technology. 2005; 96:2007-2013.

Kim, et al. Pretreatment of Corn Stover by Low-Liquid Ammonia Recycle Percolation Process. Applied Biochemistry and Biotechnology. 2006; 133:41-57.

Kim, et al. Supercritical CO2 pretreatment of lignocellulose enhances enzymatic cellulose hydrolysis. Bioresource Technology. 2001; 77:139-144.

Kimberley, et al. A colorimetric method for the quantitation of galacturonic acid. Applied biochemistry and biotechnology. 1993; 43:51-54.

Kinders, et al. Saccharification of HCl-treated substrate provided by HCL-Cleantech, Technical Report, Mar. 2010. Dyadic International Inc. // Confidential and Proprietary Information.

Kindsigo et al. Degradation of lignins by wet oxidation : model water solutions. Proc. Estonian Acad. Sci. Chem.; 2006; 55(3); 132-144.

Kintner III, et al. Carbohydrate Interference and Its Correction in Pectin Analysis Using the m-Hydroxydiphenyl Method. Journal of Food Science. 1982; 47:756-759.

Kireble, et al. The Electromotive Force Measurements of Hydrochloric Acid Solutions with and without Sucrose and their Relation to the Rate of Sucrose Hydrolysis. Chemical Laboratory of Trinity college. Jan. 1935; 57:19-22.

Kjellstrand, et al. Development of toxic degradation products during heat sterilization of glucose-containing fluids for peritoneal dialysis: influence of time and temperature. Perit Dial Int. 1995;15(1):26-32.

Klein, et al. Modelling of lignin thermolysis. MIT. 1981; 77-88.

Kobayashi, et al. A continuous process for the synthesis of hexyl beta-D-glucoside in aqueous phase using immobilized—glucosidase and with 1-hexanolextractive product recovery. Biotechnology Letters. 2000; 22:1845-1848.

Kobayashi, et al. Synthesis of alkyl glycosides through b-glucosidase-catalyzed condensation in an aqueous-organic biphasic system and estimation of the equilibrium constants fortheir formation. Journal of Molecular Catalysis B: Enzymatic. 2000; 11:13-21.

(56) References Cited

OTHER PUBLICATIONS

Kokol. Enzymatic functionalisation of fibre forming polymers using lignin substrates. Institute of Engineering Materials and Design, University of Maribor, Smetanova ul. 17, SI-2000 Maribor, Slovenia. 2008.
Kokol. Maribor Enzymatic functionalisationof fibre-forming polymers using lignin substrates. COST 50E / ILI workshop, Oct. 27-29, 2008, Dübendorf, Switzerland.
Konn et al. Chemical Reactions in Chemimechanical Pulping : Material Balances of Wood Components in a CTMP Process. Journal of pulp and paper science; 2002; 28; 395-399.
Koplan, et al. Certain Activated Carbon From China. U.S. International Trade Commission, Investigation No. 731-TA-1103 (Preliminary), Publication 3852, May 2006.
Korotkov, et al. Continuous hydrolysis of plant tissues with 46-48 hydrochloric acid. VI. The effect of heat on wood saturated with gaseous hydrogen chloride, with simultaneous increase of the partial pressure of hydrogen chloride. Sbornik Trudov, Vsesoyuznyi Nauchno-Issledovatel'skii Institut Gidroliza Rastitel'nykh Materialov (1965), 14 180-91. Abstract only.
Koski. Applicability of crude tall oil for wood protection. Acta Univ. Oul. C 293, 2008, Oulun Yliopisto, Oulu 2008.
Kosswig, et al. A new Process for Obtaining Hydrogen Chloride from Dilute Hydrochloric Acid. Chemical Economy & Engineering Review. Jun. 1983; 15(6)(No. 169):30-33.
Koullas, et al. Analytical methods for lignin characterization—differential scanning calorimetry. Cellulose Chem. Technol. 2006; 40(9-10):719-725.
Kovalev, et al. Reaction of sprucewood pulp with hydrogen chloride dissolved in dichloroethane. Sbornik Trudov Ukrainskogo Nauchno-Issledovatel'skogo Instituta Tsellyulozno-Bumazhnoi Promyshlennosti (1966), No. 9 51-69. CODEN: SUTBAU ISSN: 0453-8560. Abstract only.
Kozlowski, et al. The role of high dispersion lignin in creation of UV protection in textiles. 8 Forum ILI, Rome, 2007.
Krall, et al. Pectin Hydrolysis: Effect of Temperature , Degree of Methylation, pH, and Calcium on Hydrolysis Rates. J. Agric. Food Chem. 1998; 46:1311-1315.
Kubo, et al. Lignin-based Carbon Fibers: Effect of Synthetic Polymer Blending on Fiber Properties. Journal of Polymers and the Environment. Apr. 2005; 13(2):97-105.
Kubo, et al. Poly(Ethylene Oxide)/Organosolv Lignin Blends: Relationship between Thermal Properties, Chemical Structure, and Blend Behavior. Macromolecules. 2004; 37:6904-6911.
Kubo, et al. Preparation of carbon fibers from softwood lignin by atmospheric acetic acid pulping. Carbon. 1998; 36(7-8):1119-1124.
Kubo, et al. Surface Porosity of Lignin/PP Blend Carbon Fibers. Journal of Wood Chemistry and Technology. 2007; 27: 257-271.
Kubo, et al. Thermal Decomposition Study of Isolated Lignin Using Temperature Modulated TGA. Journal of Wood Chemistry and Technology. 2008; 28(2):106-121.
Kucuk, et al. Biomass Conversion Processes. Energy Convers. Mgmt. 1997; 38(2):151-165.
Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.
Kumar, et al. Methods for Pretreatment of Lignocellulosic Biomass for Efficient Hydrolysis and Biofuel Production. Ind. Eng. Chem. Res. 2009; 48:3713-3729.
Kunamneni, et al. Fungal laccase—a versatile enzyme for biotechnological applications. Communicating Current Research and Educational Topics and Trends in Applied Microbiology. 2007; 233-245.
Kunkes, et al. Catalytic conversion of biomass to monofunctional hydrocarbons and targeted liquid-fuel classes. Science. Oct. 17, 2008;322(5900):417-21. doi: 10.1126/science.1159210. Epub Sep. 18, 2008.
Kusama, et al. Wood saccharification by gaseous hydrogen chloride. Chisso Corp., Tokyo, Kogyo Kagaku Zasshi. 1966. Parts 1-V and VIII. Abstracts only.

Laine. Structures of hemicelluloses and pectins in wood and pulp, degree of Doctor of Science, Helsinki University of Technology,Department of Chemical Technology, Laboratory of Organic Chemistry, Espoo, Finland, 2005.
Lake. A radically-new *liquid*-lignin recovery and purification process. TechLake & Associates LLC. Feb. 25, 2010.
Lake. Potential Commercial uses for lignin. Southeastern Bioenergy Confrence, Tifton GA, Aug. 4, 2010.
Lake. Potential Commercial uses for lignin. TechLake & Associates LLC, Presentation to BDC, Durham NC, Oct. 2, 2009.
Lam, et al. Kinetic Modeling of Pseudolignin Formation in Steam Exploded Woody Biomass. 2011.
Lam. Steam explosion of biomass to produce durable wood pellets. The University of British Columbia (Vancouver). May 2011.
Lange, et al. Lignocellulose conversion: an introduction to chemistry, process and economics. Biofuels, Bioprod. Bioref. 2007; 1:39-48.
Lapan, et al. Hydrochloric and sulfuric acid hydrolyzates of fir wood. Izvestiya Nauchno-Issledovatel'skogo Instituta Nefte—i Uglekhimicheskogo Sinteza pri Irkutskom Universitete (1970), 12 102-4. CODEN: INEUBO ISSN: 0367-9195. Abstract only.
Lavarack, et al. The acid hydrolysis of sugarcane bagasse hemicellulose to produce xylose, arabinose, glucose and other products. Biomass and Bioenergy. 2002; 23:367-380.
Lebedev, et al. Hydrolysis of cellulose with concentrated hydrochloric acid at different temperatures. Sb. Tr., Gos. Nauchn.-Issled. Inst. Gidrolizn. i Sul'fitno-Spirt. Prom. (1961), 9 7-19. Abstract only.
Lebedev, et al. Hydrolysis of wood with concentrated hydrochloric acid solutions at different temperatures. Sb. Tr., Gos. Nauchn.-Issled. Inst. Gidrolizn. i Sul'fitno-Spirt. Prom. (1961), 9 20-35. Abstract only.
Lee, et al. Dilute-Acid Hydrolysis of Lignocellulosic Biomass. Advances in Biochemical Engineering/Biotechnology. 1999; 65:93-115.
Lee, et al. Ionic Liquid-Mediated Selective Extraction of Lignin From Wood Leading to Enhanced Enzymatic Cellulose Hydrolysis. Biotechnology and Bioengineering. Apr. 1, 2009; 102(5):1368-1376.
Lee, et al. Novolak PF resins prepared from phenol liquefied Cryptomeria japonica and used in manufacturing moldings. Bioresource Technology. 2008; 99:7247-7254.
Lee, et al. Solvent Extraction of Zinc from Strong Hydrochloric Acid Solution with Alamine336. Bull. Korean Chem. Soc. 2009; 30(7):1526-1530.
Leonard, et al. Fermentation of wood sugars to ethyl alcohol. US Department of Agriculture, Forest Service, Forest Products Laboratory, Madison, Wisconsin. No. R1466. Dec. 1944.
Lepifre, et al. Enzymatic lignin modification for resin applications. 6th international confrence textile and polymer biotechnology, Ghent, Sep. 2009.
Leschinsky, et al. Detailed Mass Balance of the Autohydrolysis of Eucalyptus Globulus at 170C. BioResources. 2009; 4(2): 687-703.
Leshchuk, et al. Continuous hydrolysis of plant tissue with 45-48% hydrochloric acid. V. Equilibrium in the system polysaccharides-hydrolysis products-hydrochloric acid. Gidrolizn. i Lesokhim. Prom. (1965), 18(5), 10-13. Abstract only.
Leshchuk, et al. Intensification of differential hydrolysis of softwood with concentrated hydrochloric acid in a diffusion apparatus. USSR. Sb. Tr. Vses. Nauch.-Issled. Inst. Gidroliza Rast Mater. (1968), 17 16-73. From: Ref. Zh., Khim. 1969, Abstr. No. 17P20. Abstract only.
Leshchuk, et al. Penetration of concentrated hydrochloric acid into the pores of wood particles and the formation of hydrolyzates within the particles. Sbornik Trudov. Gosudarstvennyi Nauchno-issledovatel'skii Institut Gidroliznoi i Sul'fitno-spirtovoi Promyshlennosti (1966), 15 156-67. CODEN: SGSSAC. Abstract only.
Lewkowski et al. Synthesis, chemistry and applications of 5-hydroxymethylfurfural and its derivatives. Arkivoc; 2001; I; 17-54.
Li, et al. Acidolysis of Wood in Ionic Liquids. Ind. Eng. Chem. Res. 2010; 49(7):3126-3136.

(56) References Cited

OTHER PUBLICATIONS

Li, et al. Efficient Acid-Catalyzed Hydrolysis of Cellulose in Ionic Liquid. Advanced Synthesis & Catalysis; 2007; 349; 1847-1850.
Li, et al. Ethanol Organosolv Lignin-based Rigid Polyurethane Foam Reinforced with Cellulose Nanowhiskers. Institute of Paper Science and Technology. 2011.
Li, et al. Interaction of Supercritical Fluids with Lignocellulosic Materials. Ind. Eng. Chem. Res. 1988; 27:1301-1312.
Li, et al. Kraft Lignin-based Rigid Polyurethane Foam. Institute of Paper Science and Technology. 2011.
Li, et al. Lignin depolymerization/repolymerization and its critical role for delignification of aspen wood by steam explosion. Bioresource Technology 98 (2007) 3061-3068.
Li, et al. Steam explosion lignins; their extraction, structure and potential as feedstock for biodiesel and chemicals. Bioresource Technology. 2009.
Lignimatch. Future use of lignin in value added products: A roadmap for possible Nordic/Baltic innovation. The roadmap compiles inputs from the detailed technical reports delivered in the LigniMatch project during 2007-2009. For more information, see the project website at http://www.chalmers.se/gmv/EN/projects/lignimatch.
Liitia, et al. Application of Solid-State $^{13}$C NMR Spectroscopy and Dipolar Dephasing Technique to Determine the Extent of Condensation in Technical Lignins. Solid State Nuclear Magnetic Resonance. 2002; 21:171-186.
Lin et al. Liquid phase reforming of rice straw for furfural production. International Journal of Hydrogen Energy; 2013; 4-10.
Lin, et al. Ethanol fermentation from biomass resources: current state and prospects. Appl Microbiol Biotechnol. 2006; 69:627-642.
Lin, et al. Liquid-Liquid Equilibria for Ternary Mixtures of Water + Ethanol with 1-Hexanol, Butyl Propionate, or Ethyl Caproate. J. Chem. Eng. Data. 2003; 48:587-590.
Liu et al. Effects of lignin-metal complexation on enzymatic hydrolysis of cellulose. Journal of agricultural and food chemistry. 2010; 58(12): 7233-7238.
Liu, et al. Citrus Pectin: Characterization and Inhibitory Effect on Fibroblast Growth Factor-Receptor Interaction. J. Agric. Food Chem. 2001; 49:3051-3057.
Liu, et al. Partial flow of compressed-hot water through corn stover to enhance hemicellulose sugar recovery and enzymatic digestibility of cellulose. Bioresource Technology. 2005; 96:1978-1985.
Liu, et al. Solvation of Extracted Complex Metal Acids. VII. An Improved Model. The Journal of Physical Chemistry. 1974; 78(25):2572-2575.
Liu. Understanding Starches and Their Role in Foods. Chapter 7. Copyright 2005 by Taylor & Francis Group, LLC.
Locke. Chemical Conversion Products from wood. USDA. Aug. 1960.
Loe, et al. Vanillin from wood: A CO2-friendly and sustainable bio-chemical. Lignin-based vanillin draws on the original biorefinery concept. Specialty Chemicals Magazine. May 1, 2011. 30-31.
Long, et al. Application of the Ho Acidity Function to kinetics and Mechanisms of acid Catalysis. Mar. 30, 1957; 935-1010.
Lora, et al. Recent Industrial Applications of Lignin: A Sustainable Alternative to Nonrenewable Materials. Journal of Polymers and the Environment, Apr. 2002; 10(1-2):39-48.
Lora, et al. Use of sulfur-free lignin in wood adhesives: Industrial experiences and environmental impacts. 2005; 8-14.
Lora. GreenValue-Technologies and Products. GreenValueEnterprises LLC, Media, PA, USA. 2011.
Lora. Lignin recovery technology transfer: first industrial implementation of the LPS process in India. 2005.
Lora. Non-Wood Biorefinery Developments Outside North America. 2011.
Lora., et al. Autohydrolysis sf aspen milled wood lignin. Aymanc. an. J. Chem. 1980; 58:669-676.
Lu, et al. Hydrolysis of Japanese beech by batch and semi-flow water under subcritical temperatures and pressures. Biomass and Bioenergy, Feb. 2010, pp. 1089-1097.
Lund, et al. Enzymatic modification of kraft ligninthrough oxidative coupling with water-soluble phenols. Appl Microbiol Biotechnol. 2001; 55:6*9-703.
Lynd, et al. Strategic Biorefinery Analysis: Analysis of Biorefineries, Jan. 24, 2002-Jul. 1, 2002. Subcontract Report, NREL/SR-510-35578, Jan. 10, 2005.
Ma, et al. Conversion of fructose to 5-hydroxymethylfurfural with a functionalized ionic liquid. BioResources; 2011; 7; 533-544.
Mabee, et al. Updates on Softwood-to-Ethanol Process Development. Applied Biochemistry and Biotechnology, 2006;129-132:55-70.
Macala et al. Hydrogen transfer from supercritical methanol over a solid base catalyst: a model for lignin depolymerization. ChemSusChem. 2009; 2: 215-217.
Mackenzie, et al. The solvent extraction of some major metals an overview. 2010.
Mai, et al. Biotechnology in the wood industry. Appl Microbiol Biotechnol; 2004; 63:477-494.
Malherbe, et al. Lignin Chemistry and Selected Applications. ILI— International Lignin Institute, Internal work for Umbrella. Aug. 23, 2007.
Malutan, et al. Contribution to the Study of Hydroxymethylation Reaction of Alki lignin. BioResources. 2008; 3(1):13-20.
Malutan, et al. Contributions to the lignin modification by hydroxymethylation and epoxidation. 2008.
Manninen, et al. Comparing the VOC emissions between air-dried and heat-treated Scots pine wood. Atmospheric Environment. 2002; 36:1763-1768.
Marcano, et al. Surface activity of lignin fractions obtained at different pH values. 2005.
Marchal, et al. Conversion into acetone and butanol of lignocellulosic substrates pretreated by steam explosion. Biotechnology Letters. 1986; 8(5):365-370.
Marchal, et al. Large-Scale Enzymatic Hydrolysis of Agricultural Lignocellulosic Biomass. Part 2: Conversion into Acetone-Butanol. Bioresource Technology. 1992; 42:205-217.
Marcotullio et al. Bioenergy II : Furfural Destruction Kinetics during Sulphuric Acid-Catalyzed Production from Biomass Bioenergy II : Furfural Destruction Kinetics during Sulphuric Acid-Catalyzed Production from Biomass. International journal of Chemical Reactor Engineering; 2009; 7; Article A67.
Marcotullio et al. Furfural production in modern lignocellulose-feedstock biorefineries. Presentation; Delft University of Technology; St. Petersburg; 2013.
Marcotullio. The chemistry and technology of furfural production in modern Lignicellulose-feedstock biorefineries. PhD thesis. 2011; Delft University, Italy.
Marker, et al. Optical properties of glucose. 2009.
Marone, et al. Effect of particle sizes on the kinetics of drying of a hydrochloric acid hydrolysate mass. Gidroliznaya i Lesokhimicheskaya Promyshlennost (1976), (3), 15. CODEN: GLKPA2 ISSN: 0016-9706. Abstract only.
Marsh et al. Possible Uses of Corncob Cellulose in the Explosives Industry. The journal of Industrial and Engineering Chemistry; 1921; 13(4); 296-298.
Martin, et al. Engineering a mevalonate pathway in *Escherichia coli* for production of terpenoids. Nature Biotechnology. 2003; 21(7):796-802.
Martin, et al. Studies on thermal properties of sisal fiber. Thermochemica Acta 2010, 506, 14-19.
Martinez-Inigo, et al. Time course of fungal removal of lipophilic extractives from Eucalyptus globulus wood. Journal of Biotechnology. 2000; 84:119-126.
Martin-Sampedro, et al. Combination of steam explosion and laccase-mediator treatments prior to Eucalyptus globulus kraft pulping. Bioresource Technology 2011; 102:7183-7189.
Mascal et al. Towards the efficient, total glycan utilization of biomass. ChemSusChem; 2009; 2(5); 423-426.
Mascal, et al. Direct, High Yield Conversion of Cellulose into Biofuel. Angew. Chem. Int. Ed. 2008; 7:7924-7926.
Mascal, et al. High-Yield Chemical Conversion of Biomass into Biofuels and Value added Products. Clean Technology 2010, www.ct-si.org, ISBN 978-1-4398-3419-0. 124-127.

(56) References Cited

OTHER PUBLICATIONS

Masura. A mathematical model for neutral sulfite pulping of various broadleaved wood species. Wood Science and Technology. 1998; 32:1-13.
Mathias, et al. Production of Vanillin by Oxidation of Pine Kraft Lignins with Oxygen. Holzforschung. 1995; 49:273-278. Abstract only.
Mattinen, et al. Polymerization of different lignins by laccade. BioResources. 2008; 3(2):549-565.
Mcaloon, et al. Determining the Cost of Producing Ethanol from Corn Starch and Lignocellulosic Feedstocks. National Renewable Energy Laboratory, Contract No. DE-AC36-99-GO10337, NREL/TP-580-28893. Prepared under Task No. BFP1.7110. Oct. 2000.
Mcfeeters, et al. Measurement of Pectin Methylation in Plant Cell Walls. Analytical biochemistry. 1984; 139:212-217.
Mckenzie, et al. Levulinic acid. Organic Syntheses, Coll. vol. 1, p. 335 (1941); vol. 9, p. 50 (1929). Apr. 29, 2010.
Mcmillan. Processes for Pretreating Lignocellulosic Biomass: A Review. NatioRnenaewlable Energy Laboratory, A Division of Midwest Research Institute, Operated for the U.S. Department of Energy , Under Contract No. DE-AC02-83CH 10093. Nov. 1992.
Meindersma et al. Production of discrete oxygenated target chemicals from pyrolysis oil. A Report by Eindhoven University of Technology. Netherlands. Jun. 2009.
Meister. Product synthesis, polymer characterization and applications testing of lignin graft copolymers. The international Lignin Institute, 5th international Forum' Sep. 7, 2000, Bordeaux (France).
Membralox ceramic membrane products. Pall corporation. 2004; 1-12.
Menchikov, et al. An Effective Method for Alcohol Preparation by Hydrolysis of Organohalides in the Presence of Copper and its Salts in Aqueous DMSO. Mendeleev Commun. 1995; 5(6): 223-224.
Mendes, et al. Extraction of hemicelluloses prior to kraft cooking: a step for an integrated biorefinery in the pulp mill. XXI Tecnicelpa Conference and Exhibition/VI CIADICYP 2010. Oct. 12-15, 2010.
Mesfun et al. Integration of hot water extraction in biomass based CHP plants—possibilities for green-chemicals and increased electricity production. Master's Thesis. 2010; Lulea University of Technology.
Meyer. Nanotechnology for fibers characterisation. CTP's Scientific and Technological Unit 'Process Pulp- IntechFibers', Jan. 5, 2009.
Michalka, Optimization of Sugar Consumption in the Fermentation of Temulose for Ethanol Production, 2007.
Mielenz. Ethanol production from biomass: technology and commercialization status. Current Opinion in Microbiology. 2001; 4:324-329.
Mikkola, et al. Hydrolytic decomposition of glycosides in aqueous acids. ARKIVOC 2009 (iii) 39-53.
Miljkovic. Carbohydrates, Synthesis, Mechanisms, and Stereoelectronic Effects. Springer Science+Business Media, LLC 2009.
Miller. Characteristics and Availability of Commercially Important Woods, Chapter 1. Forest Products Laboratory. 1999. Wood handbook—Wood as an engineering material.
Miller. Structure of Wood. Chapter 2. 2009.
Miller. Utilization of wood under Germany's four year plan. Forests Products Division, Bureau of Foreign and Domestic Commerce U.S. Department of Commerce, Washington. 2009; 495-503.
Miller. Vapor-Liquid Equilibria below 0° C. of Hydrogen Chloride Solutions Saturated with Calcium Chloride. J. Chem. Eng. Data. 1990; 35:436-440.
Miller. Vapor-Liquid Equilibria of Water-Hydrogen Chloride Solutions below 0° C. J. Chem. Eng. Data 1983; 28:363-367.
Miller. Vapor-Liquid Equilibria of Water-Hydrogen Chloride-Sodium Chloride-Water Solutions below 0° C. J. Chem. Eng. Data. 1985; 30:296-301.
Minina, et al. Hydrolysis of various types of cellulosic raw materials with highly concentrated hydrochloric acid. I. Effect of time, temperature, and acid ratio on the yield of sugars. USSR. Strukt. Modif. Khlop. Tsellyul. (1966), No. 3 315-24. From: Ref. Zh., Khim. 1969, Abstr. No. 1P31. Abstract only.

Miyazawa, et al. Polysaccharide Hydrolysis Accelerated by Adding Carbon Dioxide under Hydrothermal Conditions. Biotechnol. Prog. 2005; 21:1782-1785.
Moelwyn-Hughes. The kinetics of the hydrolysis of certain glucosides, part 11: trehalose, umethylglucoside and tetramethyl-a-amethyglucoside. Nov. 23, 1928; 81-92.
Mohan, et al. Pyrolysis of Wood/Biomass for Bio-oil: A Critical Review. Energy & Fuels; 2006; 20; 848-889.
Montane, et al. Activated carbons from lignin: kinetic modeling of the pyrolysis of Kraft lignin activated with phosphoric acid. Chemical Engineering Journal. 2005; 106:1-12.
Mooney, et al. The effect of initial pore volume and lignin content on the enzymatic hydrolysis of softwoods. Bioresource Technology. 1998; 64:113-119.
Moreschi, et al. Hydrolysis of Ginger Bagasse Starch in Subcritical Water and Carbon Dioxide. J. Agric. Food Chem. 2004; 52, 1753-1758.
Morreel, et al. Mass Spectrometry-Based Sequencing of Lignin Oligomers. Plant Physiology. Aug. 2010; 153:1464-1478.
Mosier, et al. Characterization of acid catalytic domains for cellulose hydrolysis and glucose degradation. Biotechnology and bioengineering, Sep. 20, 2002; 79(6):1-9.
Mosier, et al. Characterization of Dicarboxylic Acids for Cellulose Hydrolysis. Biotechnol. Prog. 2001; 17:474-480.
Mulder, et al. Lignin based controlled released coating. 2011.
Mullen, et al. Production of Deoxygenated Biomass Fast Pyrolysis Oils via Product Gas Recycling. Energy & Fuels; 2013; A-H.
Munoz, et al. Bioethanol production from bio-organosolv pulps of Pinus radiata and Acacia dealbata. J Chem Technol Biotechnol. 2007; 82:767-774.
Mussatto, et al. Production, characterization and application of activated carbon from brewer's spent grain lignin. Bioresource Technology. 2010; 101:2450-2457.
Muurinen, E. Dissertation entitled: Organosolv pulping: A review and distillation study related to peroxyacid pulping. (2000) Department of Process Engineering, Oulu University, Finland.
Myrvold. A new model for the structure of lignosulphonates. 2005.
Mythili, et al. Synthesis, mechanical, thermal and chemical properties of polyurethanes based on cardanol. Bull. Mater. Sci. Jun. 2004 ;27(3):235-241.
Naae. New lignin chemicals and applications: new uses in petroleum recovery. The international Lignin Institute, 5th international Forum' Sep. 7, 2000, Bordeaux (France).
Nagamatsu, et al. Cascade-type flow of lignocellulosic components through the phase-separation system. J. Adv. Sci. 2001; 13(3):517-520.
Nagy, et al. Catalytic hydrogenolysis of ethanol organosolv lignin. Holzforschung. 2009; 63:513-520.
Nagy, et al. Characterization of $CO_2$ precipitated Kraft lignin to promote its utilization. Green Chem. 2010; 12:31-34.
Nassar, et al. Mechanism of thermal decomposition of lignin. Wood and fiber Science. 1984; 16(3):441-453.
Navarro. Effects of furfural on ethanol fermentation by *Saccharomyces cerevisiae*: mathematical models. Current Microbiology. 1994; 29:87-90.
Neureiter et al. Dilute-acid hydrolysis of sugarcane bagasse at varying conditions. Applied Biochemistry and Biotechnology. Mar. 2002, vol. 98, Issue 1-9, pp. 49-58.
Nevell. The hydrolysis of cotton cellulose by hydrochloric acid in benzene. Dep. Polym. Fibre Sci., Univ. Manchester Inst. Sci. Technol., Manchester, UK. Carbohydrate Research (1976), 49 163-74. CODEN: CRBRAT ISSN: 0008-6215. Abstract only.
Nguyen, et al. Is gel permeation chromatography applicable to lignin? 2007.
Nguyen, et al. Molecular weight and functional group analysis of a Soda lignin fractionated by ultrafiltration and selective dissolution. 2008.
Nguyen, et al. Molecular weight in LignoAnalyse 1, "Is GPC applicable to lignin?". Rome, Forum 8, May 10-12, 2007.
Nguyen. GPC-2D FTIR : a novel technique for fractionated lignin characterization. SERMACS 2009.

(56) References Cited

OTHER PUBLICATIONS

Nikam et al. Density and Viscosity Studies of Glucose and Fructose Solutions in Aqueous and in NH4CL. Journal of Molecular Liquids; 2000; 87; 97-105.
Nitz. Lignin based polymer compounds and liquid wood. The international Lignin Institute, 5th international Forum' Sep. 7, 2000, Bordeaux (France).
Nogueira, et al. Crude tail-oil sodium salts micellization in aqueous solutions studied by static and dynamic light scattering. Colloids and Surfaces A: Physicochemical and Engineering Aspects. 2001; 191: 263-268.
Norgren. Self-Aggregation of Kraft Lignin in Aqueous Solutions. 2005; 23-30.
Norman, et al. LXXIV. Studies on pectin. V. The hydrolysis of pectin. May 1, 1930; 649-660.
Notice of allowance dated Apr. 8, 2016 for U.S. Appl. No. 13/378,657.
Notice of Allowance dated Sep. 9, 2016 for U.S. Appl. No. 14/009,858.
Notice of Allowance dated Oct. 7, 2016 for U.S. Appl. No. 14/009,858.
Novozymes application sheet. Cellic® CTec2 and HTec2—Enzymes for hydrolysis of lignocellulosic materials, Fuel Ethanol. 2010.
Novozymes application sheet. CellicTM CTec and Htec, Advanced enzymes for hydrolysis of lignocellulosic materials. Novozymes A/S No. 2009-05048-01. 2009.
Novozymes. The key to the first commercially viable enzymes for cellulosic ethanol. 2010. www.bioenergy.novozymes.com.
Nrel. Enzyme Sugar-Ethanol Platform Project. National Renewable Energy Laboratory, Operated for the U.S. Department of Energy by Midwest Research Institute • Battelle • Bechtel. 2010.
NWBC. Program, 3rd Nordic Wood Biorefinery Conference (NWBC 2011), Stockholm, Sweden, Mar. 22-24, 2011.
NWBC-2009 The 2 nd Nordic Wood Biorefinery Conference. All Presentations; 2009.
Nystrand. Feasibility of lignocellulose as feedstock for biological production of super absorbent polymers. Department of Physics, Chemistry and Biology Master's Thesis; Linköping University Department of Physics, Chemistry and Biology 581 83 Linköping. Oct. 2010.
Odincovs, et al. The influence of temperature on the hydrolysis of wood and cellulose with concentrated hydrochloric acid. Trudy Inst. Lesokhoz. Problem, Akad. Nauk Latv. S.S.R. (1951), No. 2 68-82. Abstract only.
Odintsov, et al. Hydrolysis of woods with concentrated acids. Lesokhimicheskaya Promyshlennost (1940), 3(No. 9), 14-19. Abstract only.
Office action dated Feb. 13, 2014 for U.S. Appl. No. 13/378,657.
Office action dated Feb. 22, 2016 for U.S. Appl. No. 14/009,858.
Office action dated May 10, 2016 for U.S. Appl. No. 14/033,205.
Office action dated Jun. 8, 2015 for U.S. Appl. No. 13/378,657.
Office action dated Jul. 31, 2014 for U.S. Appl. No. 13/378,657.
Office action dated Aug. 7, 2014 for U.S. Appl. No. 13/378,657.
Office action dated Aug. 24, 2013 for U.S. Appl. No. 13/380,504.
Office action dated Nov. 9, 2015 for U.S. Appl. No. 13/378,657.
Office action dated Dec. 24, 2014 for U.S. Appl. No. 13/378,657.
Oh, et al. Pretreatment of Lignocellulosic Biomass using Combination of Ammonia Recycled Percolation and Dilute-Acid Process. J. Int. Eng. Chem. 2002; 8(1):64-70.
Oliet, et al. Solvent effects in autocatalyzed alcohol-water pulping comparative study between ethanol and methanol as delignifying agents. Chemical Engineering Journal. 2002; 87:157-162.
Olsson, et al. Fermentation of lignocellulosic hydrolysates for ethanol production. Enzyme and Microbial Technology. 1996; 18:312-331.
On, et al. Studies on pulp and paper mill fiber residues as resources. (II). Studies on acid hydrolysis of sludge. Coll. Eng., Jeonbuk Univ., Jenzu, S. Korea. Poipu, Chongi Gisul (1985), 17(1), 38-44. CODEN: PCGIDY ISSN: 0253-3200. Abstract only.
Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.
Ong. Conversion of lignocellulosic biomass to fuel ethanol—a brief review. The planter kuala lumpur. 2004; 80(941 ):517-524.
Ornl. Manufacturing of Carbon Fibers Using Microwave Assisted Plasma Technology. Managed and operated by UT-Battelle, LLC for the U.S. Department of Energy under contract DE-AC05-00OR22725. 2005.
Oudia, et al. Analytical pyrolysis study of biodelignification of cloned Eucalyptus globulus (EG) clone and Pinus pinaster Aiton kraft pulp and residual lignins. J. Anal. Appl. Pyrolysis. 2009; 85:19-29.
Ouensanga, et al. Thermal degradation of sugarcane bagasse. Thermochimica acta 1988, 125, 89-97.
Ouyang, et al. Chemical modification of lignin assisted by microwave irradiation. Holzforschung, vol. 65, 2011, DOI 10.1515/HF.2011.067.
Palmqvist, et al. Fermentation of lignocellulosic hydrolysates. II: inhibitors and mechanisms of inhibition. Bioresource Technology. 2000; 74:25-33.
Pan, et al. Bioconversion of Hybrid Poplar to Ethanol and Co-Products Using an Organosolv Fractionation Process : Optimization of Process Yields. Biotechnology and bioengineering. 2006; 94: 851-861.
Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).
Pandey, et al. Lignin depolymerization and conversion: a review of thermochemical methods. Chemical Engineering and Technology. 2011; 34(1):29-41.
Papadopoulos, et al. The behavior of lignin during hydrolysis of sweetgum wood with concentrated hydrochloric acid at moderate temperatures. Dep. Wood Paper Sci., North Carolina State Univ., Raleigh, NC, USA. Holzforschung (1981), 35(6), 283-6. CODEN: HOLZAZ ISSN: 0018-3830. Abstract only.
Papadopoulou et al. The Challenge of Bio-Adhesives for the Wood Composite Industries. Report; Theassaloniki, Greece. 2012.
Papadopoulou, et al. The Challenge of Bio-Adhesives for the Wood Composite Industries. 2008.
Papadopoulous, et al. Behavior of sweetgum wood xylan and lignin during hydrolysis with concentrated hydrochloric acid at moderate temperatures. Dep. Wood Pap. Sci., North Carolina State Univ., Raleigh, NC, USA. Journal of Applied Polymer Science: Applied Polymer Symposium (1983), 37(Proc. Cellul. Conf., 9th, 1982, Part 2), 631-40. CODEN: JPSSDD ISSN: 0271-9460. Abstract only.
Papajannopoulous, et al. GC-MS analysis of oleoresin of three Greek pine species. Holz als Roh- und Werkstoff. 2001; 59:443-446.
Parisi. Advances in Lignocellulosics Hydrolysis and in the Utilization of the Hydrolyzates. Advances in Biochemical Engmeering/Biotechnology. 1989; 38:53-87.
Parpot et al. Electrochemical investigations of the oxidation-reduction of furfural in aqueous medium. Electrochimica Acta; 2004; 49; 397-403.
Pasco, et al. High Temperature Alkali Treatment of Kraft Black Liquor. This poster was presented at the 15th International Symposium on Wood, Fibre and Pulping Chemistry in Oslo on Jun. 15-18, 2009.
Pasquini, et al. Extraction of lignin from sugar cane bagasse and Pinus taeda wood chips using ethanol-water mixtures and carbon dioxide at high pressures. J. of Supercritical Fluids. 2005; 36:31-39.
Pasquini, et al. Sugar cane bagasse pulping using supercritical CO2 associated with co-solvent 1-butanol/water. J. of Supercritical Fluids. 2005; 34:125-131.
Paszner, et al. High-yield Organosolv process for conversion of cellulosic biomass to ethanol. Fac. For., Dep. Harvest. Wood Sci., Vancouver, BC, Can. Energy from Biomass and Wastes (1989), 12 1297-318. CODEN: EBWADU ISSN: 0277-7851. Abstract only.
Patel, et al. Medium and long-term Opportunities and Risks of the Biotechnological Production of Bulk Chemicals from Renewable

(56) References Cited

OTHER PUBLICATIONS

Resources—The Potential of White Biotechnology the BREW project. Utrecht University. Sep. 2006. www.chem.uu.nl/nws.
Paul, et al. Optical absorption and fluorescence studies on imidazolium ionic liquids comprising the bis (trifluoromethanesulphonyl)imide anion. J. Chem. Sci.; 2006; 118(4); 335-340.
Pazur. Reversibility of enzymatic transglucosylation reactions. Received for publication, Jan. 17, 1955, pp. 531-538.
Pearl. Vanillin from Lignin Material. J. Am. Chem. Soc., 1942; 64(6):1429-1431.
Pecina, et al. GC-MS and HPLC analyses of lignin degradation products in biomass hydrolyzates. Fresenius Z Anal Chem. 1986; 325:461-465.
Pepper, et al. Improvements in the acidolysis procedure for lignin isolation and in the procedure for the analysis of lignin oxidation products. Can J. Chem. 1961; 39:390-391.
Pepper, et al. The effect of initial acid concentration on the lignin isolated by the acidolysis of aspen wood. Can J. Chem. 1961; 39:1454-1461.
Pepper, et al. The Isolation of a Representative Lignin Fraction From Wood and Straw Meals. Canadian J. of Chemistry. 1962; 40:1026-1028.
Perez, et al. Study of the behavior of metal adsorption in acid solutions on lignin using a comparison of different adsorption isotherms. Lat. Am. appl. res. v.37 n.2 Bahia Blanca abr. 2007.
Perlack, et al. Biomass as feedstock for a bioenergy and bioproducts industry: the technical feasibility of a billion-ton annual supply. U.S. Department of Energy, under contract DE-AC05-00OR22725. Apr. 2005.
Perng et al. Pilot Treatment of OCC-based Paper Mill Wastewater Using Pulsed Electrocoagulation. Water Qual. Res. J. Canada; 2007; 42(1); 63-71.
Perng et al. Treatment of a Specialty Paper Mill Wastewater Using a Pilot-scale Pulsed Electrocoagulation Unit. Taiwan J for Sci; 2007; 22(3); 355-366.
Perry, et al. Chemical Engineers' Handbook. The McGraw-Hill Companies. 1999.
Pessoa Jr, et al. Acid hydrolysis of hemicellulose from sugarcane bagasse. Braz. J. Chem. Eng. vol. 14 No. 3 São Paulo Sep. 1997.
Peterson, et al. Thermochemical biofuel production in hydrothermal media: A review of sub and supercritical water technologies. Energy & Enviromental Science. 2008; 1:32-65.
Petkevich, et al. Hydrolysis of wood with concentrated hydrochloric acid in a pilot battery of diffusers. Sb. Tr., Gos. Nauchn.-Issled. Inst. Gidrolizn. i Sul'fitno-Spirt. Prom. (1960), 8 47-65. Abstract only.
Pettersen. The Chemical Composition of Wood. In: Rowell M., ed. The chemistry of solid wood. Advances in chemistry series 207. Washington, DC: American Chemical Society ; 1984: Chapter 2.
Philip, et al. Review Polyhydroxyalkanoates: biodegradable polymers with a range of applications. J Chem Technol Biotechnol. 2007; 82:233-247.
Phillips, et al. Thermochemical Ethanol via Indirect Gasification and Mixed Alcohol Synthesis of Lignocellulosic Biomass. National Renewable Energy Laboratory, Technical Report NREL/TP-510-41168. Apr. 2007.
Phillips. Technoeconomic Analysis of a Lignocellulosic Biomass Indirect Gasification Process to Make Ethanol. Ind. Eng. Chem. Res. 2007; 46:8887-8897.
Pielhop, et al. Two-step approach for the conversion of kraft lignin into aromatic chemicals. NWBC 2011, Stockholm, Mar. 21-24, 2011.
Pierce. Instruction Acylation Derivatization Reagents. Pierce, Rockford, IL 61105, US. 2010.
Ping, et al. Evaluation of grape stalks as bioresource. Industrial crops and products. 2011; 33:200-204.
Pisarnitsky, et al. Effect of Acid Hydrolysis of Oak Wood on Its Aroma-Forming Complex. Applied Biochemistry and Microbiology. 2004; 40(6):613-616.
Pogaku, et al. Whey Protein Isolate-Starch System—A Critical Review. International Journal of Food Engineering: vol. 3 : Iss. 6, Article 1. 2007.
Poltoratskii, et al. Liquid-Vapor Equilibrium and Ionization of HCl in the System HCl-H2S04-H20 at 298 K. Russian Journal of General Chemistry. 2002; 72(9):1339-1342.
Polymer Science. Making Polyurethane. Polymer Science Learning Center, Department of Polymer Science the University of Southern Mississippi. 2005.
Pontin. First, Cure Malaria. Next Global Warming. The New York times/SundayBusiness/Bright Ideas. Jun. 3, 2007.
Popa, et al. A comparison concerning separation and characterization of polyphenols from spruce wood bank. 2010.
Popa, et al. Composites based on natural resources: lignocelluloses, lignins and furan resins. 2008.
Popa, et al. On the interaction of lignins, furan resins and furfuryl alcohol in adhesive systems. Cellulose Chem. Technol. 2007; 41(2-3):119-123.
Pospiech, et al. Studies on iron(III) removal from chloride aqueous solutions by solvent extraction and transport through polymer inclusion membranes with D2EHPA. Physicochem. Probl. Miner. Process. 2010; 44:195-204.
Prater, et al. Determination of Sulfur Dioxide in Dehydrated Foods. Industrial and engineering chemistry. Mar. 1944; 16(3):153-157.
Priefert, et al. Biotechnological production of vanillin. Appl Microbiol Biotechnol. 2001; 56:296-314. Abstract only.
Pu, et al. Ionic Liquid as a Green Solvent for Lignin. Journal of Wood Chemistry and Technology. 2007; 27:23-33.
Pu, et al. NMR Characterization of C3H and HCT Down-Regulated Alfalfa Lignin. Bioenerg. Res. 2009; 2:198-208.
Pulping and Bleaching, PSE 476 powerpoint. 2011.
Purolite. Corn sweetener refining with ion exchange resins guide. The Purolite Compant. 2007. 60 pages, www.purolite.com.
Pye. The Alcell Process—A Proven Alternative to Kraft Pulping. 1990 Pulping Conference, TAPPI Proceedings. 991-996.
Qian, et al. Acidic Sugar Degradation Pathways an Ab Initio Molecular Dynamics Study. Applied Biochemistry and Biotechnology. 2005;121-124:989-997.
Quinde. Enzymes in the pulp and paper industry: a review. 1994.
Qvintus-Leino. Utilisation of lignin in fiber board gluing. VTT Processes , Finland. 2003.
Rabinovich. Wood hydrolysis industry in the Soviet Union and Russia: a mini-review. Cellulose Chem. Technol.2010; 44(4-6):173-186.
Radiotis, et al. Optimizing Production of Xylose and Xylooligomers from Wood Chips. 3rd NWBC, Stockholm, Sweden Mar. 23, 2011.
Rafiqul et al. Processes for the Production of Xylitol—A Review. Food Reviews International, vol. 9, Issue 29, pp. 127-156 (2013). Accepted author version posted online: Sep. 10, 2012. Published online:Mar. 13, 2013. DOI: https://doi.org/10.1080/87559129.2012.714434.
Ragan, et al. LignActiv—Activated Carbon from Renewable Resources—Lignin. Nordic Wood Biorefinery Conference. Stockholm, Mar. 24, 2011.
Ragauskas, et al. From wood to fuels Integrating biofuels and pulp production. Industrial biotechnology. 2006; 2(1):55-65.
Ragauskas, et al. The Path Forward for Biofuels and Biomaterials. Science. Jan. 26, 2006; 311:484-489.
Ragauskas. Forest BioRefinery Lignin. School of Chemistry and Biochemistry, Georgia Institute of Technology. 2010.
Ragauskas. Rediscovering the Future of Lignin Chemistry. 2003.
Ramiah, et al. TGA and DTA of Cellulose, Hemicellulose, Lignin. J. Appl. Poly. Sci. 1970, 14, 1323-1337.
Rangamannar, et al. Improved wet bulk storage of bagasse for newsprint pulp production—part 1. Pulping conference TAPPI proceedings. 1993; 391-398.
Raveendran et al. Influence of mineral matter on biomass pyrolysis characteristics. Fuel 74(12):1812-1822 (1995).
Raz. Literature review on concentrated HCl hydrolysis of lignocellulosic material. Aug. 2008.
Raz. Weyland bioethanol report. 2010.
Readnour, et al. Thermodynamic Properties for the Dissociation of Bisulfate Ion and the Partial Molal Heat Capacities of Bisulfuric

(56) References Cited

OTHER PUBLICATIONS

Acid and Sodium Bisulfate over an Extended Temperature Range. Inorganic Chemistry. Oct. 1969; 8(10):2174-2182.
Reese. A microbiological process report; enzymatic hydrolysis of cellulose. Appl Microbiol. Jan. 1956;4(1):39-45.
Reinhold. SEC of lignins. Mainz, Germany. 2007.
Reith. Development of integrated lignocellulose biorefinery for co-production of chemicals, transportation fuels, electricity and heat. EU FP6 Integrated Project Biosynergy. 2009.
Riga/Latvia. Wood-based adhesives: environmental aspects. 5th EU Programme project WOODPRO Integration of Latvian State Institute of Wood Chemistry in European Research Area. Workshop, Jul. 20-21, 2005.
Ritcey et al. Development of Industrial Solvent Extraction Processes. (Report) Gordon M. Ritcey & Associates, Inc; Nepean, Ontario, Canada.2004.
Rivas et al. Purification of Xylitol Obtained by the Fermentation of Corncob Hydrolysates. J Agric Food Chem 54:4430-4435 (2006).
Robbins, et al. Liquid-Liquid Extraction Operations and Equipment. Sec. 15. 2009.
Robertson. Factors Governing the Nitration of Cellulose. PhD Thesis; Cornell University. 1946.
Robertson. The fractional extraction and quantitative determination of pectic substances in grapes and musts. Am. J. Enol. Vitic. 1979; 30(3):182-186.
Rockwood, et al. Energy Product Options for Eucalyptus Species Grown as Short Rotation Woody Crops. Int. J. Mol. Sci. 2008; 9:1361-1378; DOI: 10.3390/ijms9081361.
Rogers, et al. The Advanced Materials Webinar Series: Carbon Fibers. Southern Advanced Materials in Transportation Alliance (SAMTA). 2011.
Roman-Leshkov et al. Production of dimethylfuran for liquid fuels from biomass-derived carbohydrates. Nature; 2007; 447; 982-985.
Rondinini, et al. Reference value standards and primary standards for pH measurements in Organic Solvents and Water + Organic Solvent Mixtures of Moderate to High Permittivities. Pure & Appl. Chem. 1987; 59(11):1549-1560.
Rout et al. Supercritical CO2 Fractionation of Bio-oil Produced from Mixed Biomass of Wheat and Wood Sawdust. Energy & Fuels; 2009; 13; 6181-6188.
Rovio, et al. Determination of monosaccharide composition in plant fiber materials by capillary zone electrophoresis. Journal of Chromatography A. 2008; 1185:139-144.
Rovio, et al. Determination of neutral carbohydrates by CZE with direct UV detection. Electrophoresis. 2007; 28:3129-3135.
Rozmarin, et al. Fermentative evaluation of prehydrolyzates from chemical cellulose manufacturing. II. Study on some factors affecting the inversion process. Rom. Revista Padurilor-Industria Lemnului-Celuloza si Hirtie: Celuloza si Hirtie (1977), 26(4), 158-62. CODEN: RPLHDX ISSN: 0258-2287. Abstract only.
Rugg. Optimization of the NYU continuous cellulose hydrolysis process. B01447 Biofuels Information Center. Dec. 1982.
Ruiz-Angel et al. Reversed-phase liquid chromatography analysis of alkyl-imidazolium ionic liquids II. Effects of different added salts and stationary phase influence. Journal of chromatography A; 2008, 1189; 476-482.
Ruiz-Rosa, et al. The production of submicron diameter carbon fibers by the electrospinning of lignin. Carbon. 2010; 48:696-705.
Rumbold. Selection of production hosts for real-life feedstock utilization. TNO Kwaliteit van Leven, Oct. 20, 2007.
Rutten, et al. Measurements of the heats of dilution and description of the system H☐O/H☐SO☐/HCl with a solvation model. Fluid Phase Equilibria. 1998; 153:317-340.
Saadatmand, et al. Prehydrolysis in softwood pulping produces a valuable biorefinery fraction for material utilization. Environ. Sci. Technol. Jul. 7, 2012; DOI: 10.1021/es301699n.
Saari et al. Adsorption Equilibria of Arabinose, Fructose, Galactose, Rhamnose, Sucrose, and Xylose on Ion-Exchange Resins. J. Chem. Eng.; 2010; 55; 3462-3467.

Saariaho. Resonance raman spextroscopy in the analysis of residual lignin and other unsaturated structures in chemical pulps. Helsinki University of Technology (Espoo, Finland) on the Jan. 14, 2005.
Saddler et al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.
Saeman. Kinetics of the hydrolysis of wood and of the decomposition of sugars in dilute acid at high tempratures. USDA. Sep. 1944.
Saha, et al. Dilute Acid Pretreatment, Enzymatic Saccharification, and Fermentation of Rice Hulls to Ethanol. Biotechnol. Prog. 2005; 21:816-822.
Sakai et al. Effect of lignocellulose-derived inhibitors on growth of and ethanol production by growth-arrested Corynebacterium glutamicum R. Applied and environmental microbiology; 2007; 73(7); 2349-2353.
Saltberg et al. Removal of metal ions from wood chips during acidic leaching 1: Comparison between Scandinavian softwood, birch and eucalyptus. Nordic Pulp and Paper Research Journal. 2006; 21: 507-512.
Saltberg, et al. Removal of metal ions from wood chips during acidic leaching 2: Modeling leaching of calcium ions from softwood chips. Nordic Pulp and Paper Research J. 2006; 21(4):513-519.
Samuel, et al. Structural Characterization and Comparison of Switchgrass Ball-milled Lignin Before and after Dilute Acid Pretreatment. Appli. Mier. BioTech. 2010, 162:62-74.
Sanchez, et al. Structural analysis of acid catalysed furfuraldehyde resins by thermal degradation techniques. Eur. Polym. J. 1994; 30(1):43-50.
Sanchez, et al. Trends in biotechnological production of fuel ethanol from different feedstocks. Bioresource Technology. 2008; 99:5270-5295.
Sanders, et al. Shuttle hydrochloric acid process for the preparation of oligosaccharides containing products from wood. Comm. Eur. Communities, [Rep.] EUR (1987), (EUR 11084, Degrad. Lignocellul. Ruminants Ind. Processes), 97-101. CODEN: CECED9 ISSN: 0303-755X. Abstract only.
Sannigrahi, et al. Cellulosic biorefineries—unleashing lignin opportunities. Current Opinion in Environmental Sustainability. 2010; 2:383-393.
Sannigrahi, et al. Effects of two-stage dilute acid pretreatment on the structure and composition of lignin and cellulose in loblolly pine. Bioenerg. Res 2008; 1 (3-4): 205-214.
Sannigrahi, et al. Lignin structural modifications resulting from ethanol organosolv treatment of loblolly pine. Energy Fuel 2010; 24(1): 683-689.
Sannigrahi, et al. Pseudo-lignin and pretreatment chemistry. Energy Environ. Sci. 2011; 4:1306-1310.
Saquin, et al. Lignin Oxidative Chemistry Using Supercritical / Expanded Media. 2005.
Sarkanen, et al. The development of plasticizers for alkylated kraft ligninbased polymeric materials. 2005.
Sasaki, et al. Cellulose hydrolysis in subcritical and supercritical water. J. of Supercritical Fluids. 1998; 13:261-268.
Sasaki, et al. Dissolution and Hydrolysis of Cellulose in Subcritical and Supercritical Water. Ind. Eng. Chem. Res. 2000, pp. 2883-2890.
Sassner, et al. Techno-economic evaluation of bioethanol production from three different lignocellulosic materials. Biomass and bioenergy. 2008; 32:422-430.
Satin Sweet® 65% High Maltose Corn Syrup. Cargill foods, www.cargillfoods.com Updated Aug. 12, 2014.
Sato, et al. Determination of monosaccharides derivatized with 2-aminobenzoic Acid by capillary electrophoresis. Ana. BioChem. 1997; 251: 119-121.
Scaringelli, et al. Pre-hydrolysis of sweetgum wood—an integrated approach to the conversion of lignocellulose from wood into useful chemicals. Report (1979), (NSF/RA-790218; Order No. PB80-108640), 38 pp. From: Gov. Rep. Announce. Index (U. S.) 1980, 80(5), 810. Abstract only.
Schaefer. Bio-Based opportunities in chemicals & energy. Novozymes. London, UBS. Nov. 17, 2010.
Schaeffer. ASTM activated carbon standards. 2002.

(56) References Cited

OTHER PUBLICATIONS

Schlamadinger, et al. Effects of the Kyoto protocol on forestry and bioenergy products for mitigation of net carbon emissions. IEA Bioenergy, proceedings of the workshop. Apr. 1998. 202 pages.
Schlea, et al. Extraction of Iron, Cobalt, and Nickel Sulfates by Organic liquids. Industrial and engineering chemistry. Jun. 1957; 49(6):1056-1057.
Schoenemann. The New Rheinau Wood Saccharification Process. Institute of Chemical Technology. Jul. 27, 1953; 1-49.
Schuchardt et al. Hydrolysis of sugar cane bagasse with hydrochloric acid, promoted by metallic cations. Journal of Chemical Technology & Biotechnology. 1986; 36:329-334.
Schultz, et al. Proposed Mechanism for the Nitrobenzene Oxidation of Lignin. Holzforschung—International Journal of the Biology, Chemistry, Physics and Technology of W. 1986; 40(2):93-97.
Schutz. The hydrolysis of wood with hydrochloric acid or chlorides as catalysts in acetic acid solution. Zellwolle, Kunstseide, Seide (1942), 47:8-9. Abstract only.
Scifinder. Steam pretreatment of wood in relation to enzymatic hydrolysis. Final report. Energy Res. Abstr. 1989, 14(17), Abstr. No. 35904.
Scurfield, et al. Amino-Acid Composition of Wood Proteins. J. Experimental Botany. 1970; 21(6):857-68.
Segatin, et al. Thermodynamics of the Solubility of Water in 1-Hexanol, 1-Octanol, 1-Decanol, and Cyclohexanol. Monatshefte fur Chemie. 2004; 135:241-248.
Sen, et al. A Review of Cellulose Non-Derivatizing Solvent Interactions with Emphasis on Activity in Inorganic Molten Salt Hydrates. Sustainable Chemistry & Engineering. 2013:858-870.
Sena-Martins, et al. Enzyme modified lignins for environment—friendly products. 2005.
Sendich, et al. Recent process improvements for the ammonia fiber expansion (AFEX) process and resulting reductions in minimum ethanol selling price. Bio. Tech. 2008; 99:8429-8435.
Sevcik, et al. Rapid analysis of carbohydrates in aqueous extracts and hydrolysates of biomass using a carbonate-modified anion-exchange column. J Chromatogr A. Mar. 4, 2011;1218(9):1236-43. doi: 10.1016/j.chroma.2011.01.002. Epub Jan. 11, 2011.
Sharkov, et al. Conversion of diffi cult-to-hydro lyze wood polysaccharides to an easy-to-hydrolyze condition with hydrogen chloride under pressure. USSR. Sb. Tr., Vses. Nauch.-Issled. Inst. Gidroliza Rast. Mater. (1971), No. 21 65-74, 205. Abstract only.
Sharkov. Production of Polyhydric Alcohols from Wood Polysaccharides. Angew. Chem. internat. Edit. 1963; 2(8):405-492.
Shatalov, et al. Kinetics of organosolv delignification of fibre crop Arundo donax L. Industrial Crops and Products. 2005; 21:203-210.
Sheehan, et al. Energy and Environmental Aspects of Using Corn Stover for Fuel Ethanol. Journal of Industrial Ecology. 2004; 7(3-4):117-146.
Shen, et al. Lignin-Based Activated Carbon Fibers and Controllable Pore Size and Properties. Journal of Applied Polymer Science. 2011; 121:989-994.
Shen, et al. Product overview and market projection of emerging bio-based plastics, Utrecht University. PRO-BIP 2009.
Sherrard, et al. Review of wood saccharification processes in the United States Prior to World War II. Industrial and Engineering Chemistry. 1945. 37(1):1-10.
Shimizu, et al. Integrated process for total utilization of wood components by steam-explosion pretreatment. Biomass and bioenergy. 1998; 14(3):195-203.
Shorr, et al. Phase equilibria and the telomerization reaction. I & EC Fundamentals. 1963; 39(1):86-87.
Shulga, et al. Effect of rheological properties of the lignin-based adhesive on aggregating of light-textured soil. 2008.
Shulga. Advanced application of lignin-based adhesives. 2005; 42-47.
Sidiras, et al. Simulation of acid-catalysed organosolv fractionation of wheat straw. Bioresource Technology. 2004; 94:91-98.
Sigma. Enzymatic Assay of α-Glucosidase. Sigma quality control test procedure. Sigma Product information, Revised: Aug. 9, 1996.
Sigma. Enzymes and Reagents for Alternative Energy. Sigma-Aldrich. Biofiles. 2010; 5(5).
Simonell, et al. Lignin Pyrolysis Products, Lignans, and Resin Acids as Specific Tracers of Plant Classes in Emissions from Biomass Combustion. Environ. Sci. Technol. 1993; 27:2533-2541.
Singh, et al. Visualization of Biomass Solubilization and Cellulose Regeneration During Ionic Liquid Pretreatment of Switchgrass. Biotechnology and Bioengineering. Sep. 1, 2009; 104(1):68-75.
Sluiter, et al. Compositional analysis of lignocellulosic feedstocks. 1. Review and description of methods. Journal of agricultural and food chemistry. 2010; 58:9043-9053.
Sluiter, et al. Determination of Ash in Biomass, Laboratory Analytical Procedure (LAP), Issue Date: Jul. 17, 2005. Technical Report, NREL/TP-510-42622, Jan. 1, 2008.
Sluiter, et al. Determination of Sugars, Byproducts, and Degradation Products in Liquid Fraction Process Samples. Laboratory Analytical Procedure (LAP), Contract No. DE-AC36-99-GG10337. Issue Date: Dec. 8, 2006.
Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.
Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.
So, et al. Economic Analysis of Selected Lignocellulose-to-Ethanol Conversion Technologies. Applied Biochemistry and Biotechnology. 1999; 77-79:633-640.
Soloman, et al. Grain and cellulosic ethanol: History, economics, and energy policy. Biomass and Bioenergy. 2007; 31:416-425.
Spaccini, et al. Molecular characteristics of humic acids extracted from compost at increasing maturity stages. Soil Biology & Biochemistry. 2009 41:1164-1172.
Srinorakutara, et al. Approach of Cassava Waste Pretreatments for Fuel Ethanol Production in Thailand. 2010.
Srinorakutara, et al. Utilization of Waste from Cassava Starch Plant for Ethanol Production. The Joint International Conference on "Sustainable Energy and Environment (SEE)" Dec. 1-3, 2004, Hua Hin, Thailand. 344-349.
Srndovic. Ultrastructure of the primary cell wall of softwood fibres studied using dynamic FT_IR spectroscopy. Licentiate Thesis, Royal Institute of Technology. Stockholm 2008.
Starr, et al. Water-enhanced solubility of carboxylic acids in organic solvents and its applications to extraction processes. Lawrence Berkeley Laboratory, University of California, Nov. 1991.
Steele. Recent breakthroughs in enzymes for biomass hydrolysis. Genecor. National Ethanol Conference, Feb. 23-25, 2009, San Antonio, Texas.
Steinbuchel. Polymeric and low molecular weight hydrophobic chemicals produced by microorganisms from renewables. Renewable Resources & Biorefineries Conference, Sep. 6-8, 2006, York, UK.
Stepnowski et al. Analysis of Environmental Fate and Quantitative Methods for Determination of Ionic Liquids. Conference report; International Conference on Enviromental Science and Technology. 2007; KOS, Greece.
Stewart. Lignin as a base material for materials applications: Chemistry, application and economics. Industrial crops and products. 2008; 207:202-207.
Stranges. Friedrich Bergius and the Rise of the German Synthetic Fuel Industry. Isis. Dec. 1984; 75(4):43-667.
Stranges. Synthetic fuel production in prewar and world war II Japan: A case study in technological failure. Annals of Science. 1993; 50:229-265.
Structure of Wood. US Department of Agriculture, Forest Service, Forest Products Laboratory , Research Note FPL-04. Mar. 1980.
Sudo, et al. A New Carbon Fiber from Lignin. Journal of Applied Polymer Science. 1992; 44:127-134.
Sudo, et al. A New Modification Method of Exploded Lignin for the Preparation of a Carbon Fiber Precursor. Journal of Applied Polymer Science. 1993; 48:1485-1491.

(56) References Cited

OTHER PUBLICATIONS

Suess. Interaction of organic compounds with calcium carbonate-I. Association phenomena and geochemical implications. Geochimia et Cosmochimic Acata. 1970; 34:157-168.
Sun, et al. Hydrolysis of lignocellulosic materials for ethanol production: a review. Bioresource Technology. 2002; 83:1-11.
Svensson. Minimizing the sulfur content in Kraft lignin. Degree Project, ECTS 30.0,At STFI-Packforsk, Stockholm, 2008.
Taherzadeh, et al. Acid-Based hydrolysis Processes for Ethanol from Lignocellulosic materials: A Review. Bioethaol review, BioResources. 2007; 2(3):472-499.
Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.
Takagaki et al. Catalytic Transformations of Biomass-Derived Materials into Value-Added Chemicals. Catalysis Surveys from Asia. 2012; 16: 164-182.
Tanaka, et al. Effect of Pore Size in Substrate and Diffusion of Enzyme on Hydrolysis of Cellulosic Materials with Cellulases. Biotechnology and Bioengineering. 1998; 32:698-706.
Tanase, et al. Mass Balance of Extractives Around Impressafiner in Mill and Pilot Scale. 2009. 1-6.
Tang, et al. Effect of Inorganic Salts on Pyrolysis of Wood, Cellulose, and Lignin Determined by Differential Thermal Analysis. U.S. Forest Service Research FPL 82 Jan. 1968.
Tappi. Acid-insoluble lignin in wood and pulp. T 222 om-88, Tappi 1988.
Tarabanko, et al. Mechanism for the Catalytic Oxidation of Lignin to Vanillin. Kinetic and Catalitysis. 2004; 45(4):569-577.
Tejado, et al. Isocyanate modified lignins for formulations of novolac resins. ILI's 7th Forum and Eurolignin meeting, Barcelona 2005.
Telysheva. Applicability of a free radical (DPPH) method for estimation of antioxidant activity of lignin and its derivatives. The international Lignin Institute, 5th international Forum' Sep. 7, 2000, Bordeaux (France).
Terashima, et al. Solid state NMR spectroscopy of specifically 13C-enriched lignin in wheat straw from coniferin. Phytochemistry. 1997; 46(5):863-870.
The US Pushes for Advanced Biofuels Market Growth. Global Data; A report.2010: 1-7.
Thielemans, et al. Lignin Esters for Use in Unsaturated Thermosets: Lignin Modification and Solubility Modeling. Biomacromolecules. 2005; 6:1895-1905.
Thompson, et al. Comparison of Pretreatment Methods on the Basis of Available Surface Area. Bioresource Technology. 1992; 39:155-163.
Thomsen. How 'green' are algae farms for biofuel production? Biofuels. 2010; 1(4):515-517.
Timell, et al. The acid hydrolysis of glycosides II. Effect of substituents at C-5. Canadian Journal of Chemistry. 1965; 43:2296-2305.
Timell. The acid hydrolysis of glycosides I. General conditions and the effect of the nature of the aglycone. Canadian Journal of Chemistry. 1964; 42:1456-1471.
Timur, et al. Characterization and application of activated carbon produced from oak cups pulp. Journal of Analytical and Applied Pyrolysis. 2010; 89:129-136.
Toledano, et al. Characterization of key functional groups of lignin. 5th Italian meeting on lignocellulosic chemistry. Sep. 1-4, 2009— Villa Monastero Varenna (Lecco) Italy.
Toledano, et al. Study of fractionation of lignin by ultrafiltration and selective recipitation. 2009.
Tomani, et al. Development and demonstration of the lignoboost process. 2007.
Trickett. Utilization of Baggase for the production of C5 and C6 sugars. MS Thesis; University of Natal, Durban, South Africa. 1982.
Trinh et al. Fast Pyrolysis of Lignin Using a Pyrolysis Centrifuge Reactor. Energy & Fuels. 2013; 27 (7): 3802-3810.
Troitskii. Colloid chemical mechanism of the separation of some elements by extraction. Russ. Chem. Rev. 163; 32:116-120.
U.S. Appl. No. 61/473,134, filed Apr. 7, 2011.
U.S. Appl. No. 61/483,777, filed May 9, 2011.
U.S. Appl. No. 61/487,319, filed May 18, 2011.
U.S. Appl. No. 61/524,350, filed Aug. 17, 2011.
U.S. Appl. No. 61/528,257, filed Aug. 28, 2011.
U.S. Appl. No. 61/539,196, filed Sep. 26, 2011.
U.S. Appl. No. 61/539,239, filed Sep. 26, 2011.
U.S. Appl. No. 61/539,272, filed Sep. 26, 2011.
U.S. Appl. No. 61/545,823, filed Oct. 11, 2011.
U.S. Appl. No. 61/552,402, filed Oct. 27, 2011.
U.S. Appl. No. 61/559,529, filed Nov. 14, 2011.
U.S. Appl. No. 61/561,181, filed Nov. 17, 2011.
UK examination report dated Jul. 30, 2012 for GB 1205500.0.
UK search and examination report dated May 11, 2012 for GB Application No. 1205501.8.
UK search and examination report dated May 27, 2014 for GB Application No. 1208154.3.
UK search and examination report dated Jul. 18, 2012 for GB Application No. 1208154.3.
UK search and examination report dated Dec. 6, 2012 for GB Application No. 1205501.8.
Unal, et al. Dechlorination of Bleached Kraft Pulp by Laccase Enzyme Produced from Some White-Rot Fungi. Turk J Biol. 2001; 25:67-72.
Updegraff et al. Semimicro determination of cellulose in biological materials. Analytical biochemistry. 1969; 32(3):420-424.
Uraki, et al. Preparation of activated carbon fibers with large specific surface area from softwood acetic acid lignin. J Wood Sci. 2001; 47:465-469.
Urban, et al. Characterization of polymer-based monolithic capillary columns by inverse sizeexclusion chromatography and mercury-intrusion porosimetry. Journal of Chromatography A. 2008; 1182:161-16.
USDA. A USDA Regional Roadmap to Meeting the Biofuels Goals of the Renewable Fuels Standard by 2022. A USDA Report. 2010.
Usde. Advanced Technologies for the Control of Sulfur Dioxide Emissions from Coal-Fired Boilers, A report on three projects conducted under separate. Clean Coal Technology. Topical Report No. 12, Jun. 1999.
Vaghela et al. Electrolytic synthesis of succinic acid in a flow reactorwith solid polymer electrolyte membrane. Journal of Applied Electrochemistry. 2002; 32: 1189-1192.
Van Bramer. An Introduction to Mass Spectrometry. Widener University, Department of Chemistry, One University Place, Chester, PA 19013. 1998.
Van Dam, et al. Emerging markets for lignin and lignin derivatives. The quest of taming the last of the "wild bio-polymers". 2005.
Van Dam. Characterization of Sulfur-free lignins from alkaline pulping of annual fibere crops. The international Lignin Institute, 5th international Forum' Sep. 7, 2000, Bordeaux (France).
Van De Pas, et al. Epoxy Resins from Lignin-derived Phenols. Scion next generation biomaterials. Poster 2009.
Van Dyke. Enzymatic Hydrolysis of Cellulose—A Kinetic Study. For the degree of Doctor of Science at the Massachusetts Institute of Technology, Sep. 1972.
Van Sprongsen, et al. Separation and recovery of the constituents from lignocellulosic biomass by using ionic liquids and acetic acid as co-solvents for mild hydrolysis. Chemical Engineering and Processing. 2011; 50:196-199.
Van-Putten et al. Hydroxymethylfurfural, a versatile platform chemical made from renewable resources. Chemical reviews. 2013;113 : 1499-1597.
Vasile, et al. Thermogravimetry (TG) and derivative thermogravimetry (DTG) of lignin. Analytical methods for lignin characterization. International Lignin Institute Version: 1.2 Last date of review: Aug. 2008.
Vassilev, et al. An overview of the chemical composition of biomass. Fuel, vol. 89, Issue 5, May 2010, pp. 913-933. Available online Nov. 10, 2009.

(56) References Cited

OTHER PUBLICATIONS

Vazquez, et al. Acetosolv pine lignin as copolymer in resins for manufacture of exterior grade plywoods. Bioresource Technology. 1999; 70:209-214.
Vazquez, et al. Effect of chemical modification of lignin on the gluebond performance of lignin-phenolic resins. Bioresource Technology. 1997; 60:191-198.
Vennestrom, et al. Beyond petrochemicals: the renewable chemicals industry. Angewandte Chemie Int. Ed. 2011; 50:10502-10509.
Von Sivers, et al. A techno-economical comparison of three processes for the production of ethanol from pine. Bioresource Technology. 1995; 51:43-52.
Vulfson, et al. Glycosidases in organic solvents: I. Alkyl-fl-glucoside synthesis in a water-organic two-phase system. Enzyme Microb. Technol. Dec. 1990; 12:950-954.
Vuori, et al. Liquefaction of Kraft Lignin: 1. Primary Reactions under Mild Thermolysis Conditions. Holzforschung—International Journal of the Biology, Chemistry, Physics and Technology of Wood , vol. 42 (3) de Gruyter—Jan. 1, 1988.
Vuyyuru et al. Conversion of Cellulosic Biomass into Chemicals using Heterogeneous and Electrochemical Catalysis. MS Thesis, Berlin University, 2012.
Wallmo, et al. Effect of precipitation conditions on properties of lignin from the LignoBoost process. 2007.
Wang et al. A Route for Lignin and Bio-Oil Conversion: Dehydroxylation of Phenols into Arenes by Catalytic Tandem Reactions. Angewandte Chemie. 2013; 52: 11499-11503.
Wang, et al. Influence of steaming explosion time on the physic-chemical properties of cellulose from Lespedeza stalks (Lespedeza crytobotrya). Bioresource Technology. 2009; 100:5288-5294.
Wang, et al. Molecular Characteristics of Kraft-AQ Pulping Lignin Fractionated by Sequential Organic Solvent Extraction. Int. J. Mol. Sci. 2010; 11:2988-3001.
Wang, et al. Understanding the Conformation of Polysaccharides. Chapter 5. Copyright 2005 by Taylor & Francis Group, LLC.
Wang, et al. Understanding the Physical Properties of Food Polysaccharides. Chapter 4. Copyright 2005 by Taylor & Francis Group, LLC.
Wang. David Wang's Wood Chemistry Class. Basic Lignin Chemistry. 2011.
Wang. Thermal Modification of Wood. Faculty of Forestry University of Toronto. 2011.
Warren. Future Lower Cost Carbon Fiber for Autos: International Scale-up & What is Needed. Oak Ridge National Laboratory, Tennessee, USA. 2007.
Wasserscheid & Welton. Ionic Liquids in Synthesis. A book ; Published by Wiley-VCH Verlag GmbH & Co. KGaA. 2007:1-709.
Wei, et al. Effects of surfactant on biochemical and hydrothermal conversion of softwood hemicellulose to ethanol and furan derivatives. Process Biochemistry. 2011; 46(9): 1785-1792.
Weingarten, et al. Kinetics of furfural production by dehydration of xylose in a biphasic reactorwith microwave heating. Green Chem. 2010; 12:1423-1429.
Werner et al. Ionic liquids in chemical engineering. Annual review of chemical and biomolecular engineering. 2010; 1: 203-230.
Williams. Ethanol production potential and costs from lignocellulosic resources in California. 15th European Biomass Conference & Exhibition, May 7-11, 2007, Berlin, Germany.
Wilson, et al. Detection of tannins in modern and fossil barks and in plant residues by high-resolution solid-state $^{13}C$ nuclear magnetic resonance. Org. Geochem. 1988; 12(6):539-546.
Winandy, et al. Wood-plastic composites using thermomechanical pulp made from oxalic acid-pretreated red pine chips. 7th Global WPC and Natural Fibre Composites Congress and Exhibition, Jun. 18-19, 2008 in Kassel / Germany.
Winston, et al. Characterization of the lignin residue from hydrolysis of sweetgum wood with superconcentrated hydrochloric acid. Holzforschung Bd. 1986; 40:Suppl. 45-50.

Wood, et al. Determination of Methanol and Its Application to Measurement of Pectin Ester Content and Pectin Methyl Esterase Activity. Analytical biochemistry. 1971; 39:418-428.
Woodbridge et al. Nitrocellulose from wood pulp. J. Ind.Eng. Chem. 1920; 12(4):380-384.
Wood-Ethanol Report. Environment Canada. 1999.
Wooley, et al. Lignocellulosic biomass to ethanol process design and economics utilizing co-current dilute acid prehydrolysis and enzymatic hydrolysis current and futuristic scenarios. National Renewable Energy Laboratory. NREL/TP 580-26157. Jul. 1999.
Wright et al. Techno-Economic Analysis of Biomass Fast Pyrolysis to Transportation Fuels. Technical Report: NREL/TP-6A20-46586. 2010.
Wyman et al. Pretreatment: The Key to Unlocking Low Cost Cellulosic Ethanol Ethanol Production in Brazil and the United States. Presentation. CAFI. 2007.
Wyman, et al. Comparative sugar recovery data from laboratory scale application of leading pretreatment technologies to corn stover. Bioresource Technology. 2005; 96: 2026-2032.
Wyman, et al. Coordinated development of leading biomass pretreatment technologies. Bioresource Technology. 2005; 96:1959-1966.
Wyman. Biomass ethanol: Technical Progress, Opportunities, and Commercial Challenges. Annu. Rev. Energy Environ. 1999; 24:189-226.
Wyman. Potential Synergies and Challenges in Refining Cellulosic Biomass to Fuels, Chemicals, and Power. Biotechnol. Prog. 2003; 19:254-262.
Wyman. Twenty Years of Trials, Tribulations, and Research Progress in Bioethanol Technology. Applied Biochemistry and Biotechnology. 2001; 91-93:5-21.
Wyman. What is (and is not) vital to advancing cellulosic ethanol. Trends in Biotechnology. 2007; 25(4):153-157.
Xiang, et al. Heterogeneous Aspects of Acid Hydrolysis of α-Cellulose. Applied Biochemistry and Biotechnology. 2003; 105-108:505-514.
Xie, et al. Opportunities with Wood Dissolved in Ionic Liquids. In Cellulose Solvents: Foe Analysis, Shaping and Chemical Modification. Chapter 19. 2010;343-363.
Xing, et al. Production of furfural and carboxylic acids from waste aqueous hemicellulose solutions from the pulp and paper and cellulosic ethanol industries. Energy & Environmental Science. 2011; 4: 2193-2205.
Yang et al. Optimization of furfural production from D-xylose with formic acid as catalyst in a reactive extraction system. Bioresource technology. 2013; 133 : 361-369.
Yang et al. Synthesis of furfural from xylose, xylan, and biomass using AlCl36H2O in biphasic media via xylose isomerization to xylulose. ChemSusChem. 2012; 5: 405-410.
Yang, et al. Pretreatment: the key to unlocking low-cost cellulosic ethanol. Biofuels, Bioprod. Bioref. 2008; 2:26-40.
Yankov, et al. Improvement of the lactic acid extraction. Extraction from aqueous solutions and simulated fermentation broth by means of mixed extractant and TOA, partially loaded with HCI. Chem. Biochem. Eng. Q. 2005; 19(1):17-24.
Ye, et al. Spontaneous High-Yield Production of Hydrogen from Cellulosic Materials and Water Catalyzed by Enzyme Cocktails. ChemSusChem. 2009; 2:149-152.
Yeoh, et al. Comparisons between different techniques for water-based extraction of pectin from orange peels. Desalination 2008; 218:229-237.
Yoshida, et al. Gasification of biomass model compounds and real biomass in supercritical water. Biomass and Bioenergy.2004; 26:71-78.
Yuan, et al. Hydrolytic degradation of alkaline lignin in hot-compressed water and ethanol. Bioresource Technology 101 (2010) 9308-9313.
Yusmawati et al. Optical Properties and Sugar Content Determination of Commercial Carbonated Drinks using Surface Plasmon Resonance. American Journal of Applied Sciences. 2007;4: 1-4.
Zahalka, et al. Esterification of 1,4-dichlorobutane with sodium formate under solid-liquid phase transfer catalysis. A kinetic study. Can. J. Chem. 1989; 67:245-249.

(56) References Cited

OTHER PUBLICATIONS

Zahalka, et al. One-Pot Conversion of Primary Alkyl Chlorides and Dichlorides into Alcohols, Diols and Ethers via Formic Ester Intermediated under Phase-Transfer Conditions. Communications, Sep. 1986; 763-765.

Zahedifar. Novel uses of lignin and hemicellulosic sugars from acidhyrolysed lignocellulosic materials, for the degree of Doctor of Philosophy, in the University of Aberdeen, Sep. 1996.

Zakzeski, et al. The Catalytic Valorization of Lignin for the Production of Renewable Chemicals. Chem. Rev. 2010; 110:3552-3599.

Zhang et al. Conversion of Xylan and Xylose into Furfural in Biorenewable Deep Eutectic Solvent with Trivalent Metal Chloride Added. BioResources; 8(4);6014-6025.

Zhang et al. Hydrodeoxygenation of Lignin-Derived Phenolic Monomers and Dimers to Alkane Fuels over Bifunctional Zeolite-Supported Metal Catalysts. Substainable Chemistry and Engineering; 2013: A-I.

Zhang, et al. Conversion of xylan, d-xylose and lignocellulosic biomass into furfural using AlCl3 as catalyst in ionic liquid. Bioresource technology. 2013; 130 : 110-116.

Zhang, et al. Quantitative 2D HSQC NMR Determination of Lignin-sub Structures by Selecting Suitable Internal Standard References. 2007.

Zhang, et al. Solid acids as catalysts for the conversion of D-xylose, xylan and lignocellulosics into furfural in ionic liquid. Bioresource technology. 2013; 136 : 515-521.

Zhang, et al. Vapor Pressure Measurements for the H2SO4/HNO3/H2O and H2SO4/HCI/H2O Systems: Incorporation of Stratospheric Acids into Background Sulfate Aerosols. J. Phys. Chem. 1993; 97:8541-8548.

Zhang, et al. Vapor-Liquid Equilibria for Water + Hydrochloric Acid + Magnesium Chloride and Water + Hydrochloric Acid + Calcium Chloride Systems at Atmospheric Pressure. Chinese J. Chem. Eng. 2006; 14(2):276-280.

Zhang. Reviving the carbohydrate economy via multi-product lignocellulose biorefineries. J Ind Microbiol Biotechnol. 2008; 35:367-375.

Zhao et al. Aromatics Production via Catalytic Pyrolysis of Pyrolytic Lignins from Bio-Oil. Energy & Fuels. 2010; 24: 5735-5740.

Zhao, et al. Small-scale mashing procedure for predicting ethanol yield of sorghum grain. Journal of Cereal Science. 2009; 49:230-238.

Zhao, et al. Supercritical hydrolysis of cellulose for oligosaccharide production in combined technology. Chem. Eng. J. 2009; 150:411-417.

Zhao, et al., Organosolv pretreatment of lignocellulosic biomass for enzymatic hydrolysis, Appl Microbiol Biotechnol (2009) 82:815-827.

Zheng, et al. Electron beam induced changes in the surface properties of starch films functionalized by lignin. Italic 5 conference—Sep. 2-4—Varenna—2009.

Zheng, et al. Overview of biomass pretreatment for cellulosic ethanol production. Int J Agric & Biol Eng. 2009; 2(3):51-68.

Zheng, et al. Phenolation of walnut shell using sulfuric acid as a catalyst and application to PF resin adhesives. Abstracts / Journal of Biotechnology 136S (2008) S402-S459, doi:10.1016/j.jbiotec.2008.07.950.

Zheng, et al. Supercritical carbon dioxide explosion as a pretreatment for cellulose hydrolysis. Biotechnology Letters. Aug. 1995; 17(8):845-850.

Zhu, et al. Understanding methanol formation in pulp mills. 1999 International Environmental Conference, pp. 139-143.

Zhuang et al. Analysis of cellulose hydrolysis products in extremely low acids. Nongye Gongcheng Xuebao, available at https://www.researchgate.net/publication/293219326_Analysis_of_cellulose_hydrolysis_products_in_extremely_low_acids. 23(2):177-182 (2007). Abstract only. 1 page.

Zimbardi, et al. Acid impregnation and steam explosion of corn stover in batch processes. Industrial Crops and Productions. 2007; 26:195-206.

Zinoviev, et al. Background Paper on biofuels Production Technologies. International Center for Science and High Technology and UNIDO. Nov. 2007; 1-106.

Zolotov. Hydration and solvation of acids and salts undergoing extraction. Russ. Chem. Rev. 1963; 32:107-116.

Zorina, et al. Study of acid heterogeneous hydrolysis of pulp. USSR. Editor(s): Kiprianov, A. I. Khim. Pererab. Drev. (1982), 35-8. Publisher: Leningr. Lesotekh. Akad., Leningrad, USSR CODEN: 49HIA6. Abstract only.

Zou, et al. Preparation of Activated Carbons from Chinese Coal and Hydrolysis Lignin. Adsorption Science & Technology. 2001; 19(1): 59-72.

Canadian Patent Application No. 2,985,478 Office Action dated Jun. 23, 2022.

Chunxun X., et al., "Research Progress in Separation and Purification of Small Molecular Derived Sugar from Hemicellulose," Advanced Sinnew and Renewable Energy, New Energy Progress, Oct. 2013, vol. 1, No. 2, 11 Pages.

Co-Pending for U.S. Appl. No. 13/132,573, filed Sep. 15, 2011.
Co-Pending for U.S. Appl. No. 13/195,721, filed Aug. 1, 2011.
Co-Pending for U.S. Appl. No. 13/316,327, filed Dec. 9, 2011.
Co-Pending for U.S. Appl. No. 13/320,535, filed Jan. 10, 2012.
Co-Pending for U.S. Appl. No. 13/378,657, filed Dec. 15, 2011.
Co-Pending for U.S. Appl. No. 13/380,504, filed Jan. 19, 2012.
Co-Pending for U.S. Appl. No. 13/491,485, filed Jun. 7, 2012.
Co-Pending for U.S. Appl. No. 13/499,638, filed Apr. 1, 2012.
Co-Pending for U.S. Appl. No. 13/577,213, filed Aug. 3, 2012.
Co-Pending for U.S. Appl. No. 13/577,215, filed Aug. 3, 2012.
Co-Pending for U.S. Appl. No. 14/537,445, filed Nov. 10, 2014.
Co-Pending for U.S. Appl. No. 14/537,494, filed Nov. 10, 2014.
Co-Pending for U.S. Appl. No. 14/537,530, filed Nov. 10, 2014.
Co-Pending for U.S. Appl. No. 61/358,894, filed Jun. 26, 2010.
Co-Pending for U.S. Appl. No. 61/483,663, filed May 7, 2011.
Co-Pending for U.S. Appl. No. 61/491,243, filed May 30, 2011.
Co-Pending for U.S. Appl. No. 61/500,169, filed Jun. 23, 2011.
Co-Pending for U.S. Appl. No. 61/513,613, filed Jul. 31, 2011.
Co-pending U.S. Appl. No. 16/560,653, inventors Jansen; Robert et al., filed Sep. 4, 2019.
Co-pending U.S. Appl. No. 16/849,831, inventors Jansen; Robert et al., filed Apr. 15, 2020.
Co-pending U.S. Appl. No. 16/922,199, inventor Eyal; Aharon, filed Jul. 7, 2020.
Co-pending U.S. Appl. No. 16/935,619, inventors Eyal; Aharon Meir et al., filed Jul. 22, 2020.
Co-pending U.S. Appl. No. 16/937,200, inventors Aharon; Eyal et al., filed Jul. 23, 2020.

EP Application No. 14197793.4 Examination Report dated Apr. 21, 2022.

European office action dated Jul. 31, 2012 for EP Application No. 09787553.8.

European Search Report and opinion dated May 4, 2015 for EP Application No. 14197793.4.

European search report and opinion dated Dec. 11, 2013 for EP Application No. 11822761, 4 pages.

European Search Report and opinion dated Nov. 18, 2015 for EP Application No. 137844221.

European Search Report and Opinion for EP Application No. 14197798.3, dated Mar. 25, 2015.

Extended European Search Report and Search Opinion dated Jun. 19, 2017 for European Patent Application No. EP11800303.7, 7 pages.

Extended European Search Report for European Application No. 20208564.3, dated Jul. 6, 2021, 11 pages.

Extended European Search Report for European application, No. EP18175599.2, dated Oct. 8, 2018, 7 pages.

Extended European Search Report for European application, No. EP19172614.0, dated Jul. 3, 2019, 8 pages.

Extended European Search Report for European application. No. EP16800678.1, dated Feb. 5, 2019, 7 pages.

Extended Search Report and Written Opinion for European app. No. EP16735376.2, dated May 9, 2018, 5 pages.

Eyal., et al., "Extraction of Metal Salts by Mixtures of Water-Immiscible Amines and Organic Acids (Acid-Base Couple Extract-

(56) References Cited

OTHER PUBLICATIONS ants). 1. A Review of Distribution and Spectroscopic Data and of Proposed Extraction Mechanisms," Ind. Eng. Chem. Res. 1994, vol. 33, pp. 1067-1075.
Fengqin W., et al., "Research Progress in Preparation of Cellulose Hydrolyzed Sugar," Journal of Cellulose Science and Technology, Mar. 2013, vol. 21, No. 1, 10 Pages.
Fourth Office Action, dated Jan. 20, 2021 for Chinese Patent Application No. 201610162095.6, 4 Pages.
Gosselink. Lignin as a renewable aromatic resource for the chemical industry. PhD Thesis, Wageningen University, Wageningen, NL (2011). 194 pages.
"Green Chemistry", Zhang long, etc. pp. 253-254, Huazhong University of Science & Technology Press, Aug. 2014.
Hedlund, et al., "High Pressure and Temperature Conversion of Lignin and Black Liquor to Liquid Fuels," Master Thesis, Chalmers University of Technology, Sweden; 2010.
International Search Report and Written Opinion for Application No. PCT/IL2008/000278, dated Jul. 4, 2008, 7 pages.
International Search Report and Written Opinion for Application No. PCT/IL2009/000392, dated Dec. 10, 2009, 15 pages.
International Search Report and Written Opinion for Application No. PCT/IL2009/000782, dated Sep. 8, 2010, 12 pages.
International Search Report and Written Opinion for Application No. PCT/IL2009/000843, dated Feb. 4, 2010, 11 pages.
International Search Report and Written Opinion for Application No. PCT/IL2009/001091, dated May 20, 2010, 8 pages.
International Search Report and Written Opinion for Application No. PCT/IL2010/000317, dated Sep. 14, 2010, 9 pages.
International Search Report and Written Opinion for Application No. PCT/IL2011/000130, dated Apr. 26, 2011, 8 pages.
International Search Report and Written Opinion for Application No. PCT/IL2011/000304, dated Sep. 23, 2011, 10 pages.
International Search Report and Written Opinion for Application No. PCT/IL2011/000517, dated Dec. 5, 2011, 13 pages.
International Search Report and Written Opinion for Application No. PCT/US2011/046153, dated Dec. 20, 2011, 15 pages.
International Search Report and Written Opinion for Application No. PCT/US2011/050435, dated Feb. 10, 2012, 20 pages.
International Search Report and Written Opinion for Application No. PCT/US2012/059542, dated Feb. 15, 2013, 16 pages.
International Search Report and Written Opinion for Application No. PCT/US2013/021055, dated Mar. 26, 2013, 16 pages.
International Search Report and Written Opinion for International PCT Patent Application No. PCT/US2016/012384, dated May 17, 2016, 12 pages.
International Search Report and Written Opinion for PCT Application No. PCT/US2013/039585, dated Dec. 13, 2013.
International Search Report for Application No. PCT/IL2010/000786, dated Aug. 10, 2011, 3 pages.
International Search Report for Application No. PCT/IL2010/001042, dated May 5, 2011, 3 pages.
International Search Report for Application No. PCT/IL2011/000131, dated Jun. 6, 2011, 4 pages.
International Search Report for Application No. PCT/IL2011/000424, dated Nov. 14, 2011, 3 pages.
International Search Report for Application No. PCT/US2016/034194, dated Aug. 29, 2016, 15 pages.
Notice of Allowance for U.S. Appl. No. 14/385,142, dated Nov. 21, 2016, 8 Pages.
Notice of Allowance for U.S. Appl. No. 14/385,142, dated Feb. 1, 2017, 15 Pages.
Notification of the Third office Action, Chinese Patent Application No. 201610162095.6, dated Jul. 16, 2020, 20 pages.
Office Action for U.S. Appl. No. 14/385,142, dated Dec. 4, 2014.
Office Action for U.S. Appl. No. 14/385,142, dated Oct. 18, 2016, 10 pages.
Office Action for U.S. Appl. No. 14/385,142, dated Jun. 25, 2015.
Office Action for U.S. Appl. No. 14/385,142, dated Jan. 29, 2016.
Office Action for U.S. Appl. No. 14/485,617, dated Dec. 4, 2014.
Office Action for U.S. Appl. No. 14/512,321, dated Dec. 4, 2014.
Office Action for U.S. Appl. No. 14/730,118, dated Oct. 18, 2016, 8 pages.
Office Action for U.S. Appl. No. 14/730,125, dated Jul. 1, 2016, 11 pages.
Office Action for U.S. Appl. No. 14/730,118, dated Jan. 26, 2017, 9 Pages.
Office Action for U.S. Appl. No. 14/730,125, dated Aug. 22, 2017, 29 Pages.
Office Action for U.S. Appl. No. 14/730,125, dated Jan. 27, 2017, 13 Pages.
Office Action for U.S. Appl. No. 15/298,145, dated Mar. 31, 2017, 84 Pages.
Office Action from Brazilian Patent Application No. BR112012032999-5, dated Mar. 8, 2022, 13 pages.
Office Action from Brazilian Patent Application No. BR112012032999-5, dated Oct. 14, 2021, 13 pages.
Office Action from Brazilian Patent Application No. BR112017014667-3, dated Nov. 3, 2021, 10 pages.
Office Action from Brazilian Patent Application No. BR112017025322-4, dated Jan. 1, 2022, 7 pages.
"Organic Chemistry", Peng zhongguo, p. 123, Sichuan Provincial Health Management Cadre College, Dec. 31, 1990.
Partial European Search Report for EP Application No. 14197787.6, dated Mar. 27, 2015.
"Plant Resource Development Research and Application", Zhang Weiming, etc., p. 364, Southeast University Press, Dec. 2005.
Restriction Requirement for U.S. Appl. No. 17/100,672 dated Jan. 31, 2022, 6 pages.
Tao Z., et al., "Review of Pretreatment for Feedstock of Lignocellulosic Ethanol," Guangdong Chemical Industry, 2013, vol. 17, pp. 108-111.
Wang Y., "The Properties of Cellulose," Carbohydrates and Proteins, Shanghai Educational Publishing House, Mar. 1983, 1st Edition, pp. 30-31.
Xia Li., "Factors affecting production of a-amylase," Practice and Guidance on Biochemical Engineering, Tianjin University Press, May 2007, 1st Edition, pp. 219-220.
Xiu-Nan Z., et al., "Research Progress in Saccharification and Detoxification of Lignocellulosic Materials," Special Wild Economic Animal and Plant Research, 2012, No. 2, pp. 71-76.
Yonglian L.I., et al., "Research Progress on Pretreatment Technologies of Lignocellulose," Guizhou Agricultural Sciences, 2013, vol. 41(10), pp. 158-161.

* cited by examiner

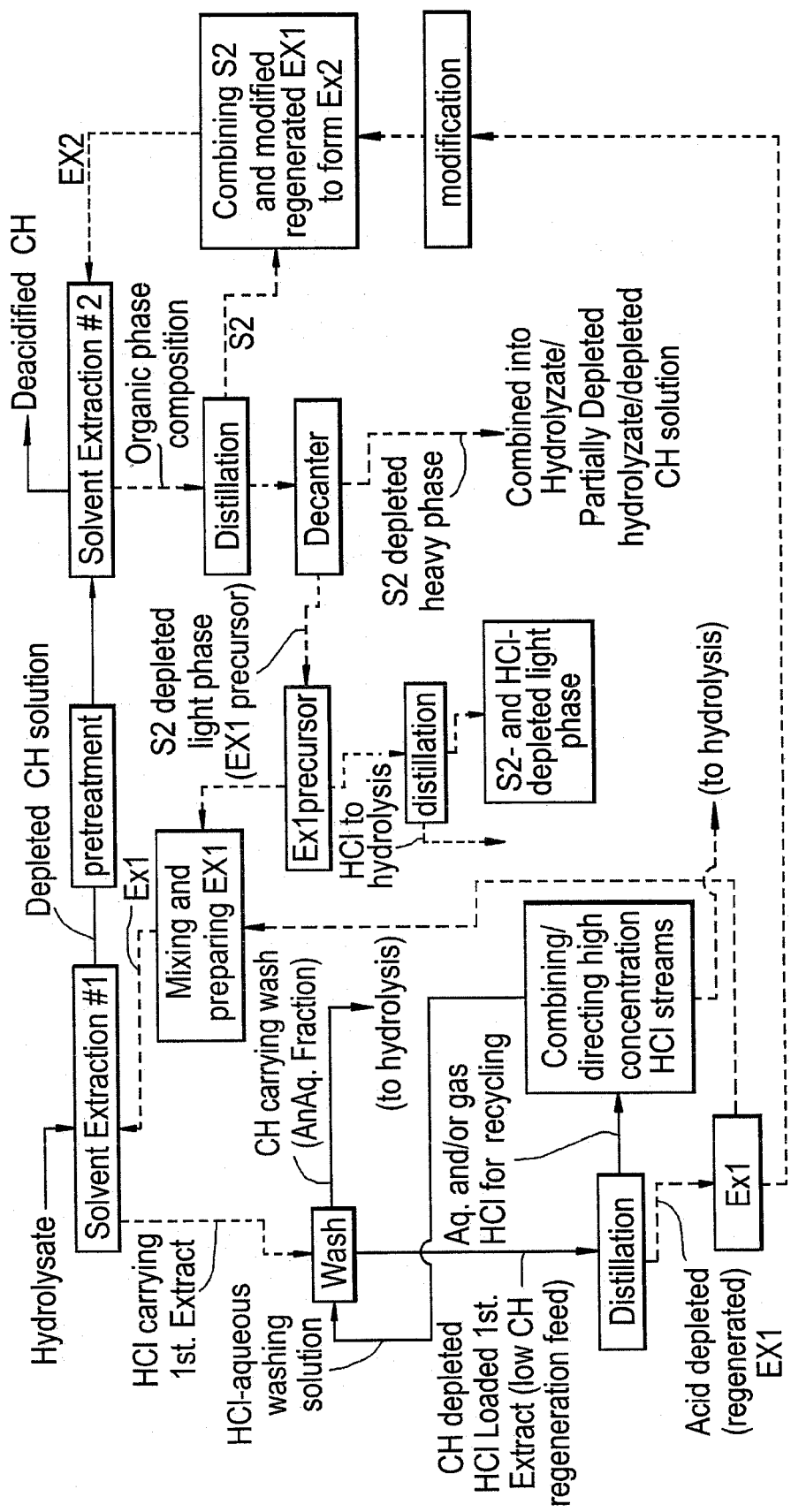

LIGNOCELLULOSIC CONVERSION PROCESSES AND PRODUCTS

RELATED APPLICATIONS

This application is a continuation of U.S. application Ser. No. 15/334,147, filed Oct. 25, 2016, now U.S. Pat. No. 10,876,178, issued Dec. 29, 2020, which is a continuation of U.S. application Ser. No. 14/009,858, filed Feb. 6, 2014, now U.S. Pat. No. 9,512,495, issued on Dec. 6, 2016, which is a U.S. National Phase Application under 35 U.S.C. § 371 of International Application No. PCT/IL2012/050118, filed Apr. 2, 2012, which claims the benefit of U.S. Provisional Application No. 61/483,663, filed May 7, 2011, and U.S. Provisional Application No. 61/473,134, filed Apr. 7, 2011 which applications are incorporated herein by reference in their entireties.

FIELD OF INVENTION

Processes for converting lignocellulose to feedstock and downstream products are disclosed. The processes may include acid treatment of lignocellulose to produce a fermentation feedstock. In various instances, the processes include recovery or recycling of acid, such as recovery of hydrochloric acid from concentrated and/or dilute streams. Downstream products may include acrylic acid-based products such as diapers, paper and paper-based products, ethanol, biofuels such as biodiesel and fuel additives, and detergents.

BACKGROUND

Industries relating to fermentation feedstock use nearly 100 million tons of carbohydrates annually to produce fuel-grade ethanol and other industrial and commercial products such as monomers for the polymer industry, e.g. lactic acid for the production of polylactide. Millions of tons of carbohydrates are also fermented every year to food and feed products, such as citric acid and lysine. Carbohydrates are attractive as an environmental-friendly substrate since they are obtained from renewable resources, presently, mainly, sucrose from sugar canes and glucose from corn and wheat starches. However, such renewable resources are limited in volume and increased consumption is predicted to increase food costs. There is therefore a need to generate carbohydrates from renewable non-food resources.

An abundant and relatively-low cost carbohydrate source is woody materials, such as wood and co-products of wood processing and residues of processing agricultural products, e.g. corn stover and cobs, sugar cane bagasse and empty fruit bunches from palm oil production. There is also the potential of growing switch grass and other "energy crops" that generate low-cost rapid growing biomass for that purpose. Such biomass contains cellulose, hemicellulose and lignin as the main components and is also referred to as lignocellulose or lignocellulosic material. Such material also contains mineral salts (ashes) and organic compounds, such as tall oils. Cellulose and hemicellulose, which together form 65-80% of lignocellulosic materials, are polysaccharides and their hydrolysis forms carbohydrates suitable for fermentation and chemical conversion to products of interest. Hydrolysis of hemicellulose is relatively easy, but hydrolysis of cellulose, which typically forms more than one half of the polysaccharides content, is difficult due to its crystalline structure.

Despite previous efforts in the field, the known technologies are expensive or industrially unacceptable. Thus, there is a need for alternative and/or lower-cost hydrolysis methods. In addition, carbohydrate costs could be lowered by recognizing the value of and utilizing co-products such as lignin and tall oils. There is therefore a need for a technology that, in addition to using low-cost hydrolysis, generates those co-products at high quality as well as generates carbohydrates that may be converted to ethanol and/or other industrially useful products.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some exemplary embodiments of the invention, there is provided a consumable product comprising a material and a marker molecule at a concentration ≥100 ppb. In some embodiments, the marker molecule is selected from the group consisting of furfural, hydroxy-methyl furfural, products of furfural or hydroxy-methylfurfural condensation, color compounds derived from sugar caramelization, levulinic acid, acetic acid, methanol, galacturonic acid, covalently-bound chlorine, alkyl chloride with at least six carbon atoms, SI solvent and glycerol. Alternatively or additionally, in some embodiments the product is selected from the group consisting of: fuel, diapers, paint, carpet, and paper. Alternatively or additionally, in some embodiments an amount of the material is derived from lignocellulose or petroleum, the amount selected from the group consisting of at least 5%, 10%, 20%, and 50% by weight. Alternatively or additionally, in some embodiments an amount of the material is produced from lignocellulosic material and an additional amount of the material is produced from a raw material other than lignocellulosic material. Alternatively or additionally, in some embodiments the material produced from lignocellulosic material and the material produced from a raw material other than lignocellulosic material are essentially of the same chemical composition.

In some exemplary embodiments of the invention, there is provided a method for producing a cellulose-derived product comprising: hydrolyzing a lignocellulosic material in an acid-comprising hydrolysis medium to generate a cellulose-enriched fraction, a sugars-enriched fraction, and a lignin-enriched fraction; using the cellulose-enriched fraction to produce the cellulose-derived product; using the sugars-enriched fraction to produce a sugar-derived consumable product; and recycling an amount of the acid selected from at least about 80%, 85%, 90%, 95%, and 99%. In some embodiments, the cellulose-derived consumable product is selected from the group consisting of paper, paper-derived products and chemically-modified cellulose. Alternatively or additionally, in some embodiments at least one of the cellulose-enriched fraction, the paper, and the paper-derived product comprise between greater than zero and less than 100 ppm sulfur. Alternatively or additionally, in some embodiments at least one of the cellulose-enriched fraction, the paper, and the paper-derived product comprise between greater than zero and less than 100 ppm wood extractives. Alternatively or additionally, in some embodiments at least one of the cellulose-enriched fraction, the paper, and the paper-derived product comprise less than 1000 ppm water-soluble carbohydrates. Alternatively or additionally, in some embodiments the weight to weight ratio between cellulose in the cellulose-enriched fraction and sugars in the sugars-enriched fraction is in a range between 0.1 and 0.5. Alternatively or additionally, in some embodiments the acid to water weight ratio in the hydrolysis medium is less than 0.65. Alternatively or additionally, in some embodiments the acid is hydrochloric acid. Alternatively or additionally, in some embodiments the hydrolyzing step comprises performing serially a plurality of hydrolysis steps at more than one concentration of acid. Alternatively or additionally, in some embodiments the hydrolyzing step is performed in a counter-current mode of operation.

In some exemplary embodiments of the invention, there is provided a lignocellulosic-derived carbohydrate mixture comprising: (i) oligomers in a proportion relative to total carbohydrate content of at least 0.06, (ii) disaccharides in a proportion relative to the total carbohydrate content of at least 0.05, (iii) pentose in a proportion relative to the total carbohydrate content of at least 0.05, (iv) an alpha-bonded carbohydrate, (v) a beta bonded carbohydrate, (vi) less than 1000 ppm furfural and (vii) more than 100 ppb solvent characterized by a water solubility of less than 10% and by at least one of (a1) having a polarity related component of Hoy's cohesion parameter (delta-P) between 5 and 10 MPa½ and (b1) having a hydrogen bonding related component of Hoy's cohesion parameter (delta-H) between 5 and 20 MPa½. In some embodiments, there is provided a fermentation broth including a carbohydrate mixture as described herein.

In some exemplary embodiments of the invention, there is provided a lignocelluloses processing unit having input capacity for processing between 5 and 200 tons of lignocellulosic material/hr on dry basis to produce a sugar mixture, characterized in green-house gas emission per pound of sugars produced of less than 0.2 kg C02 equivalent as calculated according to ISO 14040 and ISO 14044 using GaBi4 Software.

In some exemplary embodiments of the invention, there is provided a method for producing a consumer product, the method comprising: i) providing a lignocellulosic material; ii) hydrolyzing the lignocellulosic material in an HCl-comprising hydrolysis medium to form a hydrolyzate comprising carbohydrate and HCl; iii) performing partial or complete deacidification of at least a fraction of the hydrolyzate to produce an HCl fraction for recycle and an HCl-depleted hydrolyzate; and iv) processing at least one of the acid-depleted hydrolyzate or a product thereof to produce a consumer product. In some embodiments, the recycling of at least a portion of the HCl from the hydrolyzate comprises separating HCl from carbohydrate by means of contacting the HCl-depleted hydrolyzate with a resin in a chromatographic mode to form a de-acidified carbohydrate-cut solution and an acid-cut solution. Alternatively or additionally, in some embodiments the providing comprises contacting biomass material with a first extractant comprising a water-soluble organic solvent to form the provided biomass material and an extract and separating solvent from the extract to form separated solvent, an aqueous phase and an organic phase. Alternatively or additionally, in some embodiments the water-soluble organic solvent is selected from the group consisting of ketones and alcohols with up to four carbon atoms. Alternatively or additionally, in some embodiments the first extractant further comprises a weak acid. Alternatively or additionally, in some embodiments the weak acid has a boiling point lower than 100° C. at atmospheric pressure. Alternatively or additionally, in some embodiments the weak acid is selected from the group consisting of sulfurous acid and acetic acid. Alternatively or additionally, in some embodiments the biomass comprises lignin and water-insoluble cellulose, wherein providing comprises contacting biomass material with a sulfite reagent selected from S02, sulfurous acid and salts of sulfurous acid and wherein the contacting forms sulfonated lignin. Alternatively or additionally, in some embodiments the contacting biomass material with the sulfite reagent is conducted in the presence of a water-soluble organic solvent. Alternatively or additionally, in some embodiments the water-soluble organic solvent is selected from the group consisiting of alcohols, aldehydes, ketones, acetone and esters with up to 4 carbon atoms. Alternatively or additionally, in some embodiments the sulfonated lignin is water soluble and wherein the process further comprises the step of separating the water soluble lignin to form at least partially delignified water-insoluble cellulose. Alternatively or additionally, in some embodiments hydrolyzing the lignocellulosic material comprises hydrolyzing the delignified water-insoluble cellulose. Alternatively or additionally, in some embodiments the HO/water ratio in the HCl-comprising hydrolysis medium is greater than 0.6. Alternatively or additionally, in some embodiments HO/water ratio in the recycled HCl fraction is greater than 0.6. Alternatively or additionally, in some embodiments the recycling of at least a portion of the HCl from the hydrolyzate comprises (i) bringing the hydrolyzate, as such or after modification thereof, into contact with a first extractant comprising a first solvent (SI) characterized by a water solubility of less than 10% and by at least one of (a1) having a polarity related component of Hoy's cohesion parameter (delta-P) between 5 and 10 MPa½ and (b1) having a hydrogen bonding related component of Hoy's cohesion parameter (delta-H) between 5 and 20 MPa½, whereupon HCl selectively transfers to the first extractant to form an HCl-carrying first extract and an HCl-depleted aqueous feed; (ii) bringing the HCl-depleted aqueous feed solution into contact with a second extractant comprising S1 and a second solvent S2 characterized by water solubility of at least 30% and by at least one of (a2) having a delta-P greater than 8 MPa½ and (b2) having a delta-H greater than 12 MPa½, whereupon HCl selectively transfers to the second extractant to form an HCl-carrying second extract and an acid-depleted hydrolyzate; and (iii) recovering HCl from the first and second extracts. Alternatively or additionally, in some embodiments the recycling of at least a portion of the HCl from the hydrolyzate comprises: (i) bringing the hydrolyzate, as such or after modification thereof, into contact with a first extractant comprising a first solvent (SI) characterized by a water solubility of less than 15% and by at least one of (a1) having a polarity related component of Hoy's cohesion parameter (delta-P) between 5 and 10 MPa½ and (b1) having a hydrogen bonding related component of Hoy's cohesion parameter (delta-H) between 5 and 20 MPa½, whereupon at least 85% of the HCl in the hydrolyzate selectively transfers to the first extractant to form an HCl-carrying first extract and an HCl-depleted hydrolyzate; and (ii) separating HCl from carbohydrate in the HCl-depleted hydrolyzate by means of contacting the HCl-depleted hydrolyzate with a resin in a chromatographic mode to form a de-acidified carbohydrate-cut solution and an acid-cut solution. Alternatively or additionally, in some embodiments the contacting with a resin comprises introducing the HCl-depleted hydrolyzate into a resin-containing column followed by introducing an aqueous eluant into the resin-containing column, whereupon the acid-cut solution exits the column followed by the de-acidified carbohydrate-cut solution. Alternatively or additionally, in some embodiments the hydrolyzate comprises at least one monomer and at least one oligomer at a total oligomers to total monomers ratio designated OMR1, wherein the acid-cut solution comprises at least one monomer and at least one oligomer at a total oligomers to total monomers ratio designated OMR2 and wherein the de-acidified carbohydrate-cut solution comprises at least one monomer and at least one oligomer at a total oligomers to total monomers ratio designated OMR3 and wherein OMR2>OMR1>OMR3. Alternatively or additionally, in some embodiments the first solvent (SI) is hexanol, 2-ethyl-1-hexanol or a combination thereof, and the second solvent (S2) is ethanol, methanol, or a combination thereof. Alternatively or additionally, in some embodiments the acid-depleted hydrolyzate comprises predominantly glucose, sucrose, xylose, trehalose, gentiobiose, kojibiose, nigerous, sophorose, laminarobiose, arabinose, or combinations thereof. Alternatively or additionally, in some embodiments the step of processing the hydrolyzate comprises combining the hydrolyzate or a product of the hydrolyzate with at least one of a microorganism cell culture, an enzyme, and a chemical catalyst under conditions appropriate for production of a detergent precursor, a polyolefine precursor, a polylactic acid precursor, a polyhydroxyalkanoate precursor, a poly accrylate precursor or an acrylic acid precursor. Alternatively or additionally, in some embodiments the at least one of acrylic acid and polyacrylate precursor is selected from 3-hydroxypropionic acid, lactic acid and ethanol. Alternatively or additionally, in some embodiments the detergent precursor is selected from the group consisting of fatty acid methyl esters, alkanes, fatty alcohols, and farnesene. Alternatively or additionally, in some embodiments the polyhydroxyalkanoate is selected from the group consisting of poly hydroxybutyrate (PHB), poly hydroxyvalerate (PHV), poly(hydroxybutyrate-co-hydroxyvalerate) (PHBV), poly(hydroxybutyrate-co-hydroxyhexanoate) (PHBHx), polyhydroxyoctonate (PHO), PHBO and PHBOd. Alternatively or additionally, in some embodiments the step of processing the acid-depleted hydrolyzate or a product thereof comprises isolation of a mono- or disaccharide or of a combination of mono- and/or disaccharides. Alternatively or additionally, in some embodiments the consumer product is selected from the group consisting of detergent, polyethylene-based products, polypropylene-based products, polyolefin-based products, polylactic acid (polylactide)-based products, polyhydroxyalkanoate-based products and polyacrylic-based products. Alternatively or additionally, in some embodiments the detergent comprises a sugar-based surfactant, a fatty acid-based surfactant, a fatty alcohol-based surfactant, or a cell-culture derived enzyme. Alternatively or additionally, in some embodiments the polyacrylic-based product is selected from plastics, floor polishes, carpets, paints, coatings, adhesives, dispersions, flocculants, elastomers, acrylic glass, absorbent articles, incontinence pads, sanitary napkins, feminine hygene products, and diapers. Alternatively or additionally, in some embodiments the polyolefin-based products are selected from milk jugs, detergent bottles, margarine tubs, garbage containers, water pipes, absorbent articles, diapers, non wovens, HDPE toys and HDPE detergent packagings. Alternatively or additionally, in some embodiments the polypropylene based products are selected from absorbent articles, diapers and non wovens. Alternatively or additionally, in some embodiments the polylactic acid based products are selected from packaging of agriculture products and of dairy products, plastic bottles, biodegradable products and disposables. Alternatively or additionally, in some embodiments the polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastometers, films, coatings, aqueous dispersants, fibers, intermediates of pharmaceuticals and binders. Alternatively or additionally, in some embodiments the hydrolyzing and recycling steps are performed in a continuous process. Alternatively or additionally, in some embodiments the hydrolyzing and recycling steps are performed in a batch process of at least 100 kilograms of starting lignocellulose. Alternatively or additionally, in some embodiments the method is performed in a continuous process at a rate to consume at least one thousand tons of lignocellulose per year. In some exemplary embodiments of the invention, there is provided a method for producing a product based on at least one of ethanol, butanol, isobutanol, a fatty acid, a fatty acid ester, a fatty alcohol or biodiesel, comprising a method as described herein, further comprising combining the acid-depleted hydrolyzate or a product thereof and a microorganism cell culture to produce at least one of ethanol, butanol, isobutanol, a fatty acid, a fatty acid ester, a fatty alcohol, isobutene condensation products, jet fuel, gasoline, diesel fuel, drop-in fuel, diesel fuel additive, and a precursor thereof. Alternatively or additionally, in some embodiments the consumer product is ethanol-enriched gasoline, butanol-enriched gasoline, diesel fuel, gasoline, jet fuel, biodiesel or drop-in fuels. In some exemplary embodiments of the invention, there is provided a consumer product, a precursor of a consumer product, or an ingredient of a consumer product produced from lignocellulose according to a method as described herein. In some exemplary embodiments of the invention, there is provided a consumer product, a precursor of a consumer product, or an ingredient of a consumer product comprising at least one chemical produced from lignocellulose according to a method as described herein, wherein the chemical is selected from carboxylic and acids, dicarboxylic acids, hydroxylcarboxylic acids, hydroxyl dicarboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals. In some embodiments the product is ethanol-enriched gasoline, butanol-enriched gasoline, diesel fuel, gasoline, jet fuel, biodiesel or drop-in fuels. Alternatively or additionally, in some embodiments the consumer product, precursor of a consumer product, or ingredient of a consumer product as described herein has a ratio of carbon-14 to carbon-12 of about $2.0 \times 10$-13 or greater. Alternatively or additionally, in some embodiments there is provided a consumer product comprising an ingredient as described herein and an ingredient produced from a raw material other than lignocellulosic material. Alternatively or additionally, in some embodiments the consumer product according as described herein, wherein the ingredient as described herein and the ingredient produced from a raw material other than lignocellulosic material are essentially of the same chemical composition. Alternatively or additionally, in some embodiments the consumable product as described herein, includes a marker molecule at a concentration of at least 100 ppb. Alternatively or additionally, in some embodiments the consumable product as described herein includes a marker molecule selected from the group consisting of furfural, hydroxy-methyl furfural, products of furfural or hydroxymethylfurfural condensation, color compounds derived from sugar caramelization, levulinic acid, acetic acid, methanol, galacturonic acid, covalently-bound chlorine, alkyl chloride with at least six carbon atoms, S1 solvent and glycerol. Alternatively or additionally, in some embodiments of the method described herein the hydrolyzing further forms a cellulose-enriched fraction a lignin-enriched fraction, further comprising the step of using the cellulose-enriched fraction to produce the cellulose-derived product. Alternatively or additionally, in some embodiments the method described herein has a green-house gas emission per pound of sugar in the acid-depleted hydrolyzate of less than 0.2 kg $CO_2$ equivalent as calculated according to ISO 14040 and ISO 14044 using GaBi4 Software.

DESCRIPTION OF THE DRAWINGS

The novel features of the invention are set forth with particularity in the appended claims. An understanding of the features and advantages of the present invention may be obtained by reference to the following detailed description that sets forth illustrative embodiments, in which the principles of the invention are utilized, and the accompanying drawings of which:

FIG. 1 shows an embodiment of the present invention for recovery of HCl.

DETAILED DESCRIPTION

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

I. Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

As used herein, the term fermentation feedstock means a carbohydrates-comprising composition, typically an aqueous solution. According to an embodiment, said fermentation feedstock is used in fermentation as such. According to another embodiment, it is modified before being used, e.g. by changing the concentration of the carbohydrates (e.g. by diluting), by adding nutrients, by fractionation (e.g. separating pentoses from hexoses), by removal of impurities, etc.

As used herein, the phrase "essentially excluded" means that the excluded component may be present in an insubstantial amount or an amount that does not significantly contribute to the properties of the material or process.

The terms sugar, sugars, carbohydrate and carbohydrates are used herein interchangeably. The same is true for monosaccharides and monomer, disaccharides and dimers and oligosaccharides and oligomers.

As used herein and unless specified otherwise, both terms, carbohydrate and carbohydrates mean any of a single type of carbohydrate, (e.g. glucose, xylose, galactose, etc.), a plurality of carbohydrates, (e.g. mixtures of those), monosaccharides (e.g. glucose) and oligosaccharides (e.g. cellobiose or maltose) of various degrees of polymerization, (dimmers, trimers, tetramers, etc.), as long as they are soluble in the hydrolyzate, and combinations thereof.

As used here, the term higher oligosaccharides means trisaccharides, tetrasaccharides, etc.

The term monomers is used here to describe both non-polymerized carbohydrates and the units out of which oligomers are formed.

As used herein, the term lignocellulosic acid hydrolyzate means a product of hydrolyzing a lignocellulosic material in an HCl-comprising medium.

II. Lignocellulose Source and Pre-Treatment

Any source of lignocellulose consistent with the processing steps may be used.

Accordingly, a polysaccharide-comprising lignocellulosic material is provided. Said polysaccharides typically comprise cellulose and hemicelluloses. In addition, lignocellulosic material typically may comprise lignin, ash, extractives and other components. As used herein, the term extractives means wood components extractable with an organic solvent, e.g. tall oils and terpenes. Any lignocellulosic material is suitable.

Lignocellulose may refer to any cellulosic or lignocellulosic material and includes materials comprising cellulose, and optionally further comprising hemicellulose, lignin, starch, oligosaccharides and/or monosaccharides. Lignocellulose may also comprise additional components, such as protein and/or lipid. According to the present method, lignocellulose may be derived from a single source, or lignocellulose can comprise a mixture derived from more than one source; for example, lignocellulose could comprise a mixture of corn cobs and corn stover, or a mixture of grass and leaves. Lignocellulose includes, but is not limited to, bioenergy crops, agricultural residues, municipal solid waste, industrial solid waste, sludge from paper manufacture, yard waste, wood and forestry waste. Examples of lignocellulose include, but are not limited to, corn kernel fiber, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, oilseeds, trees, branches, roots, leaves, wood chips, sawdust, shrubs and bushes, vegetables, fruits, flowers and animal manure. In one embodiment, lignocellulose that is useful for the present method includes lignocellulose that has a relatively high carbohydrate value, is relatively dense, and/or is relatively easy to collect, transport, store and/or handle. In one embodiment of the invention, lignocellulose that is useful includes corn cobs, corn stover and sugar cane bagasse.

In various embodiments, lignocellulose is selected from the group consisting of: softwood chips, hardwood chips, whole tree chips from softwood or hardwood, grass, agricultural residue, and cork. In various embodiments, the lignocellulose is selected from wood and co-products of wood processing and residues of processing agricultural products, e.g. corn stover and cobs, sugarcane bagasse and empty fruit bunches from palm oil production, or from plant material such as switch grass, miscanthus, hemp, corn, poplar, willow, sorghum, and a variety of tree species, including pine, eucalyptus, and oil palm. In various embodiments, the lignocellulose is selected from wood chips, switch grass, and sugarcane. In various embodiments, the lignocellulose is selected from wood and/or wood processed products. As a non-limiting example, wood processed products may include products used for recycling, such as paper, cardboard, corrugated paper, and the like. In various embodiments, the lignocellulose may comprise post-consumer paper. In various embodiments, the lignocellulose may be a byproduct from the process of making paper, for example paper-making sludge.

III. Acid Treatment of Lignocellulose

Acid can be used as a hydrolysis catalyst in converting lignocellulose to carbohydrate. Typically, said converting to carbohydrate is conducted by contacting the biomass with an acid-comprising hydrolysis medium. Typically, the compostion of the hydrolysis medium changes during said converting, since formed carbohydrates are added to it. In various embodiments, acid may be used as the sole catalyst, while in other embodiments, acid hydrolysis is combined with further hydrolysis steps such as enzymatic hydrolysis. Since acid acts as a catalyst, it is not consumed in the process, although losses may occur through industrial processing or repeated use. Any acid compatible with the conversion of lignocellulose to carbohydrate may be used. In various embodiments, a suitable acid is defined as an acid that has the property of dissociating completely or essentially completely in water at low concentration. In various embodiments, acids that may be used include strong acids such as strong mineral acids and/or strong organic acids. For example, suitable acids may include hydrochloric acid, sulfuric acid, phosphoric acid, nitric acid, hydroiodic acid, hydrobromic acid, hydrofluoric acid, methanesulfonic acid, toluenesulfonic acid, and trifluoroacetic acid. In various embodiments, specific acids may be specifically excluded as hydrolysis catalyst. For example any one or a combination of sulfuric acid, phosphoric acid, nitric acid, hydroiodic acid, hydrobromic acid, hydrofluoric acid, methanesulfonic acid, toluenesulfonic acid, and trifluoroacetic acid may be essentially excluded. In various embodiments, sulfuric acid is essentially excluded.

In various embodiments, the acid catalyst for lignocellulose hydrolysis is hydrochloric acid. In various embodiments, the acid is greater than about 50% by weight hydrochloric acid, or greater than about 60%, greater than about 70%, greater than about 80%, greater than about 90%, greater than about 95%, greater than about 96%, greater than about 97%, greater than about 98%, or greater than about 99% by weight hydrochloric acid. HCl hydrolysis may form a hydrolyzate stream containing the carbohydrate products, other soluble components of the lignocellulosic material, and HCl. Since the lignin fraction of lignocellulosic materials does not hydrolyze and stays essentially insoluble, the process also forms a co-product stream containing the lignin dispersed in or wetted by an aqueous solution of HCl. HCl-based hydrolysis of lignocellulosic material may be implemented on an industrial scale, with or without the use of enzymes.

One method further comprises the step of converting carbohydrates of said monosaccharides-enriched hydrolyzate for a residence time suitable for the formation of a downstream product. According to various embodiments, said converting comprises fermentation, chemical reaction or a combination thereof, e.g. fermenting carbohydrate into an intermediate product that is further converted in a chemical reaction. According to a preferred embodiment, said converting comprises fermentation.

According to an embodiment, said treating with enzyme composition is conducted prior to said converting. According to another embodiment, first some of said carbohydrates in said deacidified hydrolyzate are converted, then the hydrolyzate is treated with an enzyme composition and optionally carbohydrates therein are further converted. According to other embodiments, multiple conversion steps, multiple treatment steps or both are conducted in various sequences. According to a preferred embodiment, said treating with said enzyme composition and said converting are conducted, at least partially, simultaneously. Thus, according to an embodiment, at least during part of said residence time, said converting is conducted simultaneously with said treating with an enzyme composition.

Said converting step may generate a downstream product. According to an embodiment, said downstream product is selected from the group consisting of fuels, carboxylic acids, amino acids, proteins and monomers for the polymer industry. In various embodiments, one method of the present invention is suitable for the production of a commercial product, such as an acrylic acid-based product. Such products may include diapers, various plastics, coatings, adhesives, elastomers, as well as floor polishes, and paints.

Cellulose and Hemicellulose Fraction

In various embodiments, a lignocellulosic acid hydrolyzate is produced. According to an embodiment, the lignocellulosic material results from softwood. According to an embodiment, the lignocellulosic material results from pine. According to an embodiment, said hydrolysis is conducted in a concentrated HCl-comprising hydrolysis medium. The hydrolyzate comprises carbohydrates resulting from hydrolyzing polysaccharides of the lignocellulosic material, mainly cellulose and hemicelluloses.

According to one method, polysaccharides of lignocellulosic material are hydrolyzed in an HCl-comprising hydrolysis medium to form a hydrolyzate comprising carbohydrates and HCl, also referred to herein as a hydrolyzate. Hydrolysis is catalyzed by concentrated HCl in the hydrolysis medium. The weight/weight ratio of HCl to (HCl+water) in said hydrolysis medium is at least 0.37, preferably at least 0.39 and more preferably at least 0.41. According to a preferred embodiment, said hydrolysis is conducted in a counter-current mode of operation so that a low-carbohydrate HCl solution is contacted with the lignocellulosic material after the majority of its polysaccharides are hydrolyzed, while a carbohydrate-rich HCl solution is contacted with the fresh lignocellulosic material still comprising the majority of its polysaccharides. In various embodiments, the hydrolysis is conducted at less than about 50° C., less than about 40° C., or less than about 30° C. According to another preferred embodiment, said hydrolysis is conducted at a relatively low temperature, typically of less than 25° C. Preferably, during at least a fraction of the time the hydrolysis is conducted at even lower temperature, typically of less than 20° C., preferably of less than 15° C. The hydrolysis may be conducted with active cooling or with passive cooling.

According to one method, the relative amounts of hydrolyzing medium and lignocellulosic material and the moisture of the latter are selected to form a concentrated carbohydrate solution. In said HCl-comprising hydrolyzate, the weight/weight ratio of carbohydrates to (carbohydrates+water) is at least 0.20, preferably at least 0.25 and more preferably at least 0.30.

Viscous Carbohydrate Product

A viscous fluid may be formed in the course of practicing the invention. The viscous fluid may comprise at least one carbohydrate, water, HCl and optionally also a second solvent. The viscous fluid is homogeneous according to one embodiment and heterogeneous according to another. According to an embodiment, the viscous fluid is heterogeneous and comprises a continuous phase and a dispersed phase, in which dispersed phase the major component is a solvent, according to one embodiment, and solid carbohydrate according to another.

The viscous fluid may comprise at least 75% carbohydrates, preferably at least 80%, more preferably at least 83% and most preferably at least 86% as calculated by 100CH/(CH+W), wherein CH is the amount of carbohydrates and W is the amount of water. Typically, the majority of the carbohydrates in the viscous fluid are the products of hydrolyzing the polysaccharides of the polysaccharide comprising feed to hydrolysis, typically a lignocellulosic material. Alternatively, carbohydrates from other sources are combined with products of hydrolysis to form an evaporation feed and end up in the viscous fluid. According to another embodiment, the viscous fluid comprises carbohydrates formed in isomerization of other carbohydrate, e.g. fructose formed from glucose.

According to various embodiments, the carbohydrates in the viscous solution are monomers, dimmers, trimers, higher oligomers, and their combinations. Those monomers, dimmers, trimers, and/or higher oligomers comprise monomers selected from the group consisting of glucose, xylose, mannose, arabinose, galactose, other sugar hexoses, other pentoses and combinations of those. According to a preferred embodiment, glucose is the main carbohydrate there.

The water content of the viscous fluid is between 2% wt and 25% wt, preferably between 3% wt and 20% wt, more preferably between 4% wt and 18% wt and most preferably between 5% wt and 15% wt. The HCl content of the viscous fluid is between 10% wt and 55% wt, preferably between 15% wt and 50% wt, more preferably between 18% wt and 40% wt and most preferably between 20% wt and 38% wt as calculated by 100HCl/(HCl+W), wherein HCl is the amount of HCl in the viscous fluid and W is the amount of water there. Organic solvent content of the viscous fluid may be between 0% wt and 25% wt, preferably between 1% wt and 20% wt, more preferably between 2% wt and 18% wt and most preferably between 3% wt and 15% wt.

According to an embodiment, the HCl/water weight/weight ratio in the viscous fluid is in the range between 0.20 and 1.0, preferably between 0.3 and 0.9 and more preferably between 0.4 and 0.8. According to another embodiment, the carbohydrate/water weight/weight ratio in the viscous fluid is in the range between 2 and 20, preferably between 3 and 15, more preferably between 4 and 12 and most preferably between 5 and 11. According to still another embodiment, the HCl/carbohydrate weight/weight ratio in the viscous fluid is in the range between 0.02 and 0.15, preferably between 0.03 and 0.12 and more preferably between 0.04 and 0.10.

According to an alternative embodiment said hydrolyzate, said depleted hydrolyzate, said further depleted hydrolyzate or a first aqueous stream forms the second evaporation feed as such (with no addition of the second solvent). Water and HCl are distilled from the second evaporation feed at a temperature below 100° C. and at a pressure below 1atm, whereupon a second vapor phase and a viscous fluid are formed. The viscous fluid of this alternative embodiment comprises carbohydrates, HCl and water according to the above composition, but no solvent. According to a first modification, evaporation starts in the absence of a solvent, and the second organic solvent is added to the composition during evaporation. According to a second modification, evaporation is conducted in the absence of a solvent, and the second organic solvent is added to the formed solution (distillation product) at the end of the evaporation. In both modifications, the viscous fluid comprises the second organic solvent according to the above composition.

The distillation as described herein removes much of the acid and the water left after HCl separation. According to an embodiment, combined acid removal is greater than 80% of the initial acid content of the hydrolyzate, preferably greater than 85%, more preferably greater than 90% and, most preferably greater than 95%. According to another embodiment, the combined water removal is greater than 80% of the initial water content of the hydrolyzate, preferably greater than 85%, more preferably greater than 90% and, most preferably greater than 95%. As a result of that water removal, the formed viscous fluid is highly concentrated in carbohydrates. It was surprisingly found that formed viscous fluid is fluid enough to be spray dried. Thus, according to a preferred embodiment, the viscosity of the viscous fluid, as measure at 80° C. by the Brookfield method is less than 150 cP, preferably less than 120 cP more preferably less than 100 cP, and most preferably less than 90 cP. Without wishing to be limited by theory, a possible explanation for the capability of spray drying of the viscous fluid may be some specific role the solvent plays in the viscous fluid and/or the specific composition of the carbohydrate, e.g. the mix of carbohydrates it is made of and the degree and nature of oligomerization.

According to a preferred embodiment of the invention, the ratio between the amount of first aqueous solution and the amount of the second organic solvent contacted with it is such that solvent is found in the viscous solution at the end of the distillation. According to a further preferred embodiment, the solvent/water ratio in the viscous fluid is greater than the solvent/water ratio in the water-solvent heterogeneous azeotrope. According to an embodiment of the invention, in the viscous fluid the second organic solvent/water weight/weight ratio is R2, the second organic solvent has heterogeneous azeotrope with water and the second organic solvent/water weight/weight ratio in said azeotrope is R22 and R2 is greater than R22 by at least 10%, preferably at least 25%, more preferably at least 40% and most preferably at least 50%. According to still another embodiment, the second organic solvent/water weight/weight ratio in said second evaporation feed is R23, the second organic solvent/water weight/weight ratio in said azeotrope is R22 and R23 is greater than R22 by at least 10%, preferably at least 25%, more preferably at least 40% and most preferably at least 50%.

According to an embodiment, the second organic solvent used to form the second evaporation feed is not pure, e.g. contains water and or HCl. According to a related embodiment, the used second organic solvent is recycled from another step in the process (e.g. from condensate of a distillation step). In such case, R23 refers to the ratio between the solvent on solutes free basis and water. As indicated earlier, R22 may depend on the temperature of distillation, on its pressure and on the content of the other components in the evaporation feed (including HCl and carbohydrates). As used before, R22 is referred to the second solvent/water weight/weight ratio in the solvent-water binary system. On distillation from the second evaporation feed, there is at least one additional volatile component, co-distilling with water and the solvent, i.e. HCl. Thus, this system could be referred to as a ternary system. In such system solvent/water ratio in the vapor phase may differ from that in the binary system. As indicated, that ratio may further depend on the carbohydrates concentration in the second evaporation feed. In such complex systems, R22 refers to the solvent/water ratio in the vapor phase formed on distilling from the second evaporation feed.

According to an embodiment, the method further comprising the steps of condensing the vapors in said second vapor phase to form two phases, a second organic-rich one and a first water-rich one, using said second organic solvent-rich phase in a contacting step and using said first water-rich phase for generating said hydrolysis medium. Any method of condensing is suitable, preferably comprising cooling, pressure increase or both. Typically, the solvent-rich phase also comprises water and HCl and the water-rich one also comprises solvent and HCl. Any method of separating the phases is suitable, e.g. decantation. The second organic solvent-rich phase is used as is or after some treatment, e.g. removal of dissolved water, HCl or both. The first water-rich phase is used for regenerating the hydrolysis medium as is or after some treatment.

Combined HCl removal is high, possibly exceeding 95%. Yet, some acid remains and is preferably removed for high recovery as well as for the production of low-acid product. Thus, according to a preferred embodiment, the viscous fluid is further treated. According to a related embodiment, such further treatment comprises removal of residual HCl to form de-acidified carbohydrates. According to various embodiments, removal of residual HCl involves at least one of solvent extraction, membrane separation, ion-exchange and evaporation. According to an embodiment, the viscous solution is diluted prior to such removal of HCl, while according to others it is not. According to an embodiment, the residual HCl is removed by solvent extraction, using for that purpose the extractants as described in PCT/IL2008/000278, PCT/IL2009/000392 and Israel Patent Application No: 201,330, the relevant teachings of which are incorporated herein by reference. According to another embodiment, the second organic solvent is used as the extractant for the removal of the residual HCl.

According to a particularly preferred embodiment, the method comprises removal of the residual HCl by distillation. According to a related embodiment, distillation is conducted on the viscous fluid as such or after slight modifications, such as minor adjustment of the carbohydrate concentration and changing the amount of the second organic solvent there. Such changing the amount may comprise adding or removing such solvent. Optionally, another solvent is added. According to a preferred embodiment, the ratio between the second organic solvent in the viscous fluid and the water there is such that on azeotropic distillation of water and the solvent, essentially all the water is removed, while excess solvent remains. Such excess solvent is removed, according to an embodiment, by further distillation or in a separate operation.

According to a particularly preferred embodiment, the method comprises the step of spray drying the viscous fluid to form de-acidified solid carbohydrate composition and vapors of HCl, water and optionally the solvent. Spray drying conditions are adjusted, according to an embodiment, for removing essentially all the water from the viscous solution, while some of the second organic solvent may stay and be removed subsequently. According to an embodiment, the viscous fluid is sprayed, as such or after some modification into a hot vapor stream and vaporized. Solids form as moisture quickly leaves the droplets. A nozzle is usually used to make the droplets as small as possible, maximizing heat transfer and the rate of water vaporization. Droplet sizes range, according to an embodiment, from 20 to 180 μm, depending on the nozzle. A dried powder is formed in a single step, within a short residence time and at a relatively low temperature, all of which minimize carbohydrates degradation. According to a preferred embodiment, the hot and dried powder is contacted with water in order to accelerate cooling and to form an aqueous solution of the carbohydrate. According to an embodiment, residual second solvent is distilled out of that carbohydrates solution.

One method of the present invention enables the removal of the majority of the acid at relatively low cost by combining distillation of HCl (as a nearly dry gas, as a water-HCl azeotrope, and as a mixture of HCl, water and second solvent vapors) and the efficient removal of the residual acid in spray drying. It was surprisingly found that residual HCl removal in spray drying is more efficient than suggested by the prior art. Thus, according to a preferred embodiment, in the de-acidified solid carbohydrate composition, HCl/carbohydrates weight/weight ratio is less than 0.03, preferably less than 0.02, more preferably less than 0.01 and most preferably less than 0.005. Without wishing to be limited by theory, possible explanation for the high efficiency could be some specific role the solvent plays and/or the specific composition of the carbohydrate, e.g. the mix of carbohydrates it is made of and the degree and nature of oligomerization.

Reaching low HCl concentrations in the de-acidified solid carbohydrate represents high yield of acid recovery from the hydrolyzate of the hgnocellulosic material. Thus, according to an embodiment of the method, at least 95% of the acid in the hydrolyzate is recovered, more preferably at least 96% and most preferably at least 98%.

Thus, according to an embodiment of the invention, essentially all the HCl in the hydrolyzate is removed and an essentially HCl-free carbohydrate stream is formed by a combination of distillation operations with no need for other acid removal means, such as solvent extraction or membrane separation.

In various embodiments, the present invention provides a method for the production of fermentable sugars, comprising (i) providing sugarcane material comprising water-insoluble polysaccharides, lignin and at least 1% sucrose; (ii) solubilizing sucrose and hydrolyzing water-insoluble polysaccharides in a concentrated HCl hydrolysis medium to form an HCl-comprising lignin stream and a hydrolyzate comprising biomass carbohydrates, sucrose values and HCl; and (iii) deacidifying said hydrolyzate to form recovered HCl and a deacidified carbohydrate solution comprising biomass carbohydrates and sucrose values.

According to an embodiment, the combined amount of sucrose values and biomass carbohydrates is at least 90% of the theoretical value.

According an embodiment, said hydrolyzate comprises hydroxymethylfurfural and the weight/weight ratio between hydroxymethylfurfural and carbohydrates in said hydrolyzate is less than 0.01. According another embodiment, said hydrolyzate comprises furfural and the weight/weight ratio between furfural and carbohydrates in said hydrolyzate is less than 0.01.

Lignin Fraction

In the course of acid-catalyzed hydrolysis of lignocellulosic material such as a counter-current process, a lignin fraction is generated. In various embodiments, hydrolysis of the lignin fraction may result in a lignin composition comprising between 5% wt and 50% wt lignin, less than 12% wt water, between 50% wt and 90% wt of a first organic solvent (S1) and less than 10% wt HCl, which first organic solvent is characterized by a water solubility of less than 10% and by at least one of (a1) having a delta-P between 5 and 10 MPa$^{1/2}$ and (b1) having a delta-H between 5 and 20 MPa$^{1/2}$. According to an embodiment, the lignin composition further comprises at least one carbohydrate and the concentration of said carbohydrate is less than 5% wt.

Enzymatic Treatments in Combination with Acid Treatment of Lignocellulose

In various embodiments, concentrated-acid-hydrolysis-formed carbohydrate solutions contain, in addition to monosaccharides, a significant amount of oligomers, mainly dimers, but optionally also trimers and higher oligomers. For some applications, such oligomers are acceptable. However, some fermentations do not use oligomers or use them at a lower yield. Thus, in some embodiments, methods of acid hydrolysis of lignocellulose are supplemented with enzymatic hydrolysis of oligomers in carbohydrate solutions initially produced by concentrated HCl hydrolysis of lignocellulosic material followed by deacidifying the hydrolyzate. In various embodiments, the enzymatic hydrolysis is performed without having to concentrate dilute carbohydrate solutions, i.e. the enzymatic hydrolysis is perfomed at relatively high concentration.

According to a first aspect, a method is provided for the production of a feedstock product comprising the steps of (a) providing a polysaccharide-comprising lignocellulosic material; (b) hydrolyzing said polysaccharide in an HCl-comprising hydrolysis medium to form a hydrolyzate comprising carbohydrates and HCl; (c) deacidifying said hydrolyzate to form a deacidified hydrolyzate comprising monosaccharides, disaccharides and optionally containing higher oligosaccharides; (d) treating said deacidified hydrolyzate with an enzyme composition comprising enzymes capable of hydrolyzing alpha bonds, whereupon at least 10% of said disaccharides, and optionally at least 10% of said higher oligosaccharides are hydrolyzed to form a carbohydrates-containing, monosaccharides-enriched, hydrolyzate; and (e) converting carbohydrates of said monosaccharides-enriched hydrolyzate for a residence time suitable for the formation of a fermentation product wherein (i) in said hydrolysis medium, the weight/weight ratio of HCl to (HCl+water) is at least 0.37; (ii) in said HCl-comprising hydrolyzate, the weight/weight ratio of carbohydrates to (carbohydrates+water) is at least 0.20; (iii) in said deacidified hydrolyzate, the weight/weight ratio of carbohydrates to (carbohydrates+water) is at least 0.35; and (iv) in said deacidified hydrolyzate the weight/weight ratio between disacchandes and total carbohydrates is at least 0.1.

In various embodiments, one method of the present invention comprises the step of treating deacidified hydrolyzate with an enzyme composition comprising enzymes capable of hydrolyzing alpha bonds. According to an embodiment glucose forms more than 50% of the carbohydrates in said deacidified hydrolyzate, typically more than 60% and in many cases more than 70% or more than 80%, depending on the composition of the lignocellulosic material. The glucose units in cellulose are bound via beta (1-´4) bonds. Without wishing to be bound by theory, it is therefore surprising to find that enzymes capable of hydrolyzing alpha bonds may have an important contribution to hydrolyzing of oligomers in said deacidified hydrolyzate.

According to a method of the present invention, treatment with an enzyme composition comprising enzymes capable of hydrolyzing alpha bonds results in the hydrolysis of at least 10% of the disaccharides in said hydrolyzate, preferably at least 20% and more preferably at least 30%. According to an embodiment, treating with said enzyme composition also results in the hydrolysis of at least 10% of said higher oligosaccharides.

Hydrolyzing disaccharides results in the formation of monosaccharides. Hydrolyzing oligosaccharides results in the formation of monosaccharides, oligosaccharides of lower degree of polymerization, e.g. disaccharides formation from trisaccharides, and combinations thereof. Such hydrolyzing oligosaccharides produces, according to an embodiment, disaccharides. According to said embodiment, while at least 10% of the disaccharides in said hydrolyzate are hydrolyzed to monosaccharides, the concentration of disaccharides increases on such treating with enzyme composition due to the hydrolysis of higher oligosaccharides. Yet, the hydrolysis of the disaccharides is typically reflected in increasing concentration of the monosaccharides in the treated hydrolyzate, which forms monosaccharides enriched hydrolyzate.

According to an embodiment, in said treating with enzymes the weight/weight ratio of carbohydrates to (carbohydrates+water) is at least 0.15, preferably at least 0.20.

According to an embodiment, said enzyme composition further comprises enzymes capable of hydrolyzing beta bonds. According to an embodiment, said enzyme composition comprises enzymes selected from the group consisting of cellulases, hemicellulases, transglucosidases, glucoamylases, alpha-glucosidase and pullulanase. According to various embodiments, said enzyme composition comprises a single-type enzyme or a mixture (cocktail) of enzymes. According to alternative embodiments, said treating with said enzyme composition is conducted in a single step or in multiple steps, which steps differ, according to an embodiment, in the composition of enzymes in said enzyme composition, in temperature in pH and any combination thereof. According to an embodiment, said enzyme composition comprises immobilized enzymes. According to various embodiments, all the enzymes in said enzyme composition are immobilized or only part of the enzymes there are immobilized. According to an embodiment, said treating is conducted in multiple steps and immobilized enzymes are used in some of those steps or in all of them.

IV. Recovery of Acid from Treatment of Lignocellulose

In order to provide a low-cost hydrolysis process, the HCl should be separated from the hydrolysis products and co-products and recycled for re-use. Separation and recycling of HCl presents many challenges. For example, the recovery yield of HCl needs to be high in order to minimize costs related to: acid losses, consumption of neutralizing base, and disposal of the resulting salt formed by neutralization of the residual acid in the product. In addition, residual acid content of the product and the co-products should be low in order to enable their optimal use. Acid recovery from the hydrolyzate should be conducted under conditions, i.e. temperature conditions, for minimizing thermal degradation and HQ-catalyzed carbohydrate degradation.

In addition, recovery of HCl from the lignin co-product stream is complicated by the need to deal with lignin solids and by the need to form HCl-free lignin. Washing HCl off of the lignin requires large amounts of water, resulting in a wash solution which contains dilute acid. Recycling the dilute acid back to the hydrolysis requires re-concentration of the dilute acid, which increases costs.

Another major challenge is related to the concentration of the separated and recovered acid. According to an embodiment, for high yield hydrolysis of the cellulosic fraction of the lignocellulosic material, concentrated HCl is required, typically greater than 40%. Thus, the recovered acid should be obtained at that high concentration in order to minimize re-concentration costs.

Israeli patent application number 206,152, the teachings of which are incorporated herein by reference, discloses a method for processing a lignocellulosic material and for the production of a carbohydrate composition and optionally a lignin product, comprising: (i) providing a lignocellulosic material feed comprising a polysaccharide and lignin; (ii) hydrolyzing said polysaccharide in an HQ-comprising hydrolysis medium to form a hydrolyzate, which hydrolyzate comprises at least one carbohydrate and HQ, and a lignin stream comprising lignin, HCl and water, (iii) bringing said hydrolyzate, as such or after modification thereof, into contact with a first extractant comprising a first solvent (SI) characterized by a water solubility of less than 10% and by at least one of (a1) having delta-P between 5 and 10 $MPa^{1/2}$ and (b1) having delta-H between 5 and 20 $MPa^{1/2}$, whereupon HQ selectively transfers to said first extractant to form an HQ-carrying first extract and an HQ-depleted hydrolyzate solution; (iv) recovering HQ from said first extract; (v) contacting said lignin stream, as such or after modification thereof, with S1 to form a first evaporation feed, and (vi) evaporating water, HQ and S1 from said first evaporation feed, whereupon a first vapor phase and a lignin composition are formed.

A method is provided to recover the HQ at high yield and at high concentration suitable for reuse in the hydrolysis of polysaccharides in lignocellulosic material. One method further comprises the step of deacidifying said HQ-comprising hydrolyzate to form deacidified hydrolyzate comprising monosaccharides, disaccharides and optionally higher oligosaccharides. According to an embodiment, said deacidifying comprises selective extraction of HQ with an alcohol to form an HQ-comprising organic phase. Suitable alcohols are ones with water solubility of less than 15%, e.g. alcohols with 5 to 8 carbon atoms. As used herein, selective extraction means that the HCl/carbohydrate ratio in the organic phase is greater than that ratio in the HCl-comprising hydrolyzate, preferably at least 5 folds greater, more preferably at least 10 folds. According to another embodiment, water is co-extracted with HCl and, as a result, the concentration of the carbohydrates increases. According to an embodiment, in said deacidified hydrolyzate, the weight/weight ratio of carbohydrates to (carbohydrates+water) is at least 0.35, preferably at least 0.40, more preferably at least 0.45 and most preferably at least 0.50. According to another embodiment, the deacidifying is conducted at a temperature of less than 80° C., preferably less than 70° C. and more preferably less than 60° C.

According to an embodiment, said deacidifying is conducted according to the method of Israeli patent application number 206, 152 the teachings of which are incorporated herein by reference. Thus, according to an embodiment, deacidifying is carried out by a method for the separation of HCl from a carbohydrate comprising aqueous feed, here the hydrolyzate: a. providing a hydrolyzate comprising HCl and a carbohydrate; b. bringing said hydrolyzate into contact with a first extractant comprising a first solvent (SI) characterized by a water solubility of less than 10% and by at least one of (a1) having a delta-P between 5 and 10 $MPa^{1/2}$ and (b1) having a delta-H between 5 and 20 $MPa^{1/2}$, whereupon HCl selectively transfers to said first extractant to form an HCl-carrying first extract and an HCl-depleted hydrolyzate; (c) bringing said HCl-depleted hydrolyzate into contact with a second extractant comprising S1 and a second solvent S2 characterized by water solubility of at least 30% and by at least one of (a2) having a delta-P greater than 8 $MPa^{1/2}$ and (b2) having a delta-H greater than 12 $MPa^{1/2}$, whereupon HCl selectively transfers to said second extractant to form an organic phase composition and a de-acidified hydrolyzate; and (d) recovering HCl from said first extract.

The deacidified hydrolyzate formed in said step of deacidifying comprises monosaccharides, disaccharides and optionally higher oligosaccharides. The disaccharide form a marked fraction of the carbohydrates in said deacidified hydrolyzate. Typically, in said deacidified hydrolyzate the weight/weight ratio between dimers and total carbohydrates is at least 0.1, preferably at least 0.3 and more preferably at least 0.5.

The hydrolyzate comprises at least one hexose, i.e., a C6 sugar, such as glucose and mannose, typically resulting from the hydrolysis of cellulose, and optionally at least one pentose, i.e., a C5 sugar, such as xylose and arabinose, typically resulting from the hydrolysis of hemicelluloses. According to an embodiment, said deacidified hydrolyzate comprises both pentoses and hexoses and the weight/weight ratio between pentoses and total carbohydrates is at least 0.05, preferably at least 0.1.

According to an embodiment, the HCl/carbohydrate w/w ratio in said de-acidified hydrolyzate is smaller than 0.03, preferably smaller than 0.01 and more preferably smaller than 0.005.

According to various embodiments, the HCl/water ratio in the first extract is greater than that ratio in the organic phase composition of step (iii) by at least 10%; the HCl/water ratio in the first extract is greater than that ratio in the hydrolyzate by at least 10% and/or the HCl/carbohydrate ratio in said first extract is greater than that ratio in the organic phase composition of step (iii) by at least 10%.

According to an embodiment, recovering comprises at least one of HCl distillation and back-extraction with water or with an aqueous solution. According to still another embodiment, the provided hydrolyzate comprises an impurity, the impurity/carbohydrate ratio in said feed is R3, the impurity/carbohydrate ratio in the de-acidified hydrolyzate is R2 and the R3/R2 ratio is greater than 1.5.

According to another embodiment, the first organic solvent forms a heterogeneous azeotrope with water, said first organic solvent has a boiling point at 1 atm in the range between 100° C. and 200° C. and said heterogeneous azeotrope has a boiling point at 1 atm of less than 100° C.

According to an embodiment, the carbohydrates of the hydrolyzate, of the HCl-depleted hydrolyzate and of the deacidified hydrolyzate are selected from the group consisting of glucose, mannose, xylose, galactose, arabinose, oligomers thereof and combinations thereof. According to an embodiment, essentially all the oligomers in said hydrolyzate, are water soluble.

According to an embodiment, S1 forms a heterogeneous azeotrope with water. According to a related embodiment, in the heterogeneous azeotrope with water, the first organic solvent to water weight/weight ratio is in the range between 50 and 0.02, preferably between 5 and 0.2, preferably between 4 and 0.25, more preferably between 3 and 0.3 and most preferably between 2 and 0.5. According to an embodiment, the boiling point of that heterogeneous azeotrope at atmospheric pressure is less than 100° C.

According to an embodiment SI is selected from the group consisting of aliphatic or aromatic alcohols, ketones and aldehydes having at least 5 carbon atoms, e.g. various pentanols, hexanols, heptanols, octanols, nonanols, decanols, methyl-isobutyl-ketone and methyl-butyl-ketone and combinations thereof. As used here, the term alcohols means any of mono-, di- and poly-alcohols, primary, secondary and tertiary ones, straight chain and branched alcohols and any combination of those. According to a preferred embodiment, SI is selected from hexanol and 2-ethyl-1-hexanol and a mixture thereof.

According to an embodiment, the first extractant comprises two solvents or more characterized b y a water solubility of less than 10% and by at least one of (a1) having delta-P between 5 and 10 $MPa^{1/2}$ and (b1) having delta-H between 5 and 20 $MPa^{1/2}$. SI, as used herein, means a single solvent or a combination of solvents of these characteristics.

According to an embodiment, the first extractant comprises at least one solvent other than SI, but SI forms at least 60% of the first extractant, preferably at least 80% and more preferably at least 90%. According to an embodiment, the first extractant comprises a mixture of an alkanol and the corresponding alkyl chloride. According to an embodiment, the first extractant comprises hexanol and hexyl chloride. According to another embodiment, the first extractant comprises 2-ethyl-1-hexanol and 2-ethyl-1-hexyl chloride. According to still another embodiment, the first extractant comprises hexanol, 2-ethyl-1-hexanol, hexyl chloride and 2-ethyl-1-hexyl chloride. According to a related embodiment, the alkanol/alkyl chloride weight/weight ratio is greater than 10, preferably greater than 15, more preferably greater than 20 and most preferably greater than 30.

According to one method, contacting results in selective transfer of HCl from the hydrolyzate to the first extractant to form an HCl-carrying (loaded) first extract and an HCl-depleted carbohydrate solution, which are then separated. According to an embodiment, the hydrolyzate comprises 20-80 HCl and 10-80 carbohydrates per 100 water w/w and the HCl-carrying first extract comprises 3-35 HCl and 3-35 water per 100 SI w/w. According to another embodiment, the hydrolyzate comprises 20-30 HCl and 10-40 carbohydrates per 100 water w/w and the HCl-carrying first extract comprises 3-15 HCl and 2-20 water per 100 SI w/w. According to another embodiment, the hydrolyzate comprises 30-40 HCl and 10-40 carbohydrates per 100 water w/w and the HCl-carrying first extract comprises 10-25 HCl and 10-25 water per 100 SI w/w. According to still another embodiment, the hydrolyzate comprises 40-50 HCl and 10-40 carbohydrates per 100 water w/w and the HCl-carrying first extract comprises 15-35 HCl and 15-35 water per 100 SI w/w. According to an embodiment, the hydrolyzate comprises 20-50 HCl and 10-40 carbohydrates per 100 water w/w and the HCl-carrying first extract comprises less than 3 carbohydrate per 100 S1 w/w, preferably less than 2, more preferably less than 1 and most preferably less than 0.5.

According to a preferred embodiment, the second extractant is more hydrophilic than the first one. As explained in the literature, delta-P and delta-H can be assigned to single components as well as to their mixtures. In most cases, the values to be assigned to the mixtures could be calculated from those of the single components and their proportions in the mixtures. According to an embodiment, the delta-P of the second extractant is greater than the delta-P of said first extractant by at least 0.2 $MPa^{1/2}$, preferably at least 0.4 $MPa^{1/2}$ and more preferably at least 0.6 $MPa^{1/2}$. According to another embodiment, the delta-H of the second extractant is greater than delta-H of said first extractant by at least 0.2 $MPa^{1/2}$, preferably at least 0.4 $MPa^{1/2}$ and more preferably at least 0.6 $MPa^{1/2}$. According to still another embodiment, both the delta-P and the delta-H of the second extractant are greater than those of the first extractant by at least 0.2 $MPa^{1/2}$, preferably at least 0.4 $MPa^{1/2}$ and more preferably at least 0.6 $MPa^{1/2}$.

According to an embodiment both extractants comprise SI and S2 and the S2/S1 ratio in the second extractant is greater than that ratio in the first extractant by at least 10%, preferably at least 30%, more preferably that ratio in the second extractant is at least 2 times greater than that in the first and most preferably is at least 5 times greater.

According to an embodiment, the HCl/water ratio in the first extract is greater than that ratio in the organic phase composition by at least 10%, preferably at least 30% and more preferably at least 50%.

According to another embodiment, the HCl/carbohydrate ratio in the first extract is greater than that ratio in the organic phase composition by at least 10%, preferably at least 30% and more preferably at least 50%.

In the scheme of the FIGURE, the HCl-depleted carbohydrate solution and the second extractant (Ex2) are brought in contact in the operation marked Solvent Extraction #2 (of FIG. 1). According to an embodiment, contacting consists of a multiple-stage counter-current operation conducted in commercial liquid-liquid contactors, e.g. mixers-settlers, pulsating columns or centrifugal contactor. Upon contacting, HCl transfers selectively to the second extractant to form an organic phase composition according to the first aspect and a deacidified carbohydrate solution, which according to an embodiment are separated. Thus, on a solvent-free basis, HCl concentration in the organic phase composition is greater than HCl concentration in the HCl-depleted carbohydrate solution.

According to another embodiment, the HCl-depleted hydrolyzate comprises an impurity and said impurity distributes into the second extractant preferentially to carbohydrates, leading to purification of the carbohydrate. Thus, according to an embodiment, the impurity/carbohydrate ratio in the HCl-depleted hydrolyzate is R4, the impurity/carbohydrate ratio in the deacidified hydrolyzate is R2 and the R4/R2 ratio is greater than 1.5, preferably greater than 3 and more preferably greater than 5. According to another embodiment, the impurity/carbohydrate ratio in the hydrolyzate is R3, the impurity/carbohydrate ratio in the deacidified hydrolyzate is R2 and the R3/R2 ratio is greater than 1.5, preferably greater than 3 and more preferably greater than 5.

According to an embodiment, contacting is a multiple-stage counter-current one, and water is added part of the way through the stages for controlling the concentration of carbohydrates. According to an embodiment, the distillate of concentrating the HCl-depleted hydrolyzate is added part of the way through the stages.

The formed de-acidified hydrolyzate is suitable for use, as such or after further treatment, in many processes, e.g. biological or chemical conversion into products such as fuels, food, feed and monomers for the polymer industry. According to an embodiment, the HCl/carbohydrate weight ratio in said deacidified hydrolyzate is less than 0.03, preferably less than 0.02, more preferably less than 0.01 and most preferably less than 0.005. According to an embodiment, the HCl content in the deacidified hydrolyzate is less than 5% of the initial HCl content of the hydrolyzate, preferably less than 3%, more preferably less than 2% and most preferably less than 1%. According to an embodiment, the deacidified hydrolyzate is treated prior to said use and said pre-treatment comprises, final purification, removal of residual solvent, e.g. by distillation, contacting with an adsorbent such as an activated carbon, adsorbing resin, activated earth or a combination of those, ion-exchange treatment, neutralization or removal of a residual acid and hydrolysis of oligomers, if present, e.g. acid catalyzed or enzyme catalyzed hydrolysis.

The present invention also provides an organic phase composition (also referred to herein as organic composition) comprising: (a) a first solvent (SI) characterized by a water solubility of less than 15% and by at least one of (a1) having a polarity related component of Hoy's cohesion parameter (delta-P) between 5 and 10 $MPa^{1/2}$ and (b1) having a hydrogen bonding related component of Hoy's cohesion parameter (delta-H) between 5 and 20 $MPa^{1/2}$; (b) a second solvent (S2) characterized by a water solubility of at least 30% and by at least one of (a2) having delta-P greater than 8 $MPa^{1/2}$ and (b2) having delta-H greater than 12 $MPa^{1/2}$; (c) water, (d) HCl, and (e) a carbohydrate.

According to an embodiment, said carbohydrate is selected from the group consisting of glucose, mannose, xylose, galactose, arabinose, oligomers thereof and combinations thereof.

According to an embodiment, the organic phase composition comprises a mixture of an alkanol and the corresponding alkyl chloride. According to a related embodiment, the alkanol/alkyl chloride weight/weight ratio is greater than 10, preferably greater than 15, more preferably greater than 20 and most preferably greater than 30.

According to an embodiment, the organic phase composition is formed in said contacting the HCl-depleted aqueous feed with the second extractant (in Solvent Extraction #2 of FIG. 1), the first solvent (SI) is the first solvent of the first and second extractants, the second solvent (S2) is the second solvent of the second extractant and the HCl, the water and the carbohydrate are extracted from the HCl-depleted hydrolyzate.

According to another embodiment, the weight/weight ratio of HCl/water in the organic phase composition is greater than 0.15, preferably greater than 0.20, more preferably greater than 0.25 and most preferably greater than 0.30.

According to another embodiment the weight/weight ratio of HCl/carbohydrate in the organic phase composition is greater than 5, preferably greater than 10 and more preferably greater than 15.

According to another embodiment the carbohydrate concentration in the organic phase composition is in a range between 0.01% wt and 5% wt, preferably between 0.02% wt and 4% wt and more preferably between 0.03% wt and 3% wt.

According to an embodiment, the method further comprises the step of recovering HCl from said organic phase. According to another embodiment, said organic phase is further treated.

According to an embodiment, the first extractant is formed from the organic phase composition. According to a related embodiment, the organic composition is treated to generate the SI-comprising first extractant or a precursor thereof and S2 to be used for the generation of the second extractant (see FIG. 1).

Thus, according to an embodiment, the method comprises a step of removing S2 from the organic phase composition, to form separated S2 and separated first extract or a precursor thereof. According to alternative embodiments, S2 is fully removed or only partially removed. According to an embodiment, both S2 and water are removed from the organic phase composition. The separated S2 is used, according to an embodiment, for the reformation of the second extractant by combining the separated S2 with regenerated SI. S2 separation is preferably selective so that the HCl content of the separated S2 is small.

According to a preferred embodiment, S2 is removed by distillation. The organic phase composition comprises, according to a preferred embodiment, at least three volatile components, i.e. HCl, water and S2. According to some embodiments, SI also has some volatility. In addition, HCl forms an azeotrope with water in a two-component system and according to various embodiments, at least one of SI and S2 also forms an azeotrope with water in a two-component system. The inventors have surprisingly found that, from the organic composition of the present invention, S2 can be distilled out with no major co-distillation of HCl. Thus, according to preferred embodiments, the HCl/S2 weight/weight ratio in the separated S2 is less than 0.1, preferably less than 0.05, more preferably less than 0.03 and most preferably less than 0.01.

Removal of S2 forms an S2-depleted composition. According to an embodiment, said S2-depleted composition splits into two phases, a light phase and a heavy phase, which are then separated, e.g. by known means, such as decantation (see FIG. 1) and are referred to in the following as S2-depleted light phase and S2-depleted heavy phase. According to an embodiment, the S2-depleted light phase forms said first extractant, a component of said first extractant or a precursor of said first extractant. Thus according to an embodiment, the first extractant is composed of a mixture comprising said S2-depleted light phase and regenerated first extractant formed on HCl separation from the first extract.

According to an embodiment, the HCl/water ratio in the S2-depleted heavy phase is smaller than that ratio in the HCl-depleted aqueous feed. According to another embodiment the HCl/carbohydrate ratio in that heavy phase is smaller than that ratio in the HCl-depleted aqueous feed.

The S2-depleted heavy phase comprises water, HCl and optionally also some carbohydrates. According to an embodiment of the present invention, said heavy phase is contacted with an extractant for selective extraction of HCl from it. According to various embodiment, the S2-depleted heavy phase is combined with the hydrolyzate for contacting with the first extractant, combined with the HCl-depleted hydrolyzate for contacting with the second extractant, combined with the hydrolyzate part of the way through a multiple-stage counter-current extraction with the first extractant, combined with the HCl-depleted hydrolyzate part of the way through a multiple-stage counter-current extraction with the second extractant or a combination of those. According to an embodiment, the S2-depleted heavy phase is combined with the hydrolyzate or with the HCl-depleted hydrolyzate part of the way through extraction at a point where HCl/water ratio of the S2-depleted heavy phase is between 0.7 and 1.5 of said ratio in the hydrolyzate or in the HCl-depleted hydrolyzate.

One method of the present invention comprises recovering HCl from the first extract. Such recovering forms recovered HCl and HCl-depleted first extract, also referred to herein as regenerated first extractant. According to an embodiment, said recovered HCl is used for hydrolyzing oligosaccharides of a lignocellulosic material. According to an embodiment, said recovered HCl is used to form the hydrolysis medium. According to an embodiment, the recovered HCl is obtained in a gaseous form, as an aqueous solution or as a combination thereof. According to an embodiment, HCl/water ratio in the recovered HCl (in the combination of streams, in case recovered in more than one stream) is greater than 22/78, preferably greater than 25/75 and more preferably greater than 30/70. Gaseous recovered HCl is absorbed, according to an embodiment, in an aqueous HCl solution, which is then used to form the hydrolysis medium. According various embodiments, the HCl-depleted first extract is used, as such or after some modification, to form the first extractant, the second extractant, or is split so that a fraction of it is used for the formation of the first extractant and another fraction is used for the formation of the second extractant. The first extract and the HCl-depleted first extract comprise mainly of SI. According to an embodiment, it is essentially dry. According to various embodiments, modifying said HCl-depleted first extract comprises addition of S2, removal of S2, addition or removal of another component, contacting it or a fraction of it with an adsorbent, distilling it or a fraction of it and combinations thereof.

According to an embodiment, one method of the present invention further comprises recovering HCl from the organic phase composition. According to an embodiment, S2 is first separated from the organic phase composition to form S2-depleted organic phase composition. Said S2-depleted organic phase composition separates, according to a preferred embodiment, into S2-depleted heavy phase and S2-depleted light phase. According to this embodiment, HCl recovering is from said S2-depleted light phase comprising HCl, SI and optionally also water, S2 and carbohydrates. According to an embodiment, said S2-depleted light phase is combined with the first extract or a fraction of it for the step of recovering HCl. Such recovering forms additionally recovered HCl and optionally also HCl-depleted, S2-depleted light phase. According to an embodiment, said additionally recovered HCl is used for the generation of the hydrolysis medium According to an embodiment, a regeneration feed comprises carbohydrates. In case HCl recovery comprises distillation and in case said distillation is conducted at elevated temperature, HCl-catalyzed carbohydrates degradation may take place, reduce carbohydrates production yield and generate degradation products. Such degradation products form impurities that are not desired in some carbohydrates utilization, including acting as inhibitors for some fermentation processes. According to an embodiment, such HCl distillation is conducted at a reduced pressure in order to lower its temperature. The inventors have found that costs related to such reduced-pressure distillation could be saved by highly-selective washing of carbohydrates out of the regeneration feed. Thus, according to a preferred embodiment, the regeneration feed is contacted in a wash operation of FIG. 1, with an HCl-comprising aqueous washing solution, whereupon carbohydrates selectively transfer from said regeneration feed into the aqueous washing solution to form low-carbohydrates regeneration feed (also denoted CH-depleted HCl-loaded 1st extract in FIG. 1) and a carbohydrate-comprising wash solution (also denoted CH-carrying wash in FIG. 1). According to an embodiment, the HCl-comprising aqueous washing solution is a recycled HCl solution, e.g. recycled from the HCl recovery step. According to an embodiment, HCl is distilled from said low-carbohydrates regeneration feed in Distillation operation of FIG. 1) to form the recovered HCl. According to an embodiment, the carbohydrate-comprising wash solution is used in the hydrolysis of the lignocellulosic material polysaccharides. According to an embodiment, HCl concentration in said washing solution is adjusted so that there is essentially no acid transfer from said washing solution to the regeneration feed, nor is there transfer of acid from said regeneration feed to said washing solution. As used here, essentially no transfer means transfer of less than 10% of the acid. The inventors have found that carbohydrate transfer from the regeneration feed to the washing solution is highly efficient with a distribution coefficient in favor of the washing solution of at least 10, preferably at least 30 and more preferably at least 50.

According to an embodiment, the method for the separation of HCl from a carbohydrate uses a system comprising two extraction units and a distillation unit, as shown in the FIGURE. The hydrolyzate is extracted first in Solvent Extraction #1 to form the HCl-depleted hydrolyzate, which is then extracted in Solvent Extraction #2 to form the deacidified hydrolyzate. The second extractant extracts HCl from the HCl-depleted aqueous feed in Solvent Extraction #2 to form the organic phase composition. That composition is treated in distillation to remove at least part of the S2 in it and to form the first extractant or a precursor thereof. The latter is then used to extract HCl from the aqueous feed in Solvent Extraction #1 and to form the HCl-carrying first extract.

The hydrolysis of the polysaccharide of said lignocellulosic material forms, inter alia, a lignin stream. According to an embodiment, said lignin stream is characterized by a lignin to water weight/weight ratio in the range between 0.1 and 2, preferably between 0.3 and 1.8, more preferably between 0.5 and 1.5 and most preferably between 0.8 and 1.2. Said lignin stream is further characterized by an HCl/water weight/weight ratio in the range between 0.15 and 1, preferably between 0.2 and 0.8, more preferably between 0.25 and 0.6 and most preferably between 0.3 and 0.5.

According to an embodiment, at least a fraction of the solvent is separated by filtration or centrifugation to form an S1-comprising stream, which further comprises other solutes, such as organic compounds, including tall oils, commonly referred to as extractives. According to a related embodiment, the majority of said SI comprising stream is recycled for the formation of the first evaporation stream. According to an embodiment, a fraction of said stream is treated for separation of said extractives, preferably by distilling SI therefrom to form distilled SI and extractives-comprising stream.

According to an embodiment, HCl concentration in said lignin composition, in said treated lignin composition or in both is less than 10,000 ppm, more preferably less than 5000 ppm and most preferably less than 2000 ppm.

According to various embodiments of the method, SI is used in the first extractant, in the second extractant and in the first evaporation feed. According to various embodiments, SI is recovered from various streams, such as the first extract, the organic phase composition, the lignin composition and the S1+S3 solution. According to various embodiments, SI is separated by filtration, centrifugation, distillation followed by condensation and other methods. According to various embodiments, several separated SI streams are formed, which separated streams are in the form of dry solvent or a solvent solution comprising at least one of water, HCl, S2 and possibly some impurities. As used here, the term impurity means a compound other than HCl, water, SI and S2 and S3. According to an embodiment, some SI make up is required. According to various embodiments, a separated SI or SI make up stream is used in the first extractant, in the second extractant and in the first evaporation feed. One method of the present invention provides a large degree of freedom for optimization by selecting the methods of SI separation and the way of using the separated SI. According to a preferred embodiment, the streams of the lowest impurity content, e.g. dry SI out of distillation and make up SI are used for the formation of the first extractant and the second extractant.

According to various embodiments of a method of the present invention, an HCl-comprising organic stream is formed. According to some embodiments, multiple HCl-comprising organic streams are formed. Such organic streams include, according to various embodiments, said first extract, said organic phase composition, said S2-depleted organic phase composition, said S2-depleted light phase and said modified first extract having a low-carbohydrate content. These and potentially other HCl-comprising organic streams are commonly referred to herein as a regeneration feed (this term is used for both a single stream and for multiple streams). According to an embodiment, the method further comprises the step of recovering HCl from a regeneration feed (e.g., the acid recovery in FIG. 1).

According to an embodiment, the regeneration feed further comprises water. According to an embodiment, the regeneration feed is a single phase comprising HCl, water and a solvent (typically SI, but possibly also S2 and/or another solvent). Optionally, the regeneration feed also comprises additional components, e.g. carbohydrates, but their content is typically small, e.g. less than 10% and in most cases less than 5%. Typically, the regeneration feed is of a single phase. Yet, some amount of a second phase may also be present. HCl/solvent weight/weight ratios and water/solvent weight/weight ratios in the regeneration feed may vary. Yet, according to an embodiment, on a solvent free basis, HCl concentration in said regeneration feed is greater than 20%, preferably greater than 25%, more preferably greater than 30% and most preferably greater than 35%. According to another embodiment, the water/HCl weight/weight ratio in the regeneration feed is less than 4, preferably less than 3.5 and more preferably less than 3.

Recovery of HCl from the regeneration feed forms regeneration feed recovered HCl (i.e. HCl recovered from the regeneration feed) and HCl-depleted regeneration feed. As indicated earlier, any method of HCl recovery from the regeneration feed is suitable. According to an embodiment, recovery comprises HCl distillation of HCl and optionally also of water. According to an embodiment, said regeneration feed recovered HCl is at least one of a gaseous HCl stream and an aqueous HCl stream and is typically used for the formation of said hydrolysis medium.

According to an embodiment, the HCl-depleted regeneration feed splits into an HCl-depleted regeneration feed heavy phase and an HCl-depleted regeneration feed light phase, which are also referred to herein as regeneration feed heavy phase and regeneration feed light phase. Such split takes place as a result of the recovery of HCl with no additional change in composition. According to that embodiment, the HCl-depleted regeneration feed splits into those two phases when its temperature is at 25° C. Such split into two phases is typically also observed at higher temperatures, e.g. the temperature of HCl recovery from the regeneration feed. While each of those phases may comprise HCl and both solvent and water, the water/solvent weight/weight ratio in the heavy phase is greater than that in the light phase.

According to an embodiment of the present invention, said regeneration feed heavy phase is separated from said regeneration feed light phase. According to an embodiment, said regeneration feed heavy phase is used for the formation of the hydrolysis medium.

According to an embodiment, said regeneration feed comprises water and said separated HCl-depleted regeneration feed heavy phase comprises at least 5% of the water initially contained in said regeneration feed, preferably at least 10% and more preferably at least 20%. According to another embodiment, said separated HCl-depleted regeneration feed heavy phase comprises at least 5% of the HCl initially contained in said regeneration feed, preferably at least 10% and more preferably at least 20%. According to still another embodiment, said regeneration feed comprises a carbohydrate and said separated HCl-depleted regeneration feed heavy phase comprises at least 5% of the carbohydrate initially contained in said regeneration feed, preferably at least 20% and more preferably at least 50%. According to an embodiment, said HCl-depleted regeneration feed light phase is further treated for the separation of HCl therefrom.

An extractant comprising SI and optionally also S2 and another solvent is used according to a method of the present invention for deacidification of the hydrolyzate. Differently put, such extractant is used for the separation of HCl from carbohydrates in the hydrolyzate. Optionally, the same extractant or another one with similar components is used also for the deacidification of lignin. As a result, HCl-loaded solvent (also referred to here as extract or regeneration feed) is formed. Typically, the regeneration feed also comprises water that co-extracts with the HCl. One method of the present invention typically requires recovery of the acid and the water from the regeneration feed for the reformation of the hydrolysis medium. In addition, the extractant needs to be regenerated for reuse in the process. According to a preferred embodiment of one method of the present invention, the solvent of the extractant is selected so that such recovery of the acid and the regeneration of the extractant use evaporation of water and HCl from the regeneration feed. Such evaporation is energy consuming since it requires the input of the latent heat of acid and water evaporation.

It has surprisingly been found that treating the regeneration feed according to the disclosed embodiment saves on such energy consumption. The regeneration feed is first treated for separating a fraction of the HCl it contains, e.g. by distilling gaseous HCl or gaseous HCl with some water vapors. Such separation of a fraction of the HCl increases the water/HCl weight/weight ratio in the HCl-depleted regeneration feed. When such ratio increases to greater than 3, preferably greater than 3.5 and more preferably greater than 4, a regeneration feed heavy phase splits out of the HCl-depleted regeneration feed, as such, according to an embodiment, or after some cooling, according to another. Said heavy phase comprises a significant amount of the water and of the HCl originally contained in the regeneration feed. It is separated, e.g. by decantation, from the regenerated feed light phase and used as such for the formation of the hydrolysis medium. The regeneration feed light phase is typically further distilled for the recovery of the majority of the remaining water and HCl, Yet, since part of the acid and the water are separated in the regeneration feed heavy phase and used as such in hydrolysis, the total energy cost is decreased, less water and less HCl needs to be distilled. Thus, according to the preferred embodiment, HCl recovery and extractant regeneration comprise at least three stages: distilling part of the HCl from the regeneration feed, separating the formed light phase from the formed heavy phase and distilling the rest of the acid (and water) from the separated light phase.

Operation according to the method of this embodiment provides another improvement. In the deacidification of the hydrolyzate, typically some carbohydrates co-extract with the acid (the extractant is highly selective to the acid, but extraction of some carbohydrates may still take place). The regeneration feed heavy phase carries with it a large majority of the extracted carbohydrates, which are recycled with it into the hydrolysis medium. Product losses and formation of carbohydrate degradation products are minimized Recovery of Acid from Lignin Fraction A method is provided for the deacidification of a lignin stream comprising the steps of: (i) providing a lignin stream comprising lignin, HCl and water, wherein the weight/weight ratio of lignin to water is in the range between 0.1 and 2 and wherein the weight/weight ratio of HCl to water is in the range between 0.15 and 2; (ii) contacting said lignin stream with a first solvent (SI) to form a first evaporation feed, which first solvent is characterized by a water solubility of less than 10% and by at least one of (a1) having a delta-P between 5 and 10 MPa$^{1/2}$ and (be having a delta-H between 5 and 20 MPa$^{1/2}$ and (iii) evaporating water, HCl and SI from said first evaporation feed at a temperature below 100° C. and at a pressure below 1 atm, whereupon a first vapor phase and a lignin composition are formed.

According to an embodiment, providing said lignin stream comprises hydrolyzing a lignocellulosic material in an HCl-comprising hydrolysis medium, wherein HCl concentration is greater than azeotropic.

The present method provides, according to a first aspect, a lignin composition comprising solid lignin, HCl, water, a first organic solvent (SI) characterized by a water solubility of less than 15% and by at least one of (a1) having a delta-P between 5 and 10 MPa$^{1/2}$ and (b1) having a delta-H between 5 and 20 MPa$^{1/2}$, and optionally a carbohydrate, wherein said solid lignin content is between 3 wt % and 40 wt %, the HCl/water weight/weight ratio is greater than 0.5, the HCl/solvent weight/weight ratio is greater than 0.2, the water/solvent weight/weight ratio is greater than 0.35 and the carbohydrate/lignin weight/weight ratio is less than 0.05.

The solubility of SI in water is less than 15% wt, preferably less than 5% wt, more preferably less than 2% wt and most preferably less than 1% wt. As used here and in the following, the solubility is measured by the percent weight ratio (% wt) and determined by combining an essentially pure solvent and de-ionized water at 25° C. According to an embodiment, the solubility of water in SI is less than 20% wt, preferably less than 15% wt, more preferably less than 10% wt and most preferably less than 8% wt.

According to an embodiment, SI forms with water a heterogeneous azeotrope. According to a related embodiment, in the heterogeneous azeotrope with water, the first organic solvent to water weight/weight ratio is in the range between 50 and 0.02, preferably between 5 and 0.2, preferably between 4 and 0.25, more preferably between 3 and 0.3 and most preferably between 2 and 0.5. According to an embodiment, the boiling point of that heterogeneous azeotrope at atmospheric pressure is less than 100° C.

According to an embodiment SI is selected from the group consisting of aliphatic or aromatic alcohols, ketones and aldehydes having at least 5 carbon atoms, e.g. various pentanols, hexanols, heptanols, octanols, nonanols, decanols, methyl-isobutyl-ketone and methyl-butyl-ketone and combinations thereof. As used here, the term alcohols means any of mono-, di- and poly-alcohols, primary, secondary and tertiary ones, straight chain and branched alcohols and any combination of those. According to a preferred embodiment, SI is selected from hexanol and 2-ethyl-1-hexanol and a mixture thereof.

As used herein, the term solid lignin means lignin that is not soluble in the liquid part of the composition, and which can be separated from it by known means, e.g. filtration or centrifugation. According to an embodiment, the content of the solid lignin in said lignin composition is between 3 wt % and 20 wt %, preferably between 4% wt and 15% wt. According to another embodiment, the content of the solid lignin in said lignin composition is between 10 wt % and 40 wt %, preferably between 15% wt and 30% wt.

The HCl/water weight/weight ratio is an important characteristic of the lignin composition and is greater than 0.5, preferably greater than 0.52 and more preferably greater than 0.55. HCl/solvent weight/weight ratio in the lignin composition is greater than 0.2, preferably greater than 0.25 and more preferably greater than 0.3. The water/solvent weight/weight ratio in said composition is greater than 0.35 preferably greater than 0.40 and more preferably greater than 0.45.

According to an embodiment, said lignin composition is essentially free of carbohydrates. According to another embodiment is comprises carbohydrates and the carbohydrate/lignin weight/weight ratio is less than 0.05, preferably less than 0.03 and more preferably less than 0.01. According to an embodiment, said carbohydrate is selected from the group consisting of glucose, mannose, xylose, galactose, arabinose, oligomers thereof and combinations thereof.

A lignin composition is provided which comprises solid lignin and a liquid, which liquid comprises HCl, water and SI. According to an embodiment, that lignin composition comprises a single liquid phase. As used here, comprising a single liquid phase means that, on separating the solid lignin (e.g. by filtration or centrifugation), only a single phase is observed. The number of phases may depend on the temperature. According to an embodiment, the lignin composition comprises a single liquid phase when at 25° C. That single liquid phase has a high content of water, HCl and SI.

A method is provided comprising the steps of (i) providing a lignin stream comprising solid lignin, HCl, water and optionally a carbohydrate, wherein said solid lignin content is in the range between 5% wt and 30% wt, the HCl/water weight/weight ratio is greater than 0.5 and carbohydrate/lignin weight/weight ratio is less than 0.05; (ii) contacting said lignin stream with an S1-comprising stream wherein SI is characterized by a water solubility of less than 15% and by at least one of (a1) having a delta-P between 5 and 10 MPa$^{1/2}$ and (b1) having a delta-H between 5 and 20 MPa$^{1/2}$ to form a lignin composition according to the first aspect; and (iii) separating said solid lignin to form a separated solid lignin and a separated liquid stream comprising SI, HCl and water, wherein the HCl/water weight/weight ratio is greater than 0.5, the HCl/solvent weight/weight ratio is greater than 0.2, and the water/solvent weight/weight ratio is greater than 0.35. Alternatively, acid forms a separate phase from S1 and lignin partitions to the SI layer.

Preferably, when said solid lignin comprises SI, the method further comprises a step of SI removal from said solid lignin stream by means selected from the group consisting of decantation, filtration, centrifugation, distillation, extraction with another solvent and combinations thereof to form a separated S1 and a de-solventized solid lignin.

Preferably an HCl-depleted liquid stream splits at 25° C. into an HCl-depleted heavy phase, which heavy phase comprises HCl, water and SI, and into an HCl-depleted light phase, which light phase comprises HCl, water and SI. According to an embodiment, the method further comprises the step of separating said HCl-depleted heavy phase from said HCl-depleted light phase.

In preferred embodiments, providing said lignin stream comprises hydrolyzing a lignocellulosic material in an HCl-comprising hydrolysis medium and said separated HCl-depleted heavy phase is used to form said hydrolysis medium In preferred embodiments said method further comprises a step of HCl recovery from said separated HCl-depleted light phase.

According to an embodiment, said S1-comprising stream is essentially free of HCl, essentially free of water or essentially free of both water and HCl. According to another embodiment, said S1-comprising stream comprises HCl, water or both. On contacting said S1-comprising stream with the lignin stream, the composition of the first aspect is formed. It is important that the compositions of the contacted streams (the lignin stream and the SI-comprising stream) and their ratios are selected so that the combined amount of HCl in both and the combined amount of water in both are such that the combined HCl/combined water weight/weight ratio is greater than 0.5, preferably greater than 0.52 and more preferably greater than 0.55, the combined HCl/S1 weight/weight ratio is greater than 0.2 preferably greater than 0.25 and more preferably greater than 0.3 and the combined water/S i weight/weight ratio is greater than 0.35 preferably greater than 0.40 and more preferably greater than 0.45. The compositions of the streams and their ratios are further selected so that the solid lignin content of the composition is between 3 wt % and 40 wt %. According to an embodiment, the content of the solid lignin in said lignin composition is between 3 wt % and 20 wt %, preferably between 4% wt and 15% wt. According to another embodiment, the content of the solid lignin in said lignin composition is between 10 wt % and 40 wt %, preferably between 15% wt and 30% wt.

The method of the second aspect further comprises the step of separating said solid lignin from said lignin composition to form a separated solid lignin and a separated liquid stream, comprising SI, HCl and water wherein the HCl/water weight/weight ratio is greater than 0.5, preferably greater than 0.52 and more preferably greater than 0.55, the HCl/solvent weight/weight ratio is greater than 0.2, preferably greater than 0.25 and more preferably greater than 0.3 and the water/solvent weight/weight ratio is greater than 0.35, preferably greater than 0.40 and more preferably greater than 0.45.

Any form of contacting said lignin stream and said S1-comprising stream is suitable. Any form of separating said solid lignin from said lignin composition is suitable. According to an embodiment, said lignin stream is contacted with the SI-comprising stream in a mixed vessel. According to another embodiment, the two streams are contacted in a column wherein the SI-comprising stream moves through a lignin-stream cake, the lignin stream moves against the S-1 comprising stream or the two streams move counter-currently.

Contacting should be such that it allows the formation of the lignin composition. According to an embodiment, the lignin stream comprises solid lignin wetted with or dispersed in a concentrated aqueous solution of HCl, while the S-1 comprising stream is essentially an organic phase. According to that embodiment, water and HCl of the aqueous phase transfer into the organic phase. The term transfer, as used here, does not mean to indicate a mechanism, but rather the final finding of having an organic phase containing the majority of the acid or essentially all of it, the majority of the water or essentially all of it and combinations thereof. As indicated earlier, the liquid of the lignin composition and the liquid separated later from the solid liquid are high in all three components SI, HCl and water. In that respect, it is not typical to many organic phases. Therefore, the term organic phase as used in the following means a phase comprising SI at a significant concentration, e.g. 10% wt or 20% wt. According to an embodiment, such transfer is rapid, but still requires some time, which is allowed according to an embodiment. Thus, according to an embodiment, said contacting provides residence time of at least 5 seconds, preferably at least 10 seconds. According to an embodiment, the lignin stream, the SI-comprising stream or both are flowing at a rate that provides said desired contact residence time.

It was surprisingly found that, according to another embodiment, at some modes of contacting the lignin stream with the SI-comprising stream, a major fraction of the aqueous phase separates out of the solid lignin to generate a medium comprising solid lignin, SI-comprising liquid organic solution and a liquid aqueous solution comprising a fraction of the water and a fraction of the HCl originating from the aqueous solution of the lignin stream.

According to an embodiment, such fractions are greater than 20%, preferably greater than 30% and more preferably greater than 50%. As indicated, such formation of the liquid aqueous solution could be a function of the form of contacting, of the temperature, of the ratio between the lignin stream and the SI-comprising stream, etc. Yet, according to an important embodiment of the invention, on mixing the two said liquid aqueous solution and said liquid organic solution completely or nearly completely combine into a single phase According to an embodiment said method comprises a single contacting, preferably carried out in a vessel with strong mixing. According to an alternative embodiment, it comprises multiple contacting. According to an embodiment, said multiple contacting is conducted in a cross-current mode, so that in each contact the lignin stream is contacted with a fresh S1-comprising stream. According to a related embodiment, said contacting is conducted in a counter-current mode wherein a fresh SI-comprising stream is contacted with a lignin stream, mostly depleted of its HCl content, separated, contacted with a lignin stream comprising higher HCl content, separated and further contacted with lignin stream with increasing HCl content. According to this mode the solid lignin is last contacted with a fresh S1-comprising stream, while the liquid stream is last contacted with a lignin stream highest in HCl.

According to the embodiment wherein there is a single contact, one method of the present invention comprises typically a single separation step. According to the embodiment comprising multiple contacts, the method may comprise multiple separation steps. Any method of separation is suitable. According to an embodiment, said separation comprises at least one of filtration and centrifugation. Separating according to one method of the present invention comprises forming a separated solid lignin and a separated liquid stream.

In preferred embodiments, the ratio between the lignin stream and the S1-comprising stream in said contacting is controlled as it affects several processing aspects, the degree of lignin deacidification and the cost of the overall deacidification process. On the one hand, larger proportions of the S1-comprising stream contributes to a better contact and thus better transfer of water and HCl and thus to better deacidification. Furthermore, the lignin composition formed on said contacting needs to be further treated, including separation of the solid lignin, transfer (e.g. pumping) to a means where such separating takes place, etc. Treating such a stream that comprises relatively small particles of swellable (and possibly highly swelled) solid is difficult and a larger liquid volume formed by a larger proportion of the S1-comprising stream appears to be preferable. Yet, increasing the proportion of the S1-comprising stream increases costs related to total volumes handling and the amount of separated liquid stream (formed after the separation of solid lignin) to be treated for HCl recovery therefrom, e.g. heated for HCl distillation. Furthermore, as explained hereinafter, on separating HCl from said separated liquid stream, an HCl-depleted stream is formed and splits into an HCl-depleted heavy stream and an HCl-depleted light stream. That heavy phase could be used, as such, in the formation of the hydrolysis medium. The larger the amount of HCl and water in that heavy phase, the lower are the costs related to the regeneration of the SI-comprising stream for further deacidification of lignin (less of those to be removed from the HCl-depleted light stream). However, the larger is the proportion of the S1-comprising stream in contacting with the lignin stream, the smaller is the fraction of water and HCl separating into said HCl-depleted heavy stream. The inventors have surprisingly found that high deacidification yield and suitable handling of the solid-comprising streams could be reached at relatively low ratios between the S-1 comprising stream and the lignin stream avoiding the above-described drawbacks of the high proportions. Thus, according to an embodiment, the ratio between the S-1 comprising stream and the lignin stream is in the range between 0.2 and 5, preferably between 0.25 and 3, more preferably between 0.3 and 2 and most preferably between 0.4 and 1.1. According to an embodiment of the invention, in a single stage (comprising contacting the lignin stream with the S1-comprising stream followed by the separation of the solid lignin), at least 70% of the initial HCl is removed from the lignin stream, preferably at least 75%, more preferably at least 80% and most preferably at least 85%.

The degree (yield) of HCl removal from the lignin stream is also dependent on the efficiency of separating the liquid from the solid lignin in said formed lignin composition. It was surprisingly found that separating said liquid (which comprises SI, HCl and water) from the lignin solids (of the lignin composition) is much easier than separating lignin solids from the aqueous solution (which comprise water and HCL) of the lignin stream. Thus, according to a preferred embodiment, the separated solids (which are still wetted) are of at least 25% wt dry matter, preferably at least 30% wt, more preferably at least 34% wt and most preferably at least 38% wt.

According to an embodiment, the separated solid lignin is wetted with an S1-comprising liquid. According to an embodiment, the method further comprises a step of S1 removal from said solid lignin stream by means selected from the group consisting of decantation, filtration, centrifugation, distillation, extraction with another solvent and combinations thereof to form separated SI and desolventized solid lignin.

Contacting said lignin stream with said S1-comprising stream efficiently removes HCl from said lignin stream. According to an embodiment of the invention, the HCl/lignin weight/weight ratio in said solid lignin, in said desolventized solid lignin or in both is less than 0.03, preferably less than 0.02 and more preferably less than 0.01.

As indicated earlier, SI solubility in water is limited, e.g. less than 15% wt, preferably less than 5% wt, more preferably less than 2% wt and most preferably less than 1% wt. In the separated liquid stream the water/solvent weight/weight ratio is greater than 0.35, preferably greater than 0.40 and more preferably greater than 0.45. Therefore, it was surprisingly found that, according to an important embodiment, said separated liquid stream comprises a single liquid phase. The number of phases may depend on the temperature. According to an embodiment, the separated liquid stream comprises a single liquid phase when at 25° C. As indicated earlier, the lignin stream comprises solid lignin surrounded with or dispersed in an aqueous solution highly concentrated with HCl. Without wishing to be limited by theory, it is suggested that on said contacting with an SI-comprising stream at the conditions and compositions of one method of the present invention, the aqueous solution and the SI-comprising stream (which is essentially organic) combined into a single liquid phase, which single phase is rich in SI, water and HCl. It is further suggested that said combining into a single liquid phase strongly facilitates the deacidification of the lignin.

According to one method, the separated liquid stream comprising SI, HCl and water, in which the HO/water weight/weight ratio is greater than 0.5, preferably greater than 0.52 and more preferably greater than 0.55, the HO/solvent weight/weight ratio is greater than 0.2, preferably greater than 0.25 and more preferably greater than 0.30 and the water/solvent weight/weight ratio is greater than 0.35, preferably greater than 0.40 and more preferably greater than 0.45.

One method further comprises HCl recovery from said separated liquid stream. According to an embodiment, both HCl and water are separated.

Recovery of HCl from the separated liquid stream forms separated liquid-recovered HCl (i.e. HCl recovered from the separated liquid) and HCl-depleted separated liquid. Any method of HCl recovery from the separated liquid is suitable. According to an embodiment, recovery comprises distillation of HCl and optionally also of water. According to an embodiment, said separated liquid-recovered HCl is at least one of a gaseous HCl stream and an aqueous HCl stream and is typically used for the formation of said hydrolysis medium.

According to an embodiment, the HCl-depleted separated liquid splits into an HCl-depleted separated liquid heavy phase and an HCl-depleted separated liquid light phase, which are also referred to herein as separated liquid heavy phase and separated liquid light phase. Such split takes place as a result of the recovery of HCl with no additional change in composition. According to that embodiment, the HCl-depleted separated liquid splits into those two phases when its temperature is at 25° C. Such split into two phases is typically also observed at higher temperatures, e.g. the temperature of HCl recovery from the separated liquid. While each of those phases may comprise HCl and both solvent and water, the water/solvent weight/weight ratio in the heavy phase is greater than that in the light phase.

According to an embodiment, said separated liquid heavy phase is separated from said separated liquid light phase. According to an embodiment, said separated liquid heavy phase is used for the formation of the hydrolysis medium.

According to an embodiment, said separated liquid comprises water and said separated HCl-depleted separated liquid heavy phase comprises at least 5% of the water initially contained in said separated liquid, preferably at least 10% and more preferably at least 20%. According to another embodiment, said separated HCl-depleted separated liquid heavy phase comprises at least 5% of the HCl initially contained in said separated liquid, preferably at least 10% and more preferably at least 20%. According to still another embodiment, said separated liquid comprises a carbohydrate and said separated HCl-depleted separated liquid heavy phase comprises at least 5% of the carbohydrate initially contained in said separated liquid, preferably at least 20% and more preferably at least 50%. According to an embodiment, said HCl-depleted separated liquid light phase is further treated for the separation of HCl therefrom.

An S1-comprising stream is used according to one method for the deacidification of the lignin stream. As a result, the HCl-comprising separated liquid is formed. Typically, the separated liquid also comprises water. One method typically requires recovery of the acid and the water from the separated liquid for the reformation of the hydrolysis medium. In addition, the S1-comprising stream needs to b e regenerated for reuse in lignin deacidification. According to a preferred embodiment of one method of the present invention, the solvent of the extractant is selected so that such recovery of the acid and the regeneration of the S1-comprising stream use evaporation of water and HCl from the separated liquid. Such evaporation is energy consuming since it requires the input of the latent heat of acid and water evaporation.

The inventors have surprisingly found that treating the separated liquid according to the disclosed embodiment saves on such energy consumption. The separated liquid is first treated for separating a fraction of the HCl it contains, e.g. by distilling gaseous HCl or gaseous HCl with some water vapors. Such separation of a fraction of the HCl increases the water/HCl weight/weight ratio in the HCl-depleted separated liquid. When such ratio increases, e.g. to greater than 3, preferably greater than 3.5 and more preferably greater than 4, a separated liquid heavy phase splits out of the HCl-depleted separated liquid, as such, according to an embodiment, or after some cooling, according to another. Said heavy phase comprises a significant amount of the water and of the HCl originally contained in the separated liquid. The heavy phase is separated, e.g. by decantation, from the separated liquid light phase and used as such for the formation of the hydrolysis medium. The separated liquid light phase is further distilled, according to an embodiment, for the recovery of the majority of the remaining water and HCl, Yet, since part of the acid and the water got separated in the separated liquid heavy phase and used as such in hydrolysis, the total energy cost is decreased, less water and less HCl needs to be distilled. Thus, according to the preferred embodiment, HCl recovery and extractant regeneration comprise at least three stages: distilling part of the HCl from the separated liquid, separating the formed light phase from the formed heavy phase and distilling the rest of the acid (and water), or most of it, from the separated light phase.

According to an embodiment, the separated liquid light phase is used as such, or after some modification as the S1-comprising stream for lignin deacidification. Thus, according to this alternative embodiment, treatment of the separated liquid comprise distilling part of the HCl contained in it, separating the formed heavy phase to be used, e.g. in the reformation of the hydrolysis medium, separating of the light phase and using it as such or after some modification for the deacidification of the lignin. That separated light phase may comprise some HCl. According to an embodiment, after contacting with said separated light phase, the lignin stream is further contacted with S1-comprising stream of lower HCl content. According to a related embodiment, the separated light phase is divided into at least two fractions, one of which is not treated and another treated for further removal of HCl to form HCl-depleted light phase. According to that embodiment, the lignin stream is first contacted with the untreated separated light phase and then contacted with the HCl-depleted light phase.

Operation according to the method of this embodiment provides another improvement. According to an embodiment, the lignin stream comprises a small amount of carbohydrates, which end up in the separated liquid. The separated liquid heavy phase carries with it a large majority of the extracted carbohydrates, which get recycled with it into the hydrolysis medium. Product losses and formation of carbohydrate degradation products are minimized.

The present invention provides, according to an aspect, a method for processing a lignocellulosic material and for the production of a carbohydrate composition and a lignin product, comprising: (i) providing a lignocellulosic material feed comprising a polysaccharide and lignin; (ii) hydrolyzing said polysaccharide in an HCl-comprising hydrolysis medium to form a hydrolyzate, which hydrolyzate comprises at least one carbohydrate and HCl, and to form a lignin stream comprising solid lignin, HCl and water; (iii) bringing said hydrolyzate, as such, or after modification thereof, into contact with a first extractant comprising a first solvent (SI), characterized by a water solubility of less than 10% and by at least one of (a1) having a delta-P between 5 and 10 $MPa^{1/2}$ and (b1) having a delta-H between 5 and 20 $MPa^{1/2}$, whereupon HCl selectively transfers to said first extractant to form an HCl-carrying first extract and an HCl-depleted hydrolyzate; (iv) recovering HCl from said first extract; and (v) deacidifying said lignin stream according to the method described hereinbefore.

Preferably the weight/weight ratio of carbohydrates to water in said hydrolyzate is in the range of between 0.2 and 2 and the weight/weight ratio of HCl to water in said hydrolyzate is in the range between 0.17 and 0.60.

In preferred embodiments said first extract comprises carbohydrates and the method further comprises a step of bringing said first extract, prior to said recovering, in contact with a recycled aqueous HCl solution.

In various embodiments, HCl may be recovered from lignin through extraction with a solvent that is preloaded with aqueous HCl. Without wishing to be bound by theory, it is believed that the preloaded solvent increases the overall efficiency of the process. For example, the process as described herein may decrease energy consumption (>90% of the HCl and of the water are recovered with no distillation, the majority of the solvent is not heated/cooled), reduce capital cost (a column for distilling HCl and water from the solvent is eliminated) and reduce the formation of chlorinated forms of the solvent. Thus, the present method is based on the idea of using, instead, solvent loaded with HCl and water so that a separated aqueous phase does not dissolve in the organic phase and can be removed as such. The solvent is then recycled. In various embodiments, the extraction solvent is hexanol.

Recovery of Concentrated Acid

In the recovery of concentrated acid, an aqueous feed is a hydrolyzate formed on hydrolyzing a polysaccharide contained in a lignocellulosic material in an HCl-comprising hydrolysis medium and is also referred to as the hydrolyzate. Said HCl-depleted aqueous feed is also referred to as HCl-depleted hydrolyzate and said further HCl-depleted aqueous feed is also referred to as deacidified hydrolyzate.

The feed to the process is an aqueous solution comprising HCl and a carbohydrate. According to an embodiment, said aqueous feed is a product of hydrolyzing a polysaccharide in an HCl-comprising hydrolysis medium. According to another embodiment, said polysaccharide is at least one of cellulose and hemicellulose. According to a preferred embodiment, the aqueous feed is the hydrolyzate stream formed on hydrolyzing a polysaccharide contained in a lignocellulosic material in a hydrolysis medium.

Preferably, said hydrolysis medium is a highly concentrated HCl solution.

According to an embodiment, HCl concentration in the hydrolysis medium is greater than 30%. The hydrolysis medium is formed, according to an embodiment, by contacting said lignocellulosic feed with a recycled reagent HCl stream. According to an embodiment of the invention, in said recycled reagent HCl, the concentration of HCl is greater than 30%, preferably greater than 35%, more preferably greater than 38% and most preferably greater than 40% (as calculated by 100 time HCl weight divided by the combined weights of HCl and water).

Said hydrolysis forms a hydrolyzate comprising HCl and at least one carbohydrate and a lignin stream comprising lignin, HCl and water. The lignin stream is separated from the hydrolyzate. Preferably, said hydrolyzate is essentially solids free. According to an embodiment, said hydrolyzate comprises solids and those are separated by at least one of filtration and centrifugation. According to another embodiment, the carbohydrate concentration in said hydrolyzate is greater than 15% wt (as calculated by 100CH/(CH+W), where CH and W are the weights of the carbohydrates and the water, respectively), preferably greater than 20% wt, more preferably greater than 25% wt, and most preferably greater than 30% wt.

The hydrolyzate is used as such, or after modification thereof. According to an embodiment, modification may include distilling out some of the HCl. As used herein, the term modified hydrolyzate is used herein for the separated hydrolyzate, as well as for the product of its modification.

In various embodiments, the present method provides for treating a lignin stream comprising the steps of: (a) providing a lignin stream comprising solid lignin, HCl, water, optionally cellulosic material and optionally a carbohydrate, wherein said solid lignin content is in the range of between 3% wt and 30% wt, the cellulosic material content is in the range of between 0% wt and 25% wt, the weight ratio of HCl to water is greater than 0.5 and, CI, which is the weight ratio of carbohydrates to lignin, is less than 0.05; (b) providing a recycled acid stream comprising HCl and water; (c) providing a first reactor comprising (i) a heavy aqueous liquid phase and (ii) a light organic liquid phase, said organic liquid phase comprising a first solvent SI, water and HCl, wherein SI is characterized by a water solubility of less than 15% and b y at least one of (a1) having a delta-P between 5 and 10 $MPa^{1/2}$ and (b1) having a delta-H between 5 and 20 $MPa^{1/2}$, wherein delta-P is the polarity related component of Hoy's cohesion parameter and delta-H is the hydrogen bonding related component of Hoy's cohesion parameter, wherein the weight ratio of HCl to water is greater than 0.5, wherein the weight ratio of HCl to solvent is greater than 0.1 and wherein the weight ratio of water to solvent is greater than 0.15; (d) introducing said lignin stream through at least one opening, VI, located at a lower part of said first reactor and moving said solid lignin upwards, towards at least one opening, V3, located at an upper part of the reactor; (e) contacting said solid lignin, first with said heavy liquid phase, and afterwards with said light liquid phase, to form an acid depleted solid lignin; (f) removing at least a fraction of said heavy liquid phase to form a removed heavy phase; and (g) removing said acid depleted solid lignin from said first reactor through the at least one opening V3 to form removed, acid-depleted, solid lignin. According to an embodiment, said first reactor is provided with a headspace above said light organic liquid phase and said opening V3 is located in said headspace.

According to an embodiment, the method further comprises the steps of (i) providing a lignocellulosic feed, (ii) introducing said lignocellulosic feed into at least one second reactor; (iii) contacting said lignocellulosic feed in said at least one second reactor with a hydrolysis medium to form a carbohydrate-comprising hydrolyzate stream and a lignin stream; (iv) removing said carbohydrate-comprising hydrolyzate stream from said at least one second reactor and (v) removing said lignin stream from said at least one second reactor to form said provided lignin stream.

According to an embodiment, said method further comprises the steps of deacidifying said removed acid-depleted solid lignin to form a deacidified solid lignin and desolventizing said deacidified solid lignin to form a desolventized solid lignin, wherein at least one of said deacidifying and said desolventizing is conducted at a pressure greater than 0.7 bar and at a temperature lower than 140° C.

Refining of Extractant

According to the present invention, there is now provided a method for refining a recycle extractant comprising the steps of (i) providing a recycle extractant comprising a solvent SI and at least one impurity, wherein SI is characterized by a water solubility of less than 15% and by at least one of (a1) having a polarity related component of Hoy's cohesion parameter (delta-P) between 5 and 10 $MPa^{1/2}$ and (b1) having a hydrogen bonding related component of Hoy's cohesion parameter (delta-H) between 5 and 20 $MPa^{1/2}$ and wherein said impurity has an S1/water distribution coefficient greater than 1; (ii) contacting said recycle extractant with lime to form lime-treated recycle extractant; (iii) contacting said lime-treated recycle extractant with $CO_2$ to form a slurry comprising calcium carbonate and said lime-treated recycle extractant; and (iv) separating said calcium carbonate from said lime-treated recycle extractant to form a refined recycle extractant.

The term recycle extractant refers to an extractant formed in a process comprising the steps of (i) contacting an S1-comprising extractant with an aqueous solution comprising HCl, carbohydrate, and an impurity, whereby HCl is selective extracted to form S1-comprising extract, and (ii) separating HCl from said S1-comprising extract by distillation. Said separating regenerates an S1-comprising extractant which comprises less than 2% HCl (preferably less than 1% and more preferably less than 0.5%). The regenerated S1-comprising extractant is to be reused in the step of contacting as such or after refining. That regenerated extractant is referred to herein as recycle extractant or regenerated extractant. The recycle extractant comprises at least one impurity.

As used herein, the term refining refers to the method of removing at least a fraction of an impurity in the recycle extractant. The term refined recycled extractant is used herein for recycled extractant out of which at least a fraction of said impurity was removed.

As used herein, the term impurity refers to a compound other than HCl or carbohydrate. According to an embodiment, the impurity of the recycle extractant results from an HCl-comprising aqueous solution. According to an embodiment, an impurity in the HCl-comprising aqueous solution transfers into the extract from said aqueous solution, as such or after chemical conversion. The impurity of the present invention is characterized by an SI/water distribution coefficient greater than 1, typically greater than 2, preferably greater than 3 and more preferably greater than 5. The S1/water distribution coefficient of the present invention is determined by generating a 1% solution of the impurity in SI, contacting that solution with an equivalent amount of water, equilibrating the two phases (mixing them until there is no further change in composition) to form an impurity-comprising organic phase (S1 rich) and an impurity-comprising aqueous phase, separating the two phases, analyzing each one of them for the impurity and dividing the concentration of the impurity in the organic phase by the concentration of the impurity in the aqueous phase.

According to an embodiment, said impurity is selected from the group consisting of mineral or organic acids, anionic chloride complexes of heavy metals, alkyl chlorides, alkyl acetates and hydrophobic organic compounds. According to an embodiment, said hydrophobic organic compounds are selected from the group consisting of phenols, aldehydes, fufural, hydroxymethylfurfural, tall oils, wood extractives and products of their reaction. According to an embodiment, said impurity is characterized in that the viscosity of a solution containing 95% SI and 5% impurity is greater by at least 1% compared with that of SI. According to an embodiment, said impurity has absorption in the visible spectrum.

As indicated, according to an embodiment, the recycle extractant is contacted with a lime slurry. According to an embodiment, S1 solubility in water and in the solution forming said lime suspension is less than 15%, preferably less than 10%, more preferably less than 5% and most preferably less than 1%. As a result, said recycle extractant is not soluble or has low miscibility in said lime slurry. Said contacting with lime slurry forms therefore a mixture comprising two liquid phases, an organic one consisting essentially of said lime-treated recycle extractant and an aqueous one and solid lime.

One method of the present invention further comprises contacting said lime-treated recycle extractant with $CO_2$ to form a slurry comprising calcium carbonate and said lime-treated recycle extractant. According to an embodiment, said recycle extractant is contacted with a lime slurry to form said mixture of two liquids and solid lime and said mixture is contacted with $CO_2$ to form said slurry comprising calcium carbonate and lime-treated recycle extractant. That mixture is contacted with $CO_2$ as such or after some modification. According to various embodiment, such modification comprises at least one of temperature modification, separation of part of the lime-treated recycle stream, separation of at least part of the lime slurry, adding lime, removing lime, etc.

$CO_2$ from any sources is suitable. $CO_2$ is available at low cost, e.g. from boiler exhaust, which in some cases could be used as such and in other cases, is slightly purified, e.g. by bubbling through water. According to an embodiment, the $CO_2$ to be used is provided in a gas mixture of about 10% or higher. $CO_2$ from a nearby ethanol plant is also suitable. Any form of contacting with $CO_2$ is suitable. According to an embodiment, $CO_2$ is bubbled through the mixture. Such contacting results in the formation of a slurry comprising calcium carbonate, mainly due to the reaction between lime and $CO_2$. As used herein the term calcium carbonate refers to $CaC(¾, Ca(HC(¾)_2$ and combination thereof. In the next step, said calcium carbonate is separated from said lime-treated recycle extractant to form a refined recycle extractant.

According to an embodiment, the apparent pH of the lime-treated recycle extractant in step (iii) is in the range between 6.5 and 8.5, preferably between 7.0 and 8.0. Measurement of pH in an aqueous phase is straightforward, but measuring it in an organic phase poses theoretical and practical difficulties. As used herein apparent pH of an organic solution is the pH in an aqueous solution in equilibrium with said organic solution. Contacting water with the lime-treated recycle extractant after said contacting with $CO_2$ and mixing to reach equilibrium may change the composition of that recycle extractant. Yet, at recycle extractant to water ratios greater than 10, the effect is small. Thus, according to an embodiment, on contacting said lime-treated recycle extractant after said contacting with $CO_2$ with 5% of its weight of water and mixing for equilibration, the pH measure in said aqueous medium is in the range between 6.5 and 8.5. According to another embodiment, the pH in said calcium carbonate comprising slurry is in the range between 6.5 and 8.5.

In especially preferred embodiments, the apparent pH of the lime-treated recycle extractant in step (iii) is in the range between 6.5 and 8.5.

Any form of separating said calcium carbonate from said lime-treated recycle extractant is suitable. According to an embodiment, said separating comprises press filtration. It was surprisingly found that the formed calcium carbonate is relatively easy to separate from the recycle extractant in the slurry, e.g. by filtration. Other solid components, if present, are also readily filtered out.

According to an embodiment, the $CaCO_3$ of the separated slurry is reacted with HCl-comprising byproduct streams, such as resin generation solutions and other wash solutions. Such reaction saves on alkali cost. According to another embodiment, lignocellulosic hydrolysis is conducted next to a paper mill and the separated calcium carbonate is consumed in the paper mill.

In preferred embodiments, said method further comprises the step of contacting said slurry with lime before said separating step. In other preferred embodiments of the present invention, said method further comprises the step of contacting said slurry with lime simultaneously with said separating step. According to an embodiment, contacting is with lime slurry. According to an embodiment, said contacting the slurry with lime further improves removal of said impurities, further improves color removal, further improves filtration as well as improving combination thereof.

According to an embodiment, separating said calcium carbonate leaves residual calcium compound, e.g. calcium carbonate, calcium hydroxide, calcium sulfate, or calcium phosphate, in said lime-treated recycle extractant. According to an embodiment, the method further comprising the step of removing said residual calcium salt by washing with water or with an aqueous solution. It was found that such washing of residual calcium compound requires significantly less washing water compared with washing a similar amount of residual sodium or ammonium compound, e.g. at least 10% less, preferably at least 20% less and more preferably at least 50% less.

In various embodiments, deacidifying a lignin stream comprises contacting said stream with an SI-comprising extractant to form an HCl-depleted lignin and an HCl-comprising second extract, further comprising the steps of: (a) separating acid from said HCl-comprising second extract to form separated acid and a second recycle extractant; (b) contacting said second recycle extractant with lime to form a second lime-treated recycle extractant; (c) contacting said lime-treated second recycle extractant with $CO_2$ to form a second slurry comprising calcium carbonate and refined extractant; (d) separating said calcium carbonate from said second lime-treated recycle extractant to form a second refined recycle extractant; and (e) using said second refined recycle extractant in at least one of said first extractant and said deacidifying said lignin stream.

In preferred embodiments, said method further comprises the step of contacting said first slurry, said second slurry or both with lime before said separating or simultaneously with it. Preferably said first recycle extractant, said second recycle extractant or both further comprises an ester. Preferably said ester is an acetate ester. In preferred embodiments of said methods, the apparent pH of the first refined extractant, the second refined extractant or both in said first slurry, said second slurry or both, respectively, is in the range between 6.5 and 8.5. Preferably SI is an alkanol and said recycle extractant comprises the corresponding alkyl chloride.

Resin-Based Separation of Acid and Carbohydrate

In various embodiments, acid from the hydrolysis of lignocellulosic material is recovered from the resulting hydrolyzate in a two-step process comprising a first step of extraction of acid with an organic solvent to remove a major portion of the acid followed by resin-based treatment of the acid-depleted hydrolyzate. In various embodiments, resin-based treatment of the acid-depleted hydrolyzate yields an acid-enriched sugar cut and an acid-depleted sugar cut. In various embodiments, the acid-enriched sugar cut may be added to subsequent material entering the resin-based treatment to form a processing cycle.

According to an embodiment, contacting hydrolyzate with a resin comprises introducing HQ-depleted hydrolyzate into a resin-containing column followed by introducing an aqueous eluant into said resin-containing column, whereupon acid-cut solution exits the column followed by de-acidified carbohydrate-cut solution.

According to an embodiment, the present method for processing a lignocellulosic material and for the production of a carbohydrate composition and optionally a lignin product, comprises: (i) providing a lignocellulosic material feed comprising a polysaccharide and lignin; (ii) hydrolyzing said polysaccharide in an HCl-comprising hydrolysis medium to form a lignin stream comprising lignin, HCl and water and a hydrolyzate, which hydrolyzate comprises HCl, at least one mono carbohydrate and at least one oligo carbohydrate, wherein the weight ratio of total carbohydrates to water in said hydrolyzate is at least 0.3 and wherein the total oligomers to total carbohydrate weight ratio in said hydrolyzate is at least 0.25; (iii) forming a modified hydrolyzate by combining said hydrolyzate with an adjusted and optionally concentrated acid-cut solution from a following step; (iv) bringing said modified hydrolyzate into contact with a first extractant comprising a first solvent (SI) characterized by a water solubility of less than 15% and by at least one of (a1) having a polarity related component of Hoy's cohesion parameter (delta-P) between 5 and 10 $MPa^{1/2}$ and (b1) having a hydrogen bonding related component of Hoy's cohesion parameter (delta-H) between 5 and 20 $MPa^{1/2}$; whereupon at least 85% of the HCl in said modified hydrolyzate selectively transfers to said first extractant to form an HCl-carrying first extract and an HCl-depleted hydrolyzate; (v) recovering HCl from said HCl-carrying first extract to form recovered HCl stream and recycle extractant, (vi) separating HCl from carbohydrate in said HCl-depleted hydrolyzate by means of contacting said HCl-depleted hydrolyzate with a resin in a chromatographic mode to form a de-acidified carbohydrate-cut solution and an acid-cut solution; (vii) adjusting the composition of said acid-cut solution by maintaining said composition at a temperature greater than 600 C for at least 10 minutes to form an adjusted acid-cut solution; (viii) optionally concentrating said adjusted acid-cut solution and (ix) deacidifying said lignin stream, which method is characterized in that the total weight ratio of carbohydrates to water in said carbohydrate-cut solution is at least 0.25 and in that the total oligomers to total carbohydrate weight ratio in said carbohydrate-cut solution is less than 0.15.

V. Recovery of Acid from Additional Processes

Paper Processes

Deacidifying HCl comprising streams, recovery, regeneration and/or recycle of hydrochloric acid as described herein is coupled, according to various embodiments, with industrial processes. Such industrial processes use, according to various embodiments, concentrated or dilute hydrochloric acid. For example, industrial processes for the production of corrugated containers and papers involving hydrochloric acid may be coupled with the recovery and/or regeneration of hydrochloric acid as described herein.

In various embodiments, cellulose-comprising feed material or lignocellulosic feed material is treated with aqueous hydrochloric acid solution with HCl/water weight/weight ratio of less than 0.65, preferably in the range between 0.3 and 0.6 under conditions where the hydrolysis of polysaccharides of the feed material is incomplete to form a hydrolyzate comprising HCl and at least one carbohydrate and solid cellulose, which solid cellulose is used for the production of cellulose-based consumer product, e.g. paper or paper-based products. The method further comprises deacidification of said hydrolyzate to form (i) a deacidified carbohydrates-comprising hydrolyzate, which is reacted to form carbohydrate products and (ii) recycle HCl stream, wherein HCl/water weight/weight ratio of less than 0.65, preferably in the range between 0.3 and 0.6. The costs related to the deacidification and formation of this recycle stream are lower than those of forming a recycle stream of HCl/water weight/weight ratio greater than 0.6, including reduced rate of solvent reaction with HCl, as in the case of the formation of hexyl chloride from hexanol. Thus, according to this method, cellulose-comprising feed material or lignocellulosic feed material is converted at reduced cost into a cellulose product and a carbohydrate product In various embodiments, recovery and/or regeneration of hydrochloric acid is coupled with industrial processes in the paper and pulp-making industries. In one embodiment, the industrial process in the paper and pulp-making industry is a process for the generation of paper and/or pulp from wood. Alternatively, the industrial process in the paper and pulp-making industry may be related to recycling of waste paper.

In one embodiment, waste cellulosic paper product is subjected to an acid treatment, and following the acid treatment, the acid is recycled and/or recovered. In one embodiment, acid pretreatment of waste cellulosic paper occurs prior to oxygen delignification for recycling of waste cellulosic paper.

Following treatment with acid, the waste cellulosic paper product may be treated according to any process, for example the oxygen delignification processes described by Nguyen, U.S. Pat. No. 5,302,244, which is incorporated by reference. According to Nguyen, waste cellulosic paper product may be reslushed with water, and aqueous acid is added to the reslushed waste paper product, whereafter an acid removal step may be carried out by washing or dewatering or both. Removal of the acid may be performed to avoid waste of alkaline material in a subsequent oxygen delignification step of the waste cellulosic paper product. In various embodiments, the procedures are compatible with additional steps, for example, as described in U.S. Pat. Nos. 6,461,475; 6,440,269; 5,486,268; 5,350,493; 5,302,244; 4,495,163; or U.S. Pat. No. 3,963,843, the disclosures of which are hereby incorporated by reference.

Pulp and paper sludge (a byproduct of primary pulping operations, recycle streams or waste paper pulping and the like) represents an environmental and disposal problem for manufacturers of pulp and paper. Generally, pulp and paper sludge is unsuitable for paper making, although it generally contains the same components—cellulose, lignin, hemicellulose, calcium carbonate, clay, and other inorganic components—as those present in the paper pulp itself.

Paper sludge has traditionally been disposed of by landfilling, composting, incorporation into cement, and incineration. The latter option, in turn, creates another problem, namely, disposal of the resulting ash, which often makes up to 50% (and some times as much as 80% or higher) of the volume of the sludge itself.

The principal components of ash are calcium carbonate—in the form of precipitated calcium carbonate (PCC) or ground calcium carbonate (GCC) that typically constitutes 20% and up to 75% of dry sludge content, and clay. These two minerals are typically loaded into paper as a coating and filler to improve the mechanical characteristics as well as the appearance of paper. This makes paper-making sludge, particularly mixed office paper sludge, consisting of two major components, that is fiber and minerals, finely mixed with each other.

A typical recycling mill processes 600 tons of wastepaper per day, yielding 450 tons of pulp and producing 150 tons of papermaking sludge. The 228 mills currently under operation in North America produce 9 million tons of pulp residue, approximately 5 million tons of which is cellulose. The 154 European pulp and paper mills produce about 8 million tons of pulp residue, approximately 4 million tons of which is cellulose. The conversion of such waste material into glucose as alternate source of fuels, chemicals, and other useful products by acid and/or enzymatic hydrolysis of cellulose has long been desired. However, the mineral components of papermaking sludge dramatically decrease the efficiency of enzymatic hydrolysis of the cellulose component, making it technically unrealistic and economically prohibitive. Likewise, the high content of calcium carbonate in typical papermaking sludge renders the use of acid for cellulose hydrolysis practically impossible, because calcium carbonate reacts with and neutralizes the acid. For these reasons, industry has failed to develop a feasible approach to producing glucose from papermaking sludge using acid hydrolysis; and as a result, the cellulose component of papermaking sludge is generally largely or totally wasted. At best, the prior art describes utilization of paper sludge for production of low-end products of limited market value, without their chemical conversion into value-added products.

The carbohydrate content of plant materials consists of cellulose and hemicellulose, both polysaccharides. Chemical pulping of plant materials largely removes hemicellulose, which is much more susceptible to acid treatment and depolymerizes easily compared to cellulose. Hence, acid hydrolyses of conventional, chemically intact "biomass," on the one hand, and papermaking sludge, on the other, often differ substantially: the conventional and generally milder hydrolysis of lignocellulose typically aims to produce sugars, most of which originate from hemicellulose (e.g., U.S. Pat. Nos. 2,734,836, 4,436,586, 4,511,433, 4,612,286, 4,668,340), while papermaking sludge typically contains much less hemicellulose; accordingly, the hydrolysis conditions are generally more stringent in order to break down recalcitrant cellulose into glucose.

Fagan, Grethlein et al. ("Kinetics of the Acid Hydrolysis of Cellulose Found in Paper Refuse," Env. Sci. Technol. 5(6):545-547 (1971)) detail processing of ball milled Kraft paper and municipal refuse (with no other components interfering with the hydrolysis) in the 180 C.-240 C. temperature range with sulfuric acid concentrations of 0.2%, 0.5%, and 1.0%, and on a scale of 0.5 gram with respect to paper amount. They showed that at 230 C. with 1.0% acid, 52% of the cellulose could be converted to (unspecified) sugars; with 0.5% acid, the sugar yield was 39%. Subsequently, Grethlein ("The Acid Hydrolysis of Refuse," Biotechnol. Bioeng. Symp. No. 5, pp. 303-318 (1975)) disclosed that the glucose concentration in those experiments was only about 2 g/L (due to the limit of 1% slurry in the reactor). According to Mackie et al. ("Effect of Sulphur Dioxide and Sulphuric Acid on Steam Explosion of Aspenwood," J. Wood Chem. Technol. 5(3):405-425 (1985)), the action of 0.58% (w/w) sulfuric acid on aspen wood chips for 80 sec at 200 C. liberated 16.4% pentosans (from the initial 18.3%), only 12% of which (i.e., 2.0% overall) was glucose. 70.5% of the initial wood was recovered from the reaction mixture as a solid residue (30.7% of that was lignin). Malester et al. ("Kinetics of Dilute Acid Hydrolysis of Cellulose Originating from Municipal Solid Wastes," Ind. Eng. Chem. Res. 31:1998-2003 (1992)) showed that for dilute-acid hydrolysis of cellulose derived from municipal solid wastes, the best conditions were the most severe ones among those tested: pH 0.34 and temperature of 240 C. Under these conditions, a glucose yield of 54.3% was achieved at a reaction time of 4.6 sec. The actual acid concentrations used and the concentration of glucose obtained were not reported.

Sulfuric acid has commonly been used as an active agent, though other acids, such as hydrochloric (e.g., U.S. Pat. Nos. 4,237,110, 4,645,658, 4,650,689), phosphoric (e.g., U.S. Pat. Nos. 4,409,032, 5,486,068), nitric (e.g., U.S. Pat. Nos. 5,221,357, 5,536,325), trifluoroacetic (e.g., U.S. Pat. No. 4,400,218), and also gaseous hydrogen fluoride (U.S. Pat. No. 4,556,432), sulfur dioxide (U.S. Pat. No. 4,278,471), and sulfur trioxide (U.S. Pat. No. 4,427,584) have also been used.

Materials that contain along with cellulose some other components (such as calcium carbonate in papermaking sludge) capable of effectively neutralizing an acid have not previously been considered appropriate substrates for acid hydrolysis. As a result, known techniques of acid hydrolysis of cellulose (see, e.g., U.S. Pat. Nos. 3,532,594, 3,787,241, 4,160,695, 4,174,997, 4,201,596, 4,237,226, 4,242,455, 4,266,981, 4,281,063, 4,316,747, 4,316,748, 4,384,897, 4,427,453, 4,478,644, 4,529,699, 4,556,430, 4,615,742, 4,645,541, 5,486,068, 5,536,325, 5,562,777, 5,580,389, 5,597,714) have not been applied to hydrolyze cellulose in papermaking sludge.

The present invention facilitates production of glucose by concentrated acid hydrolysis of the cellulose component of papermaking sludge (pressed/wet or dried). Generally, the invention is applied to cellulose obtained from sludge which cellulose may or may not be mixed with clay, although the approach described herein is applicable to many variants of cellulose or cellulose-clay composites regardless of their origin.

The invention generally involves a two-step procedure: (i) calcium solubilization by combining the pressed or dried sludge with acid, following which the solid content is separated from the liquid content (to yield a liquid fraction comprising a solids-free solution of the calcium salt and a solid fraction mainly comprising cellulose and clay), and (ii) acid-mediated hydrolysis by combining the pressed or dried solid residue with a concentrated acid, following which the mixture is treated with acid under atmospheric conditions and then heated only to 80-100° C. in the presence of water (in the case of concentrated acid). With a sufficiently high solid sludge-residue content in the hydrolysis reactor, such as up to 50% (with concentrated acid), the liquid obtained will contain glucose in concentrations up to 90-180 g/L (with concentrated acid). The separation of the liquid from the solid residue (if any) is preferably carried out using belt presses, screw presses, centrifuges, filters, or a combination. The solids obtained can be further washed with water in order to increase the amount of recovered glucose.

Papermaking sludge typically contains a rather high amount of $CaCO_3$ (20%-50% or more of the solids content). In the presence of many acids, CaC(¾ is solubilized as a result of conversion into the acid-anion salt in the reaction mixture. Also, CaC(¾ in the sludge is typically accompanied by aluminosilicates (clay) and other minerals (as pigments, fillers, etc.), such as those based on magnesium, potassium and others. These can be partially extracted with acids as well. Obviously, the extent of acid extraction/solubilization of the inorganic components greatly depends on the conditions of the sludge treatment with acids, nature of the acid, acid concentration, and contact time with the acid in particular.

The first step in the method of the invention (i.e., calcium solubilization) can be practiced in accordance with the the following. Removal of calcium from papermaking sludge facilitates subsequent acid-mediated hydrolysis of its cellulose component to produce glucose. Pressed or dried sludge is combined with a dilute acid, following which the solid content (mainly cellulose and clay) is separated from the liquid content (a solution of calcium and other salts). The separation of the liquid from the solid residue may be carried out using belt presses, screw presses, centrifuges, filters, or a combination. With regard to sludge, this may be mixed with a solution of an inorganic or organic acid-in concentrations generally ranging from 0.1% to 55% by weight, and most preferably 3% to 16%, the optimal concentration depending on process conditions (in particular, calcium carbonate content in the processed papermaking sludge). In preferred embodiments, the mixture is combined with 2% to 6% HCl; 2% to 8% $HNO_3$; or 2% to 16% acetic acid. Generally, the amount of acid added into the reaction mixture is 0.8 to 5.0 times the stoichiometric calcium carbonate content in the mixture, preferably 0.8 to 2.0 times the stoichiometric content, and most preferably 1.0 to 1.2 times the stoichiometric content. The acid-containing mixture is incubated (with agitation, if desired, to shorten the reaction time) to solubilize calcium carbonate and other minerals, following which the liquid phase is isolated, and the cellulose component (with or without insoluble minerals) recovered. Completion of calcium solubilization can b e verified b y determination of the calcium concentration or content in the bulk solution.

After completion of calcium solubilization and recovery of calcium carbonate-free cellulose fiber, or a mixture of fiber and clay, glucose can be obtained using either dilute or concentrated acid hydrolysis. In this step, the hydrolysis is preferably carried out with concentrated hydrochloric acid.

Concentrated-acid hydrolysis requires regeneration of spent acid to make the process economically acceptable. For example, glucose solutions derived in accordance herewith can be fermented by appropriate microorganisms, such as *Anaerobiospirillum succiniproducens*, to produce chemical, biochemical and pharmaceutical compounds. As a result, a rather complex pattern of factors should be considered in order to choose a principal mode of cellulose hydrolysis.

Concentrated-Acid Hydrolysis

In preferred embodiments, cellulose residue (with or without clay) after solubilization of calcium salts in papermaking sludge (calcium solubilization), or any other $CaCO_3$-free papermaking sludge is mixed with a solution of concentrated sulfuric acid, generally in concentration of 50% to 98% by weight, preferably 70% to 96% by weight, and most preferably 80% to 96% by weight. Generally, the ratio of solids (dry weight) to liquid in the reaction mixture is 1:0.7 to 1:7 by weight, preferably 1:1 to 1:2 by weight, and most preferably 1:1.5 by weight. Moisture content in the paper sludge residue generally is 0 to 60%, preferably 5% to 50%, and most preferably 5% to 40%. The mixture is incubated under cooling conditions (particularly when 96% sulfuric acid and/or dry sludge residue is used), preferably for 10 to 30 min, and more preferably for 15 to 20 min. The acid is then diluted with water to a concentration of 20% to 45% (preferably about 30%), and heated at 90 C. to 100 C. for 30 to 60 min (preferably about 40 min). Finally, the mixture is cooled to ambient temperature and pressed, and a liquid fraction containing glucose and other sugars in about 20% to 45% sulfuric acid, is collected. Separation of glucose can be accomplished (a) by chromatography on ion-exchange resins as described in U.S. Pat. Nos. 4,349,668, 4,608,245, 4,837,315, 5,188,673, 5,176,832, followed by regeneration, concentration, and recycling of sulfuric acid as described in U.S. Pat. No. 5,580,389; (b) by neutralization of sulfuric acid, e.g. with calcium, barium, or other appropriate metal carbonates, hydroxides, or other bases, as described in U.S. Pat. Nos. 4,384,897, 4,278,471; (c) selective extraction of glucose into a water-immisible solvent, such as long-chain alcohols (as described in U.S. Pat. Nos. 4,237,110 and 4,608,245), or acetophenone (as disclosed in U.S. Pat. No. 4,645,658, which details separation of glucose and hydrochloric acid), or propionaldehyde (as set forth herein), or other appropriate solvents.

Generally, these preferred embodiments result in solutions of up to 80-150 g/L of glucose (the precise concentration depending on ash content and moisture content in the sludge, among other factors), and a conversion ratio of cellulose into glucose as high as 60-80%.

The sugar (predominantly glucose) obtained in the liquid can be employed in solution, in a concentrated form, or in the solid state (e.g., by evaporation of the water phase) as a separate product, or can be fermented using appropriate microorganisms (such as *Anaerobiospirillum succiniproducens*) into chemicals, biochemicals and pharmaceuticals. Using the approach of the present invention, it is possible to obtain solutions of glucose from a number of papermaking sludge materials.

Additional Processes

In various embodiments, the lignocellulose-derived components according to the present invention are derived from processes as described in the following US patents, the contents of each of which are hereby incorporated by reference: U.S. Pat. No. 7,819,976 (Biomass treatment method), U.S. Pat. No. 7,781,191 (Treatment of biomass to obtain a target chemical), U.S. Pat. No. 7,682,812 (Process for producing ethanol), U.S. Pat. No. 7,625,728 (Process for the simultaneous production of xylitol and ethanol), U.S. Pat. No. 7,494,792 (Process for the production of cellulolytic and hemicellulolytic enzymes using distillation residues from the ethanolic fermentation of enzymatic hydrolyzates of (ligno)cellulosic materials), U.S. Pat. No. 7,229,558 (Chromatographic separation method), U.S. Pat. No. 5,876,505 (Method of producing glucose from papermaking sludge using concentrated or dilute acid hydrolysis), U.S. Pat. No. 5,693,296 (Calcium hydroxide pretreatment of biomass), and U.S. Pat. No. 5,571,703 (Municipal solid waste processing facility and commercial ethanol production process).

VI. Saccharification Product and Fermentation to Downstream Products

The carbohydrate compositions herein can be used in the process of making a downstream product (in whole or in part). For example, a downstream product such as a diaper can be made exclusively from lignocellulose according to the methods herein. In the alternative, a downstream product can comprise a mixture of lignocellulose derived materials and other materials (e.g., derived from petroleum). For example, downstream products, including consumer products, may be predominantly lignocellulose-derived. Alternatively, such products may be predominantly non-lignocellulose derived (such as petroleum-derived) with a minor portion of lignocellulose-derived components. In various embodiments, the proportion of lignocellulose-derived components is greater than about 10% by weight, greater than about 50% by weight, greater than about 90% by weight, or any value up to 100% by weight.

In various embodiments, the downstream product will incorporate chemicals produced during the methods described herein. For example, in various embodiments, downstream products including consumer products will include furfural. Such furfural may be present in a range of concentrations, for example, at a concentration of up to 100 ppm. Without limitation, such consumer products may include fuel, diapers, paint, carpet, and paper. In various embodiments, chemicals from the production process may serve as a chemical signature allowing for identification of the source of the consumer product.

In various embodiments, the carbohydrates of the deacidified hydrolyzate or products thereof serve as the feedstock for fermentation and/or for further processing. For example, in various embodiments, the carbohydrate is used in one or more processes as described in U.S. Pat. Nos. 7,629,010; 6,833,149; 6,610,867; 6,452,051; 6,229,046; 6,207,209; 5,959,128; 5,859,270; 5,847,238; 5,602,286; and 5,357,035, the contents of which are incorporated by reference. In various embodiments, the processes described in the above US patents are combined with one or more steps as described herein, for example, with the step of recycling hydrochloric acid as described herein.

In various embodiments, the saccharification product is a feedstock for a genetically modified organism (GMO). Any GMO is compatible with the feedstocks according to the invention. GMOs may include, but are not limited to, members of the genera *Clostridium, Escherichia, Salmonella, Zymomonas, Rhodococcus, Pseudomonas, Bacillus, Enterococcus, Alcaligenes, Lactobacillus, Klebsiella, Paenibacillus, Corynebacterium, Brevibacterium, Pichia, Candida, Hansenula* and *Saccharomyces*. Hosts that may be particularly of interest include: *Oligotropha carboxidovorans, Escherichia coli, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*. Also, any of the known strains of these species may be utilized as a starting microorganism. In various embodiments, the microorganism is an actinomycete selected from *Streptomyces coelicolor, Streptomyces lividans, Streptomyces hygroscopicus*, or *Saccharopolyspora erytlzraea*. In various embodiments, the microorganism is an *eubacterium* selected from *Escherichia coli, Pseudomonas flucrescens, Pseudomonas putida, Pseudomonas aeruginosa, Bacillus subtilis*, or *Bacillus cereus*.

In some embodiments, the GMO is a gram-negative bacterium. In some embodiments, the recombinant microorganism is selected from the genera *Zymomonas, Escherichia, Alcaligenes*, and *Klebsiella*. In some embodiments, the recombinant microorganism is selected from the species *Escherichia coli, Cupriavidus necator*, and *Oligotropha carboxidovorans*. In some embodiments, the recombinant microorganism is an *E. coli* strain.

A. Carbohydrate Fraction from Acid Catalyzed Hydrolysis of Lignocellulosic Material The carbohydrate-containing fraction (also referred to as precursor) may contain both monomers and oligomers. The majority of the oligomers may be water-soluble. The oligomers proportion relative to the total carbohydrate content of said faction may be at least 0.06, typically at least 0.10, preferably at least 0.15. According to an embodiment, in the precursor the proportion relative to the total carbohydrate content of said precursor of higher oligomers is less than 0.2, typically less than 0.15. According to an embodiment, the proportion relative to the total carbohydrate content of said precursor of higher oligomers in said fermentation feedstock precursor is less than 0.1. The carbohydrate-comprising fermentation feedstock precursor may comprise disaccharides. Any disaccharide is suitable, i.e. disaccharides composed of two sugars of the same type (e.g. two glucose molecules) and of two different sugars, disaccharides combined by an alpha bond and ones combined by a beta bonds and duisaccarides bonded via various hydroxyls on the molecule. The proportion of said disaccharides in the precursor relative to the total carbohydrate content of said precursor is at least 0.05, typically at least 0.1. According to an embodiment, the weight/weight ratio of disaccharides to monomers in the precursor is at least 0.05, typically at least 0.1. The precursor further comprises at least one pentose (C5 sugar, such as xylose and arabinose), typically resulting from the hydrolysis of hemicelluloses, and at least one hexose (C6 sugar, such as glucose and mannose). The proportion of pentoses relative to the total carbohydrate content of said precursor is at least 0.05, typically at least 0.10. As indicated, according to an embodiment, pentoses are separated from the precursor before it is used as fermentation feedstock.

The fermentation feedstock precursor may comprise at least one alpha-bonded diglucose and at least one beta-bonded diglucose. The alpha-bonded diglucose molecules of the precursor are selected from the group consisting of maltose, isomaltose, trehalose, kojibiose, nigerose, and a combination thereof, preferably from the group consisting of maltose, isomaltose trehalose and a combination thereof. The beta-bonded diglucose molecules of the precursor are selected from the group consisting of gentiobiose, sophorose, cellobiose, laminaribiose, beta-trehaose, and and a combination thereof, preferably from the group consisting of gentiobiose, sophorose, cellobiose and a combination thereof.

According to an embodiment, in said precursor, the proportion of said alpha-bonded diglucose and said beta-bonded diglucose are each at least 0.01, typically at least 0.02, preferably at least 0.03. Unless specified otherwise, the term proportion as used herein means proportion relative to the total carbohydrate content of said precursor. According to an embodiment, in said precursor, the proportion of both said alpha-bonded diglucose and said beta-bonded diglucose is at least 0.01. According to another embodiment, said precursor comprises multiple alpha-bonded diglucoses and the combined proportion of said diglucoses is at least 0.03. According to still another embodiment, said precursor comprises multiple beta-bonded diglucoses and the combined proportion of said multiple beta-bonded diglucoses is at least 0.03.

B. Carbohydrate Refining

One method further comprises the optional step of selectively reacting a first carbohydrate to form a product solution comprising a first carbohydrate product and a second carbohydrate. As used herein, selectively reacting means reacting said first carbohydrate preferably over reacting said second carbohydrate. Optionally, the method further comprises a step of treating said product solution to form a separated first carbohydrate product and a separated second carbohydrate. According to an embodiment, said first carbohydrate comprises glucose.

According to an embodiment, said reacting comprises fermenting. According to an embodiment, said first carbohydrate product is a fermentation product. According to an embodiment, said first carbohydrate product is selected from the group consisting of ethanol, alcohols, organic acids and organic acid ester of 3 to 12 carbon atoms, amino acids, peptides and proteins.

According to an embodiment, said first carbohydrate product has an atmospheric-pressure boiling point of less than 100° C., less than 90° C. and more preferably less than 80° C. According to an embodiment, said first carbohydrate product forms an azeotrope with water.

According to an embodiment, said first carbohydrate product is further reacted to form a first carbohydrate product derivative. According to an embodiment, said further reacting is of said separated first carbohydrate product after said treating. According to another embodiment said further reacting is of said first carbohydrate product, while in said product solution as such or after modification. According to a related embodiment, the method further comprises a step of treating said product solution after said further reacting or simultaneously with it to form a separated first carbohydrate product derivate and at least one of a separated second carbohydrate and a separated precursor thereof.

According to various embodiments, said second carbohydrate is selected from the group consisting of xylose, trehalose, gentiobiose, kojibiose, nigerous, sophorose, laminarobiose, arabinose and combination thereof. According to a preferred embodiment said second carbohydrate is xylose. Xylose is a C5 sugar (a pentose) of relatively high value and several applications, e.g. in the production of xylitol and in the production of rumen bypass proteins.

In various embodiments, producing a first carbohydrate product and a second carbohydrate according to one method of the present invention leads to no losses or to minimal losses of the second carbohydrate and of its precursor, where present. Their content in the product solution is similar to that in the hgnocellulosic material feed. Thus, according to an embodiment, the combined amount of said second carbohydrate and precursor thereof in said Hgnocellulosic material feed is M1, the combined amount of said second carbohydrate and precursor thereof in said product solution is M2 and the wt/wt ratio of M2 to M1 is greater than 0.85, preferably greater than 0.90 and more preferably greater than 0.95.

According to an embodiment, the ratio between the combined amount of said second carbohydrate and precursor thereof and said first carbohydrate in said hydrolyzate is R1, the ratio between the combined amount of said second carbohydrate and precursor thereof and said first carbohydrate in said product solution is R2 and the ratio of R2 to R1 is greater than 5, preferably greater than 10 and more preferably greater than 20.

According to an embodiment, the combined amount of said second carbohydrate and precursor thereof forms at least 50% of the total carbohydrates in said product solution, preferably at least 70%, more preferably at least 90% and most preferably at least 95%.

According to an embodiment, at least one of deacidifying, reacting and treating steps comprises selective water removal. As used herein, selective removal of water means preferred removal of water over removal of carbohydrates. According to an embodiment, said selective water removal (e.g. via transfer into a solvent or via distillation) results in increased concentration of the carbohydrates in the formed solution, e.g. deacidified hydrolyzate, product solution, separated second carbohydrate or separated precursor.

According to an embodiment, the combined concentration of said second carbohydrate and precursor thereof in said hydrolyzate is CI, the combined concentration of said second carbohydrate and precursor thereof in said product solution is C2 and C2/C1 is greater than 1.5, preferably greater than 2 and more preferably greater than 3. According to an embodiment, C2 is at least 30% or saturation concentration at 25° C., preferably at least 50% and more preferably at least 70%. According to an embodiment, said treating said product solution comprises crystallization of said second carbohydrate or of a precursor thereof. According to an embodiment, said treating comprises at least one of crystallization of said second carbohydrate or of a precursor thereof, crystallizing said first carbohydrate product, distilling said first carbohydrate product, membrane filtration of said first carbohydrate product, chromatographic separation and various combinations thereof. According to an embodiment, said treating comprises at least one of simulated moving bed, sequential simulated moving bed, using an ISEP and using a CSEP.

According to an embodiment, said precursor comprises an oligosaccharide comprising said second carbohydrate, e.g. a xylose-comprising disaccharide or gentiobiose-comprising trisaccharide. According to another embodiment, said second carbohydrate is a disaccharide and said precursor comprises at least two carbohydrates, each of which comprising a component of the second carbohydrate, e.g. as in the case where said second carbohydrate is a gentiobiose and the precursor comprises maltose, isomaltose or combination thereof.

According to an embodiment, a polysaccharide comprises said second carbohydrate. According to a related embodiment, at least one of said HCl-comprising hydrolyzate, said deacidified hydrolyzate and said product solution comprise said second carbohydrate. According to another embodiment, the polysaccharide comprises both said second carbohydrate and a precursor thereof. According to a related embodiment, at least one of said HCl-comprising hydrolyzate, said deacidified hydrolyzate and said product solution comprise both said second carbohydrate and a precursor thereof. According to still another embodiment, the polysaccharide comprises said precursor, but does not comprise said second carbohydrate. According to a related embodiment, said HCl-comprising hydrolyzate comprises said precursor, but not said second carbohydrate.

According to an embodiment, the method further comprises the step of reacting said second carbohydrate precursor to form said second carbohydrate. According to various embodiments, said reacting of the precursor to form said second carbohydrate is conducted in at least one of said HCl-comprising hydrolyzate, said deacidified hydrolyzate and said product solution. According to an embodiment, a separated precursor is reacted. According to an embodiment, said reacting of the precursor is conducted simultaneously with at least one of said hydrolyzing, said deacidifying and said selectively reacting said first carbohydrate According to various embodiments, said reacting of said precursor comprises hydrolysis, oligomerization, transglucosidation and combinations thereof. As used herein, the term oligomerization means combining monosaccharides and/or oligosaccharides to form an oligosaccharide of a higher degree of polymerization, e.g. combining two glucose molecules to form sophorose. As used herein, the term transglucosidation means transfer of at least one carbohydrate between oligosaccharides, e.g. as in

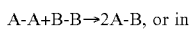

A-A+B-B→2A-B, or in

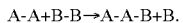

A-A+B-B→A-A-B+B.

Such reacting of the precursor may comprise a combination, e.g. of hydrolysis followed by oligomerization, as in

A-x-A→2A

2A→A-y-A where A-x-A and A-y-A are disaccharides composed of the same monosaccharides, but bound by a different bond, e.g. cellobiose and gentiobiose.

According to various embodiments, reacting said second carbohydrate precursor comprises at least one of acid catalysis and enzymatic catalysis. According to an embodiment reacting said precursor is catalyzed by HCl. According to an embodiment, reacting said precursor is catalyzed by the HCl in the hydrolyzate during said hydrolysis. According to an embodiment, reacting said precursor is facilitated by temperature elevation. According to an embodiment, reacting said precursor is conducted during deacidification. According to an embodiment reacting said precursor is enzymatically catalyzed, using enzymes selected from ones having an activity selected from alpha-glucosidase, beta-glucosidease, transglucosidases and combinations thereof. According to an embodiment, enzymatic catalysis comprises fermentation.

According to an embodiment, the total concentration of carbohydrate is adjusted before or during said reacting of said precursor. According to an embodiment, during said reacting said precursor, the concentration of total soluble carbohydrates in the solution is greater than 10% wt.

According to an embodiment the method further comprises the step of reacting said second carbohydrate to form a second carbohydrate product.

According to an embodiment said second carbohydrate is xylose and said second carbohydrate product is selected from xylitol and a rumen bypass protein, wherein xylitol is a product of reacting xylose with hydrogen and wherein rumen bypass protein is produced by reacting xylose with a protein-containing material.

According to an embodiment, said reacting said second carbohydrate is conducted simultaneously with said reacting of said first carbohydrate or after reacting said first carbohydrate. According to an embodiment, said reacting of said second carbohydrate is conducted while in the product solution. According to an embodiment, said reacting of said second carbohydrate is conducted while in the product solution and before separating said first carbohydrate product or before completely separating said first carbohydrate product. According to a related embodiment, a solution comprising both said first carbohydrate product and said second carbohydrate product ("couple-product solution") is formed. According to an embodiment, a couple-product solution is formed and the method further comprises the step of treating said solution to form a separated first carbohydrate product and a second carbohydrate product.

According to an embodiment, said treating forms a separated first carbohydrate product and a product-depleted second carbohydrate comprising product solution. According to an embodiment, said reacting of the second carbohydrate is conducted in said product-depleted product solution as such or after some modification. According to a related embodiment, said second carbohydrate is xylose, protein is combined with said product-depleted product solution and the temperature is adjusted to affect a reaction between xylose and said protein to form rumen bypass protein. According to an alternative embodiment, the separated second carbohydrate is reacted to form a second carbohydrate product.

According to an embodiment, one method of the present invention further comprises the step of reacting said first carbohydrate product to form a first carbohydrate product derivative. According to an embodiment, said first carbohydrate product and said second carbohydrate are reacted sequentially or simultaneously.

According to an embodiment, the method comprises a step of reacting said second carbohydrate, and optionally also reacting said first carbohydrate product; reacting said first carbohydrate uses a first reagent, reacting said second carbohydrate uses a second reagent and reacting said first carbohydrate product uses a third reagent and said method is further characterized by at least one of: (a) said second reagent is at least one of said first carbohydrate, said first reagent and said first carbohydrate product; (b) said second carbohydrate is at least one of said first reagent and said third reagent; (c) the second reagent is essentially of the same composition as at least one of said first reagent and said third reagents; (d) at least one of said reagents is hydrogen, and (e) both the second and the third reaction is hydrogen.

According to an embodiment, said product solution comprises said first carbohydrate product and said second carbohydrate and said method further comprises a step of treating said product solution with hydrogen to form a hydrogenated first carbohydrate product and a hydrogenated product of said second carbohydrate. According to a related embodiment, said hydrogenated first carbohydrate is ethanol. According to another related embodiment, said hydrogenated product of said second carbohydrate is xylitol.

According to an embodiment, the method comprises a step of reacting said second carbohydrate, and optionally also reacting said first carbohydrate product; reacting the first carbohydrate uses a first catalyst, reacting the second carbohydrate uses a second catalyst and reacting the first carbohydrate product uses a third catalyst and said method is further characterized by at least one of (a) the first catalysts is essentially of the same composition of the second catalyst and (b) the second catalyst is essentially of the same composition of the third catalyst.

C. Viscous Carbohydrate Product

A viscous fluid may be formed in the course of practicing the described methods. The viscous fluid may comprise at least one carbohydrate, water, HCl and optionally also a second solvent. The viscous fluid is homogeneous according to one embodiment and heterogeneous according to another. According to an embodiment, the viscous fluid is heterogeneous and comprises a continuous phase and a dispersed phase, in which dispersed phase the major component is the second solvent, according to one embodiment, and solid carbohydrate according to another.

The viscous fluid may comprise at least 75% carbohydrates, preferably at least 80%, more preferably at least 83% and most preferably at least 86% as calculated by 100CH/(CH+W), wherein CH is the amount of carbohydrates and W is the amount of water. Typically, the majority of the carbohydrates in the viscous fluid are the products of hydrolyzing the polysaccharides of the polysaccharide comprising feed to hydrolysis, typically a lignocellulosic material. Alternatively, carbohydrates from other sources are combined with products of hydrolysis to form an evaporation feed and end up in the viscous fluid. According to another embodiment, the viscous fluid comprises carbohydrates formed in isomerization of other carbohydrate, e.g. fructose formed from glucose.

According to various embodiments, the carbohydrates in the viscous solution are monomers, dimmers, trimers, higher oligomers, and their combinations. Those monomers, dimmers, trimers, and/or higher oligomers comprise monomers selected from the group consisting of glucose, xylose, mannose, arabinose, galactose, other sugar hexoses, other pentoses and combinations of those. According to a preferred embodiment, glucose is the main carbohydrate there.

The water content of the viscous fluid is between 2% wt and 25% wt, preferably between 3% wt and 20% wt, more preferably between 4% wt and 18% wt and most preferably between 5% wt and 15% wt. The HCl content of the viscous fluid is between 10% wt and 55% wt, preferably between 15% wt and 50% wt, more preferably between 18% wt and 40% wt and most preferably between 20% wt and 38% wt as calculated by 100HCl/(HCl+W), wherein HCl is the amount of HCl in the viscous fluid and W is the amount of water there. Organic solvent content of the viscous fluid may be between 0% wt and 25% wt, preferably between 1% wt and 20% wt, more preferably between 2% wt and 18% wt and most preferably between 3% wt and 15% wt.

According to an embodiment, the HCl/water weight/weight ratio in the viscous fluid is in the range between 0.20 and 1.0, preferably between 0.3 and 0.9 and more preferably between 0.4 and 0.8. According to another embodiment, the carbohydrate/water weight/weight ratio in the viscous fluid is in the range between 2 and 20, preferably between 3 and 15, more preferably between 4 and 12 and most preferably between 5 and 11. According to still another embodiment, the HCl/carbohydrate weight/weight ratio in the viscous fluid is in the range between 0.02 and 0.15, preferably between 0.03 and 0.12 and more preferably between 0.04 and 0.10.

According to an alternative embodiment said hydrolyzate, said depleted hydrolyzate, said further depleted hydrolyzate or a first aqueous stream forms the second evaporation feed as such (with no addition of the second solvent). Water and HCl are distilled from the second evaporation feed at a temperature below 100° C. and at a pressure below 1 atm, whereupon a second vapor phase and a viscous fluid are formed. The viscous fluid of this alternative embodiment comprises carbohydrates, HCl and water according to the above composition, but no solvent. According to a first modification, evaporation starts in the absence of a solvent, and the second organic solvent is added to the composition during evaporation. According to a second modification, evaporation is conducted in the absence of a solvent, and the second organic solvent is added to the formed solution (distillation product) at the end of the evaporation. In both modifications, the viscous fluid comprises the second organic solvent according to the above composition.

According to a preferred embodiment, the ratio between the amount of first aqueous solution and the amount of the second organic solvent contacted with it is such that solvent is found in the viscous solution at the end of the distillation. According to a further preferred embodiment, the solvent/water ratio in the viscous fluid is greater than the solvent/water ratio in the water-solvent heterogeneous azeotrope. According to an embodiment, in the viscous fluid the second organic solvent/water weight/weight ratio is R2, the second organic solvent has heterogeneous azeotrope with water and the second organic solvent/water weight/weight ratio in said azeotrope is R22 and R2 is greater than R22 by at least 10%, preferably at least 25%, more preferably at least 40% and most preferably at least 50%. According to still another embodiment, the second organic solvent/water weight/weight ratio in said second evaporation feed is R23, the second organic solvent/water weight/weight ratio in said azeotrope is R22 and R23 is greater than R22 by at least 10%, preferably at least 25%, more preferably at least 40% and most preferably at least 50%.

According to an embodiment, the second organic solvent used to form the second evaporation feed is not pure, e.g. contains water and or HCl. According to a related embodiment, the used second organic solvent is recycled from another step in the process (e.g. from condensate of a distillation step). In such case, R23 refers to the ratio between the solvent on solutes free basis and water. As indicated earlier, R22 may depend on the temperature of distillation, on its pressure and on the content of the other components in the evaporation feed (including HCl and carbohydrates). As used before, R22 is referred to the second solvent/water weight/weight ratio in the solvent-water binary system. On distillation from the second evaporation feed, there is at least one additional volatile component, co-distilling with water and the solvent, i.e. HCl. Thus, this system could be referred to as a ternary system. In such system solvent/water ratio in the vapor phase may differ from that in the binary system. As indicated, that ratio may further depend on the carbohydrates concentration in the second evaporation feed. In such complex systems, R22 refers to the solvent/water ratio in the vapor phase formed on distilling from the second evaporation feed.

According to an embodiment, the method further comprising the steps of condensing the vapors in said second vapor phase to form two phases, a second organic-rich one and a first water-rich one, using said second organic solvent-rich phase in a contacting step and using said first water-rich phase for generating said hydrolysis medium. Any method of condensing is suitable, preferably comprising cooling, pressure increase or both. Typically, the solvent-rich phase also comprises water and HCl and the water-rich one also comprises solvent and HCl. Any method of separating the phases is suitable, e.g. decantation. The second organic solvent-rich phase is used as is or after some treatment, e.g. removal of dissolved water, HCl or both. The first water-rich phase is used for regenerating the hydrolysis medium as is or after some treatment.

Combined HCl removal is high, possibly exceeding 95%. Yet, some acid remains and is preferably removed for high recovery as well as for the production of low-acid product. Thus, according to a preferred embodiment, the viscous fluid is further treated. According to a related embodiment, such further treatment comprises removal of residual HCl to form de-acidified carbohydrates. According to various embodiments, removal of residual HCl involves at least one of solvent extraction, membrane separation, ion-exchange and evaporation. According to an embodiment, the viscous solution is diluted prior to such removal of HCl, while according to others it is not. According to an embodiment, the residual HCl is removed by solvent extraction, using for that purpose the extractants as described in PCT/IL2008/000278, PCT/IL2009/000392 and Israel Patent Application No: 201,330, the relevant teachings of which are incorporated herein by reference. According to another embodiment, the second organic solvent is used as the extractant for the removal of the residual HCl.

According to a particularly preferred embodiment, the method comprises removal of the residual HCl by distillation. According to a related embodiment, distillation is conducted on the viscous fluid as such or after slight modifications, such as minor adjustment of the carbohydrate concentration and changing the amount of the second organic solvent there. Such changing the amount may comprise adding or removing such solvent. Optionally, another solvent is added. According to a preferred embodiment, the ratio between the second organic solvent in the viscous fluid and the water there is such that on azeotropic distillation of water and the solvent, essentially all the water is removed, while excess solvent remains. Such excess solvent is removed, according to an embodiment, by further distillation or in a separate operation.

According to a particularly preferred embodiment, the method comprises the step of spray drying the viscous fluid to form de-acidified solid carbohydrate composition and vapors of HCl, water and optionally the solvent. Spray drying conditions are adjusted, according to an embodiment, for removing essentially all the water from the viscous solution, while some of the second organic solvent may stay and be removed subsequently. According to an embodiment, the viscous fluid is sprayed, as such or after some modification into a hot vapor stream and vaporized. Solids form as moisture quickly leaves the droplets. A nozzle is usually used to make the droplets as small as possible, maximizing heat transfer and the rate of water vaporization. Droplet sizes range, according to an embodiment, from 20 to 180 μηι depending on the nozzle. A dried powder is formed in a single step, within a short residence time and at a relatively low temperature, all of which minimize carbohydrates degradation. According to a preferred embodiment, the hot and dried powder is contacted with water in order to accelerate cooling and to form an aqueous solution of the carbohydrate. According to an embodiment, residual second solvent is distilled out of that carbohydrates solution.

One method of the present invention enables the removal of the majority of the acid at relatively low cost by combining distillation of HCl (as a nearly dry gas, as a water-HCl azeotrope, and as a mixture of HCl, water and second solvent vapors) and the efficient removal of the residual acid in spray drying. It was surprisingly found that residual HCl removal in spray drying is more efficient than suggested by the prior art. Thus, according to a preferred embodiment, in the de-acidified solid carbohydrate composition, HCl/carbohydrates weight/weight ratio is less than 0.03, preferably less than 0.02, more preferably less than 0.01 and most preferably less than 0.005. Without wishing to be limited by theory, possible explanation for the high efficiency could be some specific role the solvent plays and/or the specific composition of the carbohydrate, e.g. the mix of carbohydrates it is made of and the degree and nature of oligomerization.

Reaching low HCl concentrations in the de-acidified solid carbohydrate represents high yield of acid recovery from the hydrolyzate of the hgnocellulosic material. Thus, according to an embodiment of the method, at least 95% of the acid in the hydrolyzate is recovered, more preferably at least 96% and most preferably at least 98%.

Thus, according to an embodiment, essentially all the HCl in the hydrolyzate is removed and an essentially HCl-free carbohydrate stream is formed by a combination of distillation operations with no need for other acid removal means, such as solvent extraction or membrane separation.

In various embodiments, the present invention provides a method for the production of fermentable sugars, comprising (i) providing sugarcane material comprising water-insoluble polysaccharides, lignin and at least 1% sucrose; (ii) solubilizing sucrose and hydrolyzing water-insoluble polysaccharides in a concentrated HCl hydrolysis medium to form an HCl-comprising lignin stream and a hydrolyzate comprising lignocellulose carbohydrates, sucrose values and HCl; and (iii) deacidifying said hydrolyzate to form recovered HCl and a deacidified hydrolyzate comprising lignocellulose carbohydrates and sucrose values.

According to an embodiment, the combined amount of sucrose values and lignocellulose carbohydrates is at least 90% of the theoretical value.

According an embodiment, said hydrolyzate comprises hydroxymethylfurfural and the weight/weight ratio between hydroxymethylfurfural and carbohydrates in said hydrolyzate is less than 0.01. According another embodiment, said hydrolyzate comprises furfural and the weight/weight ratio between furfural and carbohydrates in said hydrolyzate is less than 0.01.

D. Lactic Acid

The present invention provides for methods of processing lignocellulose as described herein to obtain one or more compositions comprising lactic acid derived from the lignocellulose. In various embodiments, the processing of lignocellulose to yield lactic acid according to the invention involves acid-catalyzed hydrolysis of lignocellulose and recycling of the acid catalyst. In various embodiments, the lactic acid is obtained during fermentation of the lignocellulose hydrolyzate (i.e. carbohydrate fraction from hydrolyzed lignocellulose). In various embodiments, the lactic acid is derived from further processing of hydrolyzate fractions.

In various embodiments, fermentation leads to the production of lactic acid. The potential of lactic acid as a commodity chemical, for example for use in the production of various industrial polymers, is known. This has been described, for example, in U.S. Pat. Nos. 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; and 5,594,095. (The complete disclosures of these seventeen patents, which are owned by Cargill, Inc. of Minneapolis, Minn., are incorporated herein by reference.) There has been general interest in developing improved techniques for generation and isolation of lactic acid. Also, because of their potential commercial value, there is great interest in isolation of the other valuable related lactate products such as lactide, lactate esters and amides, and oligomers; see e.g. the same 17 patents.

In general, large amounts of lactic acid can be readily generated by the conduct of large-scale, industrial, bacterially-conducted fermentation processes, particularly using carbohydrates produced according to the present invention, such as dextrose, as the feed stock, along with suitable mineral and amino acid based nutrients. Typically, such productions occur at broth temperatures of at least 45 C, usually around 48 C.

Issues of concern with respect to lactic acid generation include, inter alia, appropriate control of pH within the fermentation system to ensure proper environment for bacterial action; separation and isolation of either or both of lactic acid and lactate salts from the fermentation process; and downstream isolation and production involving the isolated lactic acid or lactic acid derived product.

In various embodiments, the lignocellulose-derived components according to the present invention are incorporated into a fermentation product as described in the following US patents, the contents of each of which are hereby incorporated by reference: U.S. Pat. Nos. 7,678,768; 7,534,597; 7,186,856; 7,144,977; 7,019,170; 6,693,188; 6,534,679; 6,452,051; 6,361,990; 6,320,077; 6,229,046; 6,187,951; 6,160,173; 6,087,532; 5,892,109; 5,780,678; and 5,510,526.

E. Biofuels

The present invention provides for methods of processing lignocellulose as described herein to obtain one or more compositions comprising ethanol derived from the lignocellulose. In various embodiments, the processing of lignocellulose to yield ethanol according to the invention involves acid-catalyzed hydrolysis of lignocellulose and recycling of the acid catalyst. In various embodiments, the ethanol is obtained during fermentation of the lignocellulose hydrolyzate (i.e. carbohydrate fraction from hydrolyzed lignocellulose). In various embodiments, the ethanol is derived from further processing of hydrolyzate fractions. Compositions comprising ethanol derived from lignocellulose according to the invention may be crude compositions (including, for example, components of cell-based fermentation systems), or may be highly purified ethanol-containing compositions.

The present invention also provides for methods of processing lignocellulose as described herein to obtain one or more compositions comprising biodiesel where the biodiesel is derived from lignocellulose via acid-catalyzed hydrolysis of the lignocellulose and recycling of the acid catalyst. For example, in various embodiments, the acid catalyst is recycled hydrochloric acid. In various embodiments, the biodiesel is comprised of fatty acid methyl esters (FAMEs). In various embodiments, the fatty acid methyl esters are derived from tall oil obtained via methods of processing lignocellulose as describe herein.

Cellulosic Streams

Implementations of cellulosic ethanol production systems may utilize various implementations of integrated processes for producing fuel ethanol and biodiesel from cellulose. A first implementation of an integrated process for producing fuel ethanol and biodiesel from cellulose may include providing a raw cellulose stream to one or more containers selected from the group consisting of a vat, a bioreactor, and a tank by mixing a waste cellulose stream and an algae cellulose stream. The process may also include hydrolyzing the raw cellulose stream to form a hydrolyzed cellulose stream and liquefying the hydrolyzed cellulose stream to produce a formed sugars stream and one or more liquefaction byproduct streams. The process may also include fermenting the formed sugars stream to produce a raw ethanol stream by reacting the sugars stream with a yeast feed in at least one fermenter and separating the raw ethanol stream to form a fuel ethanol stream. The process may include producing an algae stream by reacting at least one of the one or more liquefaction byproduct streams with algae in at least one algae bioreactor, reacting the algae stream in at least one biodiesel reactor to produce the algae cellulose stream and a biodiesel stream, and recovering the fuel ethanol and the biodiesel from their respective streams.

Implementations of a first integrated process for producing fuel ethanol and biodiesel from cellulose may include one, all, or any of the following:

One of the one or more liquefaction byproduct streams may include xylitol.

Implementations of cellulosic ethanol production systems may utilize a second implementation of a process for producing fuel ethanol and biodiesel from cellulose. The process may include providing a raw cellulose stream to one or more containers selected from the group consisting of a vat, a bioreactor, and a tank by mixing a waste cellulose stream and an algae cellulose stream. The process may also include hydrolyzing the raw cellulose stream to form a hydrolyzed cellulose stream by reacting the raw cellulose stream with HCl, liquefying the hydrolyzed cellulose stream to form a sugars stream, and separating the sugars stream to form a xylitol stream and a separated sugars stream. The process may include fermenting the separated sugars stream to form a raw ethanol stream by reacting the separated sugars stream with a yeast feed in at least one fermenter, separating the raw ethanol stream to form a fuel ethanol stream, and producing an algae stream by reacting the xylitol stream with algae in at least one algae bioreactor. The process may also include reacting the algae stream in at least one biodiesel reactor to produce the algae cellulose stream and a biodiesel stream and recovering the fuel ethanol and the biodiesel from their respective streams.

Implementations of a second integrated process for producing fuel ethanol and biodiesel from cellulose may include one, all, or some of the following:

Implementations of a first process and a second process for producing fuel ethanol and biodiesel from cellulose may include one, all, or some of the following:

Hydrolyzing the raw cellulose stream may further include reacting the raw cellulose stream with one of capsaicin, quercetin, genestine, ethanol, and any combination thereof.

Hydrolyzing the raw cellulose stream may further include reducing the concentration of auxin in the raw cellulose stream using one or more organic transport inhibitors selected from the group consisting of capsaicin, quercetin, genestine, ethanol, and any combination thereof.

Hydrolyzing the raw cellulose stream may further include adjusting the pH of the raw cellulose stream with one of capsaicin, an inorganic acid, an organic acid, and any combination thereof.

Hydrolyzing the raw cellulose stream may further include dehydrogenating the raw cellulose stream with a compound selected from the group consisting of one or more enzymes selected from the group consisting of dehydrogenase, formate, alcohol dehydrogenase E, cytosol, and excrements of cephalopods or ocean mammals, and any combination thereof, one or more organic transport inhibitors selected from the group consisting of capsaicin, quercetin, genestine, ethanol, and any combination thereof; and any combination of enzymes and organic transport inhibitors thereof.

Hydrolyzing the raw cellulose stream may further include reacting the raw cellulose stream with one or more enzymes selected from the group consisting of dehydrogenase, formate, alcohol dehydrogenase E, cytosol, and excrements of cephalopods or ocean mammals.

Implementations of cellulosic ethanol production systems may utilize implementations of a third integrated process for producing fuel ethanol and biodiesel from cellulose. The method may include providing a raw cellulose stream by mixing a waste cellulose stream and an algae cellulose stream and hydrolyzing the raw cellulose stream to form a hydrolyzed cellulose stream, a hydrolysis C02 stream, and an hydrolysis ethanol stream by reacting the raw cellulose stream with one or more fungi from the group consisting of the genera *Neocallimastix, Piromyces*, and *Orpinomyces*. The process may also include liquefying the hydrolyzed cellulose stream to produce a sugars stream by heating the hydrolyzed cellulose stream and by reacting the hydrolyzed cellulose stream with one or more enzymes, one or more bacteria, or with one or more enzymes in combination with one or more bacteria. The process may also include separating the sugars stream to produce a xylitol stream and a separated sugars stream, fermenting the separated sugars stream to produce a raw ethanol stream and a fermentation C02 stream by reacting the separated sugars stream with a yeast feed in at least one fermenter, and separating the raw ethanol stream to produce a fuel ethanol stream and a waste cellulose stream. The method may also include producing an algae stream by reacting the hydrolysis C02 stream, the fermentation C02 stream, an atmospheric C02 stream, and the xylitol stream with algae in at least one algae bioreactor. The method may include reacting the algae stream in at least one biodiesel reactor to produce the algae cellulose stream and a biodiesel stream and recovering the fuel ethanol and the biodiesel from their respective streams.

Implementations of a third integrated process for producing fuel ethanol and biodiesel from cellulose may include one, all, or any of the following:

The one or more fungi selected from the group consisting of the genera *Neocallimastix, Piromyces*, and *Orpinomyces* may be selected from the group consisting of *Neocallimastix patriciarum, Neocallimastix patriciarum* strain 27, *Neocallimastix frontalis*, and *Piromyces* sp. strain E2.

The one or more enzymes may be selected from the group consisting of alpha-amylase, beta-glucanase, cellobiase, dehydrogenase, exoglucohydrolase, formate, alcohol dehydrogenase E, cytosol, pyruvate formate lyase, lignase, and excrements of cephalopods or ocean mammals.

Separating the sugars stream may further include chromatographically separating xylitol in the sugars stream to produce the xylitol stream and the separated sugars stream.

Additional Biofuel Embodiments

In various embodiments, the lignocellulose-derived components according to the present invention are incorporated into a biofuel as described in the following US patents, the contents of each of which are hereby incorporated by reference: U.S. Pat. Nos. 7,846,225; 7,842,106; 7,840,363; 7,838,474; 7,837,891; 7,833,667; 7,831,318; 7,828,978; 7,824,453; 7,815,698; 7,806,945; 7,803,601; 7,803,337; 7,799,544; 7,790,937; 7,790,651; 7,790,429; 7,790,044; 7,759,812; 7,754,905; 7,722,755; 7,721,661; 7,713,314; 7,709,134; 7,704,723; 7,695,532; 7,691,159; 7,687,161; 7,683,232; 7,667,081; 7,666,234; 7,662,617; 7,662,616; 7,655,055; 7,645,807; 7,638,314; 7,637,969; 7,635,398; 7,628,828; 7,626,048; 7,624,878; 7,622,600; 7,619,104; 7,611,878; 7,611,835; 7,605,281; 7,579,492; 7,572,546; 7,563,915; 7,553,982; 7,550,278; 7,544,438; 7,540,889; 7,536,827; 7,534,923; 7,528,272; 7,520,905; 7,514,247; 7,507,846; 7,507,554; 7,488,357; 7,479,167; 7,473,791; 7,458,998; 7,452,515; 7,449,313; 7,439,047; 7,420,072; 7,404,411; 7,398,935; 7,388,034; 7,282,135; 7,263,934; 7,252,755; 7,169,821; 7,153,996; 7,135,308; 7,126,032; 7,112,229; 7,087,771; 6,965,044; 6,827,841; 6,824,682; 6,822,105; 6,802,897; 6,768,015; 6,719,815; 6,712,867; 6,648,930; 6,588,349; 6,409,778; 6,398,707; 6,174,501; 6,124,357; 5,891,203; 5,855,736; 5,743,923; 5,660,940; and 5,626,088.

F. Detergents

The present invention also provides for methods of processing lignocellulose as described herein to obtain one or more surfactants or detergent compositions derived from the lignocellulose. In various embodiments, the processing of lignocellulose to yield surfactants or detergent compositions according to the invention involves acid-catalyzed hydrolysis of lignocellulose and recycling of the acid catalyst. In various embodiments, the surfactants or detergent compositions are derived from tall oil obtained during lignocellulose processing. In various embodiments, the surfactants or detergent compositions are derived from further processing of hydrolyzate fractions (i.e. carbohydrate fraction from hydrolyzed lignocellulose). For example, carbohydrates produced by acid-catalyzed hydrolysis of lignocellulose may serve as a feedstock for chemical production of surfactants, or alternatively, may serve as a feedstock for the biological production of enzymes or other biologically-produced compounds useful in detergent compositions.

Surfactants

In various embodiments, the methods of processing lignocellulose according to the invention may be used to prepare compositions comprising a surfactant or a mixture thereof including nonionic surfactants, zwitterionic surfactants, anionic surfactants, cationic surfactants and/or amphoteric surfactants. Such lignocellulose-based compositions are also within the scope of the invention. As such, in another preferred embodiment of the present invention, the compositions according to the present invention comprise a sulphonated anionic surfactant. In various embodiments, the invention comprises a surfactant selected from the group consisting of nonionic surfactants, cationic surfactants, amphoteric surfactants, zwitterionic surfactants and mixtures thereof. In a preferred embodiment, the compositions according to the present invention comprise a nonionic surfactant or a zwitterionic betaine surfactant or a mixture thereof.

Typically, the compositions according to the present invention may comprise from 0.01% to 30%, preferably from 0.1% to 25% and more preferably from 0.5% to 20% by weight of the total composition of a surfactant.

Suitable nonionic surfactants include alkoxylated nonionic surfactants. Preferred alkoxylated nonionic surfactants herein are ethoxylated non ionic surfactants according to the formula RO—$(C_2H_4O)_n$H, wherein R is a $C_6$ to $C_{22}$ alkyl chain or a $C_6$ to $C_{28}$ alkyl benzene chain; and wherein n is from 0 to 20, preferably from 1 to 15 and, more preferably from 2 to 15 and most preferably from 2 to 12. The preferred R chains for use herein are the $C_8$ to $C_{22}$ alkyl chains. Propoxylated nonionic surfactants and ethoxy/propoxylated ones may also be used herein instead of the ethoxylated nonionic surfactants as defined herein above or together with said surfactants.

Preferred ethoxylated nonionic surfactants are according to the formula above and have an HLB (hydrophilic-lipophilic balance) below 16, preferably below 15, and more preferably below 14. Those ethoxylated nonionic surfactants have been found to provide good grease cutting properties.

Accordingly suitable ethoxylated nonionic surfactants for use herein are Dobanol®, Lutensol®, or Tergitol® brand surfactants. For example, Dobanol® 91-2.5 (HLB=8.1; R is a mixture of C9 and C11 alkyl chains, n is 2.5), or Lutensol® T03 (HLB=8; R is a $C_{13}$ alkyl chain, n is 3), or Lutensol® A03 (HLB=8; R is a mixture of C13 and C15 alkyl chains, n is 3), or Tergitol® 25L3 (HLB=7.7; R is in the range of C12 to C15 alkyl chain length, n is 3), or mixtures thereof. Dobanol® surfactants are commercially available from SHELL Lutensol® surfactants are commercially available from BASF and these Tergitol® surfactants are commercially available from UNION CARBIDE.

Additional nonionic surfactants may be characterized by their (net) uncharged, hydrophilic headgroups. For example, such surfactants may include Tween, Triton and Brij series surfactants, CHAPS, glycosides (i.e. octyl-thioglucoside, maltosides), bile acids such as DOC, lipids (HEGAs), or phosphine oxides.

Typical anionic detergents are alkylbenzenesulfonates. The alkylbenzene portion of these anions is highly lipophilic and the sulfonate is the hydrophilic component. In various embodiments, anionic detergents are selected from branched sodium dodecylbenzenesulfonates and linear sodium dodecylbenzenesulfonates.

Cationic detergents may be based on quaternary ammonium compounds. The ammonium center is polar and an alkyl chain provides the necessary hydrophobic components.

Suitable zwitterionic betaine surfactants for use herein contain both a cationic hydrophilic group, i.e., a quaternary ammonium group, and anionic hydrophilic group on the same molecule at a relatively wide range of pH. The typical anionic hydrophilic groups are carboxylates and sulphonates, although other groups like sulfates, phosphonates, and the like can be used.

Detergent compositions may be as described by the following US patents: U.S. Pat. Nos. 6,949,496; 6,906,012; 6,903,064; 6,884,766; 6,846,795; 6,753,307; 6,710,023; 6,579,698; 6,541,438; 6,528,471.

Polyhydroxy Fatty Acid Amide Surfactants

In various embodiments, detergents may be derived from lignocellulose and may include polyhydroxy fatty acid amide surfactant comprising compounds of the structural formula:

$$R^2—C(O)—NR^1—Z$$

wherein $R^1$ is H, $C_1$-$C_4$ hydrocarbyl, 2-hydroxy ethyl, 2-hydroxy propyl, or a mixture thereof, preferably $C_1$-$C_4$ alkyl, more preferably Ci alkyl (i.e., methyl); and $R^2$ is a $C_5$-$C_{31}$ hydrocarbyl moiety, preferably straight chain $C_7$-$C_{19}$ alkyl or alkenyl, more preferably straight chain $C_9$-$C_{17}$ alkyl or alkenyl, most preferably straight chain $C_{11}$-$C_{16}$ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2$—OH, ~CH($CH_2OH$)~$(CHOH)_{n-1}$—$CH_2$—OH, and —$CH_2$~$(CHOH)2$-(CHOR')(CHOH)—$CH_2$—OH, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)4$~$CH_2$—OH. $R^1$ can be, for example, N-methyl, N-ethyl, N-propyl, N-isopropyl, N-butyl, N-2-hydroxyethyl, or N-2-hydroxy propyl. $R^2$—CO—N<can be, for example, cocamide, stearamide, oleamide, lauramide, myrstamide, capricamide, palmitamide or tallowamide. Z can be, for example, 1-deoxyglucityl, 2-deoxyfructityl, 1-deoxymaltityl, 1-deoxylactityl, 1-deoxygalactityl, 1-deoxymannityl or 1-deoxymaltotnotityl. A preferred polyhydroxy fatty acid amide is N-cocoyl N-methyl glucamide. See, for example, U.S. Pat. No. 6,083,893 to Zint et al. (The Procter & Gamble Co.), the entire contents of which are incorporated by reference.

In various embodiments, detergents according to the invention include surface-acting polyglucosides. Surface-acting polyglucosides may be derived directly from lignocellulose or may be produced as a result of fermentation of lignocellulose. These sugar-based detergents are easily broken down by microbes, leaving no traces in the environment. They consist of a pair of glucose molecules, with hydrocarbon side chains attached to act as the hydrophobic ends. In various embodiments, they are milder than soaps, and work in hard water.

Enzymes

Proteases are enzymes that break down other proteins. Many laundry detergent manufacturers add them to detergents in order to remove protein stains for clothing. Most of these proteases are isolated from strains of Bacillus bacteria. The bacterial proteases are extremely stable at an alkaline pH, long-term storage and varying temperatures. These bacteria may be genetically engineered in order to enhance the power of the protease to withstand degradation by bleach.

In various embodiments, detergents, including laundry detergents and/or fabric care compositions, may be derived in part from lignocellulose. The laundry detergent and/or fabric care compositions may comprise one or more enzymes exhibiting endoglucanase activity specific for xyloglucan, preferably at a level of from about 0.001% to about 1%, more preferably from about 0.01% to about 0.5%, by weight of the composition. As used herein, the term "endoglucanase activity" means the capability of the enzyme to hydrolyze 1,4ˆ-D-glycosidic linkages present in any cellulosic material, such as cellulose, cellulose derivatives, lichenin, β-D-glucan, or xyloglucan. The endoglucanase activity may be determined in accordance with methods known in the art, examples of which are described in WO 94/14953 and hereinafter. One unit of endoglucanase activity (e.g. CMCU, AVIU, XGU or BGU) is defined as the production of 1 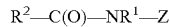 reducing sugar/min from a glucan substrate, the glucan substrate being, e.g., CMC (CMCU), acid swollen Avicell (AVIU), xyloglucan (XGU) or cereal β-glucan (BGU). The reducing sugars are determined as described in WO 94/14953 and hereinafter. The specific activity of an endoglucanase towards a substrate is defined as units/mg of protein. More specifically, compositions are envisioned relating to laundry and cleaning compositions comprising an enzyme exhibiting as its highest activity XGU endoglucanase activity (hereinafter "specific for xyloglucan"), which enzyme: i) is encoded by a DNA sequence comprising or included in at least one of the partial sequences as disclosed in U.S. Pat. No. 6,468,955 to Smets et al. (The Procter and Gamble Co.) or a sequence homologous thereto encoding a polypeptide specific for xyloglucan with endoglucanase activity, ii) is immunologically reactive with an antibody raised against a highly purified endoglucanase encoded by the DNA sequence defined in i) and derived from Aspergillus aculeatus, CBS 101.43, and is specific for xyloglucan. U.S. Pat. No. 6,468,955 to Smets et al. (The Procter and Gamble Co.) is incorporated by reference in its entirety. In various embodiments, the enzymes for incorporation into detergents may be produced by microorganisms grown on a feedstock produced by hydrolysis of lignocellulose according to the present invention.

In various embodiments, lignocellulose such as wood is processed according to the invention to yield sugar which may serve as feedstock (i.e., carbon source or growth media) for the biological production of proteases for detergent compositions. Such proteases may be engineered to be stabilized. Various descriptions of the principles of protein engineering are available, for example, Suzuki, Y. (1989); Proc. Japan Acad.; 65 Ser. B, where Suzuki states that the thermostability of a globular protein can be enhanced cumulatively to a great extent by increasing the frequency of proline occurrence at the second site of β-turns without significant alterations in the secondary and tertiary structures as well as in the catalytic function of enzymes. The principle is based on various facts and findings, among these the fact that proline residues show a strong tendency to occur preferentially at the second site of β-turns (Levitt, M (1978); Biochemistry; 17 4277-4285; and Chou, P. Y. & Fasman, G. D. (1977); J. Mol. Biol.; 115 135-175). The principle is restricted to insertion of proline into the second site of β-turns in proteins, no other sites are mentioned.

International Patent Publication WO 89/01520 (Cetus Corporation, USA) provides a method for increasing the stability of a protein by decreasing the configurational entropy of unfolding the protein. The method is applied on a *Streptomyces rubiqinosus* xylose isomerase, and it involves substitution of an amino acid with proline, or replacement of glycine with alanine, at predicted substitution sites.

In International Patent Publication WO 89/09819 (Genex Corporation, USA) a method for combining mutations for stabilization of subtilisins is provided. This publication lists a number of amino acid mutations that have been found to be thermally stabilizing mutations. The list comprises substitution of serine with proline at position 188 of subtilisins (BPN' numbering).

International Patent Publication WO 87/05050 (Genex Corporation, USA) describes a method for mutagenesis and screening. By this method one or more mutations are introduced b y treatment with mutagenizing agents, and the method includes subsequent screening for products with altered properties. As a result of this random mutagenesis a subtilisin with a proline residue at position 188 (BPN' numbering) is provided.

In various embodiments, stabilized proteases, in which a naturally occurring amino acid residue (other than proline) has been substituted with a proline residue at one or more positions, at which position(s) the dihedral angles phi and psi constitute values within the intervals (−90°<phi<−40° and −180°<psi<180°), and which positions are not located in regions in which the protease is characterized by possessing a-helical or β-sheet structure.

In the context of this invention a subtilisin is defined as a serine protease produced by gram-positive bacteria or fungi. According to another definition, a subtilisin is a serine protease, wherein the relative order of the amino acid residues in the catalytic triad is Asp-His-Ser (positions 32, 64, and 221, BPN' numbering).

A stabilized protease of this invention is a protease variant or mutated protease. By a protease variant or mutated protease is meant a protease obtainable by alteration of a DNA nucleotide sequence of the parent gene or its derivatives. The protease variant or mutated protease may be expressed and produced when the DNA nucleotide sequence encoding the protease is inserted into a suitable vector in a suitable host organism. The host organism is not necessarily identical to the organism from which the parent gene originated. Such host organism may be grown on sugars/polysaccharides/saccharides according to general feedstock processing methods.

In the context of this invention a specific numbering of amino acid residue positions in subtilisins is employed. By alignment of the amino acid sequences of various subtilisins along with subtilisin BPN', it is possible to allot a number to the amino acid residue position in any subtilisin to the number of the analogous amino acid position in subtilisin BPN' (International Patent Publications Nos. WO 89/06279 and WO 91/00345).

In describing the various protease variants produced or contemplated according to the invention, the following nomenclatures were adapted for ease of reference:

(Original amino acid; Position; Substituted amino acid) Accordingly, the substitution of alanine with proline in position 195 is designated as:

A195P

Deletion of an aspartic acid at position 36 is indicated as: D36*, and an insertion in such a position is indicated as: 36D for insertion of an aspartic acid in position 36.

Multiple mutations are separated by plusses, i.e.:

A194P+G195E representing mutations in positions 194 and 195 substituting alanine with proline and glycine with glutamic acid, respectively.

If a substitution is made by mutation in e.g. subtilisin 309, the product is designated e.g. "subtilisin 309/G195E".

In the context of this invention proteolytic activity is expressed in Kilo NOVO Protease Units (KNPU). The activity is determined relatively to an enzyme standard (SAVINASE™), and the determination is based on the digestion of a dimethyl casein (DMC) solution by the proteolytic enzyme at standard conditions, i.e. 50° C., pH 8.3, 9 min. reaction time, 3 min. measuring time.

The ability of an enzyme to catalyse the degradation of various naturally occurring substrates present on the objects to be cleaned during e.g. wash is often referred to as its washing ability, washability, detergency, or wash performance. Throughout this application the term wash performance will be used to encompass this property.

Stabilized proteases are disclosed, in which a naturally occurring amino acid residue (other than proline) has been substituted with a proline residue at one or more positions, at which position(s) the dihedral angles (phi) and (psi) constitute values in the intervals [−90<phi<−40 and −180<psi<180], preferably the intervals [−90<phi<−40 and 120<psi<180] or [−90<phi<−40 and −50<psi<10], and which position(s) is/are not located in regions, in which the protease is characterized by possessing a-helical or β-sheet structure.

Moreover, in the context of this invention, a stabilized protease is a protease having improved stability, e.g. in respect to thermal stability, storage stability, etc., when compared to the parent enzyme.

The stabilized proteases of the invention may be obtained by subjecting the protease in question to analysis for secondary structure, identifying residues in the protease having dihedral angles (phi) and (psi) constitute values in the intervals [−90<phi<−40 and −180<psi<180], preferably the intervals [−90<phi<−40 and 120<psi<180] or [−90<phi<−40 and −50<psi<10], excluding residues located in regions in which the protease is characterized by possessing a-helical or β-sheet structure, if a proline residue is not already at the identified position(s), substitution of the naturally occurring amino acid residue with a proline residue at the identified position(s), preferably by site directed mutagenesis applied on a gene encoding the protease in question, and gene expression by insertion of the gene encoding the stabilized protease in a suitable host organism, followed by cultivation of said host organism in a suitable nutrient medium, and recovery of the desired protease.

This preparation includes subjecting the protease in question to analysis for secondary structure. To perform such analysis the atomic structure of the protease has to be elucidated. The atomic structure can be determined by X-ray diffraction techniques. X-ray diffraction techniques are described by e.g. Hendrickson, W. A. [X-ray diffraction; in Protein Engineering (Ed: Oxender, D. L. and Fox, C. F.), ch. 1; Alan R. Liss, Inc. (1987)].

The crystal structure of Subtilisin 309 has been deduced [vide Beizel, B., Klupsch, S., Papendorf, G., Hastrup, S., Branner, S., and Wilson, K. S. (1992); J. Mol. Biol. 223 427-445], and the coordinates have been deposited and are available from the Brookhaven Protein Data Bank [Bernstein et al. (1977); J. Mol. Biol. 112 535-542].

When the atomic structure has been determined, it is possible to compute dihedral angles from the atomic coordinates. Moreover, it is possible to assign secondary structure elements. The secondary structure elements are defined on the basis of hydrogen bindings. Cooperative secondary structure is recognized as repeats of the elementary hydrogen-bonding patterns "turn" and "bridge". Repeating turns are "helices," repeating bridges are "ladders", connected ladders are "sheets".

Analysis for secondary structure elements requires a computerized compilation of structure assignments and geometrical features extracted from atomic coordinates. The conventional method to elucidate the secondary structure of a protein, based on its atomic coordinates, is described by Kabsch, W. and Sander, C. [Biopolymers (1983) 22 2577-2637]. In this article an algorithm for extracting structural features from the atomic coordinates by a pattern-recognition process is provided. First, H-bonds are identified based on electrostatic interactions between pairs of H-bonding groups. Next, the patterns of H-bonding are used to define secondary structure elements such as turns (M), bends (S), bridges (B), helices (G, H, I), beta-ladders (E) and beta-sheets (E).

A computer program DSSP (Define Secondary Structure of Proteins), enabling the computation of Kabsch & Sander files and written in standard PASCAL, is available from the Protein Data Bank, Chemistry Dept., Brookhaven National Laboratory, Upton, N.Y. 11973.

After the dihedral angles (phi) and (psi) for the amino acids have been calculated, based on the atomic structure in the crystalline proteases, it is possible to select position(s) which has/have dihedral phi and psi angles favourable for substitution with a proline residue. The aliphatic side chain of proline residues is bonded covalently to the nitrogen atom of the peptide group. The resulting cyclic five-membered ring consequently imposes a rigid constraint on the rotation about the N~$C_a$ bond of the peptide backbone and simultaneously prevents the formation of hydrogen bonding to the backbone N-atom. For these structural reasons, prolines are generally not compatible with alpha-helical and beta-sheet secondary conformations. Due to the same rotational constraint about the $C_a$—N bond, and due to the requirement that neighbouring amino acids in the chain are not perturbed, the magnitudes of the dihedral angles phi and psi (and in particular phi) are confined to limited intervals for proline residues in polypeptides. The dihedral angles for proline residues in polypeptides are almost exclusively within the intervals [−90<phi<−40 and −180<psi<180], preferably the intervals [−90<phi<−40 and 120<psi<180] or [−90<phi<−40 and −50<psi<10]. In this context, both cis- and trans-proline residues are considered.

A proline residue may already occur at one or more positions pointed out by the procedure described above, and then a substitution is, of course, irrelevant. Otherwise, the method includes substitution of the naturally occurring amino acid residue with a proline residue.

It is to be expected that the stabilizing (or destabilizing) effects of individual substitutions are additive, vide e.g. Wells, J. A. [Biochemistry (1990) 29 (37) 8510-8517].

If a subtilisin different from subtilisin 309 is subjected to this method (although the two subtilisins may seem very much similar), not necessarily the same number of positions, nor particularly the identical positions, may result from the method. It is likely that some of the positions may be identical, and it is likely that the numbers of positions are of equal magnitude, but it is not to be foreseen.

However, it seems likely that the stabilizing proline substitutions resulting from the above described method, applied to any specific protease, may also have a stabilizing effect on any other protease, independent of the result of the above described method applied to such a protease.

Additional details can be found in U.S. Pat. No. 5,858,757 to Van Der Osten et al. (Novo Nordisk A/S), the entire contents of which are incorporated by reference. Organisms producing such enzymes may be grown on carbohydrate feedstocks according to the present invention.

Other enzymes that can be included in the detergent compositions of the present invention include lipases. Suitable lipase enzymes for detergent usage include those produced by microorganisms of the *Pseudomonas* group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas* fluorescent IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 Lipase® and Lipomax® (Gist-Brocades) and Lipolase® and Lipolase Ultra® (Novo) which have found to be very effective when used in combination with the compositions of the present invention. Also suitable are the lipolytic enzymes described in EP 258 068, WO 92/05249 and WO 95/22615 by Novo Nordisk and in WO 94/03578, WO 95/3538 1 and WO 96/00292 by Unilever. Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor); WO 90/09446 (Plant Genetic System) and WO 94/14963 and WO 94/14964 (Unilever). Also suitable are peroxidases described in U.S. Pat. Nos. 5,605,832 and 5,648,262 by The Procter & Gamble Co.

Additional information can be found in U.S. Pat. No. 6,541,438 to Smets et al. (The Procter & Gamble Co.), which is hereby incorporated in its entirety.

Non-Phosphate Detergents

In various embodiments, the detergent according to the invention may comprise (a) a surfactant system; (b) a non-phosphate detergency builder material or a mixture thereof with a phosphate detergency builder material; and (c) sugar as herein defined to mean a mono-, di- or polysaccharide or a derivative thereof, or a degraded starch or chemically modified degraded starch which is water soluble. The saccharide repeating unit can have as few as five carbon atoms or as many as fifty carbon atoms, consistent with water-solubility. The saccharide derivative can be an alcohol or acid of the saccharide as described eg in Lehninger's Biochemistry (Worth 1970). Water-soluble in the present context means that the sugar is capable of forming a clear solution or a stable colloid dispersion in distilled water at room temperature at a concentration of 0.01 g/l. Sugars which are useful in this invention are sucrose, glucose, fructose, maltose (malt sugar), cellobiose and lactose which are disacchandes. A useful saccharide derivative is sorbitol. See, for example, U.S. Pat. No. 4,755,318 to Davies et al. (Lever Bros. Co.), which is incorporated by reference in its entirety. See also U.S. Pat. No. 3,615,811 to Barrett (Chemical Products Corporation) which discloses the use of sugars as binding agents for alkaline earth metal carbonates, such as barium carbonate, for use in the ceramic industry, the entire contents of which are incorporated by reference.

Levels of sugar may preferably be at least 1% by weight of a spray-dried composition up to 20%, although a level of 5% to 15% by weight is typical.

Surfactant systems may include an anionic surfactant and/or soap, a nonionic surfactant or a mixture of these. Typical amounts of such surfactants are from 2 to 30% by weight based on the weight of the spray-dried powder of the anionic surfactant or soap or mixtures thereof when these are used alone, from 2 to 20% by weight of nonionic surfactant when used alone and, when a binary mixture of anionic surfactant and nonionic surfactant is used, from 2 to 25% by weight of anionic surfactant and from 0.5 to 20% by weight of nonionic surfactant. Such binary mixtures can be either anionic rich or nonionic rich. When a so-called ternary mixture of anionic surfactant, nonionic surfactant and soap is used, preferred amounts of the individual components of the mixture are from 2 to 15% by weight of anionic surfactant, from 0.5 to 7.5% by weight of nonionic surfactant, and from 1 to 15% by weight of soap.

Examples of anionic surfactants which can be used are alkyl benzene sulphonates, particularly sodium alkyl benzene sulphonates having an average alkyl chain length of $C_{12}$; primary and secondary alcohol sulphates, particularly sodium C12-C15 primary alcohol sulphates, olefine sulphonates, primary and secondary alkane sulphonates, alkyl ether sulphates, amine oxides and zwitterionic compounds such as betaines and sulphobetaines.

Soaps which can be used are preferably sodium soaps derived from naturally-occurring fatty acids. In general these soaps will contain from about 12 to about 20 carbon atoms and may be saturated or partly unsaturated. Three groups of soaps are especially preferred: those derived from coconut oil and palm kernel oil, which are saturated and predominantly in the C12 to $C_{14}$ range, those derived from tallow which are saturated and predominantly in the $C_{14}$ to $C_{18}$ range, and soaps containing sodium linoleate, sodium linolenate and sodium oleate. Oils which are rich in the unsaturated substances (as glycerides) include groundnut oil, soyabean oil, sunflower oil, rapeseed oil and cottonseed oil. Of course, all of these groups of soaps may be used in admixture with each other, with other soaps not included amongst the groups enumerated, and with non-soap detergent-active material.

The nonionic surfactants which can be used are the primary and secondary alcohol ethoxylates, especially the C12-C15 primary and secondary alcohols ethoxylated with from 2 to 20 moles of ethylene oxide per mole of alcohol.

A non-phosphate detergency builder may be selected from water-insoluble ion exchange materials and water-soluble organic or inorganic materials capable of precipitating or sequestering calcium ions from hard water. Preferably the non-phosphate detergency builder is an aluminosilicate material.

Aluminosilicates will normally be sodium aluminosilicates and may be crystalline or amorphous, or a mixture thereof. They will normally contain some bound water and will normally have a calcium ion-exchange capacity of at least about 50 mg CaO/g. The preferred aluminosilicates have the general formula:

$$0.8\text{-}1.5Na_2O.Al_2O_3.0.8\text{-}6SiO_2.$$

Most preferably they contain 1.5-3.5 $SiO_2$ units in the formula above and have a particle size of not more than about 100 μηι, preferably not more than about 10 μηι. Suitable amorphous sodium aluminosilicates for detergency building use are described for example in British patent specification No. 1 473 202 (HENKEL) and European patent specification No. EP-A-150613 (UNILEVER). Alternatively, suitable crystalline sodium aluminosilicate ion-exchange detergency builders are described in UK patent specification Nos. 1 473 201 (HENKEL) and 1 429 143 (PROCTER & GAMBLE). The preferred sodium aluminosilicates of this type are the well known commercially-available zeolites A and X, and mixtures thereof.

Other non-phosphate detergency builders which can be used in the process of the present invention include water-soluble precipitating builders such as alkalimetal carbonates, and water-soluble sequestering builders such as sodium nitrilotriacetate.

The level of non-phosphate builder is preferably at least 5% by weight of the spray-dried composition, up to 75%, although a level of 20% to 50% by weight is most preferred.

Various amounts of phosphate builders maybe included in non-phosphate detergents, i.e., amounts of phosphate builders which, by weight, are less than the amounts of the non-phosphate builders.

The detergency builder material may be a mixture of an aluminosilicate material with other builders, which may be other non-phosphate builders, or phosphate builders, these other builders may be selected from sodium tripolyphosphate, sodium pyrophosphate and sodium orthophosphate, sodium nitrilotriacetate, sodium carboxymethyloxysuccinate and mixtures thereof. These materials may b e present in amounts up to about 25% by weight.

In addition to the sugar as herein defined, other structurants may be used: sodium succinate or the commercial mixture of succinic, adipic and glutaric acids sold by BASF GmbH, West Germany as Sokalan DCS™ the sodium salt of which acts as a structurant, film-forming polymers of either natural or synthetic origin such as starches, ethylene/maleic anhydride co-polymers, polyvinyl pyrrolidone, polyacrylates and cellulose ether derivatives such as Natrosol 250 MHR™ and inorganic polymers such as clays and borates of various types may be used. These materials may be present in an amount generally from about 0.5 to about 30% by weight, preferably from 1 to 10% by weight, of the spray-dried powder.

Some sodium silicate may be a desirable component of powders intended for use in washing machines. Without wishing to be bound by theory it is believed that without it, or its precipitated form which may be substantially equivalent to silica, the wash liquor containing the powders produces corrosion of vitreous enamel and/or aluminium machine parts. Against that, its presence in conjunction with non-phosphate builders may result in formation of poorly dispersing aggregates. Generally sodium silicate will not be present in amounts of more than 20%, preferably not more than 15% by weight of the spray-dried powder. It may be desired to include a water-soluble silicate material such as sodium silicate in the powder for purposes other than providing structure to the powder. In this case, in order to avoid production of a powder having poor solubility/dispersibility properties, it will be necessary to carry out the additional step of adding an acid in an amount equivalent to 1.5-3 parts by weight of hydrogen chloride per 6 parts of sodium silicate having a sodium oxide to silica ratio of 1:1.6, to precipitate at least part of the sodium silicate. This process is described in European patent specification No. EP-A-139523. Alternatively, silicates or silica may be added to the spray-dried powder in a dry-dosing step.

A sugar containing spray-dried powder may contain no water-insoluble particulate carbonate material, such as calcite.

Other components of detergent powders which may optionally be present include lather controllers, anti-redeposition agents such as sodium carboxymethyl cellulose, oxygen and chlorine bleaches, fabric softening agents, perfumes, germicides, colourants, enzymes and fluorescers. Where such optional ingredients are heat-sensitive, or in any case, they may be post-dosed to the spray-dried granules rather than be included in a crutcher slurry for spray-drying.

Additional Detergent Ingredients

Additional detergent ingredients may optionally be derived from lignocellulose according to invention, either directly or indirectly. For example, some laundry detergents contain optical brighteners. These are fluorescent dyes that glow blue-white in ultraviolet light. The blue-white color makes yellowed fabrics appear white. Laundry detergent may also contain polyethylene glycol, a polymer that prevents dirt from re-depositing on the clothes. Another polymer used for this purpose is carboxy methyl cellulose. This is derived from natural cellulose, but is very soluble in water.

Yet another ingredient in laundry detergents is Diethyl Ester Dimethyl Ammonium Chloride (DEEDMAC). It is a fabric softener which is a cationic surfactant that is rapidly biodegradable. It works by reducing the friction between fibers, and between fibers and the skin. Cationic surfactants are those where the hydrophilic part (in this case the ammonium chloride) is positively charged, and is attracted to substrates that are negatively charged, such as proteins and many synthetic fabrics. A cationic surfactant will often have an ammonium group attached to a halogen, as in the ammonium chloride mentioned above. Anionic surfactants, such as soap, often have a sodium, potassium, or ammonium group, as in sodium stearate.

Non-ionic surfactants like polyethylene glycol esters (PEG) are used as mild cleansers, or to add viscosity to a mixture like shampoo.

Amphoteric surfactants are those that are an acid and a base at the same time. Cocamidopropyl betaine is an example, used in shampoos to stabilize foam and thicken the mixture.

Some additional examples of detergents and surfactants are: Ammonium Lauryl Sulfate and Lauryl Glucoside. Classes of detergents include Alkyl benzene sulfonates (ABS), which are branched-chain, anionic surfactants; Linear Alkyl benzene sulfonates (LAS), which are straight-chain, anionic surfactants; Alkyl phenoxy polyethoxy ethanols (alcohol ethoxylates), also called nonyl phenoxy ethoxylate, or nonyl phenol; Diethanolamine and Triethanolamine, commonly used to neutralize acids in shampoos and to reduce irritation (pH balanced shampoos); Alkyl ammonium chloride (Quaternium 15), which acts as a surfactant, disinfectant, and deodorant; Alkyl glucosides, which are made from oils and sugar; Mono Ethanol Amine (MEA), which is a solvent used to dissolve other laundry detergent ingredients; Sodium carbonate peroxide, which is used as a bleach; and Sodium sulfate, which is used to dilute powdered detergents.

In various embodiments, the lignocellulose-derived components according to the present invention are incorporated into a detergent as described in the following US patents, the contents of each of which are hereby incorporated by reference: U.S. Pat. Nos. 7,854,771; 7,854,770; 7,829,517; 7,820,612; 7,820,610; 7,816,314; 7,790,664; 7,790,662; 7,772,175; 7,745,385; 7,732,394; 7,727,947; 7,714,124; 7,713,921; 7,713,920; 7,700,539; 7,671,003; 7,645,729; 7,605,116; 7,585,376; 7,582,598; 7,579,310; 7,576,048; 7,569,528; 7,563,757; 7,550,421; 7,544,651; 7,534,758; 7,534,755; 7,534,751; 7,531,493; 7,521,411; 7,494,965; 7,485,614; 7,470,654; 7,468,348; 7,468,347; 7,465,701; 7,445,643; 7,439,217; 7,439,215; 7,386,971; 7,368,415; 7,358,220; 7,338,541; 7,335,630; 7,326,677; 7,326,676; 7,323,014; 7,304,025; 7,273,837; 7,271,138; 7,262,156; 7,259,134; 7,243,664; 7,241,726; 7,214,722; 7,208,459; 7,205,269; 7,202,206; 7,202,202; 7,186,680; 7,169,741; 7,166,565; 7,125,828; 7,109,153; 7,091,171; 7,084,102; 7,084,100; 7,056,880; 7,056,879; 7,056,877; 7,049,280; 7,041,633; 7,033,988; 7,033,987; 7,033,980; 7,030,068; 7,022,660; 7,022,659; 7,018,977; 7,012,052; 7,008,915; 7,001,878; 6,995,126; 6,987,084; 6,979,667; 6,979,371; 6,974,789; 6,964,945; 6,964,942; 6,956,017; 6,951,837; 6,949,496; 6,943,200; 6,943,143; 6,933,269; 6,927,200; 6,921,743; 6,916,775; 6,916,769; 6,914,041; 6,911,422; 6,906,022; 6,906,012; 6,903,064; 6,903,059; 6,900,169; 6,897,190; 6,896,708; 6,894,018; 6,894,013; 6,884,766; 6,881,712; 6,878,680; 6,874,190; 6,858,572; 6,846,795; 6,846,794; 6,846,791; 6,835,707; 6,833,346; 6,833,336; 6,831,050; 6,827,795; 6,825,157; 6,812,198; 6,812,195; 6,809,074; 6,808,729; 6,806,246; 6,803,355; 6,797,686; 6,794,354; 6,790,821; 6,790,814; 6,784,151; 6,777,381; 6,773,737; 6,770,616; 6,770,615; 6,770,613; 6,770,609; 6,767,882; 6,767,880; 6,753,307; 6,747,000; 6,740,630; 6,740,628; 6,740,627; 6,733,538; 6,730,656; 6,730,652; 6,723,693; 6,723,687; 6,716,808; 6,716,806; 6,710,023; 6,699,828; 6,696,402; 6,696,401; 6,689,739; 6,689,737; 6,689,732; 6,686,329; 6,686,328; 6,677,491; 6,677,295; 6,677,290; 6,677,289; 6,677,287; 6,673,766; 6,667,288; 6,660,711; 6,656,898; 6,653,270; 6,645,925; 6,638,320; 6,635,612; 6,635,610; 6,630,439; 6,630,438; 6,630,436; 6,627,598; 6,627,597; 6,627,596; 6,627,590; 6,617,300; 6,613,731; 6,610,644; 6,608,021; 6,602,840; 6,602,837; 6,599,871; 6,596,683; 6,596,680; 6,596,678; 6,589,932; 6,589,931; 6,589,927; 6,589,926; 6,583,100; 6,583,098; 6,579,844; 6,579,840; 6,579,839; 6,579,698; 6,576,605;

6,576,602; 6,576,599; 6,573,234; 6,573,228; 6,566,323; 6,566,319; 6,559,115; 6,559,113; 6,557,568; 6,555,514; 6,551,983; 6,551,982; 6,548,473; 6,544,944; 6,544,943; 6,541,443; 6,541,438; 6,541,437; 6,528,477; 6,528,476; 6,528,471; 6,525,013; 6,525,012; 6,521,582; 6,521,178; 6,514,926; 6,511,956; 6,506,717; 6,506,716; 6,503,876; 6,500,797; 6,498,135; 6,497,322; 6,495,509; 6,492,319; 6,479,451; 6,479,446; 6,472,364; 6,462,012; 6,462,007; 6,455,485; 6,451,754; 6,444,631; 6,440,927; 6,440,918; 6,423,679; 6,423,265; 6,413,928; 6,410,498; 6,410,496; 6,399,564; 6,395,695; 6,387,873; 6,387,856; 6,384,008; 6,380,144; 6,376,454; 6,376,447; 6,376,445; 6,367,488; 6,362,151; 6,362,147; 6,358,911; 6,358,902; 6,326,348; 6,326,341; 6,322,595; 6,313,086; 6,306,219; 6,303,563; 6,294,513; 6,294,512; 6,291,414; 6,288,016; 6,287,346; 6,281,187; 6,281,181; 6,277,811; 6,277,804; 6,274,540; 6,274,539; 6,274,538; 6,262,005; 6,258,773; 6,255,270; 6,251,846; 6,251,845; 6,248,709; 6,242,406; 6,239,094; 6,239,087; 6,232,284; 6,232,282; 6,232,281; 6,228,829; 6,228,828; 6,221,825; 6,221,430; 6,207,631; 6,197,070; 6,194,370; 6,194,362; 6,191,100; 6,191,093; 6,187,740; 6,184,188; 6,180,586; 6,180,583; 6,177,398; 6,177,393; 6,177,389; 6,172,034; 6,172,033; 6,172,021; 6,169,063; 6,169,062; 6,165,970; 6,165,967; 6,165,966; 6,165,959; 6,162,784; 6,162,783; 6,162,778; 6,162,259; 6,159,927; 6,159,923; 6,156,722; 6,156,719; 6,156,718; 6,153,577; 6,150,323; 6,150,310; 6,147,045; 6,147,037; 6,143,711; 6,143,707; 6,140,301; 6,140,293; 6,140,292; 6,136,777; 6,136,769; 6,133,227; 6,133,224; 6,133,222; 6,133,220; 6,130,194; 6,127,331; 6,127,329; 6,121,229; 6,121,226; 6,119,705; 6,114,289; 6,113,655; 6,103,685; 6,100,232; 6,096,703; 6,096,098; 6,093,856; 6,093,691; 6,093,690; 6,093,343; 6,093,218; 6,087,321; 6,087,316; 6,087,314; 6,083,895; 6,083,892; 6,077,818; 6,075,000; 6,071,871; 6,069,122; 6,066,612; 6,063,751; 6,063,747; 6,057,278; 6,048,830; 6,048,501; 6,046,153; 6,046,149; 6,034,044; 6,030,933; 6,026,956; 6,022,844; 6,021,926; 6,020,303; 6,020,294; 6,019,252; 6,017,874; 6,017,873; 6,017,867; 6,017,865; 6,015,781; and 6,013,613.

Processes for Detergent Formulation

Following production of detergent ingredients according to the invention, such ingredients may be formulated into detergent products according to any convenient method. For example, such detergent products may be formulated by a blender process, an agglomeration process, and/or a slurry process.

In a blender process, the ingredients may be mixed in large vats before being packaged. The machines used are typically large: a common blender holds 4,000 pounds (1,816 kilograms) of mixed material, but the blenders may be able to accommodate loads ranging from 500 to 10,000 pounds (227 to 4,540 kilograms). By industry standards, small batches for which the blender process is ideal may be used. Resulting detergent is typically of high quality and can compete with detergents made by other processes.

In a blender process, ingredients are loaded into one of two machines: a tumbling blender or a ribbon blender. The tumbling blender, shaped like a rectangular box, is turned and shaken from outside b y a machine, while the ribbon blender is a cylinder fitted with blades to scrape and mix the ingredients. After the ingredients inside the blender have been mixed, a doorway at the bottom of the bowl is opened. With the blender still agitating the ingredients, the mix is allowed to run out onto a conveyor belt or other channeling device. The belt then moves the detergent to another area of the factory where it can b e dropped into boxes or cartons for delivery to wholesalers or distributors.

A second commonly used method of production is the agglomeration process Unlike the blender process, it is continuous, which makes it the choice of very large detergent manufacturers. The agglomeration process can produce between 15,000 and 50,000 pounds (6,800 and 22,700 kilograms) of detergent per hour. In this method, dry ingredients for a detergent are first fed into a large machine, such as a Shuggi agglomerator. Inside the agglomerator, sharp, whirling blades mix the material to a fine consistency; the process resembles food being textured inside a food processor. After the dry ingredients have been blended, liquid ingredients are sprayed on the dry mix through nozzles fitted into the agglomerator's walls. The blending continues, causing an exothermic (heat-producing) reaction to occur. The resulting mixture is a hot, viscous liquid similar to gelatin that hasn't hardened. Next, the liquid is allowed to flow out of the agglomerator. As it leaves the machine, it collects on a drying belt where its own heat, exposure to air, and hot air blowers render it friable—easy to crush or crumble. The newly made detergent is then pulverized and pushed through sizing screens that ensure that no large lumps of unmixed product go out to the market. The result of this process is a dry detergent made up of granules of the mixed detergent.

In the third method, dry ingredients are blended in water before being dried with hot air. In this process, ingredients are dissolved in water to create a slurry. With a pump, the slurry is blown through nozzles inside the top of a cone shaped container as hot, dry air is simultaneously forced into the bottom of the cone. As the slurry dries, "beads" of dry detergent fall to the bottom of the cone, where they can be collected for packaging.

Detergent Packaging

In various embodiments, the packaging used for a detergent or other consumer product will be based on lignocellulose according to the invention. For example, in various embodiments, the packaging is derived from polyethylene which is ultimately produced from sugarcane, wood, or any other lignocellulose according to the invention.

Polyethylene is classified into several different categories based mostly on its density and branching. The mechanical properties of PE depend significantly on variables such as the extent and type of branching, the crystal structure and the molecular weight. With regard to sold volumes, the most important polyethylene grades are HDPE, LLDPE and LDPE. Various types of polyethylene may be produced from bioethanol derived from sugarcane. Polyethylene can also be made from other feedstocks, including wheat grain and sugar beet according to the invention described herein. In various embodiments, the lignocellulose-derived components are used for packaging of a detergent.

G. Additional Fermentation Products Including Lactic Acid and 1,3-Propanediol Provided herein are methods for producing target chemicals that make use of lignocellulose. In various embodiments, the process involves optional pretreatment of lignocellulose, with a low concentration of ammonia relative to the dry weight of lignocellulose. A washing step may be included, optionally with dilute acid to remove any residual ammonia salts. Following pretreatment, the lignocellulose is treated with a saccharification enzyme consortium to produce fermentable sugars and/or with acid to achieve acid catalyzed hydrolysis. The sugars may then be contacted with a biocatalyst that can ferment the sugars and produce a target chemical.

Further provided are methods for producing target chemicals that make use of lignocellulose in the following manner: sugars are derived from lignocellulose (such as through acid catalyzed hydrolysis or enzyme-catalyzed hydrolysis), which are then used as a carbon source for the growth of microorganisms that can make target chemicals as products of their metabolism. The sugars may be released from the lignocellulose by optionally pretreating the lignocellulose, at relatively high concentration, with a relatively low concentration of ammonia relative to the dry weight of the lignocellulose. The ammonia-treated lignocellulose may optionally be pretreated to remove any residual ammonia or ammonia salts, digested with a saccharification enzyme consortium or acid such as hydrochloric acid to produce fermentable sugars. The sugars are used as a fermentation substrate for growth of a microorganism, or biocatalyst, that is able to produce a target chemical.

A target chemical that is "derivable from lignocellulose" is a target chemical produced by a process whereby lignocellulose is hydrolyzed to release fermentable sugars, and the fermentable sugars are fermented using at least one biocatalyst to produce a desired target chemical.

The terms "plasticizer" and "softening agent" refer to materials that cause a reduction in the cohesive intermolecular forces along or between polymer chains. Such materials may act, for example, to decrease crystallinity, or disrupt bonds between lignin and non-lignin carbohydrate fibers (e.g., cellulose or hemicellulose).

"Suitable conditions to produce fermentable sugars" refers to conditions such as pH, composition of medium, and temperature under which saccharification enzymes are active.

"Suitable fermentation conditions" refers to conditions that support the growth and target chemical production by a biocatalyst. Such conditions may include pH, nutrients and other medium components, temperature, atmosphere, and other factors.

The term "pretreated lignocellulose" means lignocellulose that has been subjected to pretreatment prior to saccharification.

According to the present method, an aqueous solution comprising ammonia may optionally comprise at least one additional base, such as sodium hydroxide, sodium carbonate, potassium hydroxide, potassium carbonate, calcium hydroxide and calcium carbonate. The at least one additional base may be added in an amount that is combined with ammonium to form an amount of total base that is less than about 20 weight percent relative to dry weight of lignocellulose. Preferably the total second base plus ammonia is in an amount that is less than about 15 weight percent. Additional base(s) may be utilized, for example, to neutralize acids in lignocellulose, to provide metal ions for the saccharification enzymes, or to provide metal ions for the fermentation growth medium.

In the present method, the dry weight of lignocellulose is at an initial concentration of at least about 15% up to about 80% of the weight of the lignocellulose-aqueous ammonia mixture. More suitably, the dry weight of lignocellulose is at a concentration of from about 15% to about 60% of the weight of the lignocellulose-aqueous ammonia mixture. The percent of lignocellulose in the lignocellulose-aqueous ammonia mixture is kept high to minimize the need for concentration of sugars resulting from saccharification of the pretreated lignocellulose, for use in fermentation. The high lignocellulose concentration also reduces the total volume of pretreatment material, making the process more economical.

The lignocellulose may be used directly as obtained from the source, or energy may be applied to the lignocellulose to reduce the size, increase the exposed surface area, and/or increase the availability of cellulose, hemicellulose, and/or oligosaccharides present in the lignocellulose to ammonia and to saccharification enzymes used in the second step of the method. Energy means useful for reducing the size, increasing the exposed surface area, and/or increasing the availability of cellulose, hemicellulose, and/or oligosaccharides present in the lignocellulose to ammonia and to saccharification enzymes include, but are not limited to, milling, crushing, grinding, shredding, chopping, disc refining, ultrasound, and microwave. This application of energy may occur before or during pretreatment, before or during saccharification, or any combination thereof.

In order to obtain sufficient quantities of sugars from lignocellulose, the lignocellulose may be pretreated with an aqueous ammonia solution one time or more than one time. Likewise, a saccharification reaction can be performed one or more times. Both pretreatment and saccharification processes may be repeated if desired to obtain higher yields of sugars. To assess performance of the pretreatment and saccharification processes, separately or together, the theoretical yield of sugars derivable from the starting lignocellulose can be determined and compared to measured yields.

Saccharification

Following pretreatment, the product comprises a mixture of ammonia, partially degraded lignocellulose and fermentable sugars. Prior to further processing, ammonia may be removed from the pretreated lignocellulose by applying a vacuum. Removing ammonia lowers the pH, and thus less neutralizing acid is used to obtain the desired pH for saccharification and fermentation. This results in a lower salt load in the pretreatment mixture. Typically some ammonia remains, which is desired to provide a nitrogen source for fermentation.

The pretreatment mixture is then further hydrolyzed in the presence of a saccharification enzyme consortium to release oligosaccharides and/or monosaccharides in a hydrolyzate. Saccharification enzymes and methods for lignocellulose treatment are reviewed in Lynd, L. R., et al. (Microbiol. Mol. Biol. Rev. (2002) 66:506-577). In one preferred embodiment, the entire pretreatment mixture comprising both soluble and insoluble fractions is utilized in the saccharification reaction.

In another embodiment, prior to saccharification, the aqueous fraction comprising ammonia and solubilized sugars may be separated from insoluble particulates remaining in the mixture. Methods for separating the soluble from the insoluble fractions include, but are not limited to, decantation and filtration. The insoluble particulates may be recycled to the pretreatment reactor. The insoluble particulates may optionally be washed with an aqueous solvent (e.g., water) to remove adsorbed sugars prior to being recycled to the pretreatment reactor. The insoluble fraction may then be subjected to additional treatment with aqueous ammonia solution as described above for pretreatment, followed by saccharification with a saccharification enzyme consortium. The soluble fraction may also be concentrated-prior to saccharification using a suitable process, such as evaporation.

Prior to saccharification, the pretreatment product may be treated to alter the pH, composition or temperature such that the enzymes of the saccharification enzyme consortium will be active, thus providing suitable conditions to produce fermentable sugars. The pH may be altered through the addition of acids in solid or liquid form. Alternatively, carbon dioxide (C02), which may be recovered from fermentation, may be utilized to lower the pH. For example, C02 may be collected from a fermenter and fed, such as by bubbling, into the pretreatment product while monitoring the pH, until the desired pH is achieved. The temperature may be brought to a temperature that is compatible with saccharification enzyme activity, as noted below. Any cofactors required for activity of enzymes used in saccharification may be added.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the lignocellulose component that they hydrolyze. Glycosidases useful for the present method include cellulose-hydrolyzing glycosidases (for example, cellulases, endoglucanases, exoglucanases, cellobiohydrolases, beta-glucosidases), hemicellulose-hydrolyzing glycosidases (for example, xylanases, endoxylanases, exoxylanases, beta-xylosidases, arabinoxylanases, mannases, galactases, pectinases, glucuronidases), and starch-hydrolyzing glycosidases (for example, amylases, alpha-amylases, beta-amylases, glucoamylases, alpha-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the lignocellulose. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. The pH optimum can range from about 2 to about 11. In another embodiment, the pH optimum used with the saccharification enzyme consortium in the present method ranges from about 4 to about 10.

The saccharification can be performed for a time of about several minutes to about 120 hr, and preferably from about several minutes to about 48 hr. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The degree of solubilization of sugars from lignocellulose following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentable sugars released from lignocellulose can be used by suitable microorganisms to produce target chemicals. Following saccharification, but prior to fermentation, the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the microorganism(s) used during fermentation and the pH used during saccharification, the pH may be adjusted to that suitable for fermentation. In addition, the saccharification mixture may be supplemented with additional nutrients required for microbial growth. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration. The saccharification mixture may be used as a component of a fermentation broth, for example, making up between about 100% and about 10% of the final medium. Suitable fermentation conditions are achieved by adjusting these types of factors for the growth and target chemical production by a biocatalyst.

Temperature and/or headspace gas may also be adjusted, depending on conditions useful for the fermentation microorganism(s). Fermentation may be aerobic or anaerobic.

Fermentation may occur subsequent to saccharification, or may occur concurrently with saccharification by simultaneous saccharification and fermentation (SSF). SSF can keep the sugar levels produced by saccharification low, thereby reducing potential product inhibition of the saccharification enzymes, reducing sugar availability for contaminating microorganisms, and improving the conversion of pretreated lignocellulose to monosaccharides and/or oligosaccharides.

Target chemicals that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid Amino acids include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include *Escherichia, Zymomonas, Saccharomyces, Candida, Pichia, Streptomyces, Bacillus, Lactobacillus*, and *Clostridium* In another embodiment, biocatalysts may be selected from the group consisting of recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*.

Many biocatalysts used in fermentation to produce target chemicals have been described and others may be discovered, produced through mutation, or engineered through recombinant means. Any biocatalyst that uses fermentable sugars produced in the present method may be used to make the target chemical(s) that it is known to produce, by fermentation in the present method.

Fermentation of carbohydrates to acetone, butanol, and ethanol (ABE fermentation) by solventogenic *Clostridia* is well known (Jones and Woods (1986) Microbiol. Rev. 50:484-524). See also US 2007/0219521 A1 (P&G). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Genetically modified strains of *E. coli* have also been used as biocatalysts for ethanol production (Underwood et al., (2002) Appl. Environ. Microbiol. 68:6263-6272). A genetically modified strain of *Zymomonas mobilis* that has improved production of ethanol is described in US 2003/0162271 A1.

Lactic acid has been produced in fermentations by recombinant strains of *E. coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). WO 2009/134704 A1 (P&G) describes packaging articles comprising lignocellulose-derived polylactic acid and polyolefin, the contents of which are incorporated by reference herein. Recombinant strains of *E. coli* have been used as biocatalysts in fermentation to produce 1,3 propanediol (U.S. Pat. Nos. 6,013,494, and 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17crl (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:113643). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-Ul-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid (PHBV), were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium, Brevibacterium*, and *Serratia*. For example, production of histidine using a strain resistant to a histidine analog is described in Japanese Patent Publication No. 8596/81 and using a recombinant strain is described in EP 136359. Production of tryptophan using a strain resistant to a tryptophan analog is described in Japanese Patent Publication Nos. 4505/72 and 1937/76. Production of isoleucine using a strain resistant to an isoleucine analog is described in Japanese Patent Publication Nos. 38995/72, 6237/76, 32070/79. Production of phenylalanine using a strain resistant to a phenylalanine analog is described in Japanese Patent Publication No. 10035/81. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 37235/79 and 150381/82) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. Nos. 6,861,237, 6,777,207, 6,228,630).

Target chemicals produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, Appl. Microbiol. Biotechnol. 49:639-648 (1998), Groot et al., Process. Biochem. 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

See U.S. Pat. No. 7,781,191 to Dunson et al. (E. I. DuPont de Nemours and Company), the entire contents of which are hereby incorporated by reference.

H. Acrylic-Based Products

The present invention also provides for methods of processing lignocellulose as described herein to obtain one or more acrylic-based compositions derived from the lignocellulose. In various embodiments, the processing of lignocellulose to yield acrylic-based products according to the invention involves acid-catalyzed hydrolysis of lignocellulose and recycling of the acid catalyst. In various embodiments, the acrylic-based compositions are derived from a carbohydrate fraction obtained during lignocellulose processing. In various embodiments, the acrylic-based compositions are derived from fermentation of hydrolyzate fractions (i.e. the carbohydrate fraction from hydrolyzed lignocellulose).

According to an embodiment, a downstream product is produced selected from the group consisting of monomers for the polymer industry. In various embodiments, one method of the present invention is suitable for the production of a commercial product, such as an acrylic acid-based product. Such products may include absorbent articles, diapers, incontinence pads, sanitary napkins, feminine hygene products, various plastics, coatings, adhesives, dispersions, flocculants, elastomers, as well as floor polishes, and paints. In various embodiments, the product produced is a super-absorbent polymer with acrylic acid-based monomers. In various embodiments, the acrylic-based product is produced from lignocellulose hydrolyzed with hydrochloric acid. In various embodiments, the hydrochloric acid is recycled as described herein. Such methods may be used in combination with methods for producing an acrylic-based product. See, for example, U.S. Pat. Nos. 7,799,431; 7,745, 507; 7,655,830; 7,521,587; 7,449,613; 7,166,356; 6,887, 347; 6,641,569; 6,544,642; 6,441,266; 6,232,520; 6,083, 854; 5,972,487; and US 2007/0219521 A1 (P&G), the contents of each of which are incorporated by reference.

Especially preferred absorbent articles of this invention are disposable diapers. Articles in the form of disposable diapers are described in the following: US Re. 26,151; U.S. Pat. Nos. 3,592,194; 3,489,148; and 3,860,003; which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration. In various embodiments, one or more components of the diaper are obtained from lignocellulose via an acid-catalyzed saccarification and subsequent handling to yield a carbohydrate composition suitable for further processing to acrylic acid.

Super Absorbent Polymers

In various embodiments, acrylic-based compositions are derived from a carbohydrate fraction obtained during lignocellulose processing. The acrylic-based compositions may include super absorbent polymers derived from a carbohydrate fraction obtained during lignocellulose production.

As used herein, the term "super absorbent polymer" refers to a polymer, which is water-insoluble, water-swell able or gelling, and which has a Gel Volume (GV) of at least 10 g/g. These polymers are typically lightly cross-linked polymers, which contain a multiplicity of acid functional groups such as carboxylic acid groups. Examples of acid polymers suitable for use herein include those which are prepared from polymerizable, acid-containing monomers, or monomers containing functional groups which can be converted to acid groups after polymerization. Thus, such monomers include olefinically unsaturated carboxylic acids and anhydrides, and mixtures thereof. The acid polymers can also comprise polymers that are not prepared from olefinically unsaturated monomers.

Examples of such polymers include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247, 068, issued Sep. 21, 1993 to Donachy et al., which is incorporated herein by reference.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid and anhydride monomers useful herein include the acrylic acids typified by acrylic acid itself, methacrylic acid, a-chloroacrylic acid, a-cyanoacrylic acid, β-methylacrylic acid (crotonic acid), a-phenylacrylic acid, β-acryloxypropionic acid, sorbic acid, a-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferred super-absorbent polymers contain carboxyl groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network cross linked polymers of any of the foregoing copolymers, polyacrylic acid, and slightly network cross linked polymers of polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials used for making the super-absorbent polymers herein are polyacrylates/acrylic acids and derivatives thereof, preferably (slightly) network cross linked polymers partially neutralized and ionized with sodium hydroxide polyacrylic acids and/or -starch derivatives thereof.

Most preferably, the absorbent polymers comprise from about 50-95, preferably about 75% neutralized, (slightly) network cross-linked, polyacrylic acid (i.e., poly (sodium acrylate/acrylic acid)). Network cross-linking renders the polymer substantially water-insoluble and, in part, determines the absorptive capacity and extractable polymer content characteristics of the absorbent polymers. Processes for network cross linking these polymers and typical network cross linking agents are described in greater detail in U.S. Pat. No. 4,076,663.

While the absorbent polymer is preferably of one type (i.e., homogeneous), mixtures of absorbent polymers can also be used in the present invention. For example, mixtures of starch-acrylic acid graft copolymers and slightly network crosslinked polymers of polyacrylic acid can be used in the present invention. Mixtures of (coated) polymers with different physical properties, and optionally also different chemical properties, could also be used, e.g. different mean particle size, absorbent capacity, absorbent speed, SFC value).

In absorbent structures or articles according to the present invention, there can be used one and the same super-absorbent polymer type or material throughout the total structure, or there can be different types or materials in different parts of the structure. A super-absorbent material or composition can have the same concentration throughout the structure, or can be at varying concentrations distributed there through.

Specifically, said coated super-absorbent particles can be uniformly distributed throughout the total structure of an absorbent article or structure, or there can be a gradient in the amount of super absorbent per volume unit, type, or property within the structure. This gradient can e.g. be achieved when said coating of the super absorbent is selectively applied to only a part of the super absorbent of said absorbent article or structure.

For the uncoated super absorbent polymer particles of the structures of the present invention, the particle size is preferably such that at least 90% or even at least 99% of the particles is between 45 and 850 microns, or even between 100 and 800 microns, or even between 150 and 710 microns; the mean particle size of the uncoated super absorbent polymer particles is preferably from 150 to 600, or even from 200 to 500 or even 250 to 450 microns.

The particle sizes and mean particle sizes above equally apply to the coated super absorbent polymers, as comprised by the super absorbent material herein, since the coating typically does not change the particle size much.

It is also preferred herein that the coated and uncoated super absorbent polymer particles have a specific surface area of at least 0.01 m.sup.2 per gram, preferably at least 0.1 m.sup.2 per gram, and more preferable at least 0.25 m.sup.2 per gram in accordance with the specific surface evaluation method as defined e.g. in "Modem Super Absorbent Technology" by F. L. Buchholz and A. T. Graham, published by Wiley VCH, New York, 1998.

For the purposes of this invention, particle size distributions are determined according to the method described in the Test Methods section of U.S. Pat. No. 5,419,956 (Roe et al).

The absorbent polymers useful in the present invention can be formed by any polymerization and/or cross-linking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986. Cross-linking can be affected during polymerization by incorporation of suitable cross-linking monomers. Alternatively, the polymers can be cross-linked after polymerization by reaction with a suitable reactive cross-linking agent. Surface cross-linking of the initially formed polymers is a preferred way to control to some extends the absorbent capacity, porosity and permeability.

Suitable general methods for carrying out surface cross linking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992. See also U.S. Pat. No. 7,311,968 to Ehrusperger et al. (The Procter & Gamble Company), the entire contents of which are incorporated by reference.

Additional Embodiments

In various embodiments, the lignocellulose-derived components according to the present invention are incorporated into an absorbent article as described in the following US patents, the contents of each of which are hereby incorporated by reference: U.S. Pat. No. 7,806,883 (Absorbent articles having a breathable stretch laminate), U.S. Pat. No. 7,736,349 (Absorbent article comprising an absorbent element comprising a liquid absorbent thermoplastic composition), U.S. Pat. No. 7,321,007 (Liquid absorbent thermoplastic composition comprising superabsorbent material particles of substantially angle-lacking shape), U.S. Pat. No. 5,134,007 (Multiple layer absorbent cores for absorbent articles), U.S. Pat. No. 4,988,345 (Absorbent articles with rapid acquiring absorbent cores), U.S. Pat. No. 4,988,344 (Absorbent articles with multiple layer absorbent layers), U.S. Pat. No. 4,875,974 (Absorbent vegetable material and process for making same), U.S. Pat. No. 4,783,239 (Absorbent vegetable material and process for making same), U.S. Pat. No. 4,737,582 (Absorbent vegetable materials), and US 2007/0219521 A1 (An absorbent article comprises lignocellulose-derived polypropylene/polyethylene/polyacrylic acid).

I. Polyethylene-Based Products

In various embodiments, a consumer product or its packaging will be based on lignocellulose according to the invention which is converted to polyethylene. For example, in various embodiments, a product or its packaging is derived from polyethylene which is ultimately produced from sugarcane, wood, or any other lignocellulose according to the invention.

Polyethylene is classified into several different categories based mostly on its density and branching. The mechanical properties of PE depend significantly on variables such as the extent and type of branching, the crystal structure and the molecular weight. With regard to sold volumes, the most important polyethylene grades are HDPE, LLDPE and LDPE.

UHMWPE is polyethylene with a molecular weight numbering in the millions, usually between 3.1 and 5.67 million. The high molecular weight makes it a very tough material, but results in less efficient packing of the chains into the crystal structure as evidenced by densities of less than high density polyethylene (for example, 0.930-0.935 g/cm$^3$). UHMWPE can be made through any catalyst technology, although Ziegler catalysts are most common. Because of its outstanding toughness and its cut, wear and excellent chemical resistance, UHMWPE is used in a diverse range of applications. These include can and bottle handling machine parts, moving parts on weaving machines, bearings, gears, artificial joints, edge protection on ice rinks and butchers' chopping boards. It competes with aramid polymer in bulletproof vests, under the tradenames Spectra and Dyneema, and is commonly used for the construction of articular portions of implants used for hip and knee replacements.

HDPE is defined by a density of greater or equal to 0.941 g/cm$^3$. HDPE has a low degree of branching and thus stronger intermolecular forces and tensile strength. HDPE can be produced by chromium/silica catalysts, Ziegler-Natta catalysts or metallocene catalysts. The lack of branching is ensured by an appropriate choice of catalyst (for example, chromium catalysts or Ziegler-Natta catalysts) and reaction conditions. HDPE is used in products and packaging such as milk jugs, detergent bottles, margarine tubs, garbage containers and water pipes. One third of all toys are manufactured from HDPE. In 2007 the global HDPE consumption reached a volume of more than 30 million tons.

PEX is a medium- to high-density polyethylene containing cross-link bonds introduced into the polymer structure, changing the thermoplast into an elastomer. The high-temperature properties of the polymer are improved, its flow is reduced and its chemical resistance is enhanced. PEX is used in some potable-water plumbing systems because tubes made of the material can be expanded to fit over a metal nipple and it will slowly return to its original shape, forming a permanent, water-tight, connection.

MDPE is defined by a density range of 0.926-0.940 g/cm$^3$. MDPE can be produced by chromium/silica catalysts, Ziegler-Natta catalysts or metallocene catalysts. MDPE has good shock and drop resistance properties. It also is less notch sensitive than HDPE, stress cracking resistance is better than HDPE. MDPE is typically used in gas pipes and fittings, sacks, shrink film, packaging film, carrier bags and screw closures.

LLDPE is defined by a density range of 0.915-0.925 g/cm$^3$. LLDPE is a substantially linear polymer with significant numbers of short branches, commonly made by copolymerization of ethylene with short-chain alpha-olefins (for example, 1-butene, 1-hexene and 1-octene). LLDPE has higher tensile strength than LDPE, it exhibits higher impact and puncture resistance than LDPE. Lower thickness (gauge) films can be blown, compared with LDPE, with better environmental stress cracking resistance but is not as easy to process. LLDPE is used in packaging, particularly film for bags and sheets. Lower thickness may be used compared to LDPE. Cable-covering, toys, lids, buckets, containers and pipe are typical applications. While other applications are available, LLDPE is used predominantly in film applications due to its toughness, flexibility and relative transparency. Product examples range from agricultural films, saran wrap, and bubble wrap, to multilayer and composite films. In 2009 the world LLDPE market reached a volume of almost 24 billion US-dollars (17 billion Euro).

LDPE is defined by a density range of 0.910-0.940 g/cm$^3$. LDPE has a high degree of short and long chain branching, which means that the chains do not pack into the crystal structure as well. It has, therefore, less strong intermolecular forces as the instantaneous-dipole induced-dipole attraction is less. This results in a lower tensile strength and increased ductility. LDPE is created by free radical polymerization. The high degree of branching with long chains gives molten LDPE unique and desirable flow properties. LDPE is used for both rigid containers and plastic film applications such as plastic bags and film wrap. In 2009 the global LDPE market had a volume of circa 22.2 billion US-dollars (15.9 billion Euro).

VLDPE is defined by a density range of 0.880-0.915 g/cm$^3$. VLDPE is a substantially linear polymer with high levels of short-chain branches, commonly made by copolymerization of ethylene with short-chain alpha-olefins (for example, 1-butene, 1-hexene and 1-octene). VLDPE is most commonly produced using metallocene catalysts due to the greater co-monomer incorporation exhibited by these catalysts. VLDPEs are used for hose and tubing, ice and frozen food bags, food packaging and stretch wrap as well as impact modifiers when blended with other polymers.

In addition to copolymerization with alpha-olefins, ethylene can also be copolymerized with a wide range of other monomers and ionic composition that creates ionized free radicals. Common examples include vinyl acetate (the resulting product is ethylene-vinyl acetate copolymer, or EVA, widely used in athletic-shoe sole foams) and a variety of acrylates (applications include packaging and sporting goods).

Various of the above-described types of polyethylene may be produced from bioethanol derived from sugarcane, wood, or other lignocellulose according to the invention. Polyethylene can also be made from other feedstocks, including wheat grain and sugar beet according to the invention described herein.

According to an embodiment, the biomass comprises lignin and water-insoluble cellulose and said providing comprises contacting biomass material with a sulfite reagent selected from $SO_2$, sulfurous acid and salts of sulfurous acid, including alkali and ammonium salts, such as $NaHSO_3$, $Na_2S(\frac{3}{4})$, $KHSO_3$, $K_2SO_3$, $NH_4HSO_3$, $(NH_4)_2S(\frac{3}{4})$. According to an embodiment, said contacting is at a temperature and for a residence time sufficient to at least partially sulfonate the lignin in said biomass material and to form sulfonated lignin. According to an embodiment, the degree of sulfonation is sufficiently high to make the sulfonated lignin water-soluble. According to an embodiment, said contact time is greater than an hour. According to an embodiment, said contact temperature is greater than 70° C., preferably greater than 80° C. and more preferably greater than 90° C.

According to an embodiment, said contacting biomass material with a sulfite reagent is conducted in the presence of a water-soluble organic solvent. According to an embodiment, said water-soluble organic solvent is selected from the group consisiting of alcohols, aldehydes, ketones, acetone and esters with up to 4 carbon atoms. According to a preferred embodiment, said water-soluble organic solvent is selected from the group consisiting of methanol, ethanol, isopropyl alcohol and acetone.

According to an embodiment, said contacting biomass material with a sulfite reagent generates water-soluble lignin, but has essentially no effect on said water-insoluble cellulose. According to an embodiment, hydrolysis of said cellulose during said contacting with a sulfite reagent, if any, is limited to less than 5% wt, preferably less than 1%. According to an embodiment, said process further comprises the step of separating said water soluble lignin to form a lignin stream and at least partially delignified water-insoluble cellulose. According to an embodiment, said separating of water-soluble lignin comprises at least one of filtration and centrifugation.

According to an embodiment, said separated cellulose is washed with water or with an aqueous solution. According to an embodiment, said aqueous solution comprises a sulfite reagent. According to an embodiment, hydrolyzing said biomass material comprises hydrolyzing said delignified water-insoluble cellulose. According to an embodiment, said hydrolyzing of delignified water-insoluble cellulose is at least 10% faster than hydrolyzing non-delignified cellulose in a biomass.

According to an embodiment, said biomass comprises hemicellulose. According to an embodiment, said hemicellulose is at least partially hydrolyzed into water-soluble carbohydrates during said contacting with said sulfite reagent. According to an embodiment, said hydrolyzing forms a solution comprising said water-soluble carbohydrates and optionally also said water-soluble lignin. According to an embodiment, said water-insoluble and at least partially delignified cellulose is separated from said solution prior to said hydrolyzing. According to an embodiment, said separated cellulose is washed with water or with an aqueous solution. According to an embodiment, said aqueous solution comprises a sulfite reagent.

According to a related embodiment, said contacting biomass material with a sulfite reagent is conducted in the presence of a water-soluble organic solvent and said separation of cellulose generates water-solvent solution comprising said water-soluble carbohydrates and optionally also said water-soluble lignin further comprises said solvent. According to an embodiment, said water-solvent solution is further treated to form a carbohydrate-enriched stream, a stream enriched with a sulfite reagent and optionally a stream enriched with water-soluble lignin. According to an embodiment, said treatment of said water-solvent solution comprises at least one of membrane separation, distillation, solvent extraction, addition of a solvent and addition of an anti-solvent. According to an embodiment, said carbohydrates-enriched stream comprises at least one of sulfite reagent, solvent and water-soluble lignin. According to an embodiment, said carbohydrate-enriched stream is further treated to form a carbohydrate-rich solution. According to an embodiment, said carbohydrate-rich solution is converted into a consumable product. According to an embodiment, said conversion into a consumable products comprises at least one of chemical catalysis, enzymatic catalysis and fermentation.

Lignin Products

The present invention provides, according to another aspect, a method for producing a lignin product, said method comprising (i) providing a lignocellulosic material comprising lignin and at least one polysaccharide; (ii) hydrolyzing said polysaccharide in an HCl-comprising hydrolysis medium to form water-soluble carbohydrates and a lignin stream comprising lignin and HCl; (iii) partially or completely deacidifying at least a fraction of the lignin stream to produce an HCl fraction for recycle and an acid-depleted lignin; and (iv) processing at least a fraction of said acid-depleted lignin or a product thereof to produce a lignin-comprising consumer product.

According to an embodiment, said hydrolyzing forms an aqueous medium comprising said water-soluble carbohydrates, said lignin and acid and said medium is deacidified as such or after partial removal of lignin, partial removal of carbohydrates or both. According to this embodiment, the lignin stream to deacidification comprises water-soluble carbohydrates and said acid-depleted lignin comprises water-soluble carbohydrates. According to a related embodiment, said deacidifying comprises a contact with a first organic solvent characterized by at least one of: (a1) having a polarity related component of Hoy's cohesion parameter between 0 and 15 $MPa^{1/2}$; (b1) having a Hydrogen bonding related component of Hoy's cohesion parameter between 0 and 20 $MPa^{1/2}$; and (c1) having a solubility in water of less than 15%, whereupon acid transfers into said solvent to form an acid-comprising extract. According to another related embodiment, the method further comprising the step of separating at least a fraction of said water-soluble carbohydrates from said lignin to form a deacidified hydrolyzate comprising said separated water-soluble carbohydrates and a deacidified and carbohydrates-depleted lignin.

According to an embodiment, the lignin in said lignin stream and in said deacidified lignin are water-insoluble. According to a related embodiment, said separating at least a fraction of said water-soluble carbohydrates comprises at least one of filtration, decantation and centrifugation. According to an alternative embodiment, the lignin in the carbohydrates-comprising lignin stream is water soluble, e.g. when modified by hydrolysis, sulfonation or a combination of those. According to a related embodiment, said separating at least a fraction of said water-soluble carbohydrates comprises at least one of membrane separation and ion-exchange. According to an embodiment, said separating comprises filtration via a membrane with a molecular weight cut-off in the range between 1 kiloDalton and 100 kiloDalton. According to an embodiment, said water-soluble lignin is sulfonated.

According to an embodiment, said lignin stream comprises at least a fraction of said water-soluble carbohydrates, said lignin is at least partially water soluble and said deacidifying comprises membrane separation into two streams, a deacidified lignin and a hydrolyzate comprising water-soluble carbohydrates and acid. According to an embodiment, said water-soluble lignin is sulfonated. According to a related embodiment, an aqueous solution comprising water-soluble lignin, water-soluble carbohydrate and acid is treated on a membrane with a molecular weight cut-off in the range between 1 kiloDalton and 100 kiloDalton, the water soluble lignin is retained on one side of the membrane to form the deacidified lignin, while acid and water-soluble carbohydrates permeate through the membrane to form a permeate hydrolyzate stream comprising the acid and the carbohydrates. According to an embodiment, the method further comprises the step of deacidification of said hydrolyzate.

According to an alternative embodiment, said hydrolyzing forms an aqueous medium comprising said water-soluble carbohydrates, said lignin and acid and the method further comprising a separation step of essentially fully removing water-soluble carbohydrates from said lignin to form a hydrolyzate comprising water-soluble carbohydrates and acid and a said lignin stream comprising lignin and acid. According to a related embodiment, the method further comprises the step of separating acid from said hydrolyzate to form acid-depleted hydrolyzate.

According to an embodiment, said providing comprises contacting biomass material with a sulfite reagent selected from $SO_2$, sulfurous acid and salts of sulfurous acid, including alkali and ammonium salts, such as $NaHSO_3$, $Na_2SO_3$, $KHSO_3$, $K_2SO_3$, $NH_4HSO_3$, $(NH_4)_2SO_3$. According to an embodiment, said contacting is at a temperature and for a residence time sufficient to at least partially sulfonate the lignin in said biomass material and to form sulfonated lignin. According to an embodiment, the degree of sulfonation is sufficiently high to make the sulfonated lignin water-soluble. According to an embodiment, said contact time is greater than an hour. According to an embodiment, said contact temperature is greater than 70° C., preferably greater than 80° C. and more preferably greater than 90° C.

According to an embodiment, said contacting biomass material with a sulfite reagent is conducted in the presence of a water-soluble organic solvent. According to an embodiment, said water-soluble organic solvent is selected from the group consisting of alcohols, aldehydes, ketones, acetone and esters with up to 4 carbon atoms.

EXAMPLES

The examples and preparations provided below further illustrate and exemplify the compounds of the present invention and methods of preparing such compounds. It is to be understood that the scope of the present invention is not limited in any way by the scope of the following examples and preparations.

Example 1

Commercial corrugated waste paperboard is reslushed with water and hydrochloric acid is added to a dosage of 1% based on dry waste material. The reslushed and acid washed waste at 5% consistency is maintained at 50° C. for 30 minutes, after which it is washed with water and dewatered to about 10% consistency. The hydrochloric acid is recovered as described herein.

The thus pretreated waste is digested with 5% caustic (NaOH) and 0.5% magnesium sulphate ($MgSO_4$), at 100° C. and in the presence of 100 psig oxygen gas for about 25 minutes until the pH of the mixture decreases to about 10.5, indicating that all NaOH is consumed. The yield, kappa value, viscosity, ISO brightness, and fiber strength of the pulp product are measured.

Example 2

HCl and water recovery from lignin by adding synthetic solution of Hexanol-HCl—$H_2O$ Procedure:

(i) Preparation of the lignin cake: 14 gr lignin composition, was used. An analysis showed that the concentration of HCl there was 38% and the total DS was 14%. That lignin was introduced into a vial with 30 gr HCl 37%. HCl gas was bubbled in at a temperature of about 0-2° C. After bubbling was stopped, a sample of the solution was analyzed for HCl and water. Then, the solution with the lignin was transferred into an ice-cooled column with a valve on its bottom. Liquid was drained from the column and analyzed. The remaining 15 g lignin cake was used in the experiment. The composition of that cake, as shown in Table 1, was determined from the analysis of the separated liquid and from the known amount of solid lignin.

(ii) Preparation of the solvent phase: The highly concentrated aqueous HCl solution, drained from the lignin in the lignin preparation step, was mixed with dry hexanol in an amount similar to that of the lignin cake to form a hexanol-HCl-water solution, the analysis of which is shown in Table 1. The ratio between the phases was such that, on equilibrium, two phases existed.

(iii) The lignin cake formed in (i) and the solution formed in (ii) were contacted in a column and gently mixed. Then, the total amount was transferred into a separatory funnel and allowed to settle. The composition separated into two clear regions, a heavy one that is essentially aqueous and a light one in which the solid lignin is dispersed.

(iv) The two regions were separated and analyzed. The results are summarized in Table 2. Hexanol content of the heavy phase was not determined. The lignin phase was analyzed by washing with ethanol followed by analyzing the wash solution for water and HCl. The hexanol content was determined by difference. The analysis reported in Table 2 is for the upper region liquid as such. In addition, the DS of the lignin in the upper region was determined.

TABLE 1

Initial lignin cake and hexanol-HCl-water compositions

| | Total gr | HCl Wt % | Water Wt % | Hexanol Wt % | Solids Wt % | HCl/ (HCl + $H_2O$) | Solids gr | HCl gr | Water gr | Hexanol gr |
|---|---|---|---|---|---|---|---|---|---|---|
| Lignin phase | 15 | 37.1 | 50.2 | | 12.7 | 0.425 | 1.9 | 5.6 | 7.5 | 0 |
| Hexanol-HCl-water solution | 33 | 24.0 | 31.6 | 44.35 | 0.0 | 0.432 | | 7.9 | 10.4 | 14.6 |

TABLE 2

Light and heavy regions compositions

| | Total gr | HCl Wt % | Water Wt % | Hexanol Wt % | Solids Wt % | HCl/ (HCl + H₂O) | Solids gr | HCl gr | Water gr | Hexanol gr |
|---|---|---|---|---|---|---|---|---|---|---|
| Light phase + lignin | 37 | 25.1 | 33.7 | 41.2 | 5.6 | 0.427 | 1.9 | 8.8 | 11.8 | 14.5 |
| Heavy phase | 11 | 36.8 | 63.2 | | 0.0 | 0.368 | ~0 | 4.0 | 7.0 | 0 |

According to the results, out of the HCl and water originally present in the lignin cake, 71% and 93%, respectively were found in the heavy phase. HCl concentration in the heavy phase is relatively low. Possibly, part of the HCl was lost into the atmosphere during the operations (the total amount of HCl in the final phases is ~95% of the initial). Yet, about 16% of the initial HCl in the lignin cake was transferred into the light phase, HCl concentration of which grew from 24% to 25.1%. Apparently, loading of the hexanol, prepared in (ii) above, was too low.

Example 3: HCl and Water Recovery from Lignin by Adding the Light Phase from the Previous Experiment Procedure (i) Preparation of the lignin cake: The procedure was similar to that of Example 2 starting this time with 13 gr lignin composition. See analysis in Table 3.

(ii) Preparation of the solvent phase: 32.8 gr light phase was separated from the upper phase of Example land used as such in the present example. See analysis in Table 3.

(iii) Contacting of the cake with the light phase, observations, separation and analysis were done as in Example 2. The results are reported in Table 4.

TABLE 3

Initial lignin cake and hexanol-HCl-water compositions

| | Total gr | HCl gr | HCl Wt % | Water gr | Water Wt % | Hexanol gr | Hexanol Wt % | Solids gr | Solids Wt % | HCl/ (HCl + H₂O) |
|---|---|---|---|---|---|---|---|---|---|---|
| Lignin phase | 13 | 4.9 | 37.3 | 6.7 | 51.5 | 0 | | 1.45 | 11.2 | 0.42 |
| Light phase from Ex 1 | 30 | 7.5 | 25.1 | 10.1 | 33.7 | 12.4 | 41 | | 0 | 0.427 |

TABLE 4

Light and heavy phase composition

| | Total gr | HCl gr | HCl Wt % | Water gr | Water Wt % | Hexanol gr | Hexanol Wt % | Solids gr | Solids Wt % | HCl/ (HCl + H₂O) |
|---|---|---|---|---|---|---|---|---|---|---|
| Light phase + lignin | 32.8 | 8 | 25.4 | 10.3 | 33 | 13 | 42 | 1.45 | 4.4 | 0.435 |
| Heavy phase | 10.2 | 4 | 39 | 6.3 | 61.5 | 0 | | ~0 | | 0.388 |

According to the results of the present example using solvent phase from the first one, out of the HCl and water originally present in the lignin cake, 81% and 94%, respectively were found in the heavy phase. For HCl, this is a significant increase. Compared with Example 2. HCl concentration in the heavy phase is still lower than the one in the lignin, but higher than that in Example 2 (38.8% and 36.8%, respectively). In the second example, HCl concentration in the light phase increases on contacting, as in the 1st, but significantly less (from 25.1% to 25.4%). These observations support the hypothesis made above, that HCl concentration in the hexanol was not high enough. At the correct initial HCl concentration of the light phase (which would be the case on recycling), practically all the HCl and water in the lignin cake will be rejected to the aqueous Over 90% of the HCl and of the water in the lignin (out of hydrolysis) are recovered by decantation, rather than by distillation. This provides major savings in energy.

In addition, it eliminates the corresponding distillation column.

The majority of the solvent is kept in a closed loop with no need for heating and cooling, which presents additional energy and capital savings. There is no addition of equipment. Elevated temperature contact of hexanol with HCl is minimized, which red undesired reactions. Since single phase formation is not required and since the majority of the solvent is recycled with no heating/cooling costs, the proportion of solvent can be increased beyond that considered for the previously proposed processes, which increases the recovery yield wherein recovery yield may be defined as the percentage of acid recovered from the lignin composition.

Example 4: Preparing Recycle Extractant

A hydrolyzate was prepared by hydrolyzing sugarcane bagasse in a 42% HCl solution. The concentrations of HCl and of carbohydrates in the formed hydrolyzate were 31.7% wt and 12.8% wt, respectively. That hydrolyzate was equilibrated with hexanol. HCl was selectively extracted to the solvent and an organic phase containing 14.9% wt HCl—the extract—was formed. HCl was distilled out of that extract at a pressure of 50 mm mercury. At the end of the distillation the recycle extractant was formed. HCl concentration in that recycle extractant was 0.1% wt. A sample of the recycle extractant was taken and checked for absorption at several wavelengths between 310 nm and 600 nm. The results are presented in Table 5.

Example 5: Refining of the Recycle Extractant 18 gr of recycle extractant were mixed in a vial with 5 gr of a 10% wt Ca(OH)2 slurry. Mixing duration was 3 hours. During that time, the phases were kept at 85° C. A mixture was formed containing lime-treated recycle extractant and an aqueous slurry of lime. A sample of the lime-treated recycle extractant was separated. Filtering away the lime from the organic phase was difficult. The filtered sample was taken and checked for absorption at several wavelengths between 310 nm and 600 nm. The results are presented in Table 5.

While mixing, $CO_2$ was bubbled through the mixture. Bubbling was continued until the pH of the aqueous solution reached 7.0. Then, lgr of 10% wt Ca(OH) 2 slurry was added and mixing was continued at 85° C. for another hour. The organic phase was separated. Filtering away the lime from the organic phase was much easier than that prior to the contact with $CO_2$. The filtered organic phase was washed three times with 1gr water and then analyzed. Its calcium content was 76 ppm. The washed organic phase—the refined recycle extractant—was checked for absorption at several wavelengths between 310 nm and 600 nm. The results are presented in Table 5.

TABLE 5

Absorption at various wavelengths in the UV-Vis range*

| | Wavelength | | | | | |
|---|---|---|---|---|---|---|
| | A310 | A350 | A400 | A450 | A500 | A600 |
| Recycle extractant | 28.2 | 19.5 | 9.0 | 5.0 | 3.1 | 1.4 |
| After contact with lime | 10.1 | 6.5 | 2.1 | 0.79 | 0.35 | 0.08 |
| Refined recycle extractant | 10.1 | 6.3 | 2.0 | 0.75 | 0.34 | 0.11 |

*For absorption measurements, the solutions were diluted. The figures in the table were calculated by multiplying the measured absorption by the degree of dilution.

The results in Table 5 show significant reduction in the absorption in all the measure wavelengths, confirming efficient removal of colored impurities from the recycle extractant.

Example 6

A round-bottomed flask containing 20 ml of a simulated HCl loaded extract was placed in an oil bath maintained at 180° C. The simulated extract consisted of a solution in mineral oil (boiling point above 250° C.) containing 0.2 meq/ml dinonylnaphthalene sulfonic acid (HDNNS) and 0.2 meq/ml tridodecylamine hydrochloride $(Ci_2H_{25})_3N$—HCl. A stream of nitrogen gas of about 2 ml/min was passed through the organic extract and exited through a water trap. After 90 minutes the nitrogen was stopped and the HCl in the water trap titrated. In two replications of the experiment, 98.5% and 99.3% of the HCl in the organic solution were recovered. In each experiment the remaining mineral oil was contacted with aqueous 5% NaOH and the aqueous phases checked for CI ion. Hardly any $CI^-$ could be perceived.

Example 7

A 40 ml solution of the same solutes as above, 0.1 meq of each, was prepared in a non aromatic petroleum extract (described as 98% boiling at 172° C./195° C.) simulating an HCl-carrying extract. The organic liquid was placed in a flask that was heated in a controlled fashion to distill the contents slowly, without reflux, directly into a cooled water trap. The distillation was stopped in 55 minutes when about 20 ml distillate was collected. All of the HCl in the simulated extract was found in the aqueous phase in the trap. None could be determined in the approximately 20 ml liquid that remained in the flask.

Examples 6 and 7 demonstrate that HCl carried by ABC extractants can be recovered as HCl gas by heating to a temperature that needs not exceed 200° C. while providing an inert carrier for conveying the HCl. Taken with the known art of extracting HCl from aqueous solutions thereof (as provided in U.S. Pat. No. 4,291,007 cited above) provides for designing a great variety of schemes for concentrating hydrochloric acid. For each practical problem, a practitioner can resort to the large choice of ABC extractants and the particular demands of each case.

Three general cases are represented below.

In a first case, the procedure recovers only the HCl from a part of a feed and the HCl gas thus recovered is absorbed in a second part of the feed, to obtain a concentrated hydrochloric acid. Thus, for example, a feed of 10.71% HCl (12 HCl per 100 $H_2O$) split equally will provide a product of 19.4% HCl; if split in a ratio of (3):(2)=2:1, the product will have a concentration of 26.4% HCl.

In a second case, the procedure recovers all of the HCl in a feed and absorbs it in water, which provides for easy control of concentration and for purity of the product HCl solution. A useful variant of this general procedure is to absorb the HCl gas directly in an aqueous medium of a process that requires concentrated hydrochloric acid, for instance, a slurry of a comminuted cellulosic material due to b e hydrolyzed.

In a third case, the release of HCl from an ABC extractant extract can be divided into two parts: thermal—which recovers HCl partially as gas, and liquid-liquid extraction by water—which recovers the remainder of the HCl as dilute hydrochloric acid that absorbs the HCl gas thermally released.

These are just three of the numerous flow sheet varieties, each of which can be conceived and elaborated in detail to fit the particulars of each case that involves hydrochloric acid concentration. One example is detailed below by way of illustration.

Example 8

Laboratory simulation of HCl recycling for an industrial process related to cellulose conversion to glucose by acid hydrolysis.

In this process a 32% acid is used to perform the hydrolysis. The acid (which acts as catalyst and is not consumed) yields a clarified aqueous product solution containing 172 grs/L HCl (4.7 molar and about 22% HCl with respect to the water in this product) that need be recovered as hydrochloric acid of 32%.

The HCl extraction was run in a battery of six laboratory mixer-settlers. The solvent was 0.52 molar in an ABC of 1:1 TLA:HDNNS (trilaurylamine-dinonylnaphtalene sulfonic acid) in a hydrocarbons diluent of a boiling range starting at 210° C. The volumetric ratio of extractant to aqueous feed was 10:1. The pH of the aqueous raffinate stabilized at 6.2, indicating that the extraction of HCl was practically complete. The solvent was 0.46 molar in HCl. 100 ml of this extract were heated in a glass vessel to 160° C. by immersion in a thermostatic bath maintained at this temperature. Steam superheated to 160° C./170° C. (generated by passing water through a heated copper pipe) was sparged into the liquid extract to serve as carrier for the HCl released. The gaseous mixture of $H_2O$ and HCl was passed through an externally refrigerated graphite pipe, whereby condensation to hydrochloric acid took place. The experiment was repeated with varying amounts of steam, with each replicated to obtain safe averages.

Example 9

In a conventional air-laying method, absorbent structures (diapers) are formed by air-conveying a mass of dry wood pulp fibers onto a rotating wire mesh drum. A pressure gradient is maintained over the wire mesh to ensure proper deposition of the fluff. A diaper can be made by metering various additives into the wood pulp fiber stream. Metering can be done by means of e.g., a weighing belt or a screw pump.

Feeding of hydrogel particles onto the laydown drum can be by gravity or forced air feed. In either case, a nozzle is used to spread the hydrogel particles over the crotch-width of the absorbent structure.

Since the lay-down drum rotates while wood pulp fibers are being deposited onto it, the position of the hydrogel feed nozzle with respect to the drum and the wood pulp infeed largely determines the distribution of the hydrogel particles in the structure.

The face of the structure which is in contact with the drum will become the back face. Seen from a vantage point from which the drum appears to have a clock-wise rotation, the left hand part of the wood pulp stream reaches the drum first. By placing a hydrogel in a way as to ensure predominant mixing with this left hand part of the wood pulp stream, the desired hydrogel distribution is obtained for a diaper.

Absorbent structures are made as described above, comprised of wood pulp fibers ("airfelt") and particulate cross-linked polyacrylate hydrogel derived from lignocellulose through an acid-catalyzed saccharification of lignocellulose followed by fermentation to produce a monomer for chemical conversion. Absorbent structures have a target weight of 43.58 g, 14% of which is hydrogel, and 85.1% of which is airfelt. The structures are calendered to a thickness of about 6.5 mm.

Example 10

A disposable diaper product containing particles of a lignocellulose-derived starch-acrylate material is prepared. Such an article comprises an absorbent core positioned between a polyethylene backing sheet and a hydrophobic, liquid pervious non-woven rayon topsheet. The absorbent core comprises two layers, one of which is an hourglass-shaped primary core and the other of which is a smaller oval insert placed beneath the primary core.

The hourglass consists of a homogeneous blend of southern soft wood/pine fibers and fibrous phosphorylated cellulose ("cellulose phosphate") having an ion exchange capacity of about 3.5 meq./gram. The oval insert consists of a homogeneous blend of southern soft wood/pine fibers and particles (250 microns) of acrylic acid grafted starch hydrogel derived via fermentation of carbohydrates produced from lignocellulose. The absorbent core with its two layers is overwrapped with tissue paper. The acrylate hydrogel material is derived from lignocellulose via an acid-catalyzed saccharification of lignocellulose followed by fermentation to produce a monomer for chemical conversion to acrylic acid or a derivative thereof.

Example 11

A powder detergent with the following components is prepared:

| Type | Ingredient |
| --- | --- |
| Bleach Activator | Nonanoyloxybenzenesulfonate |
| Builders | Diethylenetriamine Pentaacetate (Sodium Salt) |
| Dispersant | Sodium Polyacrylate |
| Enzyme | Protease |
| Fragrance | Fragrance |
| Fragrance Carrier | Modified Starch |
| Optical Brightener | Disodium Diaminostilbene Disulfonate |
| Oxygen Bleach | Sodium Percarbonate |
| pH Adjustment | Sodium Carbonate |
| Process Aid | Palmitic Acid |
| Process Aid | Polyethylene Glycol 4000 |
| Process Aid | Sodium Sulfate |
| Process Aid | Water |
| Removes Water Hardness | Sodium Aluminosilicate |
| Suds Suppressor | Silicone |
| Surfactant | Alkyl Sulfate |
| Surfactant | Linear Alkylbenzene Sulfonate | where at least one component is derived from carbohydrates produced by acid-catalyzed saccharification of lignocellulose to produce a detergent that is particularly effective in high efficiency and/or large washing machines.

Example 12

A liquid detergent with the following components is prepared:

| Type | Ingredient |
| --- | --- |
| Builders | Diethylenetriamine Pentaacetate (Sodium Salt) |
| Builders | Borax |
| Builders | Citric Acid |
| Colorant | LiquitintTM Blue |
| Enzyme | Amylase |
| Enzyme | Mannanase |
| Enzyme | Pectinase |
| Enzyme | Protease |
| Fragrance | Fragrance |
| Optical Brightener | Disodium Diaminostilbene Disulfonate |

| Type | Ingredient |
| --- | --- |
| Optical Brightener | Disodium Distyrylbiphenyl Disulfonate |
| pH Adjustment | Sodium Hydroxide |
| Polymer | Diquaternium Ethoxy Sulfate |
| Polymer | Polyethyleneimine Ethoxylate |
| Process Aid | Calcium Formate |
| Process Aid | Diethylene Glycol |
| Process Aid | Dimethicone |
| Process Aid | Ethanol |
| Process Aid | Ethanolamine |
| Process Aid | Polyethylene Glycol 4000 |
| Process Aid | Propylene Glycol |
| Process Aid | Sodium Cumene Sulfonate |
| Process Aid | Sodium Formate |
| Process Aid | Water |
| Surfactant | Alkyl Sulfate |
| Surfactant | Alkylethoxy Sulfate |
| Surfactant | Lauramine Oxide |
| Surfactant | Laureth-9 |
| Surfactant | Linear Alkylbenzene Sulfonate |
| Surfactant | Sodium Fatty Acids | where at least one component is derived from carbohydrates produced by acid-catalyzed saccharification of lignocellulose to produce a liquid detergent.

Example 13

5.17-0.21 gr 37% HCl solution, 0.65-1.48 gr water, 2.28-5.04 gr glucose and 1.2 gr Hexanol were introduced into vials. The vials were mixed at 50° C. The phases were then separated and analyzed for HCl concentrations by titration with NaOH, water by KF titration and glucose by HPLC. The results are presented in Table 6.

TABLE 6

| | Light phase composition | | | | heavy phase composition | | | Kd-distribution coefficient and selectivity | | | HCl/ water Selectivity | HCl/ glucose selectivity |
| --- | --- | --- | --- | --- | --- | --- | --- | --- | --- | --- | --- | --- |
| Vial No. | HCl Wt % | H$_2$O Wt % | gluc. Wt % | hexanol Wt % | HCl Wt % | H$_2$O Wt % | gluc Wt % | HCl Kd | H$_2$O Kd | Glucose Kd | | |
| 1 | 15.0 | 18.8 | 1.19 | 65.0 | 22.4 | 47.7 | 30.7 | 0.67 | 0.39 | 0.039 | 1.70 | 17.3 |
| 2 | 12.5 | 17.2 | 1.09 | 69.2 | 19.5 | 46.1 | 35.1 | 0.64 | 0.37 | 0.031 | 1.72 | 20.6 |
| 3 | 10.3 | 14.7 | 1.12 | 73.2 | 17.0 | 46.4 | 37.1 | 0.61 | 0.32 | 0.030 | 1.91 | 20.1 |
| 4 | 7.69 | 12.6 | 1.15 | 78.6 | 13.7 | 44.7 | 42.0 | 0.56 | 0.28 | 0.027 | 1.98 | 20.5 |
| 5 | 5.12 | 10.4 | 0.65 | 83.9 | 10.4 | 44.0 | 45.9 | 0.49 | 0.24 | 0.014 | 2.07 | 34.5 |
| 6 | 2.88 | 7.31 | NA | 89.8 | 7.10 | 42.5 | 50.5 | 0.41 | 0.17 | | 2.36 | |
| 7 | 0.83 | 5.9 | NA | 93.3 | 3.72 | 46.4 | 50.0 | 0.22 | 0.13 | | 1.75 | |
| 8 | 0.29 | 5.53 | NA | 94.2 | 2.09 | 45.6 | 52.4 | 0.14 | 0.12 | | 1.15 | |
| 9 | 0.11 | 5.27 | NA | 94.6 | 1.06 | 45.0 | 53.7 | 0.11 | 0.12 | | 0.91 | |
| 10 | 3.61 | 8.0 | NA | 88.4 | 6.77 | 29.6 | 63.8 | 0.53 | 0.27 | | 1.98 | |

*NA = Not Analyzed.

This example illustrates that when hexanol is used as extractant, selectivity for HCl between the two formed phases is found. Moreover, as increasing the amount of hexanol within the reaction composition the selectivity increases.

Example 14

0.05-1.66 gr 37% HCl solution, 0.93-1.76 gr water, 2.47-2.7 gr glucose, 1.53 gr hexanol and 1.3-1.8 gr MeOH were introduced into vials. The vials were mixed at 50° C. The phases were then separated and analyzed for HCl, water glucose as described above and MeOH by HPLC. The results are presented in Table 7.

TABLE 7

| | Light phase composition | | | | | heavy phase composition | | | | Kd-distribution coefficient and selectivity | | | | | |
| --- | --- | --- | --- | --- | --- | --- | --- | --- | --- | --- | --- | --- | --- | --- | --- |
| | HCl Wt % | H$_2$O Wt % | gluc Wt % | hexanol Wt % | MeOH Wt % | HCl Wt % | H$_2$O Wt % | Gluc Wt % | MeOH Wt % | HCl Kd | H$_2$O Kd | glucose Kd | MeOH Kd | water selectivity | glucose selectivity |
| 1 | 6.7 | 18 | 7.80 | 49.1 | 18.4 | 7.75 | 26.6 | 42.3 | 20.8 | 0.86 | 0.68 | 0.18 | 0.89 | 1.27 | 4.7 |
| 2 | 4.5 | 17.4 | 7.58 | 49.6 | 21.0 | 5.58 | 28.6 | 43.2 | 19.3 | 0.80 | 0.61 | 0.18 | 1.09 | 1.31 | 4.5 |
| 3 | 3.0 | 15.2 | 5.77 | 55.8 | 20.3 | 4.11 | 31.2 | 41.9 | 18.0 | 0.72 | 0.49 | 0.14 | 1.13 | 1.47 | 5.2 |
| 4 | 2.0 | 14.5 | 5.51 | 56.7 | 21.3 | 2.96 | 30.7 | 43.8 | 19.0 | 0.68 | 0.47 | 0.13 | 1.12 | 1.43 | 5.4 |
| 5 | 0.8 | 13 | NA | 59.8 | 22.5 | 1.37 | 32.0 | 44.7 | 16.7 | 0.56 | 0.41 | | 1.35 | 1.37 | |
| 6 | 0.2 | 12.3 | NA | 60.6 | 24.0 | 0.31 | 30.0 | 47.3 | 18.4 | 0.51 | 0.41 | | 1.31 | 1.25 | |
| 7 | 5.1 | 14.8 | 4.55 | 61.3 | 14.3 | 30.5 | 44.0 | 15.4 | 0.70 | 0.49 | 0.10 | 0.93 | 1.45 | 6.8 | |
| 8 | 2.7 | 13.05 | 4.00 | 63.4 | 16.8 | 7.20 | 31.4 | 46.4 | 17.3 | 0.61 | 0.41 | 0.086 | 0.97 | 1.46 | 7.0 |

TABLE 7-continued

| | Light phase composition | | | | | heavy phase composition | | | | Kd-distribution coefficient and selectivity | | | | HCl/ water selectivity | HCl/ glucose selectivity |
|---|---|---|---|---|---|---|---|---|---|---|---|---|---|---|---|
| | HCl Wt % | H₂O Wt % | gluc Wt % | hexanol Wt % | MeOH Wt % | HCl Wt % | H₂O Wt % | Gluc Wt % | MeOH Wt % | HCl Kd | H₂O Kd | glucose Kd | MeOH Kd | | |
| 9 | 1.58 | 11.6 | 3.74 | 66.8 | 16.3 | 4.54 | 32.8 | 46.7 | 14.4 | 0.53 | 0.35 | 0.080 | 1.13 | 1.50 | 6.6 |
| 10 | 0.61 | 11 | NA | 71.0 | 17.4 | 2.98 | 33.4 | 47.9 | 14.3 | 0.40 | 0.33 | | 1.22 | 1.22 | |
| 11 | 0.12 | 9.9 | NA | 71.5 | 18.5 | 1.52 | 33.9 | 48.9 | 12.2 | 0.32 | 0.29 | | 1.51 | 1.10 | |

* NA = Not Analyzed.

This example illustrates the influence of the hexanol/methanol ration on the distribution coefficient and on the selectivity of HCl. At hexanol/methanol ration of 3.7-4.3 the HCl selectivity to the carbohydrate phase increases compared with HCl selectivity at hexanol: methanol ration of 2.4-2.7, but for the respective solvents ratio the distribution coefficient of HCl decreases as the amount of methanol decreases.

Example 15

0.07-1.71 gr 37% HCl solution, 0.93-1.79 gr water, 2.5-2.7 gr glucose, 1.53 gr hexanol and 1-1.54 gr EtOH were introduced into vials. The vials were mixed at 50° C. The phases were then separated and analyzed for HCl, water glucose as described above and EtOH by HPLC. The results are presented in Tables 8-9.

TABLE 8

| | Light phase composition | | | | | Heavy Phase composition | | | |
|---|---|---|---|---|---|---|---|---|---|
| Vial No. | HCl Wt % | H₂O Wt % | gluc. Wt % | hexanol Wt % | EtOH Wt % | HCl Wt % | H₂O Wt % | gluc Wt % | EtOH Wt % |
| 1 | 6.94 | 18.4 | 6.83 | 45.2 | 22.6 | 9.62 | 34.0 | 43.1 | 11.9 |
| 2 | 3.42 | 16 | 5.20 | 47.8 | 27.6 | 4.10 | 32.7 | 49.5 | 11.3 |
| 3 | 2.04 | 15.1 | 3.58 | 49.7 | 29.5 | 2.74 | 34.0 | 50.7 | 11.1 |
| 4 | 0.93 | 13.7 | 3.29 | 50.7 | 31.4 | 1.47 | 35.6 | 51.4 | 10.8 |
| 5 | 5.04 | 16.7 | 6.1 | 43.8 | 28.3 | 7.42 | 32.6 | 50.1 | 11.3 |
| 6 | 0.145 | 12.5 | 2 | 55.1 | 30.3 | 0.43 | 36.1 | 50.3 | 10.5 |
| 7 | 1.581 | 15.3 | 4.54 | 51.0 | 27.6 | 2.37 | 34.2 | 49.5 | 10.3 |
| 8 | 0.616 | 13.67 | 2.89 | 53.4 | 29.5 | 1.17 | 35.0 | 50.6 | 10.5 |
| 9 | 0.385 | 12.54 | 2.60 | 55.7 | 28.8 | 0.82 | 34.9 | 49.7 | 10.3 |
| 10 | 1.372 | 15.2 | 3.95 | 51.0 | 28.5 | 2.09 | 34.0 | 50.3 | 10.8 |
| 12 | 6.86 | 15.7 | 4.15 | 55.3 | 18.0 | 8.51 | 38.0 | 44.3 | 8.9 |
| 13 | 3.94 | 14.2 | 2.55 | 58.5 | 20.8 | 5.49 | 36.0 | 48.7 | 8.9 |
| 14 | 2.48 | 12.4 | 2.54 | 60.9 | 21.6 | 4.00 | 38.1 | 48.4 | 8.8 |
| 15 | 1.46 | 11.6 | 2.24 | 60.4 | 24.3 | 2.74 | 40.1 | 49.4 | 9.2 |
| 16 | 0.66 | 10.8 | 1.87 | 62.7 | 23.9 | 1.61 | 38.6 | 51.2 | 8.2 |
| 17 | 0.12 | 10.7 | | 66.1 | 23.1 | 0.47 | 38.8 | 51.3 | 8.3 |
| 18 | 1.45 | 12.2 | 1.76 | 63.8 | 20.8 | 2.69 | 36.4 | 50.6 | 8.4 |
| 19 | 0.45 | 11.4 | 1.58 | 64.9 | 21.6 | 1.22 | 37.8 | 51.2 | 8.0 |
| 20 | 0.28 | 11.03 | 1.63 | 64.4 | 22.6 | 0.87 | 37.9 | 51.3 | 7.8 |
| 21 | 1.01 | 11.5 | 1.87 | 63.1 | 22.5 | 2.16 | 37.7 | 50.5 | 8.6 |

TABLE 9

| Kd-distribution coefficient and selectivity | | | | | | |
|---|---|---|---|---|---|---|
| Vial No. | HCl Kd | H₂O Kd | Glucose Kd | EtOH Kd | HCl/water selectivity | HCl/glucose selectivity |
| 1 | 0.72 | 0.54 | 0.16 | 1.90 | 1.33 | 4.6 |
| 2 | 0.84 | 0.49 | 0.10 | 2.44 | 1.71 | 8.0 |
| 3 | 0.75 | 0.44 | 0.071 | 2.67 | 1.68 | 10.6 |
| 4 | 0.63 | 0.38 | 0.06 | 2.89 | 1.64 | 9.9 |
| 5 | 0.68 | 0.51 | 0.12 | 2.50 | 1.33 | 5.6 |
| 6 | 0.33 | 0.35 | 0.04 | 2.89 | 0.97 | 8.4 |
| 7 | 0.67 | 0.45 | 0.092 | 2.69 | 1.49 | 7.3 |
| 8 | 0.53 | 0.39 | 0.057 | 2.81 | 1.35 | 9.2 |
| 9 | 0.47 | 0.36 | 0.052 | 2.81 | 1.32 | 9.0 |
| 10 | 0.66 | 0.45 | 0.079 | 2.63 | 1.47 | 8.4 |
| 12 | 0.81 | 0.41 | 0.094 | 2.02 | 1.95 | 8.6 |
| 13 | 0.72 | 0.39 | 0.052 | 2.34 | 1.82 | 13.7 |
| 14 | 0.62 | 0.33 | 0.053 | 2.46 | 1.91 | 11.8 |
| 15 | 0.53 | 0.29 | 0.045 | 2.64 | 1.85 | 11.8 |
| 16 | 0.41 | 0.28 | 0.036 | 2.91 | 1.46 | 11.2 |
| 17 | 0.26 | 0.28 | | 2.77 | 0.95 | |

TABLE 9-continued

Kd-distribution coefficient and selectivity

| Vial No. | HCl Kd | H$_2$O Kd | Glucose Kd | EtOH Kd | HCl/water selectivity | HCl/glucose selectivity |
|---|---|---|---|---|---|---|
| 18 | 0.54 | 0.33 | 0.035 | 2.49 | 1.62 | 15.5 |
| 19 | 0.37 | 0.30 | 0.031 | 2.69 | 1.23 | 12.0 |
| 20 | 0.32 | 0.29 | 0.032 | 2.90 | 1.10 | 10.0 |
| 21 | 0.47 | 0.31 | 0.037 | 2.62 | 1.53 | 12.6 |

The HCl/carbohydrate selectivity was higher than those in example 14, where methanol and hexanol were the solvents. At increased hexanol/ethanol ratio the distribution coefficient of HCl decreases while the selectivity increase, this behavior is similar to that of example 14.

Example 16

0.5-3.5 gr 37% HCl solution, 1.77-3.38 gr water, 1.37-2.2 gr glucose, and 1.9-1.6 gr 2-ethylhexanol were introduced into vials. The vials were mixed at 30° C. The phases were then separated and analyzed for HCl concentrations by titration with NaOH, water by KF titration and glucose by HPLC. The results are presented in Table 10.

TABLE 10

| | Light phase composition | | | | Heavy Phase composition | | | Kd-distribution coefficient and selectivity | | | | |
|---|---|---|---|---|---|---|---|---|---|---|---|---|
| Vial No. | HCl Wt % | H$_2$O Wt % | gluc Wt % | 2-ethyl Hexanol Wt % | HCl Wt % | H$_2$O Wt % | gluc Wt % | HCl Kd | H$_2$O Kd | glucose Kd | HCl/H$_2$O selectivity | HCl/glucose selectivity |
| 1 | 6.0 | 7.8 | 0.20 | 86.2 | 18.2 | 56.5 | 26.1 | 0.33 | 0.14 | 0.0078 | 2.38 | 42 |
| 2 | 4.6 | 6.76 | 0.13 | 88.7 | 15.4 | 57.2 | 27.8 | 0.30 | 0.12 | 0.0047 | 2.51 | 64 |
| 3 | 3.8 | 5.98 | NA | 90.2 | 13.7 | 57.7 | 28.8 | 0.28 | 0.10 | NA | 2.66 | |
| 4 | 2.7 | 5.16 | NA | 92.1 | 12.1 | 58.2 | 30.0 | 0.23 | 0.089 | NA | 2.54 | |
| 5 | 1.2 | 3.52 | NA | 95.3 | 8.9 | 59.1 | 32.1 | 0.14 | 0.060 | NA | 2.29 | |
| 6 | 0.12 | 2.56 | NA | 97.3 | 3.5 | 60.8 | 36.1 | 0.03 | 0.042 | NA | 0.78 | |
| 7 | 0.38 | 2.9 | NA | 96.7 | 5.9 | 60.0 | 34.2 | 0.06 | 0.048 | NA | 1.33 | |

The distribution coefficient of HCl herein, was lower than that in previous examples, where hexanol was tested.

Example 16

0.02-0.87 gr 37% HCl solution, 0.55-2.2 gr water, 0.9-1.12 gr glucose, 0.74-1.2 gr 2-ethylhexanol and 1.6-3 gr MeOH were introduced into vials. The vials were mixed at 30° C. The phases were then separated and analyzed for HCl concentrations by titration with NaOH, water by KF titration and glucose and MeOH by HPLC. The results are presented in Tables 11-12.

TABLE 11

| | Light phase composition | | | | | Heavy Phase composition | | | |
|---|---|---|---|---|---|---|---|---|---|
| Vial No. | HCl Wt % | H$_2$O Wt % | gluc. Wt % | 2-ethyl hexanol Wt % | MeOH Wt % | HCl Wt % | H$_2$O Wt % | glue Wt % | MeOH Wt % |
| 1 | 0.047 | NA | NA | 71.8 | 28.2 | 0.22 | 36.1 | 22.0 | 37.3 |
| 2 | 2.4 | 9.75 | NA | 69.4 | 20.9 | 6.59 | 36.3 | 20.2 | 30.2 |
| 3 | 1.5 | 9.26 | NA | 70.2 | 20.6 | 4.94 | 36.9 | 21.5 | 31.6 |
| 4 | 0.5 | 7.8 | NA | 71.5 | 20.7 | 2.34 | 38.1 | 23.4 | 32.9 |
| 5 | 0.074 | 12 | NA | 59.8 | 28.2 | 0.23 | 34.3 | 23.2 | 37.3 |
| 6 | 0.28 | 11.9 | 1.45 | 60.1 | 28.0 | 0.85 | 34.5 | 23.0 | 35.1 |
| 7 | 1.0 | 12.79 | 1.61 | 58.3 | 28.9 | 2.54 | 33.6 | 21.8 | 36.4 |
| 8 | 2.5 | 15.24 | 1.62 | 54.8 | 30.0 | 4.62 | 31.9 | 20.1 | 37.8 |

TABLE 12

Kd-distribution coefficient and selectivity

| Vial No. | HCl Kd | H$_2$O Kd | glucose Kd | MeOH Kd | HCl/water selectivity | HCl/glucose selectivity |
|---|---|---|---|---|---|---|
| 1 | 0.22 | NA | NA | 0.76 | NA | |
| 2 | 0.36 | 0.27 | NA | 0.69 | 1.36 | |
| 3 | 0.31 | 0.25 | NA | 0.65 | 1.24 | |
| 4 | 0.22 | 0.20 | NA | 0.63 | 1.09 | |
| 5 | 0.32 | 0.35 | NA | 0.76 | 0.91 | |
| 6 | 0.33 | 0.34 | 0.063 | 0.80 | 0.95 | 5.2 |
| 7 | 0.40 | 0.38 | 0.074 | 0.79 | 1.04 | 5.4 |
| 8 | 0.53 | 0.48 | 0.081 | 0.79 | 1.12 | 6.6 |

The distribution coefficients of HCl are slightly higher than those in Exp.4, but lower than that in previous examples, where hexanol was tested.

Example 17

1.3 gr 20% HCl solution, 1.42 gr water, 0.15 gr $FeCl_3 \cdot 6H_2O$, and 1.3 gr hexanol or 1.3 gr butanol were introduced into a vial. The closed vial was shaken at 25° C. for 2 min. The phases were then separated and analyzed for HCl concentrations (by titration) and Fe (with ammonium thio-cyanide). The results are presented in Table 13.

TABLE 13

| solvent | Light phase composition HCl Wt % | Light phase composition Fe Wt % | heavy Phase composition HCl Wt % | heavy Phase composition Fe Wt % | HCl distribution coefficient | Fe distribution coefficient | selectivity |
|---|---|---|---|---|---|---|---|
| hexanol | 2.28 | 0.088 | 11.5 | 1.18 | 0.20 | 0.075 | 2.67 |
| butanol | 4.88 | 0.185 | 10.5 | 1.01 | 0.46 | 0.183 | 2.52 |

These results demonstrate selective extraction of HCl from the chloride salt when a hydrophobic solvent such as hexanol is used. The results also show a selective extraction of HCL form the chloride salt when butanol is used.

Example 18

5.5 gr wet pine wood (containing 38.5% water) and 12.3-15.4 gr acetone were introduced into vials. The closed vials were shaken at 55° C. for 4 hr. Then, the liquid was filtered through and the filtrate was concentrated under reduced pressure in a 60° C. hot bath, and dried overnight at 80° C. for determining the DS. The initial composition and the composition of the acetone solution at the end of the experiment are summarized in table 14.

TABLE 14

| Vial No. | acetone-water/dry wood | total water over extractant | solids/dry wood Wt % | Solids Wt % |
|---|---|---|---|---|
| 1 | 5.6:1 | 11.11% | 1.16 | 0.0356 |
| 2 | 4.6:1 | 13.5% | 1.3 | 0.0399 |

The amount of extractant is included the moisture within the wood.

These results demonstrate extraction of pitch from the feed in the presence of acetone.

While embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A carbohydrate mixture derived from a lignocellulose material, the carbohydrate mixture comprising:
    water;
    at least one hexose selected from the group consisting of galactose and mannose;
    at least one pentose selected from the group consisting of xylose and arabinose;
    a water soluble higher oligomer of glucose, mannose, xylose, galactose, arabinose, or a combination thereof;
    furfural in a weigh/weight ratio to carbohydrates of less than 0.01; and
    an S1 solvent capable of forming a heterogeneous azeotrope with the water;
    wherein the carbohydrate mixture comprises a plurality of liquid phases.

2. The carbohydrate mixture of claim 1, wherein the at least one hexose or the at least one pentose is hemicellulose-derived.

3. The carbohydrate mixture of claim 1, wherein the at least one hexose and the at least one pentose are hemicellulose-derived.

4. The carbohydrate mixture of claim 1, comprising furfural in an amount up to 1000 ppm.

5. The carbohydrate mixture of claim 1, wherein the S1 solvent is selected from the group consisting of an aliphatic alcohol, an aromatic alcohol, a ketone having at least 5 carbon atoms, and an aldehyde having at least 5 carbon atoms.

6. The carbohydrate mixture of claim 1, wherein the S1 solvent is characterized by a water solubility of less than 10% and by at least one of:
    a polarity related component of Hoy's cohesion parameter (delta-P) between 5 and 10 $MPa^{1/2}$; and
    a hydrogen bonding related component of Hoy's cohesion parameter (delta-H) between 5 and 20 $Mpa^{1/2}$.

7. The carbohydrate mixture of claim 1, wherein the lignocellulose material comprises a material selected from the group consisting of agricultural residues, municipal solid waste, industrial solid waste, yard waste, and forestry waste.

8. The carbohydrate mixture of claim 1, wherein a weight/weight ratio between pentoses and total carbohydrates is at least 0.05.

9. The carbohydrate mixture of claim 1, further comprising at least one microorganism.

10. The carbohydrate mixture of claim 1, comprising glucose, galactose and xylose.

11. The carbohydrate mixture of claim 1, wherein the at least one pentose is present in a proportion relative to a total carbohydrate content of the carbohydrate mixture of at least 0.10.

12. The carbohydrate mixture of claim 1, wherein the higher oligomer is present in a proportion relative to a total carbohydrate content of the carbohydrate mixture of less than 0.2.

13. The carbohydrate mixture of claim 1, further comprising at least one alpha-bonded carbohydrate selected from the group consisting of maltose, isomaltose, trehalose, kojibiose and nigerose.

14. The carbohydrate mixture of claim 13, wherein the at least one alpha-bonded carbohydrate is present in a proportion relative to a total carbohydrate content of the carbohydrate mixture of at least 0.01.

15. The carbohydrate mixture of claim 1, further comprising at least one beta-bonded carbohydrate selected from the group consisting of gentiobiose, sophorose, cellobiose, laminaribiose and beta-trehalose.

16. The carbohydrate mixture of claim 15, wherein the at least one beta-bonded carbohydrate is present in a proportion relative to a total carbohydrate content of the carbohydrate mixture of at least 0.01.

17. The carbohydrate mixture of claim 1, wherein the S1 solvent comprises hexanol, 2-ethyl-1-hexanol, or a combination thereof.

18. The carbohydrate mixture of claim 1, wherein a ratio of the S1 solvent to the water is greater than a ratio of the S1 solvent to the water at the heterogeneous azeotrope.

19. The carbohydrate mixture of claim 1, wherein the water is between 3 and 20 weight percent of the carbohydrate mixture.

20. The carbohydrate mixture of claim 1, further comprising a strong acid, wherein a weight ratio of the strong acid to the water is between 0.2 and 1.0.

* * * * *